US007378506B2

(12) United States Patent
Kieliszewski

(10) Patent No.: US 7,378,506 B2
(45) Date of Patent: *May 27, 2008

(54) SYNTHETIC GENES FOR PLANT GUMS AND OTHER HYDROXYPROLINE-RICH GLYCOPROTEINS

(75) Inventor: Marcia J. Kieliszewski, Albany, OH (US)

(73) Assignee: Ohio University, Athens, OH (US)

( * ) Notice: Subject to any disclaimer, the term of this patent is extended or adjusted under 35 U.S.C. 154(b) by 272 days.

This patent is subject to a terminal disclaimer.

(21) Appl. No.: 10/418,032

(22) Filed: Apr. 16, 2003

(65) Prior Publication Data

US 2005/0074838 A1 Apr. 7, 2005

Related U.S. Application Data

(63) Continuation-in-part of application No. 09/547,693, filed on Apr. 12, 2000, now Pat. No. 6,639,050, which is a continuation-in-part of application No. 09/119,507, filed on Jul. 20, 1998, now Pat. No. 6,548,642, which is a continuation-in-part of application No. 08/897,556, filed on Jul. 21, 1997, now Pat. No. 6,570,062.

(51) Int. Cl.
*A61K 38/14* (2006.01)
*C07K 14/00* (2006.01)

(52) U.S. Cl. ............. 530/395; 530/300; 530/350; 530/370; 530/327; 530/326; 536/23.6; 435/320.1; 435/252.3

(58) Field of Classification Search ............... 530/395, 530/300, 350, 370, 327, 326; 536/23.6; 435/320.1, 435/252.3
See application file for complete search history.

(56) References Cited

U.S. PATENT DOCUMENTS

| | | | |
|---|---|---|---|
| 3,664,925 A | 5/1972 | Sonenberg et al. |
| 4,056,520 A | 11/1977 | Sonenberg et al. |
| 4,374,829 A | 2/1983 | Harris et al. |
| 4,683,195 A | 7/1987 | Mullis et al. |
| 4,683,202 A | 7/1987 | Mullis |
| 4,940,838 A | 7/1990 | Schilperoort et al. |
| 4,965,188 A | 10/1990 | Mullis et al. |
| 5,350,836 A | 9/1994 | Kopchick et al. |
| 5,352,596 A | 10/1994 | Cheung et al. |
| 5,474,925 A | 12/1995 | Maliyakal et al. |
| 5,501,967 A | 3/1996 | Offringa et al. |
| 5,506,107 A | 4/1996 | Cunningham et al. |
| 5,534,617 A | 7/1996 | Cunningham et al. |
| 5,584,807 A | 12/1996 | McCabe |
| 5,637,686 A | 6/1997 | Tjian et al. |
| 5,646,029 A | 7/1997 | Chen et al. |
| 5,681,809 A | 10/1997 | Kopchick et al. |
| 5,695,971 A | 12/1997 | Kadokami et al. |
| 5,728,810 A | 3/1998 | Lewis et al. |
| 5,733,771 A | 3/1998 | Lewis et al. |
| 5,756,677 A | 5/1998 | Lewis et al. |
| 5,763,394 A | 6/1998 | O'Connor et al. |
| 5,780,279 A | 7/1998 | Matthews et al. |
| 5,821,089 A | 10/1998 | Gruskin et al. |
| 5,830,747 A | 11/1998 | Chen et al. |
| 5,849,535 A | 12/1998 | Cunningham et al. |
| 5,958,879 A | 9/1999 | Kopchick et al. |
| 5,989,894 A | 11/1999 | Lewis et al. |
| 5,994,099 A | 11/1999 | Lewis et al. |
| 6,210,950 B1 | 4/2001 | Johnson et al. |
| 6,225,080 B1 | 5/2001 | Uhl et al. |
| 6,355,776 B1 | 3/2002 | Ferrari et al. |
| 6,486,382 B1 | 11/2002 | Gordan-Kamm et al. |
| 6,548,642 B1 | 4/2003 | Kieliszewski |
| 6,570,062 B1 | 5/2003 | Kielszewski |
| 6,583,115 B1 | 6/2003 | Kopchick et al. |
| 6,639,050 B1 | 10/2003 | Kieliszewski |
| 6,680,426 B2 | 1/2004 | Daniell et al. |
| 6,787,336 B1 | 9/2004 | Kopchick et al. |
| 2002/0127652 A1 | 9/2002 | Schambye et al. |
| 2002/0160944 A1 | 10/2002 | Boime et al. |
| 2002/0162135 A1 | 10/2002 | Daniell et al. |
| 2002/0174453 A1 | 11/2002 | Daniell |
| 2003/0009783 A1 | 1/2003 | Daniell |
| 2003/0041353 A1 | 2/2003 | Daniell |
| 2003/0167531 A1 | 9/2003 | Russell et al. |

(Continued)

FOREIGN PATENT DOCUMENTS

EP     1 156 060 A1    11/2001

(Continued)

OTHER PUBLICATIONS

Abstract No. XP-002295046, Accession No. P41479.
Alexandrou and Liakopoulou-Kyriakides, "Inhibition of Angiotensin Converting Enzyme by L-Alanyl-4 or 5-Substituted-L-Prolines and Their $N^{\alpha}$-Phosphoryl-Derivatives", *Biochemistry International* (1990) vol. 21, No. 1, pp. 271-278.
Altschul et al., "Basic Local Assignment Search Took", *J. Mol. Biol.* (1990) vol. 215, pp. 403-410.

(Continued)

*Primary Examiner*—Chih-Min Kam
(74) *Attorney, Agent, or Firm*—Calfee, Halter & Griswold LLP

(57) ABSTRACT

A new approach in the field of plant gums is described which presents a new solution to the production of hydroxyproline (Hyp)-rich glycoproteins (HRGPs), repetitive proline-rich proteins (RPRPs) and arabinogalactan-proteins (AGPs). The expression of synthetic genes designed from repetitive peptide sequences of such glycoproteins, including the peptide sequences of gum arabic glycoprotein (GAGP), is taught in host cells, including plant host cells.

7 Claims, 25 Drawing Sheets

U.S. PATENT DOCUMENTS

| | | | |
|---|---|---|---|
| 2003/0204864 A1 | 10/2003 | Daniell |
| 2004/0009555 A1 | 1/2004 | Kieliszewski |
| 2004/0009557 A1 | 1/2004 | Kieliszewski |
| 2004/0230032 A1 | 11/2004 | Kieliszewski |
| 2006/0026719 A1 | 2/2006 | Kieliszewski |
| 2006/0148680 A1 | 7/2006 | Kieliszewski |
| 2006/0252120 A1 | 11/2006 | Kieliszewski |
| 2007/0039073 A1 | 2/2007 | Kieliszewski |

FOREIGN PATENT DOCUMENTS

| | | |
|---|---|---|
| EP | 1 156 060 B1 | 6/2007 |
| WO | WO 90/04788 | 5/1990 |
| WO | WO 92/03478 | 3/1992 |
| WO | WO 92/09690 | 6/1992 |
| WO | WO 92/20713 | 11/1992 |
| WO | WO 93/00109 | 1/1993 |
| WO | WO 95/15377 | 6/1995 |
| WO | WO 97/11178 | 3/1997 |
| WO | WO 99/03978 | 1/1999 |
| WO | 00/026354 | 5/2000 |
| WO | 01/016339 | 3/2001 |
| WO | 01/049830 | 7/2001 |
| WO | 01/075132 | 10/2001 |
| WO | WO 01/078503 | 10/2001 |
| WO | 02/037313 | 5/2002 |
| WO | 05/110015 | 11/2004 |
| WO | WO 04/094590 | 11/2004 |
| WO | 05/069845 | 8/2005 |
| WO | 07/008708 | 1/2007 |

OTHER PUBLICATIONS

Amado et al., "Identification and characterization of large galactosyltransferase gene families: galactosyltransferases for all functions", *Biochimica et Biophysica Acta* (1999) vol. 1473, pp. 35-53.

An et al., "Binary Vectors", *Plant Molecular Biology Manual* (1988) vol. A3, pp. 1-19.

An, "High Efficiency Transformation of Cultured Tobacco Cells", *Plant Physiol.* (1985) vol. 79, pp. 568-570.

Averyhart-Fullard et al., "A hydroxyproline-rich protein in the soybean cell wall", *Proc. Nat. Acad. Sci. USA* (1988) vol. 85, pp. 1082-1085.

Baldwin et al., "The *ptl1* gene expressed in the transmitting tissue of *Antirrhinum* encodes an extensin-like protein", *The Plant Journal* (1992) vol. 2, No. 5, pp. 733-739.

Bergman et al., "Amino Acid Analysis by High Performance Liquid Chromatography of Phenylthiocarbamyl Derivatives", *Advanced Methods in Protein Microsequence Analysis* (1986) Wittmann-Liebold, Editor, Springer-Verlag, Berlin, pp. 45-55.

Borner et al., "Identification of Glycosylphosphatidylinositol-Anchored Proteins in Arabidopsis. A Proteomic and Genomic Analysis", *Plant Physiology* (2003) vol. 132, pp. 568-577.

Charpentier et al., "Analysis of dipeptides in urine by gas chromatography/mass spectrometry: implications for collagen breakdown in iminodipeptiduria following a study of the dipeptides by electron impact and chemical ionization", *Clinica Chimica Acta* (1984) vol. 138, pp. 299-308.

Chen et al., "In Vitro and In Vivo Studies of Antogonistic Effects ofHuman Growth Hormone Analogs", *The Journal of Biological Chemistry* (1994) vol. 269, No. 22, pp. 15892-15897.

Chen et al., "Specific Expression of an Extensin-Like Gene in the Style of *Nicotiana alata*", *The Plant Cell* (1992) vol. 4, pp. 1053-1062.

Chiu et al., "Engineered GFP as a vital reporter in plants", *Current Biology* (1996) vol. 6, No. 3, pp. 325-330.

DeCarvalho et al., "Suppression of β-1, 3-glucanase transgene expression in homozygous plants", *The EMBO Journal* (1992) vol. 11, No. 7, pp. 2595-2602.

DeLoose et al., "The extensin signal peptide allows secretion of a heterologous protein from protoplasts", *Gene* (1991) vol. 99, pp. 95-100.

Forreiter et al., "Stable transformation of an Arabidopsis cell suspension culture with firefly luciferase providing a cellular system for analysis of chaperone activity in vivo", *Plant Cell* (1997) vol. 9, No. 12, pp. 2171-2181.

Gastinel, "Galactosyltransferases: A Structural Overview of Their Function and Reaction Mechanisms", *Trends in Glycoscience and Glycotechnology* (2001) vol. 13, No. 70, pp. 131-145.

GenBank Accession No. AF227194.

GenBank Accession No. D41504.

GenBank Accession No. X69156.

Goodrum et al., "Gum arabic glycoprotein contains glycomodules of both extensin and arabinogalactan-glycoproteins", *Phytochemistry* (2000) vol. 54, pp. 99-106.

Griesbach et al., "Incorporation of the GUS Gene into Orchids through Embryo Electrophoresis", *ISHS Acta Horticulturae 336: II International Symposium on In Vitro Culture and Horticultural Breeding* (1993).

Guilley et al., "Introduction to Protein Structure and Function", *Virology* (1994) vol. 202(2), pp. 1012-1017.

Günther et al. "UDP-L-arabinose-hydroxyproline-O-glycosyltransferases in *Volvox carteri*", *FEBS* (1987) vol. 221, No. 2, pp. 293-298.

Holsters et al., "Transfection and Transformation of *Agrobacterium tumefaciens*", *Molec. Gen. Genet.* (1978) vol. 163, pp. 181-187.

Horsch et al., "A Simple and General Method for Transferring Genes into Plants", *Science* (1985) vol. 227, pp. 1229-1231.

Islam et al., "A review of recent developments on the regulatory, structural and funcitonal aspects of gum arabic", *Food Hydrocolloids* (1997) vol. 11, pp. 493-505.

Kieliszewski et al. "A Repetitive Proline-Rich Protein from the Gymnosperm Douglas Fir is a Hydroxyproline-Rich Glycoprotein", *Plant Physiol.* (1992) vol. 98, pp. 919-926.

Kieliszewski et al., "A Histidine-Rich Extensin from Zea mays is an Arabinogalactan Protein", *Plant Physiology* (1992) vol. 99, pp. 538-547.

Kieliszewski et al., "Cross-reactivities of polyclonal anitbodies against extensin precursors determined via ELISA techniques" *Phytochem.* (1986) vol. 25(3), pp. 673-677.

Kieliszewski et al., "Extensin: repetitive motifs, function sites, post-translational codes, and phylogeny", *The Plant Journal* (1994) vol. 5(2), pp. 157-172.

Kieliszewski et al., "Gum arabic glycoprotein: a new model", *FASEB* (1997) vol. 11(9), Abstract #3286.

Kieliszewski et al., "Structure of the Threonine-Rich Extensin from Zea mays", *Plant Physiology* (1990) vol. 92, pp. 316-326.

Kieliszewski et al., "Tandem mass spectrometry and structural elucidation of glycopeptidases from a hydroxyproline-rich plant cell wall glycoprotein indicate that continguous hydroxyproline residues are the major sites of hydroxyproline O-arabinosylation", *J. Biol. Chemistry* (1995) vol. 270(6), pp. 2541-2549.

Kieliszewski et al., "Potato lectin: a modular protein sharing sequence similarities with the extensin family, the hevelin lectin family, and snake venom disintegrins (platelet aggregation inhibitors)", *The Plant Journal* (1994) vol. 5, No. 6, pp. 849-861.

Kivirikko et al, "A Colorimetric Method for Determination of Hydroxyproline in Tissue Hydrolysates", *Scand. J. Clin. Lab. Invest.* (1959) vol. 11, p. 128.

Kopchick et al., "Growth Hormone Receptor Antagonists: Discovery, Development, and Use in Patients with Acromegaly", *Endocrine Reviews* (2002) vol. 23, No. 5, pp. 623-646.

Lamport et al., "Hydroxyproline in Primary Cell Walls of Higher Plants", *Nature* (1960) vol. 188, pp. 665-666.

Leonard et al., "Two novel types of O-glycans on the mugwort pollen allergen Art v 1 and their role in antibody binding", *JBC Papers in Press*, Published Dec. 10, 2004 as Manuscript M10407200.

Li et al., "A Chenopod Extensin Lacks Repetitive Tetrahydroxyproline Blocks", *Plant Physiol.* (1990), vol. 92, pp. 327-333.

Li et al., "Purification and characterization of the four beta-expansins (Zea m 1 isoforms) from maize pollen", *Plant Physiol.* (2003), vol. 132, No. 4, pp. 2073-2085.

Li et al., "Cloning and developmental/stress-regulated expression of a gene encoding a tomato arabinogalactan protein", *Plant Mol. Biol.* (1996) vol. 32, No. 4, pp. 641-652.

Mann et al., "The amino acid sequence of a type I copper protein with an unusual serine- and hydroxyproline-rich C-terminal domain isolated from cucumber peelings", *FEBS* (1992) vol. 314, No. 3, pp. 220-223.

McCormick_et al., "Leaf disc transformation of cultivated tomato (*L. esculentum*) using *Agrobacterium tumefaciens*", *Plant Cell Reports* (1986) vol. 5, pp. 81-84.

Memelink et al., "Structure and regulation of tobacco extensin", *The Plant Journal* (1993) vol. 4, No. 6, pp. 1011-1022.

Napoli et al., "Introduction of a Chimeric Chalcone Synthase Gene into Petunia Results in Reversible Co-Suppression of Homologous Genes in trans", *The Plant Cell* (1990) vol. 2, pp. 279-289.

Pagny et al., "Structural requirements for *Arabidopsis* β1,2-xylosyltransferase activity and targeting to the Golgi", *The Plant Journal* (2003) vol. 33, pp. 189-203.

Pearce et al., "Emulsifying Properties of proteins: Evaluation of a Turbidimetric Technique", *J. Agric. Food Chem.* (1978) vol. 26(3), pp. 716-723.

Sambrook et al., *Molecular Cloning Laboratory Manual* (1989) pp. 13.7-13.9 and 16.33-16.36.

Schenk et al., "Medium And Techniques For Induction And Growth Of Monocotyledonous And Dicotyledonous Plant Cell Cultures", *Can. J. Bot.* (1972) vol. 50, pp. 199-204.

Schnabelrauch et al., "Isolation of pI 4.6 extensin peroxidase from tomato cell suspension cultures and indetification of Val-Tyr-Lys as putative intermolecular cross-link site", *The Plant Journal* (1996) vol. 9, No. 4, pp. 477-489.

Shaper et al., "The Galactosyltransferases", *Carbohyd. Chem. Biol.* (2000) vol. 3, pp. 175-196.

Sheikholeslam et al., "Acetosyringone promotes high efficiency transformation of *Arabidopsis thaliana* explants by *Agrobacterium tumefaciens*", *Plant Molec. Biol.* (1987) vol. 8, pp. 291-298.

Shpak et al., "Synthetic Genes for glycoprotein design and the eludication of hydroxyproline-O-glycosylation codes", *Proc. Natl. Aca. Sci.* (1999), vol. 96, pp. 14736-14741.

Shpak et al., "Continguous Hydroxyproline Residues Direct Hydroxyproline Arabinosylation in *Nicotiana tabacum*", *The Journal of Biological Chemistry* (2001) vol. 276, No. 14, pp. 11272-11278.

Smith et al., "Tomato Extensin Precursors P1 and P2 are highly periodic structures", *Phytochemistry* (1986) vol. 25, No. 5, pp. 1021-1030.

Sticher et al., "Vacuolar Chitinases of Tobacco: A New Class of Hydroxyproline-Containing Proteins", *Science* (1992) vol. 257, No. 5070, pp. 665-657.

Stiefel et al., "Molecular cloning of cDNAs encoding a putative cell wall protein from *Zea mays* and immunological identification of related polypeptides", *Plant Molecular Biology* (1988) vol. 11, pp. 483-493.

Strahl-Bolsinger et al., "Protein O-mannosylation", *Biochimica et Biophysica acta* (1999) vol. 1426, pp. 297-307.

Stryer, *Biochemistry*, W.H. Freeman & Co., Sa Francisco, CA, (1975), pp. 17, 208-209.

Tan, Li, "O-Glycosylation Motifs in Arabinogalactan-Proteins", Doctoral Dissertation, Ohio University, presented Jun. 2003.

Tan et al., "Glycosylation Motifs That Direct Arabinogalactan Addition to Arabinogalactan-Proteins", *Plant Physiology* (2003) vol. 132, pp. 1362-1369.

Woessner et al., "Domain conservation in several volvocalean cell wall proteins", *Plant Molec. Biol.* (1994) vol. 26, pp. 947-960.

Zhao et al., "Tomato LeAGP-1 arabinogalactan-protein purified from transgenic tobacco corroborates the Hyp contiguity hypothesis", *Plant J.* (2002) vol. 31, No. 4, pp. 431-444.

Zhou et al., "Molecular cloning of a human UDP-galactose:GlcNAcβ1,3GalNAcβ1,3 galactosyltransferase gene enclding an O-linked core3-elongated enzyme", *Eur. J. Biochem.* (1999) vol. 263, pp. 571-576.

Akiyama et al., "Gum Arabic is a Kind of Arabinogalactan-Protein", *Agric. Biol. Chem.* (1984) vol. 48, pp. 235-237.

Anderson et al., "The chemical characterization of the gum exudates from eight Australia Acacia species of the series Phyllodineae", *Food Hydrocolloids* (1988) vol. 2, pp. 329-336.

Aspinall et al., "The location of a a-D-galactopyranose residues in gum arabic", *Carbohyd. Res.* (1986) vol. 157, pp. 257-260.

Aspinall, "Plant Gums", *The Carbohydrates*, (1970), vol. 2B, pp. 522-536.

Ausubel, "Current Protocols in Molecular Biology", *Chapter 3: Enzymatic Manipulation of DNA and DNA Restriction Mapping; Subcloning of DNA Fragments* (1995).

Bacic et al., "Fine Structure of the Arabinogalactan-Protein from *Lolium multiflorum*" *Carbohyd. Res.* (1987) vol. 162, pp. 85-93.

Benfey et al., "Sequence Requirements of the 5-Enolpyruvylshikimate-3-phosphate Synthase 5'-Upstream Region for Tissue-Specific Expression in Flowers and Seedings", *Plant Cell* (1990), vol. 2, pp. 849-856.

Bidney et al., "Microprojectile bombardment of plant tissues increases transformation frequency by *Agrobacterium tumefaciens*", *Plant Molec. Biol.* (1992) vol. 18, pp. 301-313.

Breton et al., "Sequence-Function Relationships of Prokaryotic and Eukaryotic Galactosyltransferases", *J. Biochem.* (Tokyo) (1998) vol. 123, pp. 1000-1009.

Churms et al., "Some New Aspects of the Molecular Structure of Acacia senegal GUM (Gum Arabic)", *Carbohydrate Research* (1983) vol. 123, pp. 267-279.

Clarke et al., "Form and Function of Arabinogalactans and arabinogalactan-Proteins", *Phytochem.* (1979) vol. 18, pp. 521-540.

Colbere-Garapin et al., "A New Dominant Hybrid Selective Marker for Higher Eukaryotic Cells", *J. Mol. Biol.* (1981) vol. 150, pp. 1-14.

Connolly et al., "Effect of a Proteinase on the Macromolecular Distribution of Acacia senegal Gum", *Carbohydrate Polymers* (1988) vol. 8, pp. 23-32.

Crimmins et al., "Increasing the Sensitivity of 6-Aminoquinolyl-N-hydroxysuccinimidyl Carbamate Amino Acid Analysis: A Simple Solution", *Analytical Biochemistry* (1997) vol. 244, pp. 407-410.

Defaye et al., "Structural Studies of Gum Arabic, the Exudate Polysaccharide from Acacia senegal", *Carbohydrate Research* (1986) vol. 150, pp. 221-231.

Delonnay, "Determination of the Protein Constitutent of Gum Arabic", *Master of Science Thesis* (1993).

Du et al., "Isolation of the Protein Backbone of an Arabinogalactan-Protein from the Styles of *Nicotiana alata* and Characterization of a Corresponding cDNA", *Plant Cell* (1994) vol. 6, p. 1643.

Dziezak, "A Focus on Gums", *Food Technology* (Mar. 1991), pp. 116-130.

Fraley et al., "Liposome-mediated delivery of tobacco mosaic virus RNA into tobacco protoplasts: A ensitive assay for monitoring liposome-protoplast interactions", *Proc. Natl. Acad. Sci. USA* (1982) vol. 79, pp. 1859-1863.

Gardiner et al., "Involvement of the Golgi Apparatus in the Synthesis and Secretion of Hydroxyproline-rich Cell Wall Glycoproteins", *Plant Physiol.* (1975) vol. 55, pp. 536-541.

Gerken et al., "Determination of the Site-Specific O-Glycosylation Pattern of the Procine Submaxillary mucin Tandem Repeat Glycopeptide", *J. Bio. Chem.* (1997) vol. 272, pp. 9709-9719.

Goodenough et al., "Crystals of the *Chlamydomonas reinhardtii* Cell Wall: Plymerization, Depolymerization, and Purification of Glycoprotein Monomers", J. Cell Biol. (1986) vol. 103, pp. 405-417.

Griesbach, "Incorporation of the gus gene into Orchids via embryo electrophoresis", *Hortscience* (1992) vol. 27, p. 620.

Haseloff et al., "Removal of a cryptic intron and subcellular localization of green fluroescent protein are required to mark transgenic Arabidopsis plants brightly", *Proc. Natl. Acad. Sci* (1997) vol. 94, pp. 2122-2127.

Idris et al., "Characterization of gum from Acacia senegal trees of different age and location using multidetection gel permeation chromatography", *Food Hydrocolloids* (1998) vol. 12, pp. 379-388.

Kieliszewski et al., "Synthetic genes for the Elucidation of Glycosylation Codes of Hydroxyproline-Rich Glycoproteins", *XVI International Botanical Congress*, St. Louis, MO, Jul. 31-Aug. 3, 1999.

Klee et al., "Agrobacterium-mediated plant transformation and its further applications to plant biology", *Ann. Rev. Plant Phys.* (1987) vol. 38, pp. 467-486.

Krens et al., "In vitro transformation of plant protoplasts with Ti-plasmid DNA", *Nature* (1982) vol. 296, pp. 72-74.

Lamport et al., "Galactosylserine in Extensin", *Biochem. J.* (1973) vol. 133, pp. 125-131.

Lamport et al., "Hydroxyproline Arabinosides in the Plant Kingdom", *Plant Physiology* (1971) vol. 48, pp. 454-456.

Lamport, "Hydroxyproline-O-glycosidic Linkage of the Plant Cell Wall glycoprotein Extensin", *Nature* (1967) vol. 216, pp. 1322-1324.

Lewis et al., "Expression and Purification of a silk spider protein: A New Strategy for Producing Repetitive Proteins", *Protein Express. Purif.* (1996) vol. 7, pp. 400-406.

McGrath et al., "Chemical and Biosynthetic Approaches to the Production of a Novel Polypeptide Materials," *Biotechnol Prog.* (1990) vol. 6, pp. 188-192.

Merkle et al., "Carbohydrate Composition Analysis of Glycoconjugates by Gas-Liquid Chromatography/Mass Spectrometry", *Methods in Enzymology* (1994) vol. 230, p. 1.

Miller et al., "Hydroxyproline Heterooligosaccharides in Chlamydomonas", *Science* (1972) vol. 176, pp. 918-920.

Mollard et al., "Acacia senegal cultured in suspension secrete a hydroxyproline-deficint rabinogalactan-protein", Plant Physiol. Biochem. (1994) vol. 32, pp. 703-709.

Nan et al., "Genetic Transformation in Dendrobium (Orchid)" In *Biotechnology in Agriculture and Forestry*, Ed. Y.P.S. Bajaj, Springer-Verlag Berling Heidelberg (1995) vol. 34, pp. 145-155.

Nothangel, "Proteoglycans and Related Components in Plant Cells", *International Review of Cytology* (1997) vol. 174, p. 195.

Osman et al., "Characterization of Gum Arabic Fractions Obtained By Anion-Exchange Chromatography", *Phytochemistry* (1995) vol. 38, pp. 409-417.

Pope, "Relationships between Hydroxyproline-containing Proteins Secreted into the Cell Wall and Medium by Suspension-cultured *Acer Pseudoplatanus* Cells", *Plant Physiology* (1977) vol. 59, pp. 894-900.

Prakash et al., "The effects of added proteins on the functionality of gum arabic in soft drink emulsion systems", *Food Hydrocolloids* (1990) vol. 4(3), pp. 177-184.

Qi et al., "Gum Arabic Glycoprotein Is A Twister Hairy Rope", *Plant Physiol.* (1991) vol. 96, pp. 848-855.

Raz et al., "The sequence of a hydroxyproline-rih glycoprotein gene from *Sorghum vulgare*", *Plant Molecular Biology* (1991) vol. 16, pp. 365-367.

Rhodes et al., "Transformation of Maize by Electroporation of Embryos", *Methods Mol. Biol.* (1995) vol. 55, pp. 121-131.

Stephens et al., "Exudate Gums", *Methods Plant Biochem.* (1990) vol. 2, pp. 483-522.

Stitcher et al., "Posttranslational Processing of a New Class fo Hydroxyproline-Containing Proteins", *Plant Physiol.* (1993) vol. 101, pp. 1239-1247.

Tsien, "The Green Fluroescent Protein", *Annu. Rev. Biochem.* (1998) vol. 67, pp. 509-544.

Van Wandelen et al., "Using quarternary high-performance liquid chromatography eluent systems for separating 6-aminoquinolyl-N-hydroxysuccinimidyl carbamate-derivatized amino acid mixtures", *J. Chromatography A* (1997) vol. 73, p. 11.

Wigler et al., "Transformation of mammalian cells with an amplifiable dominant-acting gene", *Proc. Natl. Acad. Sci.* (1980) vol. 77, pp. 3567-3570.

York et al., "Isolation and Characterization of Plant Cell Walls and Cell Wall Components", *Methods in Enzymology* (1985) vol. 118, p. 3.

Zhang et al., "Expression of an environmentally friendly synthetic protein-based polymer gene in transgenic tobacco plants", *Plant Cell Reports* (1996) vol. 16, pp. 174-179.

Office Action in U.S. Appl. No. 10/437,708, dated Aug. 11, 2004.
Office Action in U.S. Appl. No. 10/437,708, dated Nov. 26, 2004.
Office Action in U.S. Appl. No. 10/437,708, dated May 05, 2005.
Office Action in U.S. Appl. No. 10/437,708, dated Oct. 03, 2005.
Office Action in U.S. Appl. No. 10/437,708, dated Jun. 08, 2006.
Office Action in U.S. Appl. No. 10/437,708, dated Feb. 28, 2007.
Office Action in U.S. Appl. No. 11/173,811, dated Jun. 12, 2006.
Office Action in U.S. Appl. No. 11/243,295, dated Nov. 15, 2006.
Office Action in U.S. Appl. No. 11/243,295, dated Jul. 25, 2007.
Office Action in U.S. Appl. No. 11/036,257, dated Oct. 04, 2006.
Office Action in U.S. Appl. No. 11/036,257, dated Feb. 26, 2007.
Office Action in U.S. Appl. No. 11/036,256, dated Jul. 26, 2006.
Office Action in U.S. Appl. No. 11/036,256, dated Oct. 04, 2006.
Office Action in U.S. Appl. No. 11/036,256, dated Jul. 05, 2007.
International Preliminary Report on Patentability in Application No. PCT/US05/13252, dated Nov. 07, 2006.
International Search Report in Application No. PCT/US05/13252, dated Feb. 10, 2006.
Written Opinion in Application No. PCT/US05/13252, dated Feb. 10, 2006.
International Preliminary Report on Patentability in Application No. PCT/US05/01160, dated Jun. 24, 2006.
International Search Report in Application No. PCT/US05/01160, dated Jun. 24, 2006.
Written Opinion in Application No. PCT/US05/01160, dated Jun. 24, 2006.
International Preliminary Report on Patentability in Application No. PCT/US04/011174, dated Oct. 21, 2005.
International Search Report and Written Opinion in Application No. PCT/US04/011174, dated Feb. 15, 2005.
International Preliminary Examination Report in Application No. PCT/US01/12336, dated Jan. 16, 2004.
International Search Report in Application No. PCT/US01/12336, dated Jan. 27, 2003.
European Search Report from related Application No1 98944431.0, dated Oct. 15, 2004.
European Examination from related Application No. 01 927 057.8, dated Jul. 31, 2006.
European Supplementary Search Report from related Application No. 01 927 057.8, dated May 26, 2004.

Allan et al., "Identification of novel sites in the ovine growth hormone receptor involved in binding hormone. . . ", Eur. J. biochem., vol. 261, No. 2 (1999), pp. 555-561.

Bell et al., "Crystallization and Preliminary X-ray Characterization of Bovine Growth Hormone", J. Biol. Chem., vol. 260, No. 14 (1985), pp. 8520-8525.

Boutin et al., "Cloning and expression of the rat prolactin receptor, a member of the growth hormone/prolactin receptor gene family", Cell, vol 53, No. 1 (1998), pp. 69-77.

Chen et al., "Functional antagonism between endogenous mouse growth hormone (GH) and a GH analog results in dwarf transgenic mice", Endocrinolgy, vol. 129 (1991), pp. 1402-08.

Chen et al., "Glycine 119 of bovine growth hormone is critical for growth-promoting activity", Mol. Endocrinolgy, vol. 5 (1991), pp. 1845-1852.

Chen et al., "Mutations in the third α-helix of bovine growth hormone dramatically affect its intracellular distribution. . . ", J. Biol. Chem., vol. 266 (1991), pp. 2252-2258.

Chen et al., "Conformation studies of biologically active fragments of bovine growth hormone", Biochemistry, vol. 16, No. 10 (1977), pp. 2110-2118.

Chou et al., "Prediction of protein conformation", Biochemistry, vol. 13, No. 2 (1974), pp. 222-245.

Cunningham et al., "Engineering human prolactin to bind the human growth hormone receptor", Science, vol. 247 (1990), pp. 1461-1465.

Cunningham et al., "High resolution epitope mapping of hGH-receptor interactions by alainie-scanning mutagenesis", Science, vol. 284, No. 4908 (1989), pp. 1081-1085.

Cunningham et al., "Receptor and antidoby epitopes in human grwoth hormone identified by homolog-scanning mutagenesis", Science, vol. 243, No. 4896 (1989), pp. 1330-1336.

De Blank et al., "Characterization of the soybean early noduline cDNA clone GmEN0D55", Plant Mol. Biol., vol. 22 (1993), pp. 1167-1171.

De Kock et al., "Administration o bovine, porcine and equine, growth hormone to the horse: effect on insulin-like. . .", J. Endocrinol., vol. 171, No. 1 (2001), pp. 163-171.

De Vos et al., "Human Growth Hormone and Extracellular Domain of its Receptor: Crystal Structure of the Complex", Science, vol. 255 (1992), pp. 306-312.

Forsyth, "Commparative aspects of placental lactogens: structure and function", Exp. Clin. Endocrinol., vol. 102, No. 3 (1994), pp. 244-251.

Freemark et al., "Purification of a distinct platental lactogen receptor, a new member of the growth hormone/prolactin. . .", J. Clin. Investig., vol. 83 (1989), pp. 883-889.

Fuh et al., "Prolactin receptor antagonist that inhibit the growth of breast cancer cell lines", J. Biol. Chem., vol. 270, No. 22 (1995), pp. 13133-13137.

Goffin et al., "Sequence-Function Relationships Within the Expanding Family of Prolactin, Growth Hormone, Placental. . .", Endocrine Revs., vol. 17, No. 4 (1986), pp. 385-410.

Keeler et al., "The Tertiary Structure and Backbone Dynamics of Human Prolactin", J. Molec. Biol., vol. 328 (2003), pp. 1105-1221.

Kieliszewski et al., "Synthetic Genes for the Elucidation of Glycosylation Codes of Hydroxyproline-Rich. . .", Cell & Molecular Life Science, vol. 58 (2001), pp. 1386-1398.

Leung et al., "Growth Hormone receptor and serum binding protein: purification, cloning and expression", Nature, vol. 330, No. 6148 (1987), pp. 537-543.

Liu et al., "Epidsodic Evoluation of Growth Hormone in Primates and Emergence of the Species Specificity of. . .", Mol. Biology & Evolution, vol. 18, No. 6 (2001), pp. 945-953.

Miller et al., "Molecular cloning of DNA complementary to bovine growth hormone mRNA", J. Biol. Chem., vol. 255 (1980), pp. 7521-7524.

Nicoll et al., "Structural Features of Prolactins and Growth Hormones that Can Be related to Their Biological Properties", Endocrine Revs., vol. 7, No. 2 (1986), pp. 169-203.

Ross et al., "Binding and functional studies with the growth hormone receptor antagonist, B2036-PEG. . .", j. Clin. Endocrinol. Metab., vol 86, No. 4 (2001), pp. 1716-1723.

SERVICE, "Unnatural Amino Acid Could Prove Boon for Protein Therapeutics", Science, vol. 308 (2005), pp. 44+.

Takahashi et al., "Brief report: Short stature caused by a mutant growth hormone", New England J. of Med., vol. 334, No. 7 (1996), pp. 432-436.

Tan et al., "Structure of a hydroxyproline (Hyp)-arabinogalactan polysaccharide from repetitive Ala-Hyp. . .", J. Biol. Chem., vol. 264 (1989), pp. 312-316.

Watahiki et al., "conserved and unique amino acid residues in the domains of the growth hormones. . .", J. Biol. Chem., vol. 264 (1989), pp. 312-316.

Wells et al., "Structure and Function of Human Growth Hormone: Implications for the Hematopoietins", Ann. Rev. Biophys. Biomol. Struct., vol. 22 (1993), pp. 329-351.

GENBANK Accession No. AF227194 dated Feb. 21, 2003. Ishizuka et al.

GENBANK Accession No. D41504 dated Nov. 15, 1994. Takuji S.

GENBANK Accession No. P41479 dated Nov. 01, 1995. Ayres et al.

GENBANK Accession No. S50755 dated May 08, 1993. Woessner et al.

GENBANK Accession No. X69156 dated Nov. 14, 2006. Franssen H.

International Search Report for Application No. PCT/US98/15083, dated Dec. 08, 1998.

International Preliminary Examination Report for Application No. PCT/US98/15083, dated May 17, 1999.

Supplementary European Search Report for Application No. 04759826.3, dated Dec. 27 2007.

Supplementary European Search Report for Application No. 05726258.6, dated Jan. 25, 2008.

Office Action in U.S. Appl. No. 10/437,708, dated Nov. 8, 2007.

Advisory Office Action in U.S. Appl. No. 10/437,708, dated Feb. 1, 2008.

Office Action in U.S. Appl. No. 11/173,811, dated Dec. 27, 2007.

Office Action in U.S. Appl. No. 11/243,295, dated Jan. 3, 2008.

Office Action in U.S. Appl. No. 11/036,257, dated Nov. 8, 2007.

Office Action in U.S. Appl. No. 11/036,256, dated Dec.17, 2007.

Abdel-Meduid et al., "Three Dimensional Structure of a genetically engineered variate of porcine growth hormone", Proc. Nat. Acad. Sci. USA, (1987), vol. 64, pp. 6434-6437.

Bailon, et al., "Rational Design of a Potent, Long-Lasting Form of Interferon: A 40 kDa Branched Polyethylene Glyco-Conjugated Interferon α-2A for the Treatment of Hepatitis C", Bioconjugate Chem., (2001) vol. 12, No. 2, pp. 195-202.

Cabanes-Macheteau et al., "N-glycosylation of a mouse lgG expressed in transgenic tobacco plants", Glycobiology, (1999), vol. 9, pp. 365-372.

Evans et al., "The extensin gene family in oilseed rape (Brassica napus L.): characterisation of sequences of representative members of the family", Mol Gen Genet. (Sep. 1990), vol. 223, No. 2, pp. 273-87.

Fong et al., "A Gymnosperm Extensin Contains the Serine-Tetrahydroxyproline Motif", Plant Physiology, (1992), vol. 99, No. 2, pp. 548-552.

Gill et al., "Recombinant Chicken and Bovine Growth Hormones Accelerate Growth in Aquacultured Juvenile Pacific Salmon Oncorhynchus Kisutch", Biotechnology, (1985), vol. 3, pp. 643-646.

Hirsinger et al., "Characterization of tobacco extensin gene and regulation of its gene family in healthy plants and under various stress conditions", Plant Mol Biol. (Jan. 1997), vol. 33, No. 2, pp. 279-89.

Marusina et al., "Novel peptide-binding proteins and peptide transport in normal and TAP-deficient microsomes", Biochemistry (Jan. 1997), vol. 36, No. 4, pp. 856-63.

Menassa et al., "A Self-contained system for the field production of plant recombinant interleukin-10", Molecular Breeding (2001), vol. 8, pp. 177-185.

Shirsat et al., "Expression of a Brassica napus extensin gene in the vascular system of transgenic tobacco and rape plants", Plant Mol Biol. (Oct. 1991), vol. 17, No. 4, pp. 701-9.

Sommer-Knudsen et al., "Hydroxyproline-rich plant glycoproteins", Phytochemistry (1998), vol. 47, pp. 483-497.

Watanabe et al., "Cloning and expression of two genes encoding auxin-binding proteins from tobacco", PMB, (1998), vol. 36, pp. 63-74.

Xu, et al., "Production of recombinant plant gum with tobacco cell culture in bioreactor and gum characterization", Biotechnol Bioeng., (Jun. 5, 2005), vol. 90, No. 5, pp. 578-88.

Ma, et al., "The production of recombinant pharmaceutical proteins in plants", NATURE REVIEWS GENETICS, (2003) vol. 4, No. 10, pp. 153-157.

Nacka et al., "Induction of new physiocochemical and functional properties by the glycosylation of whey proteins", Journal of Protein Chemistry, (1998), vol. 17, No. 5, pp. 495-503.

Putney et al., "Improving Protein Therapeutics with Sustained-Release Formulations", Nature Biotechnology, (1998), vol. 16, pp. 153-157.

Wileman, Thomas E., "Properties of asparaginase-dextran conjugates". Adv. Drug Delivery Revs., (1991), vol. 6, pp. 167-180.

Zhang et al., "Expression of Eukaryotic Proteins in Soluble Form in Escherichia coli", Protein Expression and Purification, (1998), vol. 12, No. 2, pp. 159-165.

Lewis et al., "Structure and Properties of Members of the hGH Family: A Review," Endocrine Journal, 2000, 47, (Suppl.), pp. S1-S8.

```
BamHI    XmaI
GCT GGT TCC TCA ACC CGG GCC TCA CCA CCT CCA CCA CCC CCA TCT CCT CCT CCA|CCA CCA CCT CCT CCA|CCA CCA CCT CCT CCA|CCA CCA CCT CCT CCA|CCA CCA CCT CCT CCA CCG GTC GCC CGG GCC CGG AAT TCA CCA CCC
CGA CCA AGG AGT TGG GCC CGG AGT GGT GGA GGT GGG GGT AGA TCT AGA GGT GGG GGT|GGT GGT GGA GGA GGT|GGT GGT GGA GGA GGT|GGT GGT GGA GGA GGT|GGT GGT GGA GGA GGT GGC CAG CGG CCG TTA AGT GGT CGG
A   G   S   S   T   R   A   S   P   P   P   P   P   P   S   P   P   P   P | P   P   P   P   P | S   P   P   P   P | P   P   P   P   P | S   P   V   A   R   N   S   P   P   P
                                                                                                                                        AgeI        EcoRI
```

FIG. 1

SER-PRO INTERNAL REPEAT
5'-TCA CCC TCA CCA TCT CCT TCG CCA TCA CCC-3' (SEQ ID NO:112)
3'-GGT AGA GGA AGC GGT AGT GGG AGT GGG AGT-5' (SEQ ID NO:113)
 S   P   S   P   S   P   S   P   S   P  (SEQ ID NO:114)

GAGP INTERNAL REPEAT
5'-TCA CCC TCA CCA ACT CCT ACC GCA CCA CCT GGT GGA CCA CAC TCA CCA GGT GTG AGT GGT GGT TGT AAC AGT GGG
3'-GGT TGA GGA GGT TGA GGA TGG CGT GGT GGA CCA CCT GGT GTG AGT GGT CCA CAC TCA CCA CCA ACA TTG-3' (SEQ ID NO:115)
 S   P   S   P   T   P   T   A   P   P   G   G   P   H   S   P   G   V   S   G   G   C   N   S   G
AGT-5' (SEQ ID NO:116)
 S   P   P   P   T   L (SEQ ID NO:117)

SIGNAL SEQUENCE
5'-GCTGCCGGATCCGCAATGGGAAAAATGCTTCTCTATTGCCACACATTTTA GTGGTTTTAGTGTCACTTAGCTTAGCAC
AAACAACC-3' (SEQ ID NO:118)
3'-CACCAAAATCACAGTGAATCGAATCGTGTTTGTTGGGCCCATCATGGCGACCGAGCTCTGCCCCC-5' (SEQ ID NO:119)

5'-LINKER
5'-GCT GCC GGA TCC TCA ACC CGG GCC-3' (SEQ ID NO:120)
3'-CGA CGG CCT AGG AGT TGG GCC CGG AGT-5' (SEQ ID NO:121)
 A   A   G   S   S   T   R   A  (SEQ ID NO:122)

3'-LINKER
5'-TCA CCC TCA CCG GTC GCC GCC CGG AAT TCA CCA CCC-3' (SEQ ID NO:123)
3'-GGC CAG CGG GCC TTA AGT GGT GGG-5' (SEQ ID NO:124)
 S   P   S   P   V   A   T   N   S   P   P  (SEQ ID NO:125)

FIG. 11

A. S P S X S O X S X S O X S X (SEQ ID NO:126) S O S O S O S O S O S O S O S (SEQ ID NO:127)

B. D S O* S P T O* T A O O G P H S O O O (SEQ ID NO:128)
D S O S P T O T A O O G P H S O O P T L S S O S O T (SEQ ID NO:129)

FIG. 14

```
          HindIII BspEI              BsFl
5'-G CCA AGT TTC CGG AGT GCC GGC CCT CAT AGC CCT ACA CTT TCC CCT TCA CCA TTA TCA CCT ACT CCT CCT TTG GGA
3'-C GGT TCG AAG GCC TCA CGG CCG GGA GTA TCG GGA TGT GAA AGG GGA AGT GGT AAT AGT GGA TGA GGA GGA AAC CCT
     G   P   S   F   R   S   A   G   P   H   S   P   T   L   S   P   S   P   L   S   P   T   P   P   L   G CCA CAC AGT CCA CCC CCT ACA CCA ACC CCA CCA TTA TCA CCA CCC CCT GGT AGT CCT AGT CCT CCT CCC CCC GGG TAC-3' (SEQ ID NO:130)
GGT GTG TCA GGT GGG GGA TGT GGT TGG GGT GGT AAT AGT GGT GGG GGA CCA TCA GGA TCA GGA GGA GGG GGG CCC ATG-5'
 P   H   S   P   P   P   T   P   T   P   P   L   S   P   P   P   G   S   P   S   P   P   P   P   G  (SEQ ID NO:131)
                                                                                    XmaI
```

FIG. 16A

```
          HindIII BspEI              BsFl
5'-G CCA AGT TTC CGG AGT GCC GGC CCT CAT AGC CCT ACA CTT TCC CCT TCA CCA TTA TCA CCT ACT CCT CCT TTG GGA
3'-C GGT TCG AAG GCC TCA CGG CCG GGA GTA TCG GGA TGT GAA AGG GGA AGT GGT AAT AGT GGA TGA GGA GGA AAC CCT
     G   P   S   F   R   S   A   G   P   H   S   P   T   L   S   P   S   P   L   S   P   T   P   P   L   G CCA CAC AGT CCA CCC CCT ACA CCA ACC CCA CCA TTA TCA CCA CCC CCT GGT AGT CCT CAT AGC CCT ACA CTT TCC CCT
GGT GTG TCA GGT GGG GGA TGT GGT TGG GGT GGT AAT AGT GGT GGG GGA CCA TCA GGA GTA TCG GGA TGT GAA AGG GGA
 P   H   S   P   P   P   T   P   T   P   P   L   S   P   P   P   G   S   P   H   S   P   T   L   S   P TCA CCA TCA CCT ACT CCT CCT TTG GGA CCA CAC AGT CCA CCC CCT ACA CCA ACC CCA CCA TTA
AGT GGT AGT GGA TGA GGA GGA AAC CCT GGT GTG TCA GGT GGG GGA TGT GGT TGG GGT GGT AAT
 S   P   S   P   T   P   P   L   G   P   H   S   P   P   P   T   P   T   P   P   L TCA CCA CCC CCT GGT AGT CCT GGT CCT CCT CCC CCC GGG TAC-3' (SEQ ID NO:132)
AGT GGT GGG GGA CCA TCA GGA CCA GGA GGA GGG GGG CCC ATG-5'
 S   P   P   P   G   S   P   G   P   P   P   P   G  (SEQ ID NO:133)
                    XmaI
```

FIG. 16B

Figure 20

```
                BamHI
AGG ATC CGG TCT ATA TTT TCT TTA GCT ACC ATG GAT AGA AAA TTT GTA TTT CTA GTA TCA ATT TTG
                                         M   D   R   K   F   V   F   L   V   S   I   L
                                      XmaI
TGC ATT GTA GTG GCA AGT GTC ACG GGT CAG ACA ACC CGG GTA CCG GTC GCC ACC ATG--- EGFP---
 C   I   V   V   A   S   V   T   G   Q   T   T   R   V   P   V   A   T   M

BsrGI
GAG CTG TAC ACG GGT CAG ACA CCT GCC GCA GCA CCC GTT GGT GCT AAG GCT GGT ACT ACT CCA
 E   L   Y   T   G   Q   T   P   A   A   A   P   V   G   A   K   A   G   T   T   P
CCA GCT GCT GCA CCA ACT AAG CCG AAA ACT CCT GCT CCC GCA ACA GCA CCA GCC TCG GCC CCA
 P   A   A   A   P   T   K   P   K   T   P   A   P   A   T   A   P   A   S   A   P
CCT ACA GCT GTT CCT GTT GCT CCA GTA ACC GCT CCA GTT ACT GCT CCC ACT ACA CCT GTT GTT
 P   T   A   V   P   V   A   P   V   T   A   P   V   T   A   P   T   T   P   V   V
GCT GCA CCC GTA TCA GCA CCA GCA AGT TCT CCA CCA CTT AAA GCA CCA GCA AGT TCT CCA CCA
 A   A   P   V   S   A   P   A   S   S   P   P   L   K   A   P   A   S   S   P   P
GTA CAA TCT CCA CCA GCT CCA GCT CCA GAG GTA GCT ACA CCG CCA GCT GTT TCT ACT CCA CCG
 V   Q   S   P   P   A   P   A   P   E   V   A   T   P   P   A   V   S   T   P   P
GCT GCA GCT CCA GTT GCT GCA CCT GTT GCT TCG GAG ACA ACT CCA GCT CCG GCT CCT AGC AAA
 A   A   A   P   V   A   A   P   V   A   S   E   T   T   P   A   P   A   P   S   K
                                                       NsI
GGA AAA GTA AAG GGA AAG AAG GGA AAG AAA CAC AAT GCA TCA CCA GCA CCT TCT CCC GAT ATG
 G   K   V   K   G   K   K   G   K   K   H   N   A   S   P   A   P   S   P   D   M
ATG AGC CCA CCT GCA CCT CCT TCC GAA GCT CCT GGA CCT AGC ATG GAC TCC GAT TCA GCT CCC
 M   S   P   P   A   P   P   S   E   A   P   G   P   S   M   D   S   D   S   A   P
AGC CCA TCT CTT AAC GAT GAG AGT GGA GCA GAG AAA TTG AAG ATG CTG GGA AGT TTG GTA GCT
 S   P   S   L   N   D   E   S   G   A   E   K   L   K   M   L   G   S   L   V   A
                                                    EagI
GGA TGG GCT GTG ATG AGC TGG CTC TTG TTC TAA AGC GGC CGC ACC GCG (SEQ ID NO: 265)
 G   W   A   V   M   S   W   L   L   F   stop (SEQ ID NO: 266)
```

Figure 22

SEQUENCE LISTING

```
<160> NUMBER OF SEQ ID NOS: 274

<210> SEQ ID NO 1
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
```

```
<222> LOCATION: (14)..(16)
<223> OTHER INFORMATION: The Proline at these positions is a
      hydroxyproline.

<400> SEQUENCE: 1

Ser Pro Pro Pro Pro Leu Ser Pro Ser Pro Thr Pro Thr Pro Pro
1               5                   10                  15

Gly Pro His

<210> SEQ ID NO 2
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 2

Ser Pro Pro Pro Thr Leu Ser Pro Ser Pro Thr Pro Thr Pro Pro
1               5                   10                  15

Gly Pro His

<210> SEQ ID NO 3
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.

<400> SEQUENCE: 3

Ser Pro Pro Pro Pro
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
```

```
<223> OTHER INFORMATION: The Proline at this position is a
      hydroxyproline.

<400> SEQUENCE: 4

Pro Pro Val Tyr Lys
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Thr, Glu, hydroxyproline, Pro
      , His, and Ile.
<220> FEATURE:
<221> NAME/KEY: MISC_FEATURE
<222> LOCATION: (2)..(2)
<223> OTHER INFORMATION: The Proline at this position is a
      hydroxyproline.

<400> SEQUENCE: 5

Xaa Pro Val Tyr Lys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: Xaa can be Thr, Glu, hydroxyproline, Pr
      o, His and Ile.

<400> SEQUENCE: 6

Pro Pro Val Xaa Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa can be Thr, Glu, hydroxyproline, Pro, His
      and Ile.

<400> SEQUENCE: 7

Pro Pro Xaa Tyr Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (3)..(3)
<223> OTHER INFORMATION: Xaa can be Thr, Glu, hydroxyproline, Pr
      o, His and Ile.
<220> FEATURE:
<221> NAME/KEY: MISC_FEATURE
<222> LOCATION: (5)..(5)
<223> OTHER INFORMATION: Xaa can be Thr, Glu, hydroxyproline, Pro,
      His and Ile.

<400> SEQUENCE: 8

Pro Pro Xaa Tyr Xaa
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Thr, Glu, hydroxyproline, Pro,
      His and Ile.
<220> FEATURE:
<221> NAME/KEY: MISC_FEATURE
<222> LOCATION: (3)..(3)
<223> OTHER INFORMATION: Xaa can be Thr, Glu, hydroxyproline, Pro,
      His and Ile.

<400> SEQUENCE: 9

Xaa Pro Xaa Pro
1

<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10 ccaccaccttt cacctccacc cccatctcca                                     30

<210> SEQ ID NO 11
<211> LENGTH: 30
<212> TYPE: DNA
<213> ORGANISM: Artificial Sequence
<220> FEATURE:
<223> OTHER INFORMATION: Synthetic

<400> SEQUENCE: 11
tcaccatcac catctccttc gccatcaccc                                      30

<210> SEQ ID NO 12
<211> LENGTH: 123
<212> TYPE: DNA
<213> ORGANISM: Artificial Sequence
<220> FEATURE:
<223> OTHER INFORMATION: Synthetic

<400> SEQUENCE: 12
gctggatcct caacccgggc ctcaccacca ccaccttcac ctccaccccc atctccacca     60
ccaccttcac ctccaccccc atctccacca ccaccttcac cggtcgcccg gaattcacca   120
ccc                                                                  123
```

```
<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

Ser Pro Ser Pro Thr Pro Thr Pro Pro Pro Gly Pro
1               5                   10

<210> SEQ ID NO 14
<211> LENGTH: 34
<212> TYPE: PRT
<213> ORGANISM: Artificial Sequence
<220> FEATURE:
<223> OTHER INFORMATION: Synthetic

<400> SEQUENCE: 14

Met Gly Lys Met Ala Ser Leu Phe Ala Thr Phe Leu Val Val Leu Val
1               5                   10                  15

Ser Leu Ser Leu Ala Gln Thr Thr Arg Val Val Pro Val Ala Ser Ser
            20                  25                  30

Ala Pro

<210> SEQ ID NO 15
<211> LENGTH: 4
<212> TYPE: PRT
<213> ORGANISM: Artificial Sequence
<220> FEATURE:
<223> OTHER INFORMATION: Synthetic

<400> SEQUENCE: 15

Gly Ala Gly Pro
1

<210> SEQ ID NO 16
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 16

Ser Pro Pro Pro Pro Leu Ser Pro Ser Leu Thr Pro Thr Pro Pro Leu
1               5                   10                  15

Gly Pro
```

```
<210> SEQ ID NO 17
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 17

Ser Pro Pro Pro Pro Leu Ser Pro Ser Pro Thr Pro Thr Pro Pro Leu
1               5                   10                  15

Gly Pro

<210> SEQ ID NO 18
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.
<220> FEATURE:
<221> NAME/KEY: MISC_FEATURE
<222> LOCATION: (21)..(23)
<223> OTHER INFORMATION: The Proline at these positions is a
      hydroxyproline.

<400> SEQUENCE: 18
```

Ser Pro Pro Pro Thr Leu Ser Pro Ser Pro Thr Pro Thr Pro Pro
1               5                   10                  15

Gly Pro His Ser Pro Pro Pro
            20

<210> SEQ ID NO 19
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 19

Ser Pro Pro Pro Ser Leu Ser Pro Ser Pro Thr Pro Thr Pro Thr
1               5                   10                  15

Gly Pro His

<210> SEQ ID NO 20
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(10)
<223> OTHER INFORMATION: The Proline at these positions is a
      hydroxyproline.

<400> SEQUENCE: 20

Ser Pro Ser Pro Thr Pro Thr Pro Pro Pro Gly Pro His
1               5                   10

```
<210> SEQ ID NO 21
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(9)
<223> OTHER INFORMATION: The Proline at these positions is a
      hydroxyproline.

<400> SEQUENCE: 21

Ser Pro Ser Pro Ala Pro Thr Pro Pro Leu Gly Pro His
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(9)
<223> OTHER INFORMATION: The Proline at these positions is a
      hydroxyproline.

<400> SEQUENCE: 22

Ser Pro Leu Pro Thr Pro Thr Pro Pro Leu Gly Pro His
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
```

```
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(9)
<223> OTHER INFORMATION: The Proline at these positions is a
      hydroxyproline.

<400> SEQUENCE: 23

Ser Pro Ser Pro Thr Pro Thr Pro Pro Leu Gly Pro His
  1               5                  10

<210> SEQ ID NO 24
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: The Proline at these positions is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(9)
<223> OTHER INFORMATION: The Proline at these positions is a
      hydroxyproline.

<400> SEQUENCE: 24

Ser Pro Pro Leu Thr Pro Thr Pro Pro Leu Leu Pro His
  1               5                  10

<210> SEQ ID NO 25
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 25

Ser Pro Leu Pro Thr Leu Ser Pro Leu Pro Ala Pro Thr Pro Pro Pro
  1               5                  10                  15

Gly Pro His
```

```
<210> SEQ ID NO 26
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 26

Ser Pro Leu Pro Thr Leu Ser Pro Leu Pro Thr Pro Thr Pro Pro Pro
1               5                   10                  15

Gly Pro His

<210> SEQ ID NO 27
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 27

Ser Pro Pro Pro Thr Leu Ser Pro Ser Pro Thr Pro Thr Pro Pro Leu
1               5                   10                  15

Gly Pro His

<210> SEQ ID NO 28
<211> LENGTH: 19
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 28

Ser Pro Pro Pro Pro Leu Ser Pro Ser Pro Thr Pro Thr Pro Pro Leu
1               5                   10                  15

Gly Pro His

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Ala Gly Ser Ser Thr Arg Ala Ser Pro Pro Pro Pro
1               5                   10

<210> SEQ ID NO 30
<211> LENGTH: 27
<212> TYPE: DNA
<213> ORGANISM: Artificial Sequence
<220> FEATURE:
<223> OTHER INFORMATION: Synthetic

<400> SEQUENCE: 30
gctggatcct caacccgggc ctcacca                                        27

<210> SEQ ID NO 31
<211> LENGTH: 36
<212> TYPE: DNA
<213> ORGANISM: Artificial Sequence
<220> FEATURE:
<223> OTHER INFORMATION: Synthetic

<400> SEQUENCE: 31
aggtggtggt ggtgagcccc gggttgagga tccagc                              36

<210> SEQ ID NO 32
<211> LENGTH: 12
<212> TYPE: PRT
<213> ORGANISM: Artificial Sequence
<220> FEATURE:
```

<223> OTHER INFORMATION: Synthetic

<400> SEQUENCE: 32

Pro Pro Pro Ser Pro Val Ala Arg Asn Ser Pro Pro
1               5                   10

<210> SEQ ID NO 33
<211> LENGTH: 36
<212> TYPE: DNA
<213> ORGANISM: Artificial Sequence
<220> FEATURE:
<223> OTHER INFORMATION: Synthetic

<400> SEQUENCE: 33
ccaccacctt caccggtcgc ccggaattca ccaccc                          36

<210> SEQ ID NO 34
<211> LENGTH: 27
<212> TYPE: DNA
<213> ORGANISM: Artificial Sequence
<220> FEATURE:
<223> OTHER INFORMATION: Synthetic

<400> SEQUENCE: 34
gggtggtgaa ttccgggcga ccggtga                                    27

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ccaccacctt aatagagctc cccc                                       24

<210> SEQ ID NO 36
<211> LENGTH: 15
<212> TYPE: DNA
<213> ORGANISM: Artificial Sequence
<220> FEATURE:
<223> OTHER INFORMATION: Synthetic

<400> SEQUENCE: 36
gggggagctc tatta                                                 15

<210> SEQ ID NO 37
<211> LENGTH: 10
<212> TYPE: PRT
<213> ORGANISM: Artificial Sequence
<220> FEATURE:
<223> OTHER INFORMATION: Synthetic

<400> SEQUENCE: 37

Pro Pro Ser Pro Pro Pro Pro Ser Pro
1               5                   10

<210> SEQ ID NO 38
<211> LENGTH: 30
<212> TYPE: DNA
<213> ORGANISM: Artificial Sequence
<220> FEATURE:
<223> OTHER INFORMATION: Synthetic

<400> SEQUENCE: 38
ccaccacctt cacctccacc cccatctcca                                 30

<210> SEQ ID NO 39
<211> LENGTH: 30
<212> TYPE: DNA
<213> ORGANISM: Artificial Sequence
<220> FEATURE:
<223> OTHER INFORMATION: Synthetic

<400> SEQUENCE: 39
aggtggtggt ggagatgggg gtggaggtga                    30

<210> SEQ ID NO 40
<211> LENGTH: 11
<212> TYPE: PRT
<213> ORGANISM: Artificial Sequence
<220> FEATURE:
<223> OTHER INFORMATION: Synthetic

<400> SEQUENCE: 40

Ala Ala Gly Ser Ser Thr Arg Ala Ser Pro Ser
1               5                   10

<210> SEQ ID NO 41
<211> LENGTH: 24
<212> TYPE: DNA
<213> ORGANISM: Artificial Sequence
<220> FEATURE:
<223> OTHER INFORMATION: Synthetic

<400> SEQUENCE: 41
gctgccggat cctcaacccg ggcc                          24

<210> SEQ ID NO 42
<211> LENGTH: 33
<212> TYPE: DNA
<213> ORGANISM: Artificial Sequence
<220> FEATURE:
<223> OTHER INFORMATION: Synthetic

<400> SEQUENCE: 42
tgacggtgag gcccggttg aggatccggc agc                 33

<210> SEQ ID NO 43
<211> LENGTH: 11
<212> TYPE: PRT
<213> ORGANISM: Artificial Sequence
<220> FEATURE:
<223> OTHER INFORMATION: Synthetic

<400> SEQUENCE: 43

Ser Pro Ser Pro Val Ala Arg Asn Ser Pro Pro
1               5                   10

<210> SEQ ID NO 44
<211> LENGTH: 33
<212> TYPE: DNA
<213> ORGANISM: Artificial Sequence
<220> FEATURE:
<223> OTHER INFORMATION: Synthetic

<400> SEQUENCE: 44
tcaccctcac cggtcgcccg gaattcacca ccc                33

<210> SEQ ID NO 45
<211> LENGTH: 24
<212> TYPE: DNA

```
<213> ORGANISM: Artificial Sequence
<220> FEATURE:
<223> OTHER INFORMATION: Synthetic

<400> SEQUENCE: 45
gggtggtgaa ttccgggcga ccgg                                           24

<210> SEQ ID NO 46
<211> LENGTH: 24
<212> TYPE: DNA
<213> ORGANISM: Artificial Sequence
<220> FEATURE:
<223> OTHER INFORMATION: Synthetic

<400> SEQUENCE: 46
tcaccctcat aatagagctc cccc                                           24

<210> SEQ ID NO 47
<211> LENGTH: 15
<212> TYPE: DNA
<213> ORGANISM: Artificial Sequence
<220> FEATURE:
<223> OTHER INFORMATION: Synthetic

<400> SEQUENCE: 47
gggggagctc tatta                                                     15

<210> SEQ ID NO 48
<211> LENGTH: 19
<212> TYPE: PRT
<213> ORGANISM: Artificial Sequence
<220> FEATURE:
<223> OTHER INFORMATION: Synthetic

<400> SEQUENCE: 48

Ser Pro Ser Pro Thr Pro Thr Pro Pro Gly Pro His Ser Pro Pro
1               5                   10                  15

Pro Thr Leu

<210> SEQ ID NO 49
<211> LENGTH: 57
<212> TYPE: DNA
<213> ORGANISM: Artificial Sequence
<220> FEATURE:
<223> OTHER INFORMATION: Synthetic

<400> SEQUENCE: 49
tcaccctcac caactcctac cccaccacct ggtccacact caccaccacc aacattg       57

<210> SEQ ID NO 50
<211> LENGTH: 57
<212> TYPE: DNA
<213> ORGANISM: Artificial Sequence
<220> FEATURE:
<223> OTHER INFORMATION: Synthetic

<400> SEQUENCE: 50
tgagggtgac aatgttggtg gtggtgagtg tggaccaggt ggtggggtag gagttgg       57

<210> SEQ ID NO 51
<211> LENGTH: 11
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (8)..(8)
<223> OTHER INFORMATION: The Proline at this position is a
      hydroxyproline.

<400> SEQUENCE: 51

Val Lys Pro Tyr His Pro Thr Pro Val Tyr Lys
1               5                   10

<210> SEQ ID NO 52
<211> LENGTH: 30
<212> TYPE: DNA
<213> ORGANISM: Artificial Sequence
<220> FEATURE:
<223> OTHER INFORMATION: Synthetic

<400> SEQUENCE: 52
tcaccctcac catctccttc gccatcaccc                                      30

<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53
tgagggtgag ggtgatggcg aaggagatgg                                      30

<210> SEQ ID NO 54
<211> LENGTH: 30
<212> TYPE: DNA
<213> ORGANISM: Artificial Sequence
<220> FEATURE:
<223> OTHER INFORMATION: Synthetic

<400> SEQUENCE: 54
gctccagcac ctgccccagc ccctgcacca                                      30

<210> SEQ ID NO 55
<211> LENGTH: 21
<212> TYPE: DNA
<213> ORGANISM: Artificial Sequence
<220> FEATURE:
<223> OTHER INFORMATION: Synthetic

<400> SEQUENCE: 55
tggtgcaggg gctggggcag g                                               21

<210> SEQ ID NO 56
<211> LENGTH: 21
<212> TYPE: DNA
<213> ORGANISM: Artificial Sequence
<220> FEATURE:
<223> OTHER INFORMATION: Synthetic

<400> SEQUENCE: 56
gctgccggat cctcaacccg g                                               21

<210> SEQ ID NO 57
<211> LENGTH: 30
<212> TYPE: DNA
<213> ORGANISM: Artificial Sequence
<220> FEATURE:
<223> OTHER INFORMATION: Synthetic

<400> SEQUENCE: 57
```

```
tgctggagcc cgggttgagg atccggcagc                                    30

<210> SEQ ID NO 58
<211> LENGTH: 33
<212> TYPE: DNA
<213> ORGANISM: Artificial Sequence
<220> FEATURE:
<223> OTHER INFORMATION: Synthetic

<400> SEQUENCE: 58
gctccagcac cggtcgcccg gaattcacca ccc                                 33

<210> SEQ ID NO 59
<211> LENGTH: 24
<212> TYPE: DNA
<213> ORGANISM: Artificial Sequence
<220> FEATURE:
<223> OTHER INFORMATION: Synthetic

<400> SEQUENCE: 59
gggtggtgaa ttccgggcga ccgg                                          24

<210> SEQ ID NO 60
<211> LENGTH: 24
<212> TYPE: DNA
<213> ORGANISM: Artificial Sequence
<220> FEATURE:
<223> OTHER INFORMATION: Synthetic

<400> SEQUENCE: 60
gctccagcat aatagagctc cccc                                          24

<210> SEQ ID NO 61
<211> LENGTH: 15
<212> TYPE: DNA
<213> ORGANISM: Artificial Sequence
<220> FEATURE:
<223> OTHER INFORMATION: Synthetic

<400> SEQUENCE: 61
gggggagctc tatta                                                    15

<210> SEQ ID NO 62
<211> LENGTH: 42
<212> TYPE: DNA
<213> ORGANISM: Artificial Sequence
<220> FEATURE:
<223> OTHER INFORMATION: Synthetic

<400> SEQUENCE: 62
acaccaaccc ctactcccac gccaacacct acacccactc ca                      42

<210> SEQ ID NO 63
<211> LENGTH: 42
<212> TYPE: DNA
<213> ORGANISM: Artificial Sequence
<220> FEATURE:
<223> OTHER INFORMATION: Synthetic

<400> SEQUENCE: 63
ggttggtgtt ggagtgggtc taggtgttgg cgtgggagta gg                      42

<210> SEQ ID NO 64
<211> LENGTH: 21
<212> TYPE: DNA
```

```
<213> ORGANISM: Artificial Sequence
<220> FEATURE:
<223> OTHER INFORMATION: Synthetic

<400> SEQUENCE: 64
gctgccggat cctcaacccg g                                              21

<210> SEQ ID NO 65
<211> LENGTH: 30
<212> TYPE: DNA
<213> ORGANISM: Artificial Sequence
<220> FEATURE:
<223> OTHER INFORMATION: Synthetic

<400> SEQUENCE: 65
ggttggtgtc cgggttgagg atccggcagc                                     30

<210> SEQ ID NO 66
<211> LENGTH: 33
<212> TYPE: DNA
<213> ORGANISM: Artificial Sequence
<220> FEATURE:
<223> OTHER INFORMATION: Synthetic

<400> SEQUENCE: 66
acaccaaccc cggtcgcccg gaattcacca ccc                                 33

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
gggtggtgaa ttccgggcga ccgg                                           24

<210> SEQ ID NO 68
<211> LENGTH: 24
<212> TYPE: DNA
<213> ORGANISM: Artificial Sequence
<220> FEATURE:
<223> OTHER INFORMATION: Synthetic

<400> SEQUENCE: 68
acaccaacct aatagagctc cccc                                           24

<210> SEQ ID NO 69
<211> LENGTH: 15
<212> TYPE: DNA
<213> ORGANISM: Artificial Sequence
<220> FEATURE:
<223> OTHER INFORMATION: Synthetic

<400> SEQUENCE: 69
gggggagctc tatta                                                     15

<210> SEQ ID NO 70
<211> LENGTH: 45
<212> TYPE: DNA
<213> ORGANISM: Artificial Sequence
<220> FEATURE:
<223> OTHER INFORMATION: Synthetic

<400> SEQUENCE: 70
ccaccatcac caccctctcc tccatcaccc ccatccccac catca                    45
```

<210> SEQ ID NO 71
<211> LENGTH: 45
<212> TYPE: DNA
<213> ORGANISM: Artificial Sequence
<220> FEATURE:
<223> OTHER INFORMATION: Synthetic

<400> SEQUENCE: 71
tgatggtggt gatggtgggg atgggggtga tggaggagag ggtgg        45

<210> SEQ ID NO 72
<211> LENGTH: 24
<212> TYPE: DNA
<213> ORGANISM: Artificial Sequence
<220> FEATURE:
<223> OTHER INFORMATION: Synthetic

<400> SEQUENCE: 72
gctgccggat cctcaacccg ggcc        24

<210> SEQ ID NO 73
<211> LENGTH: 33
<212> TYPE: DNA
<213> ORGANISM: Artificial Sequence
<220> FEATURE:
<223> OTHER INFORMATION: Synthetic

<400> SEQUENCE: 73
tgatggtggg gcccggggttg aggatccggc agc        33

<210> SEQ ID NO 74
<211> LENGTH: 33
<212> TYPE: DNA
<213> ORGANISM: Artificial Sequence
<220> FEATURE:
<223> OTHER INFORMATION: Synthetic

<400> SEQUENCE: 74
ccaccatcac cggtcgcccg gaattcacca ccc        33

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
gggtggtgaa ttccgggcga ccgg        24

<210> SEQ ID NO 76
<211> LENGTH: 24
<212> TYPE: DNA
<213> ORGANISM: Artificial Sequence
<220> FEATURE:
<223> OTHER INFORMATION: Synthetic

<400> SEQUENCE: 76
ccaccatcat aatagagctc cccc        24

<210> SEQ ID NO 77
<211> LENGTH: 15
<212> TYPE: DNA
<213> ORGANISM: Artificial Sequence
<220> FEATURE:

<223> OTHER INFORMATION: Synthetic

<400> SEQUENCE: 77 ggggagctc tatta                                                          15

<210> SEQ ID NO 78
<211> LENGTH: 48
<212> TYPE: DNA
<213> ORGANISM: Artificial Sequence
<220> FEATURE:
<223> OTHER INFORMATION: Synthetic

<400> SEQUENCE: 78 ccaccaccctt caccacctcc atctccccca ccttcccctc caccatca                     48

<210> SEQ ID NO 79
<211> LENGTH: 48
<212> TYPE: DNA
<213> ORGANISM: Artificial Sequence
<220> FEATURE:
<223> OTHER INFORMATION: Synthetic

<400> SEQUENCE: 79
aggtggtggt gatggtggag gggaaggtgg gggagatgga ggtggtga                      48

<210> SEQ ID NO 80
<211> LENGTH: 24
<212> TYPE: DNA
<213> ORGANISM: Artificial Sequence
<220> FEATURE:
<223> OTHER INFORMATION: Synthetic

<400> SEQUENCE: 80
gctggatcct caacccgggc ctca                                                24

<210> SEQ ID NO 81
<211> LENGTH: 33
<212> TYPE: DNA
<213> ORGANISM: Artificial Sequence
<220> FEATURE:
<223> OTHER INFORMATION: Synthetic

<400> SEQUENCE: 81
aggtggtggt gaggcccggg ttgaggatcc agc                                      33

<210> SEQ ID NO 82
<211> LENGTH: 36
<212> TYPE: DNA
<213> ORGANISM: Artificial Sequence
<220> FEATURE:
<223> OTHER INFORMATION: Synthetic

<400> SEQUENCE: 82
ccaccacctt caccggtcgc ccggaattca ccaccc                                   36

<210> SEQ ID NO 83
<211> LENGTH: 27
<212> TYPE: DNA
<213> ORGANISM: Artificial Sequence
<220> FEATURE:
<223> OTHER INFORMATION: Synthetic

<400> SEQUENCE: 83
gggtggtgaa ttccgggcga ccggtga                                             27

<210> SEQ ID NO 84
<211> LENGTH: 24
<212> TYPE: DNA
<213> ORGANISM: Artificial Sequence
<220> FEATURE:
<223> OTHER INFORMATION: Synthetic

<400> SEQUENCE: 84
ccaccacctt aatagagctc cccc                                          24

<210> SEQ ID NO 85
<211> LENGTH: 15
<212> TYPE: DNA
<213> ORGANISM: Artificial Sequence
<220> FEATURE:
<223> OTHER INFORMATION: Synthetic

<400> SEQUENCE: 85
gggggagctc tatta                                                    15

<210> SEQ ID NO 86
<211> LENGTH: 42
<212> TYPE: DNA
<213> ORGANISM: Artificial Sequence
<220> FEATURE:
<223> OTHER INFORMATION: Synthetic

<400> SEQUENCE: 86
ccaccacctt caccctctcc acctccacca tctccgtcac ca                      42

<210> SEQ ID NO 87
<211> LENGTH: 42
<212> TYPE: DNA
<213> ORGANISM: Artificial Sequence
<220> FEATURE:
<223> OTHER INFORMATION: Synthetic

<400> SEQUENCE: 87
aggtggtggt ggtgacggag atggtggagg tggagagggt ga                      42

<210> SEQ ID NO 88
<211> LENGTH: 48
<212> TYPE: DNA
<213> ORGANISM: Artificial Sequence
<220> FEATURE:
<223> OTHER INFORMATION: Synthetic

<400> SEQUENCE: 88
ccaccacctt caccccatc tccacctcca ccatctccac cgtcacca                 48

<210> SEQ ID NO 89
<211> LENGTH: 48
<212> TYPE: DNA
<213> ORGANISM: Artificial Sequence
<220> FEATURE:
<223> OTHER INFORMATION: Synthetic

<400> SEQUENCE: 89
aggtggtggt ggtgacggtg gagatggtgg aggtggagat gggggtga                48

<210> SEQ ID NO 90
<211> LENGTH: 60
<212> TYPE: DNA
<213> ORGANISM: Artificial Sequence
<220> FEATURE:
<223> OTHER INFORMATION: Synthetic

```
<400> SEQUENCE: 90
ccaccaccta ctcccgttta caaatcacca ccaccaccta ctcccgttta caaatcacca    60

<210> SEQ ID NO 91
<211> LENGTH: 60
<212> TYPE: DNA
<213> ORGANISM: Artificial Sequence
<220> FEATURE:
<223> OTHER INFORMATION: Synthetic

<400> SEQUENCE: 91
aggtggtggt ggtgatttgt aaacgggagt aggtggtggt ggtgatttgt aaacgggagt    60

<210> SEQ ID NO 92
<211> LENGTH: 48
<212> TYPE: DNA
<213> ORGANISM: Artificial Sequence
<220> FEATURE:
<223> OTHER INFORMATION: Synthetic

<400> SEQUENCE: 92
ccaccacctg tcaagcctta ccaccccact cccgtttttc tttcacca                 48

<210> SEQ ID NO 93
<211> LENGTH: 48
<212> TYPE: DNA
<213> ORGANISM: Artificial Sequence
<220> FEATURE:
<223> OTHER INFORMATION: Synthetic

<400> SEQUENCE: 93
aggtggtggt ggtgaaagaa aaacgggagt ggggtggtaa ggcttgac                 48

<210> SEQ ID NO 94
<211> LENGTH: 48
<212> TYPE: DNA
<213> ORGANISM: Artificial Sequence
<220> FEATURE:
<223> OTHER INFORMATION: Synthetic

<400> SEQUENCE: 94
ccaccacctg tcttaccttt ccaccccact cccgtttaca aatcacca                 48

<210> SEQ ID NO 95
<211> LENGTH: 48
<212> TYPE: DNA
<213> ORGANISM: Artificial Sequence
<220> FEATURE:
<223> OTHER INFORMATION: Synthetic

<400> SEQUENCE: 95
aggtggtggt ggtgatttgt aaacgggagt ggggtggaaa ggtaagac                 48

<210> SEQ ID NO 96
<211> LENGTH: 21
<212> TYPE: DNA
<213> ORGANISM: Artificial Sequence
<220> FEATURE:
<223> OTHER INFORMATION: Synthetic

<400> SEQUENCE: 96
ggccgcgagc tccagcacgg g                                              21

<210> SEQ ID NO 97
<211> LENGTH: 17
```

```
<212> TYPE: DNA
<213> ORGANISM: Artificial Sequence
<220> FEATURE:
<223> OTHER INFORMATION: Synthetic

<400> SEQUENCE: 97
cccgtgctgg agctcgc                                                  17

<210> SEQ ID NO 98
<211> LENGTH: 121
<212> TYPE: DNA
<213> ORGANISM: Artificial Sequence
<220> FEATURE:
<223> OTHER INFORMATION: Synthetic

<400> SEQUENCE: 98
gatccgcaat gggaaaaatg gcttctctat ttgccacatt tttagtggtt ttagtgtcac    60
ttagcttagc acaaacaacc cgggtaccgg tcgccaccat ggtgtaaagc ggccgcgagc   120
t                                                                  121

<210> SEQ ID NO 99
<211> LENGTH: 113
<212> TYPE: DNA
<213> ORGANISM: Artificial Sequence
<220> FEATURE:
<223> OTHER INFORMATION: Synthetic

<400> SEQUENCE: 99
cgcggccgct ttacaccatg gtggcgaccg gtacccgggt tgtttgtgct aagctaagtg    60
acactaaaac cactaaaaat gtggcaaata gagaagccat ttttcccatt gcg          113

<210> SEQ ID NO 100
<211> LENGTH: 19
<212> TYPE: PRT
<213> ORGANISM: Artificial Sequence
<220> FEATURE:
<223> OTHER INFORMATION: Synthetic

<400> SEQUENCE: 100

Ser Pro Ser Pro Thr Pro Thr Ala Pro Pro Gly Pro His Ser Pro Pro
1               5                   10                  15

Pro Thr Leu

<210> SEQ ID NO 101
<211> LENGTH: 57
<212> TYPE: DNA
<213> ORGANISM: Artificial Sequence
<220> FEATURE:
<223> OTHER INFORMATION: Synthetic

<400> SEQUENCE: 101
tcaccctcac caactcctac cgcaccacct ggtccacact ctccaccacc aacattg       57

<210> SEQ ID NO 102
<211> LENGTH: 57
<212> TYPE: DNA
<213> ORGANISM: Artificial Sequence
<220> FEATURE:
<223> OTHER INFORMATION: Synthetic

<400> SEQUENCE: 102
caatgttggt ggtggagagt gtggaccagg tggtgcggta ggagttggtg agggtga       57
```

<210> SEQ ID NO 103
<211> LENGTH: 19
<212> TYPE: PRT
<213> ORGANISM: Artificial Sequence
<220> FEATURE:
<223> OTHER INFORMATION: Synthetic

<400> SEQUENCE: 103

Ser Pro Ser Pro Thr Pro Thr Ala Pro Pro Gly Pro His Ser Pro Pro
1               5                   10                  15

Pro Ser Leu

<210> SEQ ID NO 104
<211> LENGTH: 57
<212> TYPE: DNA
<213> ORGANISM: Artificial Sequence
<220> FEATURE:
<223> OTHER INFORMATION: Synthetic

<400> SEQUENCE: 104
tcaccctcac caactcctac cgcaccacct ggtccacact ctccaccacc atcattg       57

<210> SEQ ID NO 105
<211> LENGTH: 57
<212> TYPE: DNA
<213> ORGANISM: Artificial Sequence
<220> FEATURE:
<223> OTHER INFORMATION: Synthetic

<400> SEQUENCE: 105
caatgatggt ggtggagagt gtggaccagg tggtgcggta ggagttggtg agggtga       57

<210> SEQ ID NO 106
<211> LENGTH: 279
<212> TYPE: DNA
<213> ORGANISM: Artificial Sequence
<220> FEATURE:
<223> OTHER INFORMATION: Synthetic

<400> SEQUENCE: 106
ggatccgcaa tgggaaaaat ggcttctcta tttgccacat ttttagtcgt tttagtgtca      60
cttagcttag cacaaacaac ccgggactca ccctcaccaa ctcctaccgc accacctggt     120
ccacactctc caccaccaac attgtcaccc tcaccaactc ctaccgcacc acctggtcca     180
cactcaccac caccaacatt gtcaccctca ccaactccta ccgcaccacc tggtccacac     240
tcaccaccac catcattgtc accctcaccg gtcgccacc                            279

<210> SEQ ID NO 107
<211> LENGTH: 88
<212> TYPE: PRT
<213> ORGANISM: Artificial Sequence
<220> FEATURE:
<223> OTHER INFORMATION: Synthetic

<400> SEQUENCE: 107

Met Gly Lys Met Ala Ser Leu Phe Ala Thr Phe Leu Val Val Leu Val
1               5                   10                  15

Ser Leu Ser Leu Ala Gln Thr Thr Arg Asp Ser Pro Ser Pro Thr Pro
            20                  25                  30

Thr Ala Pro Pro Gly Pro His Ser Pro Pro Pro Thr Leu Ser Pro Ser
        35                  40                  45

Pro Thr Pro Thr Ala Pro Pro Gly Pro His Ser Pro Pro Pro Thr Leu
    50                  55                  60

```
Ser Pro Ser Pro Thr Pro Thr Ala Pro Pro Gly Pro His Ser Pro Pro
 65                  70                  75                  80

Pro Ser Leu Ser Pro Ser Pro Val
                 85
```

<210> SEQ ID NO 108
<211> LENGTH: 13
<212> TYPE: PRT
<213> ORGANISM: Artificial Sequence
<220> FEATURE:
<223> OTHER INFORMATION: Synthetic

<400> SEQUENCE: 108

```
Ser Pro Ser Pro Ser Pro Ser Pro Ser Pro Ser Pro Ser
1               5                   10
```

<210> SEQ ID NO 109
<211> LENGTH: 30
<212> TYPE: DNA
<213> ORGANISM: Artificial Sequence
<220> FEATURE:
<223> OTHER INFORMATION: Synthetic

<400> SEQUENCE: 109
tcaccctcac catctccttc gccatcaccc                                        30

<210> SEQ ID NO 110
<211> LENGTH: 30
<212> TYPE: DNA
<213> ORGANISM: Artificial Sequence
<220> FEATURE:
<223> OTHER INFORMATION: Synthetic

<400> SEQUENCE: 110
tgagggtgag ggtgatggcg aaggagatgg                                        30

<210> SEQ ID NO 111
<211> LENGTH: 288
<212> TYPE: DNA
<213> ORGANISM: Artificial Sequence
<220> FEATURE:
<223> OTHER INFORMATION: Synthetic

<400> SEQUENCE: 111
ggatccgcaa tgggaaaaat ggcttctcta tttgccacat ttttagtggt tttagtgtca       60
cttagcttag cacaaacaac ccgggcctca ccctcaccat ctccttcgcc atcaccctca      120
ccctcaccat ctccttcgcc atcaccctca ccctcaccat ctccttcgcc atcaccctca      180
ccctcaccat ctccttcgcc atcaccctca ccctcaccat ctccttcgcc atcaccctca      240
ccctcaccat ctccttcgcc atcaccctca ccctcaccgg tcgccacc                   288

<210> SEQ ID NO 112
<211> LENGTH: 30
<212> TYPE: DNA
<213> ORGANISM: Artificial Sequence
<220> FEATURE:
<223> OTHER INFORMATION: Synthetic

<400> SEQUENCE: 112
tcaccctcac catctccttc gccatcaccc                                        30

<210> SEQ ID NO 113
<211> LENGTH: 30

```
<212> TYPE: DNA
<213> ORGANISM: Artificial Sequence
<220> FEATURE:
<223> OTHER INFORMATION: Synthetic

<400> SEQUENCE: 113
tgagggtgag ggtgatggcg aaggagatgg                                    30

<210> SEQ ID NO 114
<211> LENGTH: 10
<212> TYPE: PRT
<213> ORGANISM: Artificial Sequence
<220> FEATURE:
<223> OTHER INFORMATION: Synthetic

<400> SEQUENCE: 114

Ser Pro Ser Pro Ser Pro Ser Pro Ser Pro
1               5                   10

<210> SEQ ID NO 115
<211> LENGTH: 57
<212> TYPE: DNA
<213> ORGANISM: Artificial Sequence
<220> FEATURE:
<223> OTHER INFORMATION: Synthetic

<400> SEQUENCE: 115
tcaccctcac caactcctac cgcaccacct ggtccacact caccaccacc aacattg     57

<210> SEQ ID NO 116
<211> LENGTH: 57
<212> TYPE: DNA
<213> ORGANISM: Artificial Sequence
<220> FEATURE:
<223> OTHER INFORMATION: Synthetic

<400> SEQUENCE: 116
tgagggtgac aatgttggtg gtggtgagtg tggaccaggt ggtgcggtag gagttgg     57

<210> SEQ ID NO 117
<211> LENGTH: 19
<212> TYPE: PRT
<213> ORGANISM: Artificial Sequence
<220> FEATURE:
<223> OTHER INFORMATION: Synthetic

<400> SEQUENCE: 117

Ser Pro Ser Pro Thr Pro Thr Ala Pro Pro Gly Pro His Ser Pro Pro
1               5                   10                  15

Pro Thr Leu

<210> SEQ ID NO 118
<211> LENGTH: 87
<212> TYPE: DNA
<213> ORGANISM: Artificial Sequence
<220> FEATURE:
<223> OTHER INFORMATION: Synthetic

<400> SEQUENCE: 118
gctgccggat ccgcaatggg aaaaatggct tctctatttg ccacattttt agtggttta    60 gtgtcactta gcttagcaca aacaacc                                       87

<210> SEQ ID NO 119
<211> LENGTH: 66
<212> TYPE: DNA
```

<213> ORGANISM: Artificial Sequence
<220> FEATURE:
<223> OTHER INFORMATION: Synthetic

<400> SEQUENCE: 119

```
cccccgtctc dacgccagcg gtactacccg ggttgtttgt gctaagctaa gtgacactaa    60
aaccac                                                                66
```

<210> SEQ ID NO 120
<211> LENGTH: 24
<212> TYPE: DNA
<213> ORGANISM: Artificial Sequence
<220> FEATURE:
<223> OTHER INFORMATION: Synthetic

<400> SEQUENCE: 120

```
gctgccggat cctcaacccg ggcc                                            24
```

<210> SEQ ID NO 121
<211> LENGTH: 33
<212> TYPE: DNA
<213> ORGANISM: Artificial Sequence
<220> FEATURE:
<223> OTHER INFORMATION: Synthetic

<400> SEQUENCE: 121

```
tgagggtgag gcccggggttg aggatccggc agc                                 33
```

<210> SEQ ID NO 122
<211> LENGTH: 8
<212> TYPE: PRT
<213> ORGANISM: Artificial Sequence
<220> FEATURE:
<223> OTHER INFORMATION: Synthetic

<400> SEQUENCE: 122

```
Ala Ala Gly Ser Ser Thr Arg Ala
1               5
```

<210> SEQ ID NO 123
<211> LENGTH: 33
<212> TYPE: DNA
<213> ORGANISM: Artificial Sequence
<220> FEATURE:
<223> OTHER INFORMATION: Synthetic

<400> SEQUENCE: 123

```
tcaccctcac cggtcgcccg gaattcacca ccc                                  33
```

<210> SEQ ID NO 124
<211> LENGTH: 24
<212> TYPE: DNA
<213> ORGANISM: Artificial Sequence
<220> FEATURE:
<223> OTHER INFORMATION: Synthetic

<400> SEQUENCE: 124

```
gggtggtgaa ttccgggcga ccgg                                            24
```

<210> SEQ ID NO 125
<211> LENGTH: 11
<212> TYPE: PRT
<213> ORGANISM: Artificial Sequence
<220> FEATURE:
<223> OTHER INFORMATION: Synthetic

```
<400> SEQUENCE: 125

Ser Pro Ser Pro Val Ala Thr Asn Ser Pro Pro
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.

<400> SEQUENCE: 126

Ser Pro Ser Pro Ser Pro Ser Pro Ser Pro Ser Pro
1               5                   10

<210> SEQ ID NO 127
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
```

```
      hydroxyproline.
<220> FEATURE:
<221> NAME/KEY: MISC_FEATURE
<222> LOCATION: (14)..(14)
<223> OTHER INFORMATION: The Proline at this position is a
      hydroxyproline.
<220> FEATURE:
<221> NAME/KEY: MISC_FEATURE
<222> LOCATION: (16)..(16)
<223> OTHER INFORMATION: The Proline at this position is a
      hydroxyproline.
<220> FEATURE:
<221> NAME/KEY: MISC_FEATURE
<222> LOCATION: (18)..(18)
<223> OTHER INFORMATION: The Proline at this position is a
      hydroxyproline.
<220> FEATURE:
<221> NAME/KEY: MISC_FEATURE
<222> LOCATION: (20)..(20)
<223> OTHER INFORMATION: The Proline at this position is a
      hydroxyproline.
<220> FEATURE:
<221> NAME/KEY: MISC_FEATURE
<222> LOCATION: (22)..(22)
<223> OTHER INFORMATION: The Proline at this position is a
      hydroxyproline.

<400> SEQUENCE: 127

Ser Pro Ser Pro Ser Pro Ser Pro Ser Pro Ser Pro Ser Pro Ser Pro
1               5                   10                  15

Ser Pro Ser Pro Ser Pro
            20

<210> SEQ ID NO 128
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: The Proline at this position is a
      hydroxyproline.
<220> FEATURE:
<221> NAME/KEY: MISC_FEATURE
<222> LOCATION: (5)..(5)
<223> OTHER INFORMATION: The Proline at this position is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.
<220> FEATURE:
<221> NAME/KEY: MISC_FEATURE
<222> LOCATION: (10)..(11)
<223> OTHER INFORMATION: The Proline at these positions is a
      hydroxyproline.
<220> FEATURE:
<221> NAME/KEY: MISC_FEATURE
<222> LOCATION: (16)..(18)
<223> OTHER INFORMATION: The Proline at these positions is a
      hydroxyproline.

<400> SEQUENCE: 128

Asp Ser Pro Ser Pro Thr Pro Thr Ala Pro Pro Gly Pro His Ser Pro
1               5                   10                  15

Pro Pro

<210> SEQ ID NO 129
<211> LENGTH: 25
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: The Proline at this position is a
      hydroxyproline.
<220> FEATURE:
<221> NAME/KEY: MISC_FEATURE
<222> LOCATION: (5)..(5)
<223> OTHER INFORMATION: The Proline at this position is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.
<220> FEATURE:
<221> NAME/KEY: MISC_FEATURE
<222> LOCATION: (10)..(11)
<223> OTHER INFORMATION: The Proline at these positions is a
      hydroxyproline.
<220> FEATURE:
<221> NAME/KEY: MISC_FEATURE
<222> LOCATION: (16)..(16)
<223> OTHER INFORMATION: The Proline at this position is a
      hydroxyproline.
<220> FEATURE:
<221> NAME/KEY: MISC_FEATURE
<222> LOCATION: (18)..(18)
<223> OTHER INFORMATION: The Proline at this position is a
      hydroxyproline.
<220> FEATURE:
<221> NAME/KEY: MISC_FEATURE
<222> LOCATION: (22)..(22)
<223> OTHER INFORMATION: The Proline at this position is a
      hydroxyproline.
<220> FEATURE:
<221> NAME/KEY: MISC_FEATURE
<222> LOCATION: (24)..(24)
<223> OTHER INFORMATION: The Proline at this position is a
      hydroxyproline.

<400> SEQUENCE: 129

Asp Ser Pro Ser Pro Thr Pro Thr Ala Pro Pro Gly Pro His Ser Pro
1               5                   10                  15

Pro Pro Thr Leu Ser Pro Ser Pro Thr
            20                  25

<210> SEQ ID NO 130
<211> LENGTH: 139
<212> TYPE: DNA
<213> ORGANISM: Artificial Sequence
<220> FEATURE:
<223> OTHER INFORMATION: Synthetic

<400> SEQUENCE: 130
gccaagcttc cggagtgccg gccctcatag cccacctcca ccattatcac catcacctac      60
tccaactcct cctttgggac cacacagtcc acccctaca ctttccccctt caccaacccc    120 aacaccaccc cccgggtac                                                  139

<210> SEQ ID NO 131
<211> LENGTH: 39
<212> TYPE: PRT
<213> ORGANISM: Artificial Sequence
<220> FEATURE:
<223> OTHER INFORMATION: Synthetic

<400> SEQUENCE: 131

Gly Pro His Ser Pro Pro Pro Pro Leu Ser Pro Ser Pro Thr Pro Thr
```

```
                1               5              10              15
Pro Pro Leu Gly Pro His Ser Pro Pro Pro Thr Leu Ser Pro Ser Pro
                20                  25                  30

Thr Pro Thr Pro Pro Pro Gly
            35
```

<210> SEQ ID NO 132
<211> LENGTH: 253
<212> TYPE: DNA
<213> ORGANISM: Artificial Sequence
<220> FEATURE:
<223> OTHER INFORMATION: Synthetic

<400> SEQUENCE: 132

```
gccaagcttc cggagtgccg gccctcatag cccacctcca ccattatcac catcacctac      60
tccaactcct cctttgggac cacacagtcc accccctaca ctttcccctt caccaacccc     120
aacaccaccc cccggccctc atagcccacc tccaccatta tcaccatcac ctactccaac     180
tcctcctttg gaccacacag tccacccccc tacactttcc ccttcaccaa ccccaacacc     240
accccccggg tac                                                        253
```

<210> SEQ ID NO 133
<211> LENGTH: 74
<212> TYPE: PRT
<213> ORGANISM: Artificial Sequence
<220> FEATURE:
<223> OTHER INFORMATION: Synthetic

<400> SEQUENCE: 133

```
Gly Pro His Ser Pro Pro Pro Leu Ser Pro Ser Pro Thr Pro Thr
1               5                  10                  15

Pro Pro Leu Gly Pro His Ser Pro Pro Pro Thr Leu Ser Pro Ser Pro
                20                  25                  30

Thr Pro Thr Pro Pro Pro Gly Pro His Ser Pro Pro Pro Leu Ser
            35                  40                  45

Pro Ser Pro Thr Pro Thr Pro Pro Leu Gly Pro His Ser Pro Pro Pro
    50                  55                  60

Thr Leu Ser Pro Ser Pro Thr Pro Thr Pro
65                  70
```

<210> SEQ ID NO 134
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The amino acid at this position is selected from Ser, Thr, and
      Ala.
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (3)..(3)
<223> OTHER INFORMATION: The amino acid at this position is selected from Hyp, Pro, Leu,
      and Ile.
<220> FEATURE:
<221> NAME/KEY: MISC_FEATURE

```
<222> LOCATION: (4)..(4)
<223> OTHER INFORMATION: The amino acid at this position is selected fr
      om Pro and Hyp.
<220> FEATURE:
<221> NAME/KEY: MISC_FEATURE
<222> LOCATION: (5)..(5)
<223> OTHER INFORMATION: The amino acid at this position is selected from
      Hyp, Pro, Ser, Thr, and Ala.
<220> FEATURE:
<221> NAME/KEY: MISC_FEATURE
<222> LOCATION: (6)..(6)
<223> OTHER INFORMATION: The amino acid at this position is selected from
      Leu and Ile.
<220> FEATURE:
<221> NAME/KEY: MISC_FEATURE
<222> LOCATION: (7)..(7)
<223> OTHER INFORMATION: The amino acid at this position is selected from Ser,
      Thr, and Ala.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (9)..(9)
<223> OTHER INFORMATION: The amino acid at this position is selected from
      Ser, Leu, Hyp,
      Thr, Ala, and Ile.
<220> FEATURE:
<221> NAME/KEY: MISC_FEATURE
<222> LOCATION: (10)..(10)
<223> OTHER INFORMATION: The amino acid at this position is selected from
      Hyp, Pro, Leu,
      and Ile.
<220> FEATURE:
<221> NAME/KEY: MISC_FEATURE
<222> LOCATION: (11)..(11)
<223> OTHER INFORMATION: The amino acid at this position is selected fro
      m Thr, Ala, and
      Ser.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (13)..(13)
<223> OTHER INFORMATION: The amino acid at this position is selected fro
      m Thr, Ser, and
      Ala.
<220> FEATURE:
<221> NAME/KEY: MISC_FEATURE
<222> LOCATION: (14)..(15)
<223> OTHER INFORMATION: The Proline at these positions is a
      hydroxyproline.
<220> FEATURE:
<221> NAME/KEY: MISC_FEATURE
<222> LOCATION: (16)..(16)
<223> OTHER INFORMATION: The amino acid at this position is selected from
      Thr, Leu, Hyp,
      Ser, Ala, and Ile.
<220> FEATURE:
<221> NAME/KEY: MISC_FEATURE
<222> LOCATION: (17)..(17)
<223> OTHER INFORMATION: The amino acid at this position is selected from
      Gly, Leu, Ala, and Ile.
<220> FEATURE:
<221> NAME/KEY: MISC_FEATURE
<222> LOCATION: (19)..(19)
<223> OTHER INFORMATION: The amino acid at this position is selected fr
      om His and Pro.

<400> SEQUENCE: 134

Xaa Pro Xaa Xaa Xaa Xaa Xaa Pro Xaa Xaa Xaa Pro Xaa Pro Pro Xaa
1               5                   10                  15
```

Xaa Pro Xaa

<210> SEQ ID NO 135
<211> LENGTH: 11
<212> TYPE: PRT
<213> ORGANISM: Acacia senegal
<220> FEATURE:
<221> NAME/KEY: MISC_FEATURE
<222> LOCATION: (1)..(4)
<223> OTHER INFORMATION: The Proline at these positions is a
      hydroxyproline.

<400> SEQUENCE: 135

Pro Pro Pro Pro Ser Ser Thr Pro Gly Leu His
1               5                   10

<210> SEQ ID NO 136
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The amino acid at this position is selected fro
      m Ser, Thr, and
      Ala.
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (3)..(3)
<223> OTHER INFORMATION: The amino acid at this position is selected
      from Hyp, Pro, Leu, and Ile.
<220> FEATURE:
<221> NAME/KEY: MISC_FEATURE
<222> LOCATION: (4)..(4)
<223> OTHER INFORMATION: The amino acid at this position is selected
      from Pro and Hyp.
<220> FEATURE:
<221> NAME/KEY: MISC_FEATURE
<222> LOCATION: (5)..(5)
<223> OTHER INFORMATION: The amino acid at this position is selected
      from Hyp, Pro, Ser,
      Thr, and Ala.
<220> FEATURE:
<221> NAME/KEY: MISC_FEATURE
<222> LOCATION: (6)..(6)
<223> OTHER INFORMATION: The amino acid at this position is selected
      from Leu and Ile.
<220> FEATURE:
<221> NAME/KEY: MISC_FEATURE
<222> LOCATION: (7)..(7)
<223> OTHER INFORMATION: The amino acid at this position is selected
      from Ser, Thr, and
      Ala.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (9)..(9)
<223> OTHER INFORMATION: The amino acid at this position is selected
      from Ser, Leu, Hyp,
      Thr, Ala, and Ile.
<220> FEATURE:
<221> NAME/KEY: MISC_FEATURE
<222> LOCATION: (10)..(10)
<223> OTHER INFORMATION: The amino acid at this position is selected
      from Hyp, Pro, Leu,

```
        and Ile.
<220> FEATURE:
<221> NAME/KEY: MISC_FEATURE
<222> LOCATION: (11)..(11)
<223> OTHER INFORMATION: The amino acid at this position is selected
      from Thr, Ala, and
      Ser.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (13)..(13)
<223> OTHER INFORMATION: The amino acid at this position is selected
      from Thr, Ser, and
      Ala.
<220> FEATURE:
<221> NAME/KEY: MISC_FEATURE
<222> LOCATION: (14)..(15)
<223> OTHER INFORMATION: The Proline at these positions is a
      hydroxyproline.
<220> FEATURE:
<221> NAME/KEY: MISC_FEATURE
<222> LOCATION: (16)..(16)
<223> OTHER INFORMATION: The amino acid at this position is selected
      from Thr, Leu, Hyp,
      Ser, Ala, and Ile.
<220> FEATURE:
<221> NAME/KEY: MISC_FEATURE
<222> LOCATION: (17)..(17)
<223> OTHER INFORMATION: The amino acid at this position is selected
      from Gly, Leu, Ala,
      and Ile.
<220> FEATURE:
<221> NAME/KEY: MISC_FEATURE
<222> LOCATION: (19)..(19)
<223> OTHER INFORMATION: The amino acid at this position is selected
      from His and Pro.

<400> SEQUENCE: 136

Xaa Pro Xaa Xaa Xaa Xaa Xaa Pro Xaa Xaa Xaa Pro Xaa Pro Pro Xaa
1               5                   10                  15

Xaa Pro Xaa

<210> SEQ ID NO 137
<211> LENGTH: 6
<212> TYPE: PRT
<213> ORGANISM: Acacia senegal
<220> FEATURE:
<221> NAME/KEY: MISC_FEATURE
<222> LOCATION: (1)..(1)
<223> OTHER INFORMATION: The amino acid at this position is selected
      from Ser, Thr, and
      Ala.
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (3)..(3)
<223> OTHER INFORMATION: The amino acid at this position is selected
      from Ser, Leu, Hyp,
      Thr, Ala, and Ile.
<220> FEATURE:
<221> NAME/KEY: MISC_FEATURE
<222> LOCATION: (4)..(4)
<223> OTHER INFORMATION: The amino acid at this position is selected
      from Hyp, Pro, Leu,
      and Ile.
<220> FEATURE:
<221> NAME/KEY: MISC_FEATURE
<222> LOCATION: (5)..(5)
```

```
<223> OTHER INFORMATION: The amino acid at this position is selected
      from Thr, Ala, and
      Ser.
<220> FEATURE:
<221> NAME/KEY: MISC_FEATURE
<222> LOCATION: (6)..(6)
<223> OTHER INFORMATION: The Proline at this position is a
      hydroxyproline.

<400> SEQUENCE: 137

Xaa Pro Xaa Xaa Xaa Pro
1               5

<210> SEQ ID NO 138
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.

<400> SEQUENCE: 138

Ser Pro Ser Pro Thr Pro
1               5

<210> SEQ ID NO 139
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The amino acid at this position is selected
      from Ser, Thr, and
      Ala.
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (3)..(3)
<223> OTHER INFORMATION: The amino acid at this position is selected
      from Hyp, Leu, and
      Ile.
<220> FEATURE:
<221> NAME/KEY: MISC_FEATURE
<222> LOCATION: (4)..(4)
<223> OTHER INFORMATION: The amino acid at this position is selected
      from Pro and Hyp.
<220> FEATURE:
<221> NAME/KEY: MISC_FEATURE
<222> LOCATION: (5)..(5)
<223> OTHER INFORMATION: The amino acid at this position is selected
      from Hyp, Ser, Thr,
      and Ala.
<220> FEATURE:
<221> NAME/KEY: MISC_FEATURE
```

```
<222> LOCATION: (6)..(6)
<223> OTHER INFORMATION: The amino acid at this position is selected
      from Leu and Ile.

<400> SEQUENCE: 139

Ala Pro Asx Cys Asp Glu
1               5

<210> SEQ ID NO 140
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (5)..(5)
<223> OTHER INFORMATION: The amino acid at this position is selected
      from Hyp, Thr, and
      Ser.

<400> SEQUENCE: 140

Ser Pro Pro Pro Xaa Leu
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The amino acid at this position is selected
      from Thr, Ser, and
      Ala.
<220> FEATURE:
<221> NAME/KEY: MISC_FEATURE
<222> LOCATION: (2)..(3)
<223> OTHER INFORMATION: The Proline at these positions is a
      hydroxyproline.
<220> FEATURE:
<221> NAME/KEY: MISC_FEATURE
<222> LOCATION: (4)..(4)
<223> OTHER INFORMATION: The amino acid at this position is selected
      from Thr, Leu, Hyp,
      Ser, Ala, and Ile.
<220> FEATURE:
<221> NAME/KEY: MISC_FEATURE
<222> LOCATION: (5)..(5)
<223> OTHER INFORMATION: The amino acid at this position is selected
      from Gly, Leu, Ala,
      and Ile.
<220> FEATURE:
<221> NAME/KEY: MISC_FEATURE
<222> LOCATION: (7)..(7)
<223> OTHER INFORMATION: The amino acid at this position is selected
      from His and Pro.

<400> SEQUENCE: 141

Xaa Pro Pro Xaa Xaa Pro Xaa
1               5

<210> SEQ ID NO 142
<211> LENGTH: 12
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Proline at this position is a
      hydroxyproline.
<220> FEATURE:
<221> NAME/KEY: MISC_FEATURE
<222> LOCATION: (3)..(3)
<223> OTHER INFORMATION: The Proline at this position is a
      hydroxyproline.
<220> FEATURE:
<221> NAME/KEY: MISC_FEATURE
<222> LOCATION: (5)..(5)
<223> OTHER INFORMATION: The Proline at this position is a
      hydroxyproline.
<220> FEATURE:
<221> NAME/KEY: MISC_FEATURE
<222> LOCATION: (7)..(8)
<223> OTHER INFORMATION: The Proline at these positions is a
      hydroxyproline.
<220> FEATURE:
<221> NAME/KEY: MISC_FEATURE
<222> LOCATION: (9)..(9)
<223> OTHER INFORMATION: The amino acid at this position is selected
      from Hyp and Leu.

<400> SEQUENCE: 142

Pro Ser Pro Thr Pro Thr Pro Pro Xaa Gly Pro His
1               5                   10

<210> SEQ ID NO 143
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 143

Ser Pro Pro Pro Pro Leu Ser Pro Ser Pro Thr Pro Thr Pro Pro Leu
1               5                   10                  15

Gly Pro His

<210> SEQ ID NO 144
<211> LENGTH: 19
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 144

Ser Pro Pro Pro Thr Leu Ser Pro Ser Pro Thr Pro Thr Pro Pro
1               5                   10                  15

Gly Pro His

<210> SEQ ID NO 145
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 145

Ser Pro Pro Pro Ser Leu Ser Pro Ser Pro Thr Pro Thr Pro Thr
1               5                   10                  15

Gly Pro His

<210> SEQ ID NO 146
<211> LENGTH: 19
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.
<220> FEATURE:
<221> NAME/KEY: MISC_FEATURE
<222> LOCATION: (19)..(19)
<223> OTHER INFORMATION: The Proline at this position is a
      hydroxyproline.

<400> SEQUENCE: 146

Ser Pro Pro Pro Pro Leu Ser Pro Ser Pro Thr Pro Thr Pro Pro Pro
1               5                   10                  15

Gly Pro Pro

<210> SEQ ID NO 147
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 147

Ser Pro Leu Pro Thr Leu Ser Pro Leu Pro Thr Pro Thr Pro Pro Pro
1               5                   10                  15

Gly Pro His
```

<210> SEQ ID NO 148
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 148

Ser Pro Leu Pro Thr Leu Ser Pro Leu Pro Ala Pro Thr Pro Pro Pro
1               5                   10                  15

Gly Pro His

<210> SEQ ID NO 149
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.
<220> FEATURE:
<221> NAME/KEY: MISC_FEATURE
<222> LOCATION: (19)..(19)
<223> OTHER INFORMATION: The Proline at this position is a
      hydroxyproline.

<400> SEQUENCE: 149

Ser Pro Pro Pro Pro Leu Ser Pro Ser Leu Thr Pro Thr Pro Pro Leu
1               5                   10                  15

Gly Pro Pro

<210> SEQ ID NO 150
<211> LENGTH: 19

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 150

Ser Pro Pro Pro Pro Leu Ser Pro Ser Pro Thr Pro Thr Pro Pro Pro
1               5                   10                  15

Gly Pro His

<210> SEQ ID NO 151
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 151

Ser Pro Pro Pro Thr Leu Ser Pro Ser Pro Thr Pro Thr Pro Pro Pro
1               5                   10                  15

Gly Pro His

<210> SEQ ID NO 152
```

```
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 152

Ser Pro Pro Pro Pro Leu Ser Pro Ser Pro Ala Pro Thr Pro Pro Pro
1               5                   10                  15

Gly Pro His

<210> SEQ ID NO 153
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 153

Ser Pro Pro Pro Pro Leu Ser Pro Leu Pro Thr Pro Thr Pro Pro Leu
1               5                   10                  15

Gly Pro His

<210> SEQ ID NO 154
<211> LENGTH: 19
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 154

Ser Pro Pro Pro Ser Leu Ser Pro Leu Pro Thr Pro Thr Pro Pro Leu
1               5                   10                  15

Gly Pro His

<210> SEQ ID NO 155
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(9)
<223> OTHER INFORMATION: The Proline at these positions is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 155

Ser Pro Pro Pro Thr Leu Ser Pro Pro Leu Thr Pro Thr Pro Pro Leu
1               5                   10                  15

Leu Pro His

<210> SEQ ID NO 156
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: The Proline at these positions is a
      hydroxyproline.
<220> FEATURE:
<221> NAME/KEY: MISC_FEATURE
<222> LOCATION: (6)..(7)
```

```
<223> OTHER INFORMATION: The Proline at these positions is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(13)
<223> OTHER INFORMATION: The Proline at these positions is a
      hydroxyproline.

<400> SEQUENCE: 156

Pro Pro Thr Leu Ser Pro Pro Leu Thr Pro Thr Pro Pro Leu Leu Pro
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 157

Ser Pro Pro Pro Ser Leu Ser Pro Leu Pro Thr Pro Thr Pro Pro Leu
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: The Proline at these positions is a
      hydroxyproline.
<220> FEATURE:
<221> NAME/KEY: MISC_FEATURE
<222> LOCATION: (5)..(5)
<223> OTHER INFORMATION: The Proline at this position is a
      hydroxyproline.
<220> FEATURE:
<221> NAME/KEY: MISC_FEATURE
<222> LOCATION: (9)..(9)
<223> OTHER INFORMATION: The Proline at this position is a
      hydroxyproline.
<220> FEATURE:
<221> NAME/KEY: MISC_FEATURE
<222> LOCATION: (11)..(12)
<223> OTHER INFORMATION: The Proline at these positions is a
      hydroxyproline.
```

-continued

<400> SEQUENCE: 158

Pro Pro Leu Ser Pro Leu Pro Thr Pro Thr Pro Pro Leu Gly Pro His
1               5                   10                  15

<210> SEQ ID NO 159
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(14)
<223> OTHER INFORMATION: The Proline at this position is a
      hydroxyproline.

<400> SEQUENCE: 159

Ser Pro Pro Pro Thr Leu Ser Pro Ser Pro Thr Pro Thr Pro
1               5                   10

<210> SEQ ID NO 160
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: The Proline at this position is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.
<220> FEATURE:
<221> NAME/KEY: MISC_FEATURE
<222> LOCATION: (9)..(10)
<223> OTHER INFORMATION: The Proline at these positions is a
      hydroxyproline.
<220> FEATURE:
<221> NAME/KEY: MISC_FEATURE
<222> LOCATION: (14)..(14)
<223> OTHER INFORMATION: The Proline at this position is a
      hydroxyproline.

<400> SEQUENCE: 160

Leu Ser Pro Ser Leu Thr Pro Thr Pro Pro Leu Gly Pro Pro
1               5                   10

<210> SEQ ID NO 161
<211> LENGTH: 14

```
-continued

<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Proline at this position is a
      hydroxyproline.
<220> FEATURE:
<221> NAME/KEY: MISC_FEATURE
<222> LOCATION: (5)..(5)
<223> OTHER INFORMATION: The Proline at this position is a
      hydroxyproline.
<220> FEATURE:
<221> NAME/KEY: MISC_FEATURE
<222> LOCATION: (9)..(9)
<223> OTHER INFORMATION: The Proline at this position is a
      hydroxyproline.
<220> FEATURE:
<221> NAME/KEY: MISC_FEATURE
<222> LOCATION: (11)..(13)
<223> OTHER INFORMATION: The Proline at these positions is a
      hydroxyproline.

<400> SEQUENCE: 161

Pro Thr Leu Ser Pro Leu Pro Ala Pro Thr Pro Pro Pro Gly
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.

<400> SEQUENCE: 162

Ser Pro Pro Pro Pro Leu Ser Pro Ser Pro Thr Pro
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
```

```
          hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(11)
<223> OTHER INFORMATION: The Proline at these positions is a
      hydroxyproline.

<400> SEQUENCE: 163

Ser Leu Ser Pro Ser Pro Thr Pro Thr Pro Pro Thr
1               5                  10

<210> SEQ ID NO 164
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: The Proline at these positions is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.

<400> SEQUENCE: 164

Pro Pro Thr Leu Ser Pro Ser Pro Thr Pro Thr Pro
1               5                  10

<210> SEQ ID NO 165
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Proline at this position is a
      hydroxyproline.
<220> FEATURE:
<221> NAME/KEY: MISC_FEATURE
<222> LOCATION: (3)..(3)
<223> OTHER INFORMATION: The Proline at this position is a
      hydroxyproline.
<220> FEATURE:
<221> NAME/KEY: MISC_FEATURE
<222> LOCATION: (5)..(6)
<223> OTHER INFORMATION: The Proline at these positions is a
      hydroxyproline.

<400> SEQUENCE: 165
```

```
Pro Thr Pro Thr Pro Pro Leu Gly Pro His
1               5                   10

<210> SEQ ID NO 166
<211> LENGTH: 10
<212> TYPE: PRT
<213> ORGANISM: Artificial Sequence
<220> FEATURE:
<221> NAME/KEY: MISC_FEATURE
<222> LOCATION: (1)..(2)
<223> OTHER INFORMATION: The Proline at these positions is a
      hydroxyproline.
<220> FEATURE:
<221> NAME/KEY: MISC_FEATURE
<222> LOCATION: (6)..(7)
<223> OTHER INFORMATION: The Proline at these positions is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.

<400> SEQUENCE: 166

Pro Pro Thr Leu Ser Pro Pro Leu Thr Pro
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.

<400> SEQUENCE: 167

Ser Pro Pro Pro Ser Leu Ser Pro Leu Pro
1               5                   10

<210> SEQ ID NO 168
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Proline at this position is a
      hydroxyproline.
<220> FEATURE:
<221> NAME/KEY: MISC_FEATURE
<222> LOCATION: (3)..(4)
<223> OTHER INFORMATION: The Proline at these positions is a
      hydroxyproline.

<400> SEQUENCE: 168

Pro Thr Pro Pro Leu Gly Pro His
1               5

<210> SEQ ID NO 169
<211> LENGTH: 8
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.

<400> SEQUENCE: 169

Pro Leu Ser Pro Ser Pro Ala Pro
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: The Proline at these positions is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.

<400> SEQUENCE: 170

Pro Pro Pro Thr Leu Ser Pro Ser
1               5

<210> SEQ ID NO 171
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.

<400> SEQUENCE: 171

Thr Pro Pro Pro Gly Pro
1               5

<210> SEQ ID NO 172
<211> LENGTH: 6
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(2)
<223> OTHER INFORMATION: The Proline at these positions is a
      hydroxyproline.
<220> FEATURE:
<221> NAME/KEY: MISC_FEATURE
<222> LOCATION: (5)..(5)
<223> OTHER INFORMATION: The Proline at this position is a
      hydroxyproline.

<400> SEQUENCE: 172

Pro Pro Leu Ser Pro Ser
1               5

<210> SEQ ID NO 173
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.

<400> SEQUENCE: 173

Ser Pro Leu Pro Ala Pro
1               5

<210> SEQ ID NO 174
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: The Proline at this position is a
      hydroxyproline.

<400> SEQUENCE: 174

Leu Pro Thr Leu Ser Pro
1               5

<210> SEQ ID NO 175
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.

<400> SEQUENCE: 175

Ser Pro Ser Pro
1
```

```
<210> SEQ ID NO 176
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The proline at this position is a
      hydroxyproline.
<220> FEATURE:
<221> NAME/KEY: MISC_FEATURE
<222> LOCATION: (4)..(4)
<223> OTHER INFORMATION: The proline at this position is a
      hydroxyproline.

<400> SEQUENCE: 176

Ser Pro Thr Pro
1

<210> SEQ ID NO 177
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.

<400> SEQUENCE: 177

Thr Pro Thr Pro
1

<210> SEQ ID NO 178
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.

<400> SEQUENCE: 178

Thr Pro Pro Pro
1

<210> SEQ ID NO 179
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (5)..(5)
```

```
<223> OTHER INFORMATION: The amino acid at this position is selected fro
      m Hyp, Thr, and
      Ser.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.
<220> FEATURE:
<221> NAME/KEY: MISC_FEATURE
<222> LOCATION: (16)..(16)
<223> OTHER INFORMATION: The amino acid at this position is selected fr
      om Hyp and Leu.

<400> SEQUENCE: 179

Ser Pro Pro Pro Xaa Leu Ser Pro Ser Pro Thr Pro Thr Pro Pro Xaa
1               5                   10                  15

Gly Pro His

<210> SEQ ID NO 180
<211> LENGTH: 38
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: The Proline at this position is a
      hydroxyproline.
<220> FEATURE:
<221> NAME/KEY: MISC_FEATURE
<222> LOCATION: (5)..(7)
<223> OTHER INFORMATION: The Proline at these positions is a
      hydroxyproline.
<220> FEATURE:
<221> NAME/KEY: MISC_FEATURE
<222> LOCATION: (11)..(12)
<223> OTHER INFORMATION: The Proline at these positions is a
      hydroxyproline.
<220> FEATURE:
<221> NAME/KEY: MISC_FEATURE
<222> LOCATION: (15)..(15)
<223> OTHER INFORMATION: The Proline at this position is a
      hydroxyproline.
<220> FEATURE:
<221> NAME/KEY: MISC_FEATURE
<222> LOCATION: (17)..(18)
<223> OTHER INFORMATION: The Proline at these positions is a
      hydroxyproline.
<220> FEATURE:
<221> NAME/KEY: MISC_FEATURE
<222> LOCATION: (24)..(27)
<223> OTHER INFORMATION: The Proline at these positions is a
      hydroxyproline.
<220> FEATURE:
<221> NAME/KEY: MISC_FEATURE
<222> LOCATION: (30)..(30)
<223> OTHER INFORMATION: The Proline at this position is a
      hydroxyproline.
<220> FEATURE:
```

```
<221> NAME/KEY: MISC_FEATURE
<222> LOCATION: (34)..(34)
<223> OTHER INFORMATION: The Proline at this position is a
      hydroxyproline.
<220> FEATURE:
<221> NAME/KEY: MISC_FEATURE
<222> LOCATION: (36)..(37)
<223> OTHER INFORMATION: The Proline at these positions is a
      hydroxyproline.

<400> SEQUENCE: 180

Gly Pro Pro Ser Pro Pro Pro Thr Leu Ser Pro Pro Leu Thr Pro Thr
1               5                   10                  15

Pro Pro Leu Leu Pro His Ser Pro Pro Pro Leu Ser Pro Ser Leu
            20                  25                  30

Thr Pro Thr Pro Pro Leu
            35

<210> SEQ ID NO 181
<211> LENGTH: 38
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(8)
<223> OTHER INFORMATION: The Proline at these positions is a
      hydroxyproline.
<220> FEATURE:
<221> NAME/KEY: MISC_FEATURE
<222> LOCATION: (11)..(11)
<223> OTHER INFORMATION: The Proline at this position is a
      hydroxyproline.
<220> FEATURE:
<221> NAME/KEY: MISC_FEATURE
<222> LOCATION: (13)..(13)
<223> OTHER INFORMATION: The Proline at this position is a
      hydroxyproline.
<220> FEATURE:
<221> NAME/KEY: MISC_FEATURE
<222> LOCATION: (15)..(15)
<223> OTHER INFORMATION: The Proline at this position is a
      hydroxyproline.
<220> FEATURE:
<221> NAME/KEY: MISC_FEATURE
<222> LOCATION: (17)..(19)
<223> OTHER INFORMATION: The Proline at these positions is a
      hydroxyproline.
<220> FEATURE:
<221> NAME/KEY: MISC_FEATURE
<222> LOCATION: (24)..(26)
<223> OTHER INFORMATION: The Proline at these positions is a
      hydroxyproline.
<220> FEATURE:
<221> NAME/KEY: MISC_FEATURE
<222> LOCATION: (30)..(34)
<223> OTHER INFORMATION: The Proline at these positions is a
      hydroxyproline.
<220> FEATURE:
<221> NAME/KEY: MISC_FEATURE
<222> LOCATION: (36)..(37)
<223> OTHER INFORMATION: The Proline at these positions is a
      hydroxyproline.

<400> SEQUENCE: 181

Gly Pro His Ser Pro Pro Pro Leu Ser Pro Ser Pro Ala Pro Thr
1               5                   10                  15

Pro Pro Pro Gly Pro His Ser Pro Pro Ser Leu Ser Pro Leu Pro
            20                  25                  30

Thr Pro Thr Pro Pro Leu
            35
```

```
<210> SEQ ID NO 182
<211> LENGTH: 2
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: The seq  Xaa-Pro is repeated x times, x being
      an integer from 1 to 1000.  Xaa is any amino acid other than
      hydroxyproline.  Each of the Proline residues is a hydroxyproline.

<400> SEQUENCE: 182

Xaa Pro
1

<210> SEQ ID NO 183
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid other than
      hydroxyproline.
<220> FEATURE:
<221> NAME/KEY: MISC_FEATURE
<222> LOCATION: (2)..(2)
<223> OTHER INFORMATION: The Proline at this position is
      hydroxyproline.
<220> FEATURE:
<221> NAME/KEY: MISC_FEATURE
<222> LOCATION: (3)..(4)
<223> OTHER INFORMATION: Xaa at these positions is any amino
      acid other than
      hydroxyproline.
<220> FEATURE:
<221> NAME/KEY: MISC_FEATURE
<222> LOCATION: (5)..(5)
<223> OTHER INFORMATION: The Proline at this position is
      hydroxyproline.
<220> FEATURE:
<221> NAME/KEY: MISC_FEATURE
<222> LOCATION: (6)..(6)
<223> OTHER INFORMATION: Xaa is any amino acid other than
      hydroxyproline.

<400> SEQUENCE: 183

Xaa Pro Xaa Xaa Pro Xaa
1               5

<210> SEQ ID NO 184
<211> LENGTH: 23
<212> TYPE: PRT
<213> ORGANISM: Acacia senegal
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
```

```
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.
<220> FEATURE:
<221> NAME/KEY: MISC_FEATURE
<222> LOCATION: (21)..(23)
<223> OTHER INFORMATION: The Proline at these positions is a
      hydroxyproline.

<400> SEQUENCE: 184

Ser Pro Pro Pro Thr Leu Ser Pro Ser Pro Thr Pro Thr Pro Pro Pro
1               5                   10                  15

Gly Pro His Ser Pro Pro Pro
            20

<210> SEQ ID NO 185
<211> LENGTH: 24
<212> TYPE: PRT
<213> ORGANISM: Acacia senegal
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.
<220> FEATURE:
<221> NAME/KEY: MISC_FEATURE
<222> LOCATION: (21)..(24)
<223> OTHER INFORMATION: The Proline at these positions is a
      hydroxyproline.

<400> SEQUENCE: 185

Ser Pro Pro Pro Thr Leu Ser Pro Ser Pro Thr Pro Thr Pro Pro Pro
1               5                   10                  15

Gly Pro His Ser Pro Pro Pro Pro
            20

<210> SEQ ID NO 186
<211> LENGTH: 16
<212> TYPE: PRT
<213> ORGANISM: Acacia senegal
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
```

```
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: misc_feature
<222> LOCATION: (14)..(14)
<223> OTHER INFORMATION: Xaa can be any naturally occur
      ring amino acid
<220> FEATURE:
<221> NAME/KEY: MISC_FEATURE
<222> LOCATION: (15)..(16)
<223> OTHER INFORMATION: The Proline at these positions is a
      hydroxyproline.

<400> SEQUENCE: 186

Ser Pro Pro Pro Thr Leu Ser Pro Ser Pro Thr Pro Thr Xaa Pro Pro
1               5                   10                  15

<210> SEQ ID NO 187
<211> LENGTH: 16
<212> TYPE: PRT
<213> ORGANISM: Acacia senegal
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: misc_feature
<222> LOCATION: (14)..(14)
<223> OTHER INFORMATION: Xaa can be any naturally occur
      ring amino acid
<220> FEATURE:
<221> NAME/KEY: MISC_FEATURE
<222> LOCATION: (15)..(16)
<223> OTHER INFORMATION: The Proline at these positions is a
      hydroxyproline.

<400> SEQUENCE: 187

Ser Pro Pro Pro Ser Leu Ser Pro Ser Pro Thr Pro Thr Xaa Pro Pro
1               5                   10                  15

<210> SEQ ID NO 188
<211> LENGTH: 12
<212> TYPE: PRT
<213> ORGANISM: Acacia senegal
<220> FEATURE:
<221> NAME/KEY: MISC_FEATURE
<222> LOCATION: (2)..(2)
```

```
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(10)
<223> OTHER INFORMATION: The Proline at these positions is a
      hydroxyproline.

<400> SEQUENCE: 188

Ser Pro Ser Pro Thr Pro Thr Pro Pro Pro Gly Pro
1               5                   10

<210> SEQ ID NO 189
<211> LENGTH: 19
<212> TYPE: PRT
<213> ORGANISM: Acacia senegal
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 189

Ser Pro Pro Pro Ser Leu Ser Pro Ser Pro Thr Pro Thr Pro Pro Thr
1               5                   10                  15

Gly Pro His

<210> SEQ ID NO 190
<211> LENGTH: 18
<212> TYPE: PRT
<213> ORGANISM: Acacia senegal
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
```

```
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 190

Ser Pro Pro Pro Pro Leu Ser Pro Ser Pro Thr Pro Thr Pro Pro Pro
1               5                   10                  15

Gly Pro

<210> SEQ ID NO 191
<211> LENGTH: 19
<212> TYPE: PRT
<213> ORGANISM: Acacia senegal
<220> FEATURE:
<221> NAME/KEY: MISC_FEATURE
<222> LOCATION: (2)..(2)
<223> OTHER INFORMATION: The proline at this position is a
      hydroxyproline.
<220> FEATURE:
<221> NAME/KEY: MISC_FEATURE
<222> LOCATION: (8)..(8)
<223> OTHER INFORMATION: The proline at this position is a
      hydroxyproline.
<220> FEATURE:
<221> NAME/KEY: MISC_FEATURE
<222> LOCATION: (12)..(12)
<223> OTHER INFORMATION: The proline at this position is a
      hydroxyproline.
<220> FEATURE:
<221> NAME/KEY: MISC_FEATURE
<222> LOCATION: (14)..(16)
<223> OTHER INFORMATION: The proline at these positions is a
      hydroxyproline.

<400> SEQUENCE: 191

Ser Pro Leu Pro Thr Leu Ser Pro Leu Pro Ala Pro Thr Pro Pro Pro
1               5                   10                  15

Gly Pro His

<210> SEQ ID NO 192
<211> LENGTH: 19
<212> TYPE: PRT
<213> ORGANISM: Acacia senegal
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(16)
<223> OTHER INFORMATION: The Proline at these positions is a
      hydroxyproline.

<400> SEQUENCE: 192

Ser Pro Leu Pro Thr Leu Ser Pro Leu Pro Thr Pro Thr Pro Pro Pro
1               5                   10                  15
```

Gly Pro His

<210> SEQ ID NO 193
<211> LENGTH: 18
<212> TYPE: PRT
<213> ORGANISM: Acacia senegal
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 193

Ser Pro Pro Pro Pro Leu Ser Pro Ser Leu Thr Pro Thr Pro Pro Leu
1               5                   10                  15

Gly Pro

<210> SEQ ID NO 194
<211> LENGTH: 13
<212> TYPE: PRT
<213> ORGANISM: Acacia senegal
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(10)
<223> OTHER INFORMATION: The Proline at these positions is a
      hydroxyproline.

<400> SEQUENCE: 194

Ser Pro Ser Pro Thr Pro Thr Pro Pro Pro Gly Pro His
1               5                   10

<210> SEQ ID NO 195
<211> LENGTH: 13
<212> TYPE: PRT
<213> ORGANISM: Acacia senegal
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)

```
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(9)
<223> OTHER INFORMATION: The Proline at these positions is a
      hydroxyproline.

<400> SEQUENCE: 195

Ser Pro Ser Pro Ala Pro Thr Pro Pro Leu Gly Pro His
1               5                   10

<210> SEQ ID NO 196
<211> LENGTH: 14
<212> TYPE: PRT
<213> ORGANISM: Acacia senegal
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(9)
<223> OTHER INFORMATION: The Proline at these positions is a
      hydroxyproline.

<400> SEQUENCE: 196

Ser Pro Leu Pro Thr Pro Thr Pro Pro Leu Gly Pro His Ser
1               5                   10

<210> SEQ ID NO 197
<211> LENGTH: 13
<212> TYPE: PRT
<213> ORGANISM: Acacia senegal
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(9)
<223> OTHER INFORMATION: The Proline at these positions is a
      hydroxyproline.

<400> SEQUENCE: 197

Ser Pro Ser Pro Thr Pro Thr Pro Pro Leu Gly Pro His
1               5                   10

<210> SEQ ID NO 198
<211> LENGTH: 13
<212> TYPE: PRT
```

```
<213> ORGANISM: Acacia senegal
<220> FEATURE:
<221> NAME/KEY: MISC_FEATURE
<222> LOCATION: (2)..(3)
<223> OTHER INFORMATION: The Proline at these positions is a
      hydroxyproline.
<220> FEATURE:
<221> NAME/KEY: MISC_FEATURE
<222> LOCATION: (6)..(6)
<223> OTHER INFORMATION: The Proline at this position is a
      hydroxyproline.
<220> FEATURE:
<221> NAME/KEY: MISC_FEATURE
<222> LOCATION: (8)..(9)
<223> OTHER INFORMATION: The Proline at these positions is a
      hydroxyproline.

<400> SEQUENCE: 198

Ser Pro Pro Leu Thr Pro Thr Pro Pro Leu Leu Pro His
1               5                   10

<210> SEQ ID NO 199
<211> LENGTH: 11
<212> TYPE: PRT
<213> ORGANISM: Acacia senegal
<220> FEATURE:
<221> NAME/KEY: MISC_FEATURE
<222> LOCATION: (1)..(4)
<223> OTHER INFORMATION: The Proline at these positions is a
      hydroxyproline.

<400> SEQUENCE: 199

Pro Pro Pro Pro Ser Ser Thr Pro Gly Leu His
1               5                   10

<210> SEQ ID NO 200
<211> LENGTH: 1
<212> TYPE: PRT
<213> ORGANISM: Acacia senegal
<220> FEATURE:
<221> NAME/KEY: MISC_FEATURE
<222> LOCATION: (1)..(1)
<223> OTHER INFORMATION: The Proline is hydroxyproline linked to
      Ara Ara Ara Ara.

<400> SEQUENCE: 200

Pro
1

<210> SEQ ID NO 201
<211> LENGTH: 1
<212> TYPE: PRT
<213> ORGANISM: Acacia senegal
<220> FEATURE:
<221> NAME/KEY: MISC_FEATURE
<222> LOCATION: (1)..(1)
<223> OTHER INFORMATION: The Proline is hydroxyproline linked to Ara
      Ara Ara.

<400> SEQUENCE: 201

Pro
1

<210> SEQ ID NO 202
<211> LENGTH: 1
<212> TYPE: PRT
<213> ORGANISM: Acacia senegal
<220> FEATURE:
<221> NAME/KEY: MISC_FEATURE
<222> LOCATION: (1)..(1)
<223> OTHER INFORMATION: The Proline is hydroxyproline linked to Ara
```

Ara.

<400> SEQUENCE: 202

Pro
1

<210> SEQ ID NO 203
<211> LENGTH: 1
<212> TYPE: PRT
<213> ORGANISM: Acacia senegal
<220> FEATURE:
<221> NAME/KEY: MISC_FEATURE
<222> LOCATION: (1)..(1)
<223> OTHER INFORMATION: The Proline is hydroxyproline linked to Ara.

<400> SEQUENCE: 203

Pro
1

<210> SEQ ID NO 204
<211> LENGTH: 30
<212> TYPE: DNA
<213> ORGANISM: Artificial Sequence
<220> FEATURE:
<223> OTHER INFORMATION: Synthetic

<400> SEQUENCE: 204
gataccgcga gacccacgct caccagctcc                                         30

<210> SEQ ID NO 205
<211> LENGTH: 21
<212> TYPE: DNA
<213> ORGANISM: Artificial Sequence
<220> FEATURE:
<223> OTHER INFORMATION: Synthetic

<400> SEQUENCE: 205
ctcggtcgcc gcatacacta t                                                  21

<210> SEQ ID NO 206
<211> LENGTH: 87
<212> TYPE: DNA
<213> ORGANISM: Artificial Sequence
<220> FEATURE:
<223> OTHER INFORMATION: Synthetic

<400> SEQUENCE: 206
ggcaagcttc cggagtgccg gccctcatag cccacctcca ccattatcac catcacctac         60
tccaactcct cctttgggac cacacag                                            87

<210> SEQ ID NO 207
<211> LENGTH: 72
<212> TYPE: DNA
<213> ORGANISM: Artificial Sequence
<220> FEATURE:
<223> OTHER INFORMATION: Synthetic

<400> SEQUENCE: 207
ggtcccgggg ggtggtgttg gggttggtga aggggaaagt gtaggggtg gactgtgtgg          60 tcccaaagga gg                                                            72

<210> SEQ ID NO 208
<211> LENGTH: 19
<212> TYPE: PRT
<213> ORGANISM: Artificial Sequence

```
<220> FEATURE:
<223> OTHER INFORMATION: Synthetic

<400> SEQUENCE: 208

Ser Pro Ser Pro Thr Pro Thr Pro Pro Gly Pro His Ser Pro Pro
1               5                   10                  15

Pro Thr Leu

<210> SEQ ID NO 209
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid other than
      hydroxyproline.
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (3)..(3)
<223> OTHER INFORMATION: The hydroxyproline at this position is
      repeated n times, n being an integer from 1 to 100.  Each of
      the proline residues at positions 3 - 102 is hydroxyproline.

<400> SEQUENCE: 209

Xaa Pro Pro
1

<210> SEQ ID NO 210
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa at this position is any amino acid other
      than hydroxyproline.
<220> FEATURE:
<221> NAME/KEY: MISC_FEATURE
<222> LOCATION: (3)..(3)
<223> OTHER INFORMATION: The hydroxyproline at this position is
      repeated n times, n being an integer from 1 to 100.  Each of the
      proline residues at positions 3 - 102 is hydroxyproline.

<400> SEQUENCE: 210

Xaa Pro Pro
1

<210> SEQ ID NO 211
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: The Proline at these positions is a
      hydroxyproline.

<400> SEQUENCE: 211

Ser Pro Pro
```

<210> SEQ ID NO 212
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.

<400> SEQUENCE: 212

Ser Pro Pro Pro
1

<210> SEQ ID NO 213
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: The Proline at these positions is a
      hydroxyproline.

<400> SEQUENCE: 213

Thr Pro Pro
1

<210> SEQ ID NO 214
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.

<400> SEQUENCE: 214

Thr Pro Pro Pro
1

<210> SEQ ID NO 215
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: The Proline at these positions is a
      hydroxyproline.

<400> SEQUENCE: 215

Ser Pro Pro Pro
1

<210> SEQ ID NO 216
<211> LENGTH: 5
<212> TYPE: PRT
<213> ORGANISM: Artificial Sequence

```
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: The Proline at these positions is a
      hydroxyproline.
<220> FEATURE:
<221> NAME/KEY: MISC_FEATURE
<222> LOCATION: (5)..(5)
<223> OTHER INFORMATION: The Proline at this position is a
      hydroxyproline.

<400> SEQUENCE: 216

Ser Pro Pro Pro Pro
1               5

<210> SEQ ID NO 217
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 217

Ser Pro Pro Pro Pro Leu Ser Pro Ser Pro Thr Pro Thr Pro Pro Leu
1               5                   10                  15

Gly Pro His

<210> SEQ ID NO 218
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
```

```
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 218

Ser Pro Pro Pro Pro Leu Ser Pro Ser Pro Thr Pro Thr Pro Pro Leu
1               5                   10                  15

Gly Pro His

<210> SEQ ID NO 219
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 219

Ser Pro Pro Pro Pro Leu Ser Pro Ser Pro Thr Pro Thr Pro Pro Leu
1               5                   10                  15

Gly Pro His

<210> SEQ ID NO 220
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (8)..(8)
```

```
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 220

Ser Pro Pro Pro Pro Leu Ser Pro Ser Pro Thr Pro Thr Pro Pro Leu
1               5                   10                  15

Gly Pro His

<210> SEQ ID NO 221
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 221

Ser Pro Pro Pro Pro Leu Ser Pro Ser Pro Thr Pro Thr Pro Pro Leu
1               5                   10                  15

Gly Pro His

<210> SEQ ID NO 222
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: The Proline at these positions is a
      hydroxyproline.
<220> FEATURE:
<221> NAME/KEY: MISC_FEATURE
```

```
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 222

Ser Pro Pro Pro Pro Leu Ser Pro Ser Pro Thr Pro Thr Pro Pro Leu
1               5                   10                  15

Gly Pro His

<210> SEQ ID NO 223
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 223

Ser Pro Pro Pro Pro Leu Ser Pro Ser Pro Thr Pro Thr Pro Pro Leu
1               5                   10                  15

Gly Pro His

<210> SEQ ID NO 224
<211> LENGTH: 19
<212> TYPE: PRT
<213> ORGANISM: Artificial Sequence
<220> FEATURE:
<221> NAME/KEY: MISC_FEATURE
<222> LOCATION: (2)..(4)
```

```
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 224

Ser Pro Pro Pro Pro Leu Ser Pro Ser Pro Thr Pro Thr Pro Pro Leu
1               5                   10                  15

Gly Pro His

<210> SEQ ID NO 225
<211> LENGTH: 19
<212> TYPE: PRT
<213> ORGANISM: Artificial Sequence
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.

<400> SEQUENCE: 225

Ser Pro Pro Pro Pro Leu Ser Pro Ser Leu Thr Pro Thr Pro Pro Leu
1               5                   10                  15

Gly Pro His

<210> SEQ ID NO 226
<211> LENGTH: 23
<212> TYPE: DNA
<213> ORGANISM: Artificial Sequence
<220> FEATURE:
<223> OTHER INFORMATION: Synthetic

<400> SEQUENCE: 226
gaagatggtg cgctcctgga cgt                                      23

<210> SEQ ID NO 227
<211> LENGTH: 38
<212> TYPE: DNA
<213> ORGANISM: Artificial Sequence
<220> FEATURE:
<223> OTHER INFORMATION: Synthetic

<400> SEQUENCE: 227
```

```
ctcttttct ctggatccgg tctatatttt cttttagc                            38
```

<210> SEQ ID NO 228
<211> LENGTH: 37
<212> TYPE: DNA
<213> ORGANISM: Artificial Sequence
<220> FEATURE:
<223> OTHER INFORMATION: Synthetic

<400> SEQUENCE: 228

```
cgggtgctgc ccgggttgtc tgacccgtga cacttgc                            37
```

<210> SEQ ID NO 229
<211> LENGTH: 334
<212> TYPE: DNA
<213> ORGANISM: Artificial Sequence
<220> FEATURE:
<223> OTHER INFORMATION: Synthetic

<400> SEQUENCE: 229

```
ggatccgcaa tgggaaaaat ggcttctcta tttgccacat ttttagtggt tttaggtgtc    60
acttagctta gcacaaacaa cccgggcccc accttcaccc ccatctccac cgagtccacc   120
atccccacct tcaccccat ctccaccgag tccaccatcc ccaccttcac ccccatctcc   180
accgagtcca ccatccccac cttcaccccc atctccaccg agtccaccat ccccaccttc   240
accccatct ccaccgagtc caccatcccc accttcaccc ccatctccac cgagtccacc   300
atccccacct tcatccatgg cataatagag ctcg                              334
```

<210> SEQ ID NO 230
<211> LENGTH: 105
<212> TYPE: PRT
<213> ORGANISM: Artificial Sequence
<220> FEATURE:
<223> OTHER INFORMATION: Synthetic

<400> SEQUENCE: 230

Ser Ala Met Gly Lys Met Ala Ser Leu Phe Ala Thr Phe Leu Val Val
1               5                   10                  15

Leu Val Ser Leu Val Leu Ala Gln Thr Thr Arg Ala Pro Pro Ser Pro
            20                  25                  30

Pro Ser Pro Pro Ser Pro Pro Ser Pro Pro Ser Pro Pro Ser Pro Pro
        35                  40                  45

Ser Pro Pro Ser Pro Pro Ser Pro Pro Ser Pro Pro Ser Pro Pro Ser
    50                  55                  60

Pro Pro Ser Pro Pro Ser Pro Pro Ser Pro Pro Ser Pro Pro Ser Pro
65                  70                  75                  80

Pro Ser Pro Pro Ser Pro Pro Ser Pro Pro Ser Pro Pro Ser Pro Pro
                85                  90                  95

Ser Pro Pro Ser Pro Ser Ser Met Ala
            100                 105

<210> SEQ ID NO 231
<211> LENGTH: 72
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a

```
        hydroxyproline.
<220> FEATURE:
<221> NAME/KEY: MISC_FEATURE
<222> LOCATION: (4)..(5)
<223> OTHER INFORMATION: The Proline at these positions is a
        hydroxyproline.
<220> FEATURE:
<221> NAME/KEY: MISC_FEATURE
<222> LOCATION: (7)..(8)
<223> OTHER INFORMATION: The Proline at these positions is a
        hydroxyproline.
<220> FEATURE:
<221> NAME/KEY: MISC_FEATURE
<222> LOCATION: (10)..(11)
<223> OTHER INFORMATION: The Proline at these positions is a
        hydroxyproline.
<220> FEATURE:
<221> NAME/KEY: MISC_FEATURE
<222> LOCATION: (14)..(14)
<223> OTHER INFORMATION: The Proline at this position is a
        hydroxyproline.
<220> FEATURE:
<221> NAME/KEY: MISC_FEATURE
<222> LOCATION: (16)..(17)
<223> OTHER INFORMATION: The Proline at these positions is a
        hydroxyproline.
<220> FEATURE:
<221> NAME/KEY: MISC_FEATURE
<222> LOCATION: (19)..(20)
<223> OTHER INFORMATION: The Proline at these positions is a
        hydroxyproline.
<220> FEATURE:
<221> NAME/KEY: MISC_FEATURE
<222> LOCATION: (22)..(23)
<223> OTHER INFORMATION: The Proline at these positions is a
        hydroxyproline.
<220> FEATURE:
<221> NAME/KEY: MISC_FEATURE
<222> LOCATION: (26)..(26)
<223> OTHER INFORMATION: The Proline at this position is a
        hydroxyproline.
<220> FEATURE:
<221> NAME/KEY: MISC_FEATURE
<222> LOCATION: (28)..(29)
<223> OTHER INFORMATION: The Proline at these positions is a
        hydroxyproline.
<220> FEATURE:
<221> NAME/KEY: MISC_FEATURE
<222> LOCATION: (31)..(32)
<223> OTHER INFORMATION: The Proline at these positions is a
        hydroxyproline.
<220> FEATURE:
<221> NAME/KEY: MISC_FEATURE
<222> LOCATION: (34)..(35)
<223> OTHER INFORMATION: The Proline at these positions is a
        hydroxyproline.
<220> FEATURE:
<221> NAME/KEY: MISC_FEATURE
<222> LOCATION: (38)..(38)
<223> OTHER INFORMATION: The Proline at this position is a
        hydroxyproline.
<220> FEATURE:
<221> NAME/KEY: MISC_FEATURE
<222> LOCATION: (40)..(41)
<223> OTHER INFORMATION: The Proline at these positions is a
        hydroxyproline.
<220> FEATURE:
<221> NAME/KEY: MISC_FEATURE
<222> LOCATION: (43)..(44)
<223> OTHER INFORMATION: The Proline at these positions is a
        hydroxyproline.
<220> FEATURE:
<221> NAME/KEY: MISC_FEATURE
<222> LOCATION: (46)..(47)
<223> OTHER INFORMATION: The Proline at these positions is a
        hydroxyproline.
<220> FEATURE:
<221> NAME/KEY: MISC_FEATURE
<222> LOCATION: (50)..(50)
```

```
<223> OTHER INFORMATION: The Proline at this position is a
      hydroxyproline.
<220> FEATURE:
<221> NAME/KEY: MISC_FEATURE
<222> LOCATION: (52)..(53)
<223> OTHER INFORMATION: The Proline at these positions is a
      hydroxyproline.
<220> FEATURE:
<221> NAME/KEY: MISC_FEATURE
<222> LOCATION: (55)..(56)
<223> OTHER INFORMATION: The Proline at these positions is a
      hydroxyproline.
<220> FEATURE:
<221> NAME/KEY: MISC_FEATURE
<222> LOCATION: (58)..(59)
<223> OTHER INFORMATION: The Proline at these positions is a
      hydroxyproline.
<220> FEATURE:
<221> NAME/KEY: MISC_FEATURE
<222> LOCATION: (62)..(62)
<223> OTHER INFORMATION: The Proline at this position is a
      hydroxyproline.
<220> FEATURE:
<221> NAME/KEY: MISC_FEATURE
<222> LOCATION: (64)..(65)
<223> OTHER INFORMATION: The Proline at these positions is a
      hydroxyproline.
<220> FEATURE:
<221> NAME/KEY: MISC_FEATURE
<222> LOCATION: (67)..(68)
<223> OTHER INFORMATION: The Proline at these positions is a
      hydroxyproline.
<220> FEATURE:
<221> NAME/KEY: MISC_FEATURE
<222> LOCATION: (70)..(71)
<223> OTHER INFORMATION: The Proline at these positions is a
      hydroxyproline.

<400> SEQUENCE: 231

Pro Pro Ser Pro Pro Ser Pro Pro Ser Pro Pro Ser Pro Pro Ser Pro
1               5                   10                  15

Pro Ser Pro Pro Ser Pro Pro Ser Pro Pro Ser Pro Pro Ser Pro Pro
            20                  25                  30

Ser Pro Pro Ser Pro Pro Ser Pro Pro Ser Pro Pro Ser Pro Pro Ser
        35                  40                  45

Pro Pro Ser Pro Pro Ser Pro Pro Ser Pro Pro Ser Pro Pro Ser Pro
    50                  55                  60

Pro Ser Pro Pro Ser Pro Pro Ser
65                  70

<210> SEQ ID NO 232
<211> LENGTH: 246
<212> TYPE: DNA
<213> ORGANISM: Artificial Sequence
<220> FEATURE:
<223> OTHER INFORMATION: Synthetic

<400> SEQUENCE: 232
ggatcctcaa cccgggcctc accaccacca ccttctccac ctccatcacc cccaccttcg      60
cctccaccat ccccaccacc ttctccacct ccatcacccc cacccttcgcc tccaccatcc    120 ccaccacctt ctccacctcc atcaccccca ccttcgcctc caccatcccc accaccttct    180
ccacctccat caccccccacc ttcgcctcca ccatcccctt ccatggcata atagagctcg    240
aattcg                                                                246

<210> SEQ ID NO 233
<211> LENGTH: 76
<212> TYPE: PRT
```

<213> ORGANISM: Artificial Sequence
<220> FEATURE:
<223> OTHER INFORMATION: Synthetic

<400> SEQUENCE: 233

Gly Ser Ser Thr Arg Ala Ser Pro Pro Pro Ser Pro Pro Pro Ser
1               5                   10                  15
Pro Pro Pro Ser Pro Pro Pro Ser Pro Pro Pro Ser Pro Pro Pro
                20                  25                  30
Pro Pro Pro Ser Pro Pro Pro Ser Pro Pro Pro Ser Pro Pro Pro
            35                  40                  45
Pro Pro Pro Ser Pro Pro Ser Pro Pro Pro Ser Pro Pro Pro Ser
        50                  55                  60
Pro Pro Pro Ser Pro Pro Pro Ser Pro Ser Met Ala
65                  70                  75

<210> SEQ ID NO 234
<211> LENGTH: 324
<212> TYPE: DNA
<213> ORGANISM: Artificial Sequence
<220> FEATURE:
<223> OTHER INFORMATION: Synthetic

<400> SEQUENCE: 234

```
ggatcctcaa cccgggcctc accaccacca ccttcacctc accccccatc tccaccacca      60
ccttcacctc accccccatc tccaccacca ccttcacctc accccccatc tccaccacca     120
ccttcacctc accccccatc tccaccacca ccttcacctc accccccatc tccaccacca     180
ccttcacctc accccccatc tccaccacca ccttcacctc accccccatc tccaccacca     240
ccttcacctc accccccatc tccaccacca ccttcacctc accccccatc tccaccacca     300
ccttccatgg cattatagag ctcg                                            324
```

<210> SEQ ID NO 235
<211> LENGTH: 104
<212> TYPE: PRT
<213> ORGANISM: Artificial Sequence
<220> FEATURE:
<223> OTHER INFORMATION: Synthetic

<400> SEQUENCE: 235

Gly Ser Ser Thr Arg Ala Ser Pro Pro Pro Ser Pro Pro Pro Pro
1               5                   10                  15
Ser Pro Pro Pro Pro Ser Pro Pro Pro Ser Pro Pro Pro Pro Ser
                20                  25                  30
Pro Pro Pro Ser Pro Pro Pro Pro Ser Pro Pro Pro Ser Pro Pro
            35                  40                  45
Pro Pro Ser Pro Pro Pro Pro Ser Pro Pro Pro Pro Ser Pro Pro
        50                  55                  60
Pro Pro Ser Pro Pro Pro Ser Pro Pro Pro Pro Ser Pro Pro Pro
65                  70                  75                  80
Pro Ser Pro Pro Pro Ser Pro Pro Pro Ser Pro Pro Pro Pro
                85                  90                  95
Ser Pro Pro Pro Pro Ser Met Ala
            100

<210> SEQ ID NO 236
<211> LENGTH: 96
<212> TYPE: PRT
<213> ORGANISM: Artificial Sequence

```
<220> FEATURE:
<223> OTHER INFORMATION: Synthetic

<400> SEQUENCE: 236

Gly Ser Ala Met Gly Lys Met Ala Ser Leu Phe Ala Thr Phe Leu Val
1               5                   10                  15

Val Leu Val Ser Leu Ser Leu Ala Gln Thr Thr Arg Ala Ser Pro Ser
            20                  25                  30

Pro Ser Pro Ser Pro Ser Pro Ser Pro Ser Pro Ser Pro Ser Pro Ser
        35                  40                  45

Pro Ser Pro Ser Pro Ser Pro Ser Pro Ser Pro Ser Pro Ser Pro Ser
    50                  55                  60

Pro Ser Pro Ser Pro Ser Pro Ser Pro Ser Pro Ser Pro Ser Pro Ser
65                  70                  75                  80

Pro Ser Pro Ser Pro Ser Pro Ser Pro Ser Pro Ser Pro Val Ala Thr
                85                  90                  95

<210> SEQ ID NO 237
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.

<400> SEQUENCE: 237

Ser Pro Pro Pro Pro Thr Pro Val Tyr Lys
1               5                   10

<210> SEQ ID NO 238
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.
<220> FEATURE:
<221> NAME/KEY: MISC_FEATURE
<222> LOCATION: (9)..(14)
<223> OTHER INFORMATION: The Proline at these positions is a
      hydroxyproline.

<400> SEQUENCE: 238

Ser Pro Pro Pro Pro Ser Pro Ser Pro Pro Pro Pro Pro Pro Tyr Tyr
1               5                   10                  15

Tyr Lys

<210> SEQ ID NO 239
<211> LENGTH: 5
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.

<400> SEQUENCE: 239

Pro Pro Val Tyr Lys
1               5

<210> SEQ ID NO 240
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (4)..(4)
<223> OTHER INFORMATION: The Proline at this position is a
      hydroxyproline.

<400> SEQUENCE: 240

Ala Pro Ala Pro
1

<210> SEQ ID NO 241
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Ser, Ala, or Thr.
<220> FEATURE:
<221> NAME/KEY: MISC_FEATURE
<222> LOCATION: (2)..(5)
<223> OTHER INFORMATION: The Proline at these positions is a
      hydroxyproline.

<400> SEQUENCE: 241

Xaa Pro Pro Pro Pro
1               5

<210> SEQ ID NO 242
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Ser, Ala, or Thr.
<220> FEATURE:
<221> NAME/KEY: MISC_FEATURE
<222> LOCATION: (2)..(2)
<223> OTHER INFORMATION: The Proline at this position is a hydroxyproline
      , and is always
      arabinosylated.
<220> FEATURE:
<221> NAME/KEY: MISC_FEATURE
```

```
<222> LOCATION: (3)..(3)
<223> OTHER INFORMATION: The Proline at this position is a hydroxy
      proline, and is
      occasionally arabinosylated.

<400> SEQUENCE: 242

Xaa Pro Pro
1

<210> SEQ ID NO 243
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X can be Ser or Ala.
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (3)..(3)
<223> OTHER INFORMATION: Xaa can be Ser or Ala.
<220> FEATURE:
<221> NAME/KEY: MISC_FEATURE
<222> LOCATION: (4)..(4)
<223> OTHER INFORMATION: The Proline at this position is a
      hydroxyproline.

<400> SEQUENCE: 243

Xaa Pro Xaa Pro
1

<210> SEQ ID NO 244
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Thr, Glu, Pro, His, or Ile.
<220> FEATURE:
<221> NAME/KEY: MISC_FEATURE
<222> LOCATION: (2)..(2)
<223> OTHER INFORMATION: The Proline at this position is a
      hydroxyproline.

<400> SEQUENCE: 244

Xaa Pro Val Tyr Lys
1               5

<210> SEQ ID NO 245
<211> LENGTH: 4
<212> TYPE: PRT
<213> ORGANISM: Artificial Sequence
<220> FEATURE:
<223> OTHER INFORMATION: Synthetic

<400> SEQUENCE: 245

Tyr Tyr Tyr Lys
1

<210> SEQ ID NO 246
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 246

Tyr Lys Tyr Lys
1

<210> SEQ ID NO 247
<211> LENGTH: 2
<212> TYPE: PRT
<213> ORGANISM: Artificial Sequence
<220> FEATURE:
<223> OTHER INFORMATION: Synthetic

<400> SEQUENCE: 247

Lys Pro
1

<210> SEQ ID NO 248
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.
<220> FEATURE:
<221> NAME/KEY: MISC_FEATURE
<222> LOCATION: (9)..(12)
<223> OTHER INFORMATION: The Proline at these positions is a
      hydroxyproline.

<400> SEQUENCE: 248

Ser Pro Pro Pro Pro Ser Pro Ser Pro Pro Pro Tyr Tyr Tyr Lys
1               5                   10                  15

<210> SEQ ID NO 249
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.
<220> FEATURE:
<221> NAME/KEY: MISC_FEATURE
<222> LOCATION: (9)..(12)
<223> OTHER INFORMATION: The Proline at these positions is a
      hydroxyproline.

<400> SEQUENCE: 249

Ser Pro Pro Pro Pro Ser Pro Ser Pro Pro Pro
1               5                   10
```

```
<210> SEQ ID NO 250
<211> LENGTH: 4
<212> TYPE: PRT
<213> ORGANISM: Artificial Sequence
<220> FEATURE:
<223> OTHER INFORMATION: Synthetic

<400> SEQUENCE: 250

Tyr Tyr Tyr Lys
1

<210> SEQ ID NO 251
<211> LENGTH: 4
<212> TYPE: PRT
<213> ORGANISM: Artificial Sequence
<220> FEATURE:
<223> OTHER INFORMATION: Synthetic

<400> SEQUENCE: 251

Phe Phe Phe Lys
1

<210> SEQ ID NO 252
<211> LENGTH: 4
<212> TYPE: PRT
<213> ORGANISM: Artificial Sequence
<220> FEATURE:
<223> OTHER INFORMATION: Synthetic

<400> SEQUENCE: 252

Tyr Tyr Tyr Leu
1

<210> SEQ ID NO 253
<211> LENGTH: 4
<212> TYPE: PRT
<213> ORGANISM: Artificial Sequence
<220> FEATURE:
<223> OTHER INFORMATION: Synthetic

<400> SEQUENCE: 253

Phe Phe Phe Leu
1

<210> SEQ ID NO 254
<211> LENGTH: 10
<212> TYPE: PRT
<213> ORGANISM: Artificial Sequence
<220> FEATURE:
<223> OTHER INFORMATION: Synthetic

<400> SEQUENCE: 254

Ser Pro Pro Pro Pro Thr Pro Val Tyr Lys
1               5                   10

<210> SEQ ID NO 255
<211> LENGTH: 16
<212> TYPE: PRT
<213> ORGANISM: Artificial Sequence
<220> FEATURE:
<223> OTHER INFORMATION: Synthetic

<400> SEQUENCE: 255

Ser Pro Pro Pro Pro Val Lys Pro Tyr His Pro Thr Pro Val Tyr Lys
1               5                   10                  15
```

```
<210> SEQ ID NO 256
<211> LENGTH: 3
<212> TYPE: PRT
<213> ORGANISM: Artificial Sequence
<220> FEATURE:
<223> OTHER INFORMATION: Synthetic

<400> SEQUENCE: 256

Val Tyr Lys
1

<210> SEQ ID NO 257
<211> LENGTH: 7
<212> TYPE: PRT
<213> ORGANISM: Artificial Sequence
<220> FEATURE:
<223> OTHER INFORMATION: Synthetic

<400> SEQUENCE: 257

Ser Pro Pro Pro Pro Thr Pro
1               5

<210> SEQ ID NO 258
<211> LENGTH: 3
<212> TYPE: PRT
<213> ORGANISM: Artificial Sequence
<220> FEATURE:
<223> OTHER INFORMATION: Synthetic

<400> SEQUENCE: 258

Val Phe Leu
1

<210> SEQ ID NO 259
<211> LENGTH: 10
<212> TYPE: PRT
<213> ORGANISM: Artificial Sequence
<220> FEATURE:
<223> OTHER INFORMATION: Synthetic

<400> SEQUENCE: 259

Ser Pro Pro Pro Pro Thr Pro Val Phe Leu
1               5                   10

<210> SEQ ID NO 260
<211> LENGTH: 37
<212> TYPE: DNA
<213> ORGANISM: Artificial Sequence
<220> FEATURE:
<223> OTHER INFORMATION: Synthetic

<400> SEQUENCE: 260
cgggtgctgc ccgggttgtc tgacccgtga cacttgc                    37

<210> SEQ ID NO 261
<211> LENGTH: 40
<212> TYPE: DNA
<213> ORGANISM: Artificial Sequence
<220> FEATURE:
<223> OTHER INFORMATION: Synthetic

<400> SEQUENCE: 261
gcaatgtaca cgggtcagac acctgccgca gcacccgttg                 40

<210> SEQ ID NO 262
<211> LENGTH: 42
<212> TYPE: DNA
```

<213> ORGANISM: Artificial Sequence
<220> FEATURE:
<223> OTHER INFORMATION: Synthetic

<400> SEQUENCE: 262

```
gacgtcacgg ccgctttaga acaagagcca gctcatcaca gc                          42
```

<210> SEQ ID NO 263
<211> LENGTH: 38
<212> TYPE: DNA
<213> ORGANISM: Artificial Sequence
<220> FEATURE:
<223> OTHER INFORMATION: Synthetic

<400> SEQUENCE: 263

```
actttcatg cattaggagc cggagctgga gttgtctc                                38
```

<210> SEQ ID NO 264
<211> LENGTH: 43
<212> TYPE: DNA
<213> ORGANISM: Artificial Sequence
<220> FEATURE:
<223> OTHER INFORMATION: Synthetic

<400> SEQUENCE: 264

```
caatttgcgg ccgctttact catcgttaag agatgggctg gga                         43
```

<210> SEQ ID NO 265
<211> LENGTH: 738
<212> TYPE: DNA
<213> ORGANISM: Lycopersicon esculentum

<400> SEQUENCE: 265

```
aggatccggt ctatattttc tttagctacc atggatagaa aatttgtatt tctagtatca       60
attttgtgca ttgtagtggc aagtgtcacg ggtcagacaa cccgggtacc ggtcgccacc      120
atggagctgt acacgggtca gacacctgcc gcagcacccg ttggtgctaa ggctggtact      180
actccaccag ctgctgcacc aactaagccg aaaactcctg ctcccgcaac agcaccagcc      240
tcggccccac ctacagctgt tcctgttgct ccagtaaccg ctccagttac tgctcccact      300
acacctgttg ttgctgcacc cgtatcagca ccagcaagtt ctccaccact aaagcacca      360
gcaagttctc caccagtaca atctccacca gctccagctc cagaggtagc tacaccgcca      420
gctgtttcta ctccaccggc tgcagctcca gttgctgcac ctgttgcttc ggagacaact      480
ccagctccgg ctcctagcaa aggaaaagta agggaaaga agggaaagaa acacaatgca      540
tcaccagcac cttctcccga tatgatgagc ccacctgcac ctccttccga agctcctgga      600
cctagcatgg actccgattc agctcccagc ccatctctta acgatgagag tggagcagag      660
aaattgaaga tgctgggaag tttggtagct ggatgggctg tgatgagctg gctcttgttc      720
taaagcggcg gcaccgcg                                                    738
```

<210> SEQ ID NO 266
<211> LENGTH: 230
<212> TYPE: PRT
<213> ORGANISM: Artificial Sequence
<220> FEATURE:
<223> OTHER INFORMATION: Synthetic

<400> SEQUENCE: 266

```
Met Asp Arg Lys Phe Val Phe Leu Val Ser Ile Leu Cys Ile Val Val
1               5                   10                  15
```

```
Ala Ser Val Thr Gly Gln Thr Thr Arg Val Pro Val Ala Thr Met Glu
            20                  25                  30

Leu Tyr Thr Gly Gln Thr Pro Ala Ala Ala Pro Val Gly Ala Lys Ala
            35                  40                  45

Gly Thr Thr Pro Pro Ala Ala Ala Pro Thr Lys Pro Lys Thr Pro Ala
     50                  55                  60

Pro Ala Thr Ala Pro Ala Ser Ala Pro Pro Thr Ala Val Pro Val Ala
 65                  70                  75                  80

Pro Val Thr Ala Pro Val Thr Ala Pro Thr Thr Pro Val Val Ala Ala
                 85                  90                  95

Pro Val Ser Ala Pro Ala Ser Ser Pro Pro Leu Lys Ala Pro Ala Ser
                100                 105                 110

Ser Pro Pro Val Gln Ser Pro Pro Ala Pro Ala Pro Glu Val Ala Thr
            115                 120                 125

Pro Pro Ala Val Ser Thr Pro Pro Ala Ala Pro Val Ala Ala Pro
        130                 135                 140

Val Ala Ser Glu Thr Thr Pro Ala Pro Ala Pro Ser Lys Gly Lys Val
145                 150                 155                 160

Lys Gly Lys Lys Gly Lys Lys His Asn Ala Ser Pro Ala Pro Ser Pro
                165                 170                 175

Asp Met Met Ser Pro Ala Pro Pro Ser Glu Ala Pro Gly Pro Ser
            180                 185                 190

Met Asp Ser Asp Ser Ala Pro Ser Pro Ser Leu Asn Asp Glu Ser Gly
        195                 200                 205

Ala Glu Lys Leu Lys Met Leu Gly Ser Leu Val Ala Gly Trp Ala Val
        210                 215                 220

Met Ser Trp Leu Leu Phe
225                 230

<210> SEQ ID NO 267
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.

<400> SEQUENCE: 267

Thr Pro Val Tyr Lys
1               5

<210> SEQ ID NO 268
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.

<400> SEQUENCE: 268
```

Ser Pro Pro Pro Pro Thr Pro Val Tyr Lys
1               5                   10

<210> SEQ ID NO 269
<211> LENGTH: 230
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.
<220> FEATURE:
<221> NAME/KEY: MISC_FEATURE
<222> LOCATION: (12)..(15)
<223> OTHER INFORMATION: The Proline at these positions is a
      hydroxyproline.
<220> FEATURE:
<221> NAME/KEY: MISC_FEATURE
<222> LOCATION: (17)..(17)
<223> OTHER INFORMATION: The Proline at this position is a
      hydroxyproline.
<220> FEATURE:
<221> NAME/KEY: MISC_FEATURE
<222> LOCATION: (22)..(25)
<223> OTHER INFORMATION: The Proline at these positions is a
      hydroxyproline.
<220> FEATURE:
<221> NAME/KEY: MISC_FEATURE
<222> LOCATION: (29)..(29)
<223> OTHER INFORMATION: The Proline at this position is a
      hydroxyproline.
<220> FEATURE:
<221> NAME/KEY: MISC_FEATURE
<222> LOCATION: (34)..(34)
<223> OTHER INFORMATION: The Proline at this position is a
      hydroxyproline.
<220> FEATURE:
<221> NAME/KEY: MISC_FEATURE
<222> LOCATION: (39)..(39)
<223> OTHER INFORMATION: The Proline at this position is a
      hydroxyproline.
<220> FEATURE:
<221> NAME/KEY: MISC_FEATURE
<222> LOCATION: (44)..(44)
<223> OTHER INFORMATION: The Proline at this position is a
      hydroxyproline.
<220> FEATURE:
<221> NAME/KEY: MISC_FEATURE
<222> LOCATION: (49)..(49)
<223> OTHER INFORMATION: The Proline at this position is a
      hydroxyproline.
<220> FEATURE:
<221> NAME/KEY: MISC_FEATURE
<222> LOCATION: (54)..(54)
<223> OTHER INFORMATION: The Proline at this position is a
      hydroxyproline.
<220> FEATURE:
<221> NAME/KEY: MISC_FEATURE
<222> LOCATION: (59)..(59)
<223> OTHER INFORMATION: The Proline at this position is a
      hydroxyproline.
<220> FEATURE:
<221> NAME/KEY: MISC_FEATURE
<222> LOCATION: (64)..(64)
<223> OTHER INFORMATION: The Proline at this position is a
      hydroxyproline.
<220> FEATURE:
<221> NAME/KEY: MISC_FEATURE
<222> LOCATION: (69)..(69)

```
<223> OTHER INFORMATION: The Proline at this position is a
      hydroxyproline.
<220> FEATURE:
<221> NAME/KEY: MISC_FEATURE
<222> LOCATION: (74)..(74)
<223> OTHER INFORMATION: The Proline at this position is a
      hydroxyproline.
<220> FEATURE:
<221> NAME/KEY: MISC_FEATURE
<222> LOCATION: (79)..(79)
<223> OTHER INFORMATION: The Proline at this position is a
      hydroxyproline.
<220> FEATURE:
<221> NAME/KEY: MISC_FEATURE
<222> LOCATION: (84)..(84)
<223> OTHER INFORMATION: The Proline at these positions is a
      hydroxyproline.
<220> FEATURE:
<221> NAME/KEY: MISC_FEATURE
<222> LOCATION: (84)..(84)
<223> OTHER INFORMATION: The Proline at this position is a
      hydroxyproline.
<220> FEATURE:
<221> NAME/KEY: MISC_FEATURE
<222> LOCATION: (87)..(90)
<223> OTHER INFORMATION: The Proline at these positions is a
      hydroxyproline.
<220> FEATURE:
<221> NAME/KEY: MISC_FEATURE
<222> LOCATION: (92)..(95)
<223> OTHER INFORMATION: The Proline at these positions is a
      hydroxyproline.
<220> FEATURE:
<221> NAME/KEY: MISC_FEATURE
<222> LOCATION: (97)..(100)
<223> OTHER INFORMATION: The Proline at these positions is a
      hydroxyproline.
<220> FEATURE:
<221> NAME/KEY: MISC_FEATURE
<222> LOCATION: (102)..(105)
<223> OTHER INFORMATION: The Proline at these positions is a
      hydroxyproline.
<220> FEATURE:
<221> NAME/KEY: MISC_FEATURE
<222> LOCATION: (107)..(110)
<223> OTHER INFORMATION: The Proline at these positions is a
      hydroxyproline.
<220> FEATURE:
<221> NAME/KEY: MISC_FEATURE
<222> LOCATION: (112)..(115)
<223> OTHER INFORMATION: The Proline at these positions is a
      hydroxyproline.
<220> FEATURE:
<221> NAME/KEY: MISC_FEATURE
<222> LOCATION: (117)..(120)
<223> OTHER INFORMATION: The Proline at these positions is a
      hydroxyproline.
<220> FEATURE:
<221> NAME/KEY: MISC_FEATURE
<222> LOCATION: (122)..(125)
<223> OTHER INFORMATION: The Proline at these positions is a
      hydroxyproline.
<220> FEATURE:
<221> NAME/KEY: MISC_FEATURE
<222> LOCATION: (127)..(130)
<223> OTHER INFORMATION: The Proline at these positions is a
      hydroxyproline.
<220> FEATURE:
<221> NAME/KEY: MISC_FEATURE
<222> LOCATION: (132)..(135)
<223> OTHER INFORMATION: The Proline at these positions is a
      hydroxyproline.
<220> FEATURE:
<221> NAME/KEY: MISC_FEATURE
<222> LOCATION: (137)..(140)
<223> OTHER INFORMATION: The Proline at these positions is a
      hydroxyproline.
<220> FEATURE:
<221> NAME/KEY: MISC_FEATURE
```

```
<222> LOCATION: (142)..(145)
<223> OTHER INFORMATION: The Proline at these positions is a
      hydroxyproline.
<220> FEATURE:
<221> NAME/KEY: MISC_FEATURE
<222> LOCATION: (147)..(150)
<223> OTHER INFORMATION: The Proline at these positions is a
      hydroxyproline.
<220> FEATURE:
<221> NAME/KEY: MISC_FEATURE
<222> LOCATION: (152)..(155)
<223> OTHER INFORMATION: The Proline at these positions is a
      hydroxyproline.
<220> FEATURE:
<221> NAME/KEY: MISC_FEATURE
<222> LOCATION: (157)..(160)
<223> OTHER INFORMATION: The Proline at these positions is a
      hydroxyproline.
<220> FEATURE:
<221> NAME/KEY: MISC_FEATURE
<222> LOCATION: (162)..(165)
<223> OTHER INFORMATION: The Proline at these positions is a
      hydroxyproline.
<220> FEATURE:
<221> NAME/KEY: MISC_FEATURE
<222> LOCATION: (167)..(170)
<223> OTHER INFORMATION: The Proline at these positions is a
      hydroxyproline.
<220> FEATURE:
<221> NAME/KEY: MISC_FEATURE
<222> LOCATION: (172)..(175)
<223> OTHER INFORMATION: The Proline at these positions is a
      hydroxyproline.
<220> FEATURE:
<221> NAME/KEY: MISC_FEATURE
<222> LOCATION: (179)..(179)
<223> OTHER INFORMATION: The Proline at this position is a
      hydroxyproline.
<220> FEATURE:
<221> NAME/KEY: MISC_FEATURE
<222> LOCATION: (184)..(184)
<223> OTHER INFORMATION: The Proline at this position is a
      hydroxyproline.
<220> FEATURE:
<221> NAME/KEY: MISC_FEATURE
<222> LOCATION: (189)..(189)
<223> OTHER INFORMATION: The Proline at this position is a
      hydroxyproline.
<220> FEATURE:
<221> NAME/KEY: MISC_FEATURE
<222> LOCATION: (194)..(194)
<223> OTHER INFORMATION: The Proline at this position is a
      hydroxyproline.
<220> FEATURE:
<221> NAME/KEY: MISC_FEATURE
<222> LOCATION: (199)..(199)
<223> OTHER INFORMATION: The Proline at this position is a
      hydroxyproline.
<220> FEATURE:
<221> NAME/KEY: MISC_FEATURE
<222> LOCATION: (204)..(204)
<223> OTHER INFORMATION: The Proline at this position is a
      hydroxyproline.
<220> FEATURE:
<221> NAME/KEY: MISC_FEATURE
<222> LOCATION: (207)..(210)
<223> OTHER INFORMATION: The Proline at these positions is a
      hydroxyproline.
<220> FEATURE:
<221> NAME/KEY: MISC_FEATURE
<222> LOCATION: (212)..(212)
<223> OTHER INFORMATION: The Proline at this position is a
      hydroxyproline.
<220> FEATURE:
<221> NAME/KEY: MISC_FEATURE
<222> LOCATION: (217)..(220)
<223> OTHER INFORMATION: The Proline at these positions is a
      hydroxyproline.
<220> FEATURE:
```

```
<221> NAME/KEY: MISC_FEATURE
<222> LOCATION: (222)..(222)
<223> OTHER INFORMATION: The Proline at this position is a
      hydroxyproline.
<220> FEATURE:
<221> NAME/KEY: MISC_FEATURE
<222> LOCATION: (227)..(230)
<223> OTHER INFORMATION: The Proline at these positions is a
      hydroxyproline.

<400> SEQUENCE: 269

Ser Pro Pro Pro Thr Pro Val Tyr Lys Ser Pro Pro Pro Thr
 1               5                  10                  15

Pro Val Tyr Lys Ser Pro Pro Pro Val Gly Val Pro Gly Val Gly
                20                  25                  30

Val Pro Gly Val Gly Val Pro Gly Val Gly Val Pro Gly Val Gly Val
            35                  40                  45

Pro Gly Val Gly Val Pro Gly Val Gly Val Pro Gly Val Gly Val Pro
            50                  55                  60

Gly Val Gly Val Pro Gly Val Gly Val Pro Gly Val Gly Val Pro Gly
 65                  70                  75                  80

Val Gly Val Pro Gly Ser Pro Pro Pro Ser Pro Pro Pro Ser
                85                  90                  95

Pro Pro Pro Ser Pro Pro Pro Ser Pro Pro Pro Ser Pro
                100                 105                 110

Pro Pro Ser Pro Pro Pro Ser Pro Pro Pro Ser Pro Pro
            115                 120                 125

Pro Pro Ser Pro Pro Pro Ser Pro Pro Pro Ser Pro Pro Pro
        130                 135                 140

Pro Ser Pro Pro Pro Ser Pro Pro Pro Ser Pro Pro Pro Pro
145                 150                 155                 160

Ser Pro Pro Pro Ser Pro Pro Pro Ser Pro Pro Pro Val
                165                 170                 175

Gly Val Pro Gly Val Gly Val Pro Gly Val Gly Val Pro Gly Val Gly
                180                 185                 190

Val Pro Gly Val Gly Val Pro Gly Val Gly Val Pro Gly Ser Pro Pro
            195                 200                 205

Pro Pro Thr Pro Val Tyr Lys Ser Pro Pro Pro Thr Pro Val Tyr
        210                 215                 220

Lys Ser Pro Pro Pro Pro
225                 230

<210> SEQ ID NO 270
<211> LENGTH: 284
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.
<220> FEATURE:
<221> NAME/KEY: MISC_FEATURE
<222> LOCATION: (12)..(15)
<223> OTHER INFORMATION: The Proline at these positions is a
      hydroxyproline.
```

```
-continued

<220> FEATURE:
<221> NAME/KEY: MISC_FEATURE
<222> LOCATION: (17)..(17)
<223> OTHER INFORMATION: The Proline at this position is a
      hydroxyproline.
<220> FEATURE:
<221> NAME/KEY: MISC_FEATURE
<222> LOCATION: (22)..(25)
<223> OTHER INFORMATION: The Proline at these positions is a
      hydroxyproline.
<220> FEATURE:
<221> NAME/KEY: MISC_FEATURE
<222> LOCATION: (29)..(29)
<223> OTHER INFORMATION: The Proline at this position is a
      hydroxyproline.
<220> FEATURE:
<221> NAME/KEY: MISC_FEATURE
<222> LOCATION: (34)..(34)
<223> OTHER INFORMATION: The Proline at this position is a
      hydroxyproline.
<220> FEATURE:
<221> NAME/KEY: MISC_FEATURE
<222> LOCATION: (39)..(39)
<223> OTHER INFORMATION: The Proline at this position is a
      hydroxyproline.
<220> FEATURE:
<221> NAME/KEY: MISC_FEATURE
<222> LOCATION: (44)..(44)
<223> OTHER INFORMATION: The Proline at this position is a
      hydroxyproline.
<220> FEATURE:
<221> NAME/KEY: MISC_FEATURE
<222> LOCATION: (49)..(49)
<223> OTHER INFORMATION: The Proline at this position is a
      hydroxyproline.
<220> FEATURE:
<221> NAME/KEY: MISC_FEATURE
<222> LOCATION: (54)..(54)
<223> OTHER INFORMATION: The Proline at this position is a
      hydroxyproline.
<220> FEATURE:
<221> NAME/KEY: MISC_FEATURE
<222> LOCATION: (59)..(59)
<223> OTHER INFORMATION: The Proline at this position is a
      hydroxyproline.
<220> FEATURE:
<221> NAME/KEY: MISC_FEATURE
<222> LOCATION: (64)..(64)
<223> OTHER INFORMATION: The Proline at this position is a
      hydroxyproline.
<220> FEATURE:
<221> NAME/KEY: MISC_FEATURE
<222> LOCATION: (69)..(69)
<223> OTHER INFORMATION: The Proline at this position is a
      hydroxyproline.
<220> FEATURE:
<221> NAME/KEY: MISC_FEATURE
<222> LOCATION: (74)..(74)
<223> OTHER INFORMATION: The Proline at this position is a
      hydroxyproline.
<220> FEATURE:
<221> NAME/KEY: MISC_FEATURE
<222> LOCATION: (79)..(79)
<223> OTHER INFORMATION: The Proline at this position is a
      hydroxyproline.
<220> FEATURE:
<221> NAME/KEY: MISC_FEATURE
<222> LOCATION: (84)..(84)
<223> OTHER INFORMATION: The Proline at this position is a
      hydroxyproline.
<220> FEATURE:
<221> NAME/KEY: MISC_FEATURE
<222> LOCATION: (87)..(87)
<223> OTHER INFORMATION: The Proline at this position is a
      hydroxyproline.
<220> FEATURE:
<221> NAME/KEY: MISC_FEATURE
<222> LOCATION: (89)..(89)
<223> OTHER INFORMATION: The Proline at this position is a
```

```
      hydroxyproline.
<220> FEATURE:
<221> NAME/KEY: MISC_FEATURE
<222> LOCATION: (91)..(91)
<223> OTHER INFORMATION: The Proline at this position is a
      hydroxyproline.
<220> FEATURE:
<221> NAME/KEY: MISC_FEATURE
<222> LOCATION: (93)..(93)
<223> OTHER INFORMATION: The Proline at this position is a
      hydroxyproline.
<220> FEATURE:
<221> NAME/KEY: MISC_FEATURE
<222> LOCATION: (95)..(95)
<223> OTHER INFORMATION: The Proline at this position is a
      hydroxyproline.
<220> FEATURE:
<221> NAME/KEY: MISC_FEATURE
<222> LOCATION: (97)..(97)
<223> OTHER INFORMATION: The Proline at this position is a
      hydroxyproline.
<220> FEATURE:
<221> NAME/KEY: MISC_FEATURE
<222> LOCATION: (99)..(99)
<223> OTHER INFORMATION: The Proline at this position is a
      hydroxyproline.
<220> FEATURE:
<221> NAME/KEY: MISC_FEATURE
<222> LOCATION: (101)..(101)
<223> OTHER INFORMATION: The Proline at this position is a
      hydroxyproline.
<220> FEATURE:
<221> NAME/KEY: MISC_FEATURE
<222> LOCATION: (103)..(103)
<223> OTHER INFORMATION: The Proline at this position is a
      hydroxyproline.
<220> FEATURE:
<221> NAME/KEY: MISC_FEATURE
<222> LOCATION: (105)..(105)
<223> OTHER INFORMATION: The Proline at this position is a
      hydroxyproline.
<220> FEATURE:
<221> NAME/KEY: MISC_FEATURE
<222> LOCATION: (107)..(107)
<223> OTHER INFORMATION: The Proline at this position is a
      hydroxyproline.
<220> FEATURE:
<221> NAME/KEY: MISC_FEATURE
<222> LOCATION: (109)..(109)
<223> OTHER INFORMATION: The Proline at this position is a
      hydroxyproline.
<220> FEATURE:
<221> NAME/KEY: MISC_FEATURE
<222> LOCATION: (111)..(111)
<223> OTHER INFORMATION: The Proline at this position is a
      hydroxyproline.
<220> FEATURE:
<221> NAME/KEY: MISC_FEATURE
<222> LOCATION: (113)..(113)
<223> OTHER INFORMATION: The Proline at this position is a
      hydroxyproline.
<220> FEATURE:
<221> NAME/KEY: MISC_FEATURE
<222> LOCATION: (115)..(115)
<223> OTHER INFORMATION: The Proline at this position is a
      hydroxyproline.
<220> FEATURE:
<221> NAME/KEY: MISC_FEATURE
<222> LOCATION: (117)..(117)
<223> OTHER INFORMATION: The Proline at this position is a
      hydroxyproline.
<220> FEATURE:
<221> NAME/KEY: MISC_FEATURE
<222> LOCATION: (119)..(119)
<223> OTHER INFORMATION: The Proline at this position is a
      hydroxyproline.
<220> FEATURE:
<221> NAME/KEY: MISC_FEATURE
<222> LOCATION: (121)..(121)
```

```
<223> OTHER INFORMATION: The Proline at this position is a
      hydroxyproline.
<220> FEATURE:
<221> NAME/KEY: MISC_FEATURE
<222> LOCATION: (123)..(123)
<223> OTHER INFORMATION: The Proline at this position is a
      hydroxyproline.
<220> FEATURE:
<221> NAME/KEY: MISC_FEATURE
<222> LOCATION: (125)..(125)
<223> OTHER INFORMATION: The Proline at this position is a
      hydroxyproline.
<220> FEATURE:
<221> NAME/KEY: MISC_FEATURE
<222> LOCATION: (127)..(127)
<223> OTHER INFORMATION: The Proline at this position is a
      hydroxyproline.
<220> FEATURE:
<221> NAME/KEY: MISC_FEATURE
<222> LOCATION: (129)..(129)
<223> OTHER INFORMATION: The Proline at this position is a
      hydroxyproline.
<220> FEATURE:
<221> NAME/KEY: MISC_FEATURE
<222> LOCATION: (131)..(131)
<223> OTHER INFORMATION: The Proline at this position is a
      hydroxyproline.
<220> FEATURE:
<221> NAME/KEY: MISC_FEATURE
<222> LOCATION: (133)..(133)
<223> OTHER INFORMATION: The Proline at this position is a
      hydroxyproline.
<220> FEATURE:
<221> NAME/KEY: MISC_FEATURE
<222> LOCATION: (135)..(135)
<223> OTHER INFORMATION: The Proline at this position is a
      hydroxyproline.
<220> FEATURE:
<221> NAME/KEY: MISC_FEATURE
<222> LOCATION: (137)..(137)
<223> OTHER INFORMATION: The Proline at this position is a
      hydroxyproline.
<220> FEATURE:
<221> NAME/KEY: MISC_FEATURE
<222> LOCATION: (139)..(139)
<223> OTHER INFORMATION: The Proline at this position is a
      hydroxyproline.
<220> FEATURE:
<221> NAME/KEY: MISC_FEATURE
<222> LOCATION: (141)..(141)
<223> OTHER INFORMATION: The Proline at this position is a
      hydroxyproline.
<220> FEATURE:
<221> NAME/KEY: MISC_FEATURE
<222> LOCATION: (143)..(143)
<223> OTHER INFORMATION: The Proline at this position is a
      hydroxyproline.
<220> FEATURE:
<221> NAME/KEY: MISC_FEATURE
<222> LOCATION: (145)..(145)
<223> OTHER INFORMATION: The Proline at this position is a
      hydroxyproline.
<220> FEATURE:
<221> NAME/KEY: MISC_FEATURE
<222> LOCATION: (147)..(147)
<223> OTHER INFORMATION: The Proline at this position is a
      hydroxyproline.
<220> FEATURE:
<221> NAME/KEY: MISC_FEATURE
<222> LOCATION: (149)..(149)
<223> OTHER INFORMATION: The Proline at this position is a
      hydroxyproline.
<220> FEATURE:
<221> NAME/KEY: MISC_FEATURE
<222> LOCATION: (151)..(151)
<223> OTHER INFORMATION: The Proline at this position is a
      hydroxyproline.
<220> FEATURE:
<221> NAME/KEY: MISC_FEATURE
```

-continued

```
<222> LOCATION: (153)..(153)
<223> OTHER INFORMATION: The Proline at this position is a
      hydroxyproline.
<220> FEATURE:
<221> NAME/KEY: MISC_FEATURE
<222> LOCATION: (155)..(155)
<223> OTHER INFORMATION: The Proline at this position is a
      hydroxyproline.
<220> FEATURE:
<221> NAME/KEY: MISC_FEATURE
<222> LOCATION: (157)..(157)
<223> OTHER INFORMATION: The Proline at this position is a
      hydroxyproline.
<220> FEATURE:
<221> NAME/KEY: MISC_FEATURE
<222> LOCATION: (159)..(159)
<223> OTHER INFORMATION: The Proline at this position is a
      hydroxyproline.
<220> FEATURE:
<221> NAME/KEY: MISC_FEATURE
<222> LOCATION: (161)..(161)
<223> OTHER INFORMATION: The Proline at this position is a
      hydroxyproline.
<220> FEATURE:
<221> NAME/KEY: MISC_FEATURE
<222> LOCATION: (163)..(163)
<223> OTHER INFORMATION: The Proline at this position is a
      hydroxyproline.
<220> FEATURE:
<221> NAME/KEY: MISC_FEATURE
<222> LOCATION: (165)..(165)
<223> OTHER INFORMATION: The Proline at this position is a
      hydroxyproline.
<220> FEATURE:
<221> NAME/KEY: MISC_FEATURE
<222> LOCATION: (167)..(167)
<223> OTHER INFORMATION: The Proline at this position is a
      hydroxyproline.
<220> FEATURE:
<221> NAME/KEY: MISC_FEATURE
<222> LOCATION: (169)..(169)
<223> OTHER INFORMATION: The Proline at this position is a
      hydroxyproline.
<220> FEATURE:
<221> NAME/KEY: MISC_FEATURE
<222> LOCATION: (171)..(171)
<223> OTHER INFORMATION: The Proline at this position is a
      hydroxyproline.
<220> FEATURE:
<221> NAME/KEY: MISC_FEATURE
<222> LOCATION: (173)..(173)
<223> OTHER INFORMATION: The Proline at this position is a
      hydroxyproline.
<220> FEATURE:
<221> NAME/KEY: MISC_FEATURE
<222> LOCATION: (175)..(175)
<223> OTHER INFORMATION: The Proline at this position is a
      hydroxyproline.
<220> FEATURE:
<221> NAME/KEY: MISC_FEATURE
<222> LOCATION: (177)..(177)
<223> OTHER INFORMATION: The Proline at this position is a
      hydroxyproline.
<220> FEATURE:
<221> NAME/KEY: MISC_FEATURE
<222> LOCATION: (179)..(179)
<223> OTHER INFORMATION: The Proline at this position is a
      hydroxyproline.
<220> FEATURE:
<221> NAME/KEY: MISC_FEATURE
<222> LOCATION: (181)..(181)
<223> OTHER INFORMATION: The Proline at this position is a
      hydroxyproline.
<220> FEATURE:
<221> NAME/KEY: MISC_FEATURE
<222> LOCATION: (183)..(183)
<223> OTHER INFORMATION: The Proline at this position is a
      hydroxyproline.
<220> FEATURE:
```

```
<221> NAME/KEY: MISC_FEATURE
<222> LOCATION: (185)..(185)
<223> OTHER INFORMATION: The Proline at this position is a
      hydroxyproline.
<220> FEATURE:
<221> NAME/KEY: MISC_FEATURE
<222> LOCATION: (187)..(187)
<223> OTHER INFORMATION: The Proline at this position is a
      hydroxyproline.
<220> FEATURE:
<221> NAME/KEY: MISC_FEATURE
<222> LOCATION: (189)..(189)
<223> OTHER INFORMATION: The Proline at this position is a
      hydroxyproline.
<220> FEATURE:
<221> NAME/KEY: MISC_FEATURE
<222> LOCATION: (191)..(191)
<223> OTHER INFORMATION: The Proline at this position is a
      hydroxyproline.
<220> FEATURE:
<221> NAME/KEY: MISC_FEATURE
<222> LOCATION: (193)..(193)
<223> OTHER INFORMATION: The Proline at this position is a
      hydroxyproline.
<220> FEATURE:
<221> NAME/KEY: MISC_FEATURE
<222> LOCATION: (195)..(195)
<223> OTHER INFORMATION: The Proline at this position is a
      hydroxyproline.
<220> FEATURE:
<221> NAME/KEY: MISC_FEATURE
<222> LOCATION: (197)..(197)
<223> OTHER INFORMATION: The Proline at this position is a
      hydroxyproline.
<220> FEATURE:
<221> NAME/KEY: MISC_FEATURE
<222> LOCATION: (199)..(199)
<223> OTHER INFORMATION: The Proline at this position is a
      hydroxyproline.
<220> FEATURE:
<221> NAME/KEY: MISC_FEATURE
<222> LOCATION: (201)..(201)
<223> OTHER INFORMATION: The Proline at this position is a
      hydroxyproline.
<220> FEATURE:
<221> NAME/KEY: MISC_FEATURE
<222> LOCATION: (203)..(203)
<223> OTHER INFORMATION: The Proline at this position is a
      hydroxyproline.
<220> FEATURE:
<221> NAME/KEY: MISC_FEATURE
<222> LOCATION: (205)..(205)
<223> OTHER INFORMATION: The Proline at this position is a
      hydroxyproline.
<220> FEATURE:
<221> NAME/KEY: MISC_FEATURE
<222> LOCATION: (207)..(207)
<223> OTHER INFORMATION: The Proline at this position is a
      hydroxyproline.
<220> FEATURE:
<221> NAME/KEY: MISC_FEATURE
<222> LOCATION: (209)..(209)
<223> OTHER INFORMATION: The Proline at this position is a
      hydroxyproline.
<220> FEATURE:
<221> NAME/KEY: MISC_FEATURE
<222> LOCATION: (211)..(211)
<223> OTHER INFORMATION: The Proline at this position is a
      hydroxyproline.
<220> FEATURE:
<221> NAME/KEY: MISC_FEATURE
<222> LOCATION: (213)..(213)
<223> OTHER INFORMATION: The Proline at this position is a
      hydroxyproline.
<220> FEATURE:
<221> NAME/KEY: MISC_FEATURE
<222> LOCATION: (215)..(215)
<223> OTHER INFORMATION: The Proline at this position is a
      hydroxyproline.
```

```
-continued

<220> FEATURE:
<221> NAME/KEY: MISC_FEATURE
<222> LOCATION: (217)..(217)
<223> OTHER INFORMATION: The Proline at this position is a
      hydroxyproline.
<220> FEATURE:
<221> NAME/KEY: MISC_FEATURE
<222> LOCATION: (219)..(219)
<223> OTHER INFORMATION: The Proline at this position is a
      hydroxyproline.
<220> FEATURE:
<221> NAME/KEY: MISC_FEATURE
<222> LOCATION: (221)..(221)
<223> OTHER INFORMATION: The Proline at this position is a
      hydroxyproline.
<220> FEATURE:
<221> NAME/KEY: MISC_FEATURE
<222> LOCATION: (223)..(223)
<223> OTHER INFORMATION: The Proline at this position is a
      hydroxyproline.
<220> FEATURE:
<221> NAME/KEY: MISC_FEATURE
<222> LOCATION: (225)..(225)
<223> OTHER INFORMATION: The Proline at this position is a
      hydroxyproline.
<220> FEATURE:
<221> NAME/KEY: MISC_FEATURE
<222> LOCATION: (227)..(227)
<223> OTHER INFORMATION: The Proline at this position is a
      hydroxyproline.
<220> FEATURE:
<221> NAME/KEY: MISC_FEATURE
<222> LOCATION: (229)..(229)
<223> OTHER INFORMATION: The Proline at this position is a
      hydroxyproline.
<220> FEATURE:
<221> NAME/KEY: MISC_FEATURE
<222> LOCATION: (233)..(233)
<223> OTHER INFORMATION: The Proline at this position is a
      hydroxyproline.
<220> FEATURE:
<221> NAME/KEY: MISC_FEATURE
<222> LOCATION: (238)..(238)
<223> OTHER INFORMATION: The Proline at this position is a
      hydroxyproline.
<220> FEATURE:
<221> NAME/KEY: MISC_FEATURE
<222> LOCATION: (243)..(243)
<223> OTHER INFORMATION: The Proline at this position is a
      hydroxyproline.
<220> FEATURE:
<221> NAME/KEY: MISC_FEATURE
<222> LOCATION: (248)..(248)
<223> OTHER INFORMATION: The Proline at this position is a
      hydroxyproline.
<220> FEATURE:
<221> NAME/KEY: MISC_FEATURE
<222> LOCATION: (253)..(253)
<223> OTHER INFORMATION: The Proline at this position is a
      hydroxyproline.
<220> FEATURE:
<221> NAME/KEY: MISC_FEATURE
<222> LOCATION: (258)..(258)
<223> OTHER INFORMATION: The Proline at this position is a
      hydroxyproline.
<220> FEATURE:
<221> NAME/KEY: MISC_FEATURE
<222> LOCATION: (261)..(264)
<223> OTHER INFORMATION: The Proline at these positions is a
      hydroxyproline.
<220> FEATURE:
<221> NAME/KEY: MISC_FEATURE
<222> LOCATION: (266)..(266)
<223> OTHER INFORMATION: The Proline at this position is a
      hydroxyproline.
<220> FEATURE:
<221> NAME/KEY: MISC_FEATURE
<222> LOCATION: (271)..(274)
<223> OTHER INFORMATION: The Proline at these positions is a
```

```
          hydroxyproline.
<220> FEATURE:
<221> NAME/KEY: MISC_FEATURE
<222> LOCATION: (276)..(276)
<223> OTHER INFORMATION: The Proline at this position is a
      hydroxyproline.
<220> FEATURE:
<221> NAME/KEY: MISC_FEATURE
<222> LOCATION: (281)..(284)
<223> OTHER INFORMATION: The Proline at these positions is a
      hydroxyproline.

<400> SEQUENCE: 270

Ser Pro Pro Pro Pro Thr Pro Val Tyr Lys Ser Pro Pro Pro Pro Thr
1               5                   10                  15

Pro Val Tyr Lys Ser Pro Pro Pro Val Gly Val Pro Gly Val Pro Gly
            20                  25                  30

Val Pro Gly Val Gly Val Pro Gly Val Gly Val Pro Gly Val Gly Val
        35                  40                  45

Pro Gly Val Gly Val Pro Gly Val Gly Val Pro Gly Val Gly Val Pro
    50                  55                  60

Gly Val Gly Val Pro Gly Val Gly Val Pro Gly Val Gly Val Pro Gly
65                  70                  75                  80

Val Gly Val Pro Gly Ser Pro Ser Pro Ser Pro Ser Pro Ser Pro Ser
                85                  90                  95

Pro Ser Pro Ser Pro Ser Pro Ser Pro Ser Pro Ser Pro Ser Pro Ser
            100                 105                 110

Pro Ser Pro Ser Pro Ser Pro Ser Pro Ser Pro Ser Pro Ser Pro Ser
        115                 120                 125

Pro Ser Pro Ser Pro Ser Pro Ser Pro Ser Pro Ser Pro Ser Pro Ser
    130                 135                 140

Pro Ser Pro Ser Pro Ser Pro Ser Pro Ser Pro Ser Pro Ser Pro Ser
145                 150                 155                 160

Pro Ser Pro Ser Pro Ser Pro Ser Pro Ser Pro Ser Pro Ser Pro Ser
                165                 170                 175

Pro Ser Pro Ser Pro Ser Pro Ser Pro Ser Pro Ser Pro Ser Pro Ser
            180                 185                 190

Pro Ser Pro Ser Pro Ser Pro Ser Pro Ser Pro Ser Pro Ser Pro Ser
        195                 200                 205

Pro Ser Pro Ser Pro Ser Pro Ser Pro Ser Pro Ser Pro Ser Pro Ser
    210                 215                 220

Pro Ser Pro Ser Pro Val Gly Val Pro Gly Val Gly Val Pro Gly Val
225                 230                 235                 240

Gly Val Pro Gly Val Gly Val Pro Gly Val Gly Val Pro Gly Val Gly
                245                 250                 255

Val Pro Gly Ser Pro Pro Pro Thr Pro Val Tyr Lys Ser Pro Pro Pro
            260                 265                 270

Pro Pro Thr Pro Val Tyr Lys Ser Pro Pro Pro Pro
        275                 280

<210> SEQ ID NO 271
<211> LENGTH: 284
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: The Proline at these positions is a
```

```
      hydroxyproline.
<220> FEATURE:
<221> NAME/KEY: MISC_FEATURE
<222> LOCATION: (7)..(7)
<223> OTHER INFORMATION: The Proline at this position is a
      hydroxyproline.
<220> FEATURE:
<221> NAME/KEY: MISC_FEATURE
<222> LOCATION: (12)..(15)
<223> OTHER INFORMATION: The Proline at these positions is a
      hydroxyproline.
<220> FEATURE:
<221> NAME/KEY: MISC_FEATURE
<222> LOCATION: (17)..(17)
<223> OTHER INFORMATION: The Proline at this position is a
      hydroxyproline.
<220> FEATURE:
<221> NAME/KEY: MISC_FEATURE
<222> LOCATION: (22)..(25)
<223> OTHER INFORMATION: The Proline at these positions is a
      hydroxyproline.
<220> FEATURE:
<221> NAME/KEY: MISC_FEATURE
<222> LOCATION: (29)..(29)
<223> OTHER INFORMATION: The Proline at this position is a
      hydroxyproline.
<220> FEATURE:
<221> NAME/KEY: MISC_FEATURE
<222> LOCATION: (34)..(34)
<223> OTHER INFORMATION: The Proline at this position is a
      hydroxyproline.
<220> FEATURE:
<221> NAME/KEY: MISC_FEATURE
<222> LOCATION: (39)..(39)
<223> OTHER INFORMATION: The Proline at this position is a
      hydroxyproline.
<220> FEATURE:
<221> NAME/KEY: MISC_FEATURE
<222> LOCATION: (44)..(44)
<223> OTHER INFORMATION: The Proline at this position is a
      hydroxyproline.
<220> FEATURE:
<221> NAME/KEY: MISC_FEATURE
<222> LOCATION: (49)..(49)
<223> OTHER INFORMATION: The Proline at this position is a
      hydroxyproline.
<220> FEATURE:
<221> NAME/KEY: MISC_FEATURE
<222> LOCATION: (54)..(54)
<223> OTHER INFORMATION: The Proline at this position is a
      hydroxyproline.
<220> FEATURE:
<221> NAME/KEY: MISC_FEATURE
<222> LOCATION: (59)..(59)
<223> OTHER INFORMATION: The Proline at this position is a
      hydroxyproline.
<220> FEATURE:
<221> NAME/KEY: MISC_FEATURE
<222> LOCATION: (64)..(64)
<223> OTHER INFORMATION: The Proline at this position is a
      hydroxyproline.
<220> FEATURE:
<221> NAME/KEY: MISC_FEATURE
<222> LOCATION: (69)..(69)
<223> OTHER INFORMATION: The Proline at this position is a
      hydroxyproline.
<220> FEATURE:
<221> NAME/KEY: MISC_FEATURE
<222> LOCATION: (74)..(74)
<223> OTHER INFORMATION: The Proline at this position is a
      hydroxyproline.
<220> FEATURE:
<221> NAME/KEY: MISC_FEATURE
<222> LOCATION: (79)..(79)
<223> OTHER INFORMATION: The Proline at this position is a
      hydroxyproline.
<220> FEATURE:
<221> NAME/KEY: MISC_FEATURE
<222> LOCATION: (84)..(84)
```

```
-continued

<223> OTHER INFORMATION: The Proline at this position is a
      hydroxyproline.
<220> FEATURE:
<221> NAME/KEY: MISC_FEATURE
<222> LOCATION: (87)..(87)
<223> OTHER INFORMATION: The Proline at this position is a
      hydroxyproline.
<220> FEATURE:
<221> NAME/KEY: MISC_FEATURE
<222> LOCATION: (89)..(89)
<223> OTHER INFORMATION: The Proline at this position is a
      hydroxyproline.
<220> FEATURE:
<221> NAME/KEY: MISC_FEATURE
<222> LOCATION: (91)..(91)
<223> OTHER INFORMATION: The Proline at this position is a
      hydroxyproline.
<220> FEATURE:
<221> NAME/KEY: MISC_FEATURE
<222> LOCATION: (93)..(93)
<223> OTHER INFORMATION: The Proline at this position is a
      hydroxyproline.
<220> FEATURE:
<221> NAME/KEY: MISC_FEATURE
<222> LOCATION: (95)..(95)
<223> OTHER INFORMATION: The Proline at this position is a
      hydroxyproline.
<220> FEATURE:
<221> NAME/KEY: MISC_FEATURE
<222> LOCATION: (97)..(97)
<223> OTHER INFORMATION: The Proline at this position is a
      hydroxyproline.
<220> FEATURE:
<221> NAME/KEY: MISC_FEATURE
<222> LOCATION: (99)..(99)
<223> OTHER INFORMATION: The Proline at this position is a
      hydroxyproline.
<220> FEATURE:
<221> NAME/KEY: MISC_FEATURE
<222> LOCATION: (101)..(101)
<223> OTHER INFORMATION: The Proline at this position is a
      hydroxyproline.
<220> FEATURE:
<221> NAME/KEY: MISC_FEATURE
<222> LOCATION: (103)..(103)
<223> OTHER INFORMATION: The Proline at this position is a
      hydroxyproline.
<220> FEATURE:
<221> NAME/KEY: MISC_FEATURE
<222> LOCATION: (105)..(105)
<223> OTHER INFORMATION: The Proline at this position is a
      hydroxyproline.
<220> FEATURE:
<221> NAME/KEY: MISC_FEATURE
<222> LOCATION: (107)..(107)
<223> OTHER INFORMATION: The Proline at this position is a
      hydroxyproline.
<220> FEATURE:
<221> NAME/KEY: MISC_FEATURE
<222> LOCATION: (109)..(109)
<223> OTHER INFORMATION: The Proline at this position is a
      hydroxyproline.
<220> FEATURE:
<221> NAME/KEY: MISC_FEATURE
<222> LOCATION: (111)..(111)
<223> OTHER INFORMATION: The Proline at this position is a
      hydroxyproline.
<220> FEATURE:
<221> NAME/KEY: MISC_FEATURE
<222> LOCATION: (113)..(113)
<223> OTHER INFORMATION: The Proline at this position is a
      hydroxyproline.
<220> FEATURE:
<221> NAME/KEY: MISC_FEATURE
<222> LOCATION: (115)..(115)
<223> OTHER INFORMATION: The Proline at this position is a
      hydroxyproline.
<220> FEATURE:
<221> NAME/KEY: MISC_FEATURE
```

```
<222> LOCATION: (117)..(117)
<223> OTHER INFORMATION: The Proline at this position is a
      hydroxyproline.
<220> FEATURE:
<221> NAME/KEY: MISC_FEATURE
<222> LOCATION: (119)..(119)
<223> OTHER INFORMATION: The Proline at this position is a
      hydroxyproline.
<220> FEATURE:
<221> NAME/KEY: MISC_FEATURE
<222> LOCATION: (121)..(121)
<223> OTHER INFORMATION: The Proline at this position is a
      hydroxyproline.
<220> FEATURE:
<221> NAME/KEY: MISC_FEATURE
<222> LOCATION: (123)..(123)
<223> OTHER INFORMATION: The Proline at this position is a
      hydroxyproline.
<220> FEATURE:
<221> NAME/KEY: MISC_FEATURE
<222> LOCATION: (125)..(125)
<223> OTHER INFORMATION: The Proline at this position is a
      hydroxyproline.
<220> FEATURE:
<221> NAME/KEY: MISC_FEATURE
<222> LOCATION: (127)..(127)
<223> OTHER INFORMATION: The Proline at this position is a
      hydroxyproline.
<220> FEATURE:
<221> NAME/KEY: MISC_FEATURE
<222> LOCATION: (129)..(129)
<223> OTHER INFORMATION: The Proline at this position is a
      hydroxyproline.
<220> FEATURE:
<221> NAME/KEY: MISC_FEATURE
<222> LOCATION: (131)..(131)
<223> OTHER INFORMATION: The Proline at this position is a
      hydroxyproline.
<220> FEATURE:
<221> NAME/KEY: MISC_FEATURE
<222> LOCATION: (133)..(133)
<223> OTHER INFORMATION: The Proline at this position is a
      hydroxyproline.
<220> FEATURE:
<221> NAME/KEY: MISC_FEATURE
<222> LOCATION: (135)..(135)
<223> OTHER INFORMATION: The Proline at this position is a
      hydroxyproline.
<220> FEATURE:
<221> NAME/KEY: MISC_FEATURE
<222> LOCATION: (137)..(137)
<223> OTHER INFORMATION: The Proline at this position is a
      hydroxyproline.
<220> FEATURE:
<221> NAME/KEY: MISC_FEATURE
<222> LOCATION: (139)..(139)
<223> OTHER INFORMATION: The Proline at this position is a
      hydroxyproline.
<220> FEATURE:
<221> NAME/KEY: MISC_FEATURE
<222> LOCATION: (141)..(141)
<223> OTHER INFORMATION: The Proline at this position is a
      hydroxyproline.
<220> FEATURE:
<221> NAME/KEY: MISC_FEATURE
<222> LOCATION: (143)..(143)
<223> OTHER INFORMATION: The Proline at this position is a
      hydroxyproline.
<220> FEATURE:
<221> NAME/KEY: MISC_FEATURE
<222> LOCATION: (145)..(145)
<223> OTHER INFORMATION: The Proline at this position is a
      hydroxyproline.
<220> FEATURE:
<221> NAME/KEY: MISC_FEATURE
<222> LOCATION: (147)..(147)
<223> OTHER INFORMATION: The Proline at this position is a
      hydroxyproline.
<220> FEATURE:
```

```
<221> NAME/KEY: MISC_FEATURE
<222> LOCATION: (149)..(149)
<223> OTHER INFORMATION: The Proline at this position is a
      hydroxyproline.
<220> FEATURE:
<221> NAME/KEY: MISC_FEATURE
<222> LOCATION: (151)..(151)
<223> OTHER INFORMATION: The Proline at this position is a
      hydroxyproline.
<220> FEATURE:
<221> NAME/KEY: MISC_FEATURE
<222> LOCATION: (153)..(153)
<223> OTHER INFORMATION: The Proline at this position is a
      hydroxyproline.
<220> FEATURE:
<221> NAME/KEY: MISC_FEATURE
<222> LOCATION: (155)..(155)
<223> OTHER INFORMATION: The Proline at this position is a
      hydroxyproline.
<220> FEATURE:
<221> NAME/KEY: MISC_FEATURE
<222> LOCATION: (157)..(157)
<223> OTHER INFORMATION: The Proline at this position is a
      hydroxyproline.
<220> FEATURE:
<221> NAME/KEY: MISC_FEATURE
<222> LOCATION: (159)..(159)
<223> OTHER INFORMATION: The Proline at this position is a
      hydroxyproline.
<220> FEATURE:
<221> NAME/KEY: MISC_FEATURE
<222> LOCATION: (161)..(161)
<223> OTHER INFORMATION: The Proline at this position is a
      hydroxyproline.
<220> FEATURE:
<221> NAME/KEY: MISC_FEATURE
<222> LOCATION: (163)..(163)
<223> OTHER INFORMATION: The Proline at this position is a
      hydroxyproline.
<220> FEATURE:
<221> NAME/KEY: MISC_FEATURE
<222> LOCATION: (165)..(165)
<223> OTHER INFORMATION: The Proline at this position is a
      hydroxyproline.
<220> FEATURE:
<221> NAME/KEY: MISC_FEATURE
<222> LOCATION: (167)..(167)
<223> OTHER INFORMATION: The Proline at this position is a
      hydroxyproline.
<220> FEATURE:
<221> NAME/KEY: MISC_FEATURE
<222> LOCATION: (169)..(169)
<223> OTHER INFORMATION: The Proline at this position is a
      hydroxyproline.
<220> FEATURE:
<221> NAME/KEY: MISC_FEATURE
<222> LOCATION: (171)..(171)
<223> OTHER INFORMATION: The Proline at this position is a
      hydroxyproline.
<220> FEATURE:
<221> NAME/KEY: MISC_FEATURE
<222> LOCATION: (173)..(173)
<223> OTHER INFORMATION: The Proline at this position is a
      hydroxyproline.
<220> FEATURE:
<221> NAME/KEY: MISC_FEATURE
<222> LOCATION: (175)..(175)
<223> OTHER INFORMATION: The Proline at this position is a
      hydroxyproline.
<220> FEATURE:
<221> NAME/KEY: MISC_FEATURE
<222> LOCATION: (177)..(177)
<223> OTHER INFORMATION: The Proline at this position is a
      hydroxyproline.
<220> FEATURE:
<221> NAME/KEY: MISC_FEATURE
<222> LOCATION: (179)..(179)
<223> OTHER INFORMATION: The Proline at this position is a
      hydroxyproline.
```

```
<220> FEATURE:
<221> NAME/KEY: MISC_FEATURE
<222> LOCATION: (181)..(181)
<223> OTHER INFORMATION: The Proline at this position is a
      hydroxyproline.
<220> FEATURE:
<221> NAME/KEY: MISC_FEATURE
<222> LOCATION: (183)..(183)
<223> OTHER INFORMATION: The Proline at this position is a
      hydroxyproline.
<220> FEATURE:
<221> NAME/KEY: MISC_FEATURE
<222> LOCATION: (185)..(185)
<223> OTHER INFORMATION: The Proline at this position is a
      hydroxyproline.
<220> FEATURE:
<221> NAME/KEY: MISC_FEATURE
<222> LOCATION: (187)..(187)
<223> OTHER INFORMATION: The Proline at this position is a
      hydroxyproline.
<220> FEATURE:
<221> NAME/KEY: MISC_FEATURE
<222> LOCATION: (189)..(189)
<223> OTHER INFORMATION: The Proline at this position is a
      hydroxyproline.
<220> FEATURE:
<221> NAME/KEY: MISC_FEATURE
<222> LOCATION: (191)..(191)
<223> OTHER INFORMATION: The Proline at this position is a
      hydroxyproline.
<220> FEATURE:
<221> NAME/KEY: MISC_FEATURE
<222> LOCATION: (193)..(193)
<223> OTHER INFORMATION: The Proline at this position is a
      hydroxyproline.
<220> FEATURE:
<221> NAME/KEY: MISC_FEATURE
<222> LOCATION: (195)..(195)
<223> OTHER INFORMATION: The Proline at this position is a
      hydroxyproline.
<220> FEATURE:
<221> NAME/KEY: MISC_FEATURE
<222> LOCATION: (197)..(197)
<223> OTHER INFORMATION: The Proline at this position is a
      hydroxyproline.
<220> FEATURE:
<221> NAME/KEY: MISC_FEATURE
<222> LOCATION: (199)..(199)
<223> OTHER INFORMATION: The Proline at this position is a
      hydroxyproline.
<220> FEATURE:
<221> NAME/KEY: MISC_FEATURE
<222> LOCATION: (201)..(201)
<223> OTHER INFORMATION: The Proline at this position is a
      hydroxyproline.
<220> FEATURE:
<221> NAME/KEY: MISC_FEATURE
<222> LOCATION: (203)..(203)
<223> OTHER INFORMATION: The Proline at this position is a
      hydroxyproline.
<220> FEATURE:
<221> NAME/KEY: MISC_FEATURE
<222> LOCATION: (205)..(205)
<223> OTHER INFORMATION: The Proline at this position is a
      hydroxyproline.
<220> FEATURE:
<221> NAME/KEY: MISC_FEATURE
<222> LOCATION: (207)..(207)
<223> OTHER INFORMATION: The Proline at this position is a
      hydroxyproline.
<220> FEATURE:
<221> NAME/KEY: MISC_FEATURE
<222> LOCATION: (209)..(209)
<223> OTHER INFORMATION: The Proline at this position is a
      hydroxyproline.
<220> FEATURE:
<221> NAME/KEY: MISC_FEATURE
<222> LOCATION: (211)..(211)
<223> OTHER INFORMATION: The Proline at this position is a
```

```
      hydroxyproline.
<220> FEATURE:
<221> NAME/KEY: MISC_FEATURE
<222> LOCATION: (213)..(213)
<223> OTHER INFORMATION: The Proline at this position is a
      hydroxyproline.
<220> FEATURE:
<221> NAME/KEY: MISC_FEATURE
<222> LOCATION: (215)..(215)
<223> OTHER INFORMATION: The Proline at this position is a
      hydroxyproline.
<220> FEATURE:
<221> NAME/KEY: MISC_FEATURE
<222> LOCATION: (217)..(217)
<223> OTHER INFORMATION: The Proline at this position is a
      hydroxyproline.
<220> FEATURE:
<221> NAME/KEY: MISC_FEATURE
<222> LOCATION: (219)..(219)
<223> OTHER INFORMATION: The Proline at this position is a
      hydroxyproline.
<220> FEATURE:
<221> NAME/KEY: MISC_FEATURE
<222> LOCATION: (221)..(221)
<223> OTHER INFORMATION: The Proline at this position is a
      hydroxyproline.
<220> FEATURE:
<221> NAME/KEY: MISC_FEATURE
<222> LOCATION: (223)..(223)
<223> OTHER INFORMATION: The Proline at this position is a
      hydroxyproline.
<220> FEATURE:
<221> NAME/KEY: MISC_FEATURE
<222> LOCATION: (225)..(225)
<223> OTHER INFORMATION: The Proline at this position is a
      hydroxyproline.
<220> FEATURE:
<221> NAME/KEY: MISC_FEATURE
<222> LOCATION: (227)..(227)
<223> OTHER INFORMATION: The Proline at this position is a
      hydroxyproline.
<220> FEATURE:
<221> NAME/KEY: MISC_FEATURE
<222> LOCATION: (229)..(229)
<223> OTHER INFORMATION: The Proline at this position is a
      hydroxyproline.
<220> FEATURE:
<221> NAME/KEY: MISC_FEATURE
<222> LOCATION: (233)..(233)
<223> OTHER INFORMATION: The Proline at this position is a
      hydroxyproline.
<220> FEATURE:
<221> NAME/KEY: MISC_FEATURE
<222> LOCATION: (238)..(238)
<223> OTHER INFORMATION: The Proline at this position is a
      hydroxyproline.
<220> FEATURE:
<221> NAME/KEY: MISC_FEATURE
<222> LOCATION: (243)..(243)
<223> OTHER INFORMATION: The Proline at this position is a
      hydroxyproline.
<220> FEATURE:
<221> NAME/KEY: MISC_FEATURE
<222> LOCATION: (248)..(248)
<223> OTHER INFORMATION: The Proline at this position is a
      hydroxyproline.
<220> FEATURE:
<221> NAME/KEY: MISC_FEATURE
<222> LOCATION: (253)..(253)
<223> OTHER INFORMATION: The Proline at this position is a
      hydroxyproline.
<220> FEATURE:
<221> NAME/KEY: MISC_FEATURE
<222> LOCATION: (258)..(258)
<223> OTHER INFORMATION: The Proline at this position is a
      hydroxyproline.
<220> FEATURE:
<221> NAME/KEY: MISC_FEATURE
<222> LOCATION: (261)..(264)
```

<223> OTHER INFORMATION: The Proline at these positions is a
      hydroxyproline.
<220> FEATURE:
<221> NAME/KEY: MISC_FEATURE
<222> LOCATION: (266)..(266)
<223> OTHER INFORMATION: The Proline at this position is a
      hydroxyproline.
<220> FEATURE:
<221> NAME/KEY: MISC_FEATURE
<222> LOCATION: (271)..(274)
<223> OTHER INFORMATION: The Proline at these positions is a
      hydroxyproline.
<220> FEATURE:
<221> NAME/KEY: MISC_FEATURE
<222> LOCATION: (276)..(276)
<223> OTHER INFORMATION: The Proline at this position is a
      hydroxyproline.
<220> FEATURE:
<221> NAME/KEY: MISC_FEATURE
<222> LOCATION: (281)..(284)
<223> OTHER INFORMATION: The Proline at these positions is a
      hydroxyproline.

<400> SEQUENCE: 271

Ser Pro Pro Pro Pro Thr Pro Val Tyr Lys Ser Pro Pro Pro Pro Thr
1               5                   10                  15

Pro Val Tyr Lys Ser Pro Pro Pro Val Gly Val Pro Gly Val Gly
            20                  25                  30

Val Pro Gly Val Gly Val Pro Gly Val Gly Val Pro Gly Val Gly Val
            35                  40                  45

Pro Gly Val Gly Val Pro Gly Val Gly Val Pro Gly Val Gly Val Pro
        50                  55                  60

Gly Val Gly Val Pro Gly Val Gly Val Pro Gly Val Gly Val Pro Gly
65                  70                  75                  80

Val Gly Val Pro Gly Ala Pro Ala Pro Ala Pro Ala Pro Ala Pro Ala
                85                  90                  95

Pro Ala Pro Ala Pro Ala Pro Ala Pro Ala Pro Ala Pro Ala Pro Ala
            100                 105                 110

Pro Ala Pro Ala Pro Ala Pro Ala Pro Ala Pro Ala Pro Ala Pro Ala
            115                 120                 125

Pro Ala Pro Ala Pro Ala Pro Ala Pro Ala Pro Ala Pro Ala Pro Ala
            130                 135                 140

Pro Ala Pro Ala Pro Ala Pro Ala Pro Ala Pro Ala Pro Ala Pro Ala
145                 150                 155                 160

Pro Ala Pro Ala Pro Ala Pro Ala Pro Ala Pro Ala Pro Ala Pro Ala
            165                 170                 175

Pro Ala Pro Ala Pro Ala Pro Ala Pro Ala Pro Ala Pro Ala Pro Ala
            180                 185                 190

Pro Ala Pro Ala Pro Ala Pro Ala Pro Ala Pro Ala Pro Ala Pro Ala
            195                 200                 205

Pro Ala Pro Ala Pro Ala Pro Ala Pro Ala Pro Ala Pro Ala Pro Ala
        210                 215                 220

Pro Ala Pro Ala Pro Val Gly Val Pro Gly Val Gly Val Pro Gly Val
225                 230                 235                 240

Gly Val Pro Gly Val Gly Val Pro Gly Val Gly Val Pro Gly Val Gly
                245                 250                 255

Val Pro Gly Ser Pro Pro Pro Pro Thr Pro Val Tyr Lys Ser Pro Pro
            260                 265                 270

Pro Pro Thr Pro Val Tyr Lys Ser Pro Pro Pro Pro
        275                 280

-continued

```
<210> SEQ ID NO 272
<211> LENGTH: 84
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Proline at this position is a
      hydroxyproline.
<220> FEATURE:
<221> NAME/KEY: MISC_FEATURE
<222> LOCATION: (5)..(5)
<223> OTHER INFORMATION: The Proline at this position is a
      hydroxyproline.
<220> FEATURE:
<221> NAME/KEY: MISC_FEATURE
<222> LOCATION: (9)..(9)
<223> OTHER INFORMATION: The Proline at this position is a
      hydroxyproline.
<220> FEATURE:
<221> NAME/KEY: MISC_FEATURE
<222> LOCATION: (11)..(11)
<223> OTHER INFORMATION: The Proline at this position is a
      hydroxyproline.
<220> FEATURE:
<221> NAME/KEY: MISC_FEATURE
<222> LOCATION: (14)..(14)
<223> OTHER INFORMATION: The Proline at this position is a
      hydroxyproline.
<220> FEATURE:
<221> NAME/KEY: MISC_FEATURE
<222> LOCATION: (16)..(16)
<223> OTHER INFORMATION: The Proline at this position is a
      hydroxyproline.
<220> FEATURE:
<221> NAME/KEY: MISC_FEATURE
<222> LOCATION: (18)..(18)
<223> OTHER INFORMATION: The Proline at this position is a
      hydroxyproline.
<220> FEATURE:
<221> NAME/KEY: MISC_FEATURE
<222> LOCATION: (20)..(20)
<223> OTHER INFORMATION: The Proline at this position is a
      hydroxyproline.
<220> FEATURE:
<221> NAME/KEY: MISC_FEATURE
<222> LOCATION: (22)..(22)
<223> OTHER INFORMATION: The Proline at this position is a
      hydroxyproline.
<220> FEATURE:
<221> NAME/KEY: MISC_FEATURE
<222> LOCATION: (24)..(24)
<223> OTHER INFORMATION: The Proline at this position is a
      hydroxyproline.
<220> FEATURE:
<221> NAME/KEY: MISC_FEATURE
<222> LOCATION: (26)..(26)
<223> OTHER INFORMATION: The Proline at this position is a
      hydroxyproline.
<220> FEATURE:
<221> NAME/KEY: MISC_FEATURE
<222> LOCATION: (28)..(28)
<223> OTHER INFORMATION: The Proline at this position is a
      hydroxyproline.
<220> FEATURE:
<221> NAME/KEY: MISC_FEATURE
<222> LOCATION: (30)..(30)
<223> OTHER INFORMATION: The Proline at this position is a
      hydroxyproline.
<220> FEATURE:
<221> NAME/KEY: MISC_FEATURE
<222> LOCATION: (32)..(32)
<223> OTHER INFORMATION: The Proline at this position is a
      hydroxyproline.
<220> FEATURE:
<221> NAME/KEY: MISC_FEATURE
```

```
<222> LOCATION: (34)..(34)
<223> OTHER INFORMATION: The Proline at this position is a
      hydroxyproline.
<220> FEATURE:
<221> NAME/KEY: MISC_FEATURE
<222> LOCATION: (36)..(36)
<223> OTHER INFORMATION: The Proline at this position is a
      hydroxyproline.
<220> FEATURE:
<221> NAME/KEY: MISC_FEATURE
<222> LOCATION: (38)..(38)
<223> OTHER INFORMATION: The Proline at this position is a
      hydroxyproline.
<220> FEATURE:
<221> NAME/KEY: MISC_FEATURE
<222> LOCATION: (40)..(40)
<223> OTHER INFORMATION: The Proline at this position is a
      hydroxyproline.
<220> FEATURE:
<221> NAME/KEY: MISC_FEATURE
<222> LOCATION: (42)..(42)
<223> OTHER INFORMATION: The Proline at this position is a
      hydroxyproline.
<220> FEATURE:
<221> NAME/KEY: MISC_FEATURE
<222> LOCATION: (44)..(44)
<223> OTHER INFORMATION: The Proline at this position is a
      hydroxyproline.
<220> FEATURE:
<221> NAME/KEY: MISC_FEATURE
<222> LOCATION: (46)..(46)
<223> OTHER INFORMATION: The Proline at this position is a
      hydroxyproline.
<220> FEATURE:
<221> NAME/KEY: MISC_FEATURE
<222> LOCATION: (48)..(48)
<223> OTHER INFORMATION: The Proline at this position is a
      hydroxyproline.
<220> FEATURE:
<221> NAME/KEY: MISC_FEATURE
<222> LOCATION: (50)..(50)
<223> OTHER INFORMATION: The Proline at this position is a
      hydroxyproline.
<220> FEATURE:
<221> NAME/KEY: MISC_FEATURE
<222> LOCATION: (52)..(52)
<223> OTHER INFORMATION: The Proline at this position is a
      hydroxyproline.
<220> FEATURE:
<221> NAME/KEY: MISC_FEATURE
<222> LOCATION: (54)..(54)
<223> OTHER INFORMATION: The Proline at this position is a
      hydroxyproline.
<220> FEATURE:
<221> NAME/KEY: MISC_FEATURE
<222> LOCATION: (56)..(56)
<223> OTHER INFORMATION: The Proline at this position is a
      hydroxyproline.
<220> FEATURE:
<221> NAME/KEY: MISC_FEATURE
<222> LOCATION: (58)..(58)
<223> OTHER INFORMATION: The Proline at this position is a
      hydroxyproline.
<220> FEATURE:
<221> NAME/KEY: MISC_FEATURE
<222> LOCATION: (60)..(60)
<223> OTHER INFORMATION: The Proline at this position is a
      hydroxyproline.
<220> FEATURE:
<221> NAME/KEY: MISC_FEATURE
<222> LOCATION: (62)..(62)
<223> OTHER INFORMATION: The Proline at this position is a
      hydroxyproline.
<220> FEATURE:
<221> NAME/KEY: MISC_FEATURE
<222> LOCATION: (64)..(64)
<223> OTHER INFORMATION: The Proline at this position is a
      hydroxyproline.
<220> FEATURE:
```

```
<221> NAME/KEY: MISC_FEATURE
<222> LOCATION: (66)..(66)
<223> OTHER INFORMATION: The Proline at this position is a
      hydroxyproline.
<220> FEATURE:
<221> NAME/KEY: MISC_FEATURE
<222> LOCATION: (68)..(68)
<223> OTHER INFORMATION: The Proline at this position is a
      hydroxyproline.
<220> FEATURE:
<221> NAME/KEY: MISC_FEATURE
<222> LOCATION: (70)..(70)
<223> OTHER INFORMATION: The Proline at this position is a
      hydroxyproline.
<220> FEATURE:
<221> NAME/KEY: MISC_FEATURE
<222> LOCATION: (72)..(72)
<223> OTHER INFORMATION: The Proline at this position is a
      hydroxyproline.
<220> FEATURE:
<221> NAME/KEY: MISC_FEATURE
<222> LOCATION: (74)..(74)
<223> OTHER INFORMATION: The Proline at this position is a
      hydroxyproline.
<220> FEATURE:
<221> NAME/KEY: MISC_FEATURE
<222> LOCATION: (77)..(77)
<223> OTHER INFORMATION: The Proline at this position is a
      hydroxyproline.
<220> FEATURE:
<221> NAME/KEY: MISC_FEATURE
<222> LOCATION: (80)..(80)
<223> OTHER INFORMATION: The Proline at this position is a
      hydroxyproline.
<220> FEATURE:
<221> NAME/KEY: MISC_FEATURE
<222> LOCATION: (83)..(83)
<223> OTHER INFORMATION: The Proline at this position is a
      hydroxyproline.

<400> SEQUENCE: 272

Val Pro Gly Val Pro Gly Val Gly Pro Val Pro Gly Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro Ala Pro Ala Pro Ala Pro Ala Pro
        35                  40                  45

Ala Pro Ala Pro Ala Pro Ala Pro Ala Pro Ala Pro Ala Pro Ala Pro
    50                  55                  60

Ala Pro Ala Pro Ala Pro Ala Pro Val Pro Gly Val Pro Gly Val Pro
65                  70                  75                  80

Gly Val Pro Gly

<210> SEQ ID NO 273
<211> LENGTH: 186
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Proline at these positions is a
      hydroxyproline.
<220> FEATURE:
<221> NAME/KEY: MISC_FEATURE
<222> LOCATION: (8)..(8)
<223> OTHER INFORMATION: The Proline at this position is a
      hydroxyproline.
<220> FEATURE:
<221> NAME/KEY: MISC_FEATURE
<222> LOCATION: (10)..(10)
```

```
<223> OTHER INFORMATION: The Proline at this position is a
      hydroxyproline.
<220> FEATURE:
<221> NAME/KEY: MISC_FEATURE
<222> LOCATION: (12)..(12)
<223> OTHER INFORMATION: The Proline at this position is a
      hydroxyproline.
<220> FEATURE:
<221> NAME/KEY: MISC_FEATURE
<222> LOCATION: (14)..(15)
<223> OTHER INFORMATION: The Proline at these positions is a
      hydroxyproline.
<220> FEATURE:
<221> NAME/KEY: MISC_FEATURE
<222> LOCATION: (18)..(18)
<223> OTHER INFORMATION: The Proline at this position is a
      hydroxyproline.
<220> FEATURE:
<221> NAME/KEY: MISC_FEATURE
<222> LOCATION: (21)..(23)
<223> OTHER INFORMATION: The Proline at these positions is a
      hydroxyproline.
<220> FEATURE:
<221> NAME/KEY: MISC_FEATURE
<222> LOCATION: (27)..(27)
<223> OTHER INFORMATION: The Proline at this position is a
      hydroxyproline.
<220> FEATURE:
<221> NAME/KEY: MISC_FEATURE
<222> LOCATION: (29)..(29)
<223> OTHER INFORMATION: The Proline at this position is a
      hydroxyproline.
<220> FEATURE:
<221> NAME/KEY: MISC_FEATURE
<222> LOCATION: (31)..(31)
<223> OTHER INFORMATION: The Proline at this position is a
      hydroxyproline.
<220> FEATURE:
<221> NAME/KEY: MISC_FEATURE
<222> LOCATION: (33)..(34)
<223> OTHER INFORMATION: The Proline at these positions is a
      hydroxyproline.
<220> FEATURE:
<221> NAME/KEY: MISC_FEATURE
<222> LOCATION: (37)..(37)
<223> OTHER INFORMATION: The Proline at this position is a
      hydroxyproline.
<220> FEATURE:
<221> NAME/KEY: MISC_FEATURE
<222> LOCATION: (40)..(40)
<223> OTHER INFORMATION: The Proline at this position is a
      hydroxyproline.
<220> FEATURE:
<221> NAME/KEY: MISC_FEATURE
<222> LOCATION: (45)..(47)
<223> OTHER INFORMATION: The Proline at these positions is a
      hydroxyproline.
<220> FEATURE:
<221> NAME/KEY: MISC_FEATURE
<222> LOCATION: (51)..(51)
<223> OTHER INFORMATION: The Proline at this position is a
      hydroxyproline.
<220> FEATURE:
<221> NAME/KEY: MISC_FEATURE
<222> LOCATION: (53)..(53)
<223> OTHER INFORMATION: The Proline at this position is a
      hydroxyproline.
<220> FEATURE:
<221> NAME/KEY: MISC_FEATURE
<222> LOCATION: (55)..(55)
<223> OTHER INFORMATION: The Proline at this position is a
      hydroxyproline.
<220> FEATURE:
<221> NAME/KEY: MISC_FEATURE
<222> LOCATION: (57)..(57)
<223> OTHER INFORMATION: The Proline at this position is a
      hydroxyproline.
<220> FEATURE:
<221> NAME/KEY: MISC_FEATURE
```

```
<222> LOCATION: (57)..(58)
<223> OTHER INFORMATION: The Proline at these positions is a
      hydroxyproline.
<220> FEATURE:
<221> NAME/KEY: MISC_FEATURE
<222> LOCATION: (61)..(61)
<223> OTHER INFORMATION: The Proline at this position is a
      hydroxyproline.
<220> FEATURE:
<221> NAME/KEY: MISC_FEATURE
<222> LOCATION: (64)..(66)
<223> OTHER INFORMATION: The Proline at these positions is a
      hydroxyproline.
<220> FEATURE:
<221> NAME/KEY: MISC_FEATURE
<222> LOCATION: (70)..(70)
<223> OTHER INFORMATION: The Proline at this position is a
      hydroxyproline.
<220> FEATURE:
<221> NAME/KEY: MISC_FEATURE
<222> LOCATION: (72)..(72)
<223> OTHER INFORMATION: The Proline at this position is a
      hydroxyproline.
<220> FEATURE:
<221> NAME/KEY: MISC_FEATURE
<222> LOCATION: (74)..(74)
<223> OTHER INFORMATION: The Proline at this position is a
      hydroxyproline.
<220> FEATURE:
<221> NAME/KEY: MISC_FEATURE
<222> LOCATION: (76)..(77)
<223> OTHER INFORMATION: The Proline at these positions is a
      hydroxyproline.
<220> FEATURE:
<221> NAME/KEY: MISC_FEATURE
<222> LOCATION: (80)..(80)
<223> OTHER INFORMATION: The Proline at this position is a
      hydroxyproline.
<220> FEATURE:
<221> NAME/KEY: MISC_FEATURE
<222> LOCATION: (83)..(83)
<223> OTHER INFORMATION: The Proline at this position is a
      hydroxyproline.
<220> FEATURE:
<221> NAME/KEY: MISC_FEATURE
<222> LOCATION: (88)..(90)
<223> OTHER INFORMATION: The Proline at these positions is a
      hydroxyproline.
<220> FEATURE:
<221> NAME/KEY: MISC_FEATURE
<222> LOCATION: (94)..(94)
<223> OTHER INFORMATION: The Proline at this position is a
      hydroxyproline.
<220> FEATURE:
<221> NAME/KEY: MISC_FEATURE
<222> LOCATION: (96)..(96)
<223> OTHER INFORMATION: The Proline at this position is a
      hydroxyproline.
<220> FEATURE:
<221> NAME/KEY: MISC_FEATURE
<222> LOCATION: (98)..(98)
<223> OTHER INFORMATION: The Proline at this position is a
      hydroxyproline.
<220> FEATURE:
<221> NAME/KEY: MISC_FEATURE
<222> LOCATION: (100)..(101)
<223> OTHER INFORMATION: The Proline at these positions is a
      hydroxyproline.
<220> FEATURE:
<221> NAME/KEY: MISC_FEATURE
<222> LOCATION: (104)..(104)
<223> OTHER INFORMATION: The Proline at this position is a
      hydroxyproline.
<220> FEATURE:
<221> NAME/KEY: MISC_FEATURE
<222> LOCATION: (107)..(109)
<223> OTHER INFORMATION: The Proline at these positions is a
      hydroxyproline.
<220> FEATURE:
```

-continued

```
<221> NAME/KEY: MISC_FEATURE
<222> LOCATION: (113)..(113)
<223> OTHER INFORMATION: The Proline at this position is a
      hydroxyproline.
<220> FEATURE:
<221> NAME/KEY: MISC_FEATURE
<222> LOCATION: (115)..(115)
<223> OTHER INFORMATION: The Proline at this position is a
      hydroxyproline.
<220> FEATURE:
<221> NAME/KEY: MISC_FEATURE
<222> LOCATION: (117)..(117)
<223> OTHER INFORMATION: The Proline at this position is a
      hydroxyproline.
<220> FEATURE:
<221> NAME/KEY: MISC_FEATURE
<222> LOCATION: (119)..(120)
<223> OTHER INFORMATION: The Proline at these positions is a
      hydroxyproline.
<220> FEATURE:
<221> NAME/KEY: MISC_FEATURE
<222> LOCATION: (123)..(123)
<223> OTHER INFORMATION: The Proline at this position is a
      hydroxyproline.
<220> FEATURE:
<221> NAME/KEY: MISC_FEATURE
<222> LOCATION: (126)..(126)
<223> OTHER INFORMATION: The Proline at this position is a
      hydroxyproline.
<220> FEATURE:
<221> NAME/KEY: MISC_FEATURE
<222> LOCATION: (131)..(133)
<223> OTHER INFORMATION: The Proline at these positions is a
      hydroxyproline.
<220> FEATURE:
<221> NAME/KEY: MISC_FEATURE
<222> LOCATION: (137)..(137)
<223> OTHER INFORMATION: The Proline at this position is a
      hydroxyproline.
<220> FEATURE:
<221> NAME/KEY: MISC_FEATURE
<222> LOCATION: (139)..(139)
<223> OTHER INFORMATION: The Proline at this position is a
      hydroxyproline.
<220> FEATURE:
<221> NAME/KEY: MISC_FEATURE
<222> LOCATION: (141)..(141)
<223> OTHER INFORMATION: The Proline at this position is a
      hydroxyproline.
<220> FEATURE:
<221> NAME/KEY: MISC_FEATURE
<222> LOCATION: (143)..(144)
<223> OTHER INFORMATION: The Proline at these positions is a
      hydroxyproline.
<220> FEATURE:
<221> NAME/KEY: MISC_FEATURE
<222> LOCATION: (146)..(146)
<223> OTHER INFORMATION: The Proline at this position is a
      hydroxyproline.
<220> FEATURE:
<221> NAME/KEY: MISC_FEATURE
<222> LOCATION: (150)..(150)
<223> OTHER INFORMATION: The Proline at this position is a
      hydroxyproline.
<220> FEATURE:
<221> NAME/KEY: MISC_FEATURE
<222> LOCATION: (152)..(152)
<223> OTHER INFORMATION: The Proline at this position is a
      hydroxyproline.
<220> FEATURE:
<221> NAME/KEY: MISC_FEATURE
<222> LOCATION: (156)..(156)
<223> OTHER INFORMATION: The Proline at this position is a
      hydroxyproline.
<220> FEATURE:
<221> NAME/KEY: MISC_FEATURE
<222> LOCATION: (158)..(158)
<223> OTHER INFORMATION: The Proline at this position is a
      hydroxyproline.
```

```
<220> FEATURE:
<221> NAME/KEY: MISC_FEATURE
<222> LOCATION: (160)..(160)
<223> OTHER INFORMATION: The Proline at this position is a
      hydroxyproline.
<220> FEATURE:
<221> NAME/KEY: MISC_FEATURE
<222> LOCATION: (162)..(163)
<223> OTHER INFORMATION: The Proline at these positions is a
      hydroxyproline.
<220> FEATURE:
<221> NAME/KEY: MISC_FEATURE
<222> LOCATION: (166)..(166)
<223> OTHER INFORMATION: The Proline at this position is a
      hydroxyproline.
<220> FEATURE:
<221> NAME/KEY: MISC_FEATURE
<222> LOCATION: (169)..(169)
<223> OTHER INFORMATION: The Proline at this position is a
      hydroxyproline.
<220> FEATURE:
<221> NAME/KEY: MISC_FEATURE
<222> LOCATION: (171)..(171)
<223> OTHER INFORMATION: The Proline at this position is a
      hydroxyproline.
<220> FEATURE:
<221> NAME/KEY: MISC_FEATURE
<222> LOCATION: (175)..(175)
<223> OTHER INFORMATION: The Proline at this position is a
      hydroxyproline.
<220> FEATURE:
<221> NAME/KEY: MISC_FEATURE
<222> LOCATION: (177)..(177)
<223> OTHER INFORMATION: The Proline at this position is a
      hydroxyproline.
<220> FEATURE:
<221> NAME/KEY: MISC_FEATURE
<222> LOCATION: (179)..(179)
<223> OTHER INFORMATION: The Proline at this position is a
      hydroxyproline.
<220> FEATURE:
<221> NAME/KEY: MISC_FEATURE
<222> LOCATION: (181)..(182)
<223> OTHER INFORMATION: The Proline at these positions is a
      hydroxyproline.
<220> FEATURE:
<221> NAME/KEY: MISC_FEATURE
<222> LOCATION: (185)..(185)
<223> OTHER INFORMATION: The Proline at this position is a
      hydroxyproline.

<400> SEQUENCE: 273

Ser Pro Pro Pro Thr Leu Ser Pro Ser Pro Thr Pro Pro Leu
1               5                   10                  15

Gly Pro His Ser Pro Pro Thr Leu Ser Pro Ser Pro Thr Pro Thr
            20                  25                  30

Pro Pro Leu Gly Pro His Thr Pro Val Tyr Lys Ser Pro Pro Thr
            35                  40                  45

Leu Ser Pro Ser Pro Thr Pro Thr Pro Leu Gly Pro His Ser Pro
        50                  55                  60

Pro Pro Thr Leu Ser Pro Ser Pro Thr Pro Thr Pro Leu Gly Pro
65                  70                  75                  80

His Thr Pro Val Tyr Lys Ser Pro Pro Thr Leu Ser Pro Ser Pro
                85                  90                  95

Thr Pro Thr Pro Pro Leu Gly Pro His Ser Pro Pro Pro Thr Leu Ser
                100                 105                 110

Pro Ser Pro Thr Pro Thr Pro Leu Gly Pro His Thr Pro Val Tyr
            115                 120                 125

Lys Ser Pro Pro Pro Thr Leu Ser Pro Ser Pro Thr Pro Thr Pro Pro
        130                 135                 140
```

```
Leu Pro Gly His Ser Pro Leu Pro Thr Leu Ser Pro Leu Pro Thr Pro
145                 150                 155                 160

Thr Pro Pro Leu Leu Pro His Ser Pro Leu Pro Thr Leu Ser Pro Leu
            165                 170                 175

Pro Thr Pro Thr Pro Pro Leu Leu Pro His
            180                 185

<210> SEQ ID NO 274
<211> LENGTH: 32
<212> TYPE: DNA
<213> ORGANISM: Artificial Sequence
<220> FEATURE:
<223> OTHER INFORMATION: Synthetic

<400> SEQUENCE: 274
ctcttttctg gatccggtct atatctttta gc                              32
```

SYNTHETIC GENES FOR PLANT GUMS AND OTHER HYDROXYPROLINE-RICH GLYCOPROTEINS

This application is a continuation-in-part application of U.S. patent application Ser. No. 09/547,693, filed on Apr. 12, 2000, now U.S. Pat. No. 6,639,050, which is a continuation-in-part application of U.S. patent application Ser. No. 09/119,507, filed on Jul. 20, 1998, now U.S. Pat. No. 6,548,642, which is a continuation-in-part application of U.S. patent application Ser. No. 08/897,556, filed on Jul. 21, 1997, now U.S. Pat. No. 6,570,062.

SEQUENCE LISTING

The instant application contains a "lengthy" Sequence Listing which has been submitted via CD-R in lieu of a printed paper copy, and hereby incorporated by reference in its entirety. Said CD-R recorded on Aug. 25, 2005 are labeled CRF, "Copy 1" and "Copy 2", respectively, and each contains only one identical 316 Kb file (27211499.APP).

FIELD OF THE INVENTION

The present invention relates generally to the field of plant gums and other hydroxyproline-rich glycoproteins, and in particular, to the expression of synthetic genes designed from repetitive peptide sequences.

BACKGROUND

Gummosis is a common wound response that results in the exudation of a gum sealant at the site of cracks in bark. A. M. Stephen et al., "Exudate Gums", *Methods Plant Biochem.* (1990). Generally the exudate is a composite of polysaccharides and glycoproteins structurally related to cell wall components such as galactans [G. O. Aspinall, "Plant Gums", *The Carbohydrates* 2B:522536 (1970)] and hydroxyproline-rich glycoproteins [Anderson and McDougall, "The chemical characterization of the gum exudates from eight Australian *Acacia* species of the series *Phyllodineae.*" *Food Hydrocolloids*, 2: 329 (1988)].

Gum arabic is probably the best characterized of these exudates (although it has been largely refractory to chemical analysis). It is a natural plant exudate secreted by various species of Acacia trees. *Acacia senegal* accounts for approximately 80% of the production of gum arabic with *Acacia seyal, Acacia laeta, Acacia camplylacantha,* and *Acacia drepanolobium* supplying the remaining 20%. The gum is gathered by hand in Africa. It is a tedious process involving piercing and stripping the bark of the trees, then returning later to gather the dried tear drop shaped, spherical balls that form in response to mechanical wounding.

The exact chemical nature of gum arabic has not been elucidated. It is believed to consist of two major components, a microheterogeneous glucurono-arabinorhamnogalactan polysaccharide and a higher molecular weight hydroxyproline-rich glycoprotein. Osman et al.,"Characterization of Gum Arabic Fractions Obtained By Anion-Exchange Chromatography" Phytochemistry 38:409 (1984) and Qi et al., "Gum Arabic Glycoprotein Is A Twisted Hairy Rope" Plant Physiol. 96:848 (1991). While the amino composition of the protein portion has been examined, little is known with regard to the precise amino acid sequence.

While the precise chemical nature of gum arabic is elusive, the gum is nonetheless particularly useful due to its high solubility and low viscosity compared to other gums. The FDA declared the gum to be a GRAS food additive. Consequently, it is widely used in the food industry as a thickener, emulsifier, stabilizer, surfactant, protective colloid, and flavor fixative or preservative. J. Dziezak, "A Focus on Gums" *Food Technology* (March 1991). It is also used extensively in the cosmetics industry.

Normally, the world production of gum arabic is over 100,000 tons per year. However, this production depends on the environmental and political stability of the region producing the gum. In the early 1970s, for example, a severe drought reduced gum production to 30,00 tons. Again in 1985, drought brought about shortages of the gum, resulting in a 600% price increase.

Three approaches have been used to deal with the somewhat precarious supply problem of gum arabic. First, other gums have been sought out in other regions of the world. Second, additives have been investigated to supplement inferior gum arabic. Third, production has been investigated in cultured cells.

The effort to find other gums in other regions of the world has met with some limited success. However, the solubility of gum arabic from *Acacia* is superior to other gums because it dissolves well in either hot or cold water. Moreover, while other exudates are limited to a 5% solution because of their excessive viscosity, gum arabic can be dissolved readily to make 55% solutions.

Some additives have been identified to supplement gum arabic. For example, whey proteins can be used to increase the functionality of gum arabic. A. Prakash et al., "The effects of added proteins on the functionality of gum arabic in soft drink emulsion systems," *Food Hydrocolloids* 4:177 (1990). However, this approach has limitations. Only low concentrations of such additives can be used without producing off-flavors in the final food product.

Attempts to produce gum arabic in cultured *Acacia senegal* cells has been explored. Unfortunately, conditions have not been found which lead to the expression of gum arabic in culture. A. Mollard and J-P. Joseleau, "*Acacia senegal* cells cultured in suspension secrete a hydroxyproline-deficient arabinogalactan-protein" *Plant Physiol. Biochem.* 32:703 (1994).

Clearly, new approaches to improve gum arabic production are needed. Such approaches should not be dependent on environmental or political factors. Ideally, such approaches should simplify production and be relatively inexpensive.

SUMMARY OF THE INVENTION

The present invention involves a new approach in the field of plant gums and presents a new solution to the production of hydroxyproline(Hyp)-rich glycoproteins (HRGPs), repetitive proline-rich proteins (RPRPs) and arabinogalactan-proteins (AGPs). The present invention contemplates the expression of synthetic genes designed from repetitive peptide sequences of such glycoproteins, including the peptide sequences of gum arabic glycoprotein (GAGP).

With respect to GAGP, the present invention contemplates a substantially purified polypeptide comprising at least a portion of the amino acid sequence Ser-Hyp-Hyp-Hyp-[Hyp/Thr]-Leu-Ser-Hyp-Ser-Hyp-Thr-Hyp-Thr-Hyp-Hyp-Hyp-Gly-Pro-His (SEQ ID NO:1 and SEQ ID NO:2) or variants thereof. By "variants" it is meant that the sequence need not comprise the exact sequence; up to five (5) amino acid substitutions are contemplated. For example, a Leu or Hyp may be substituted for the Gly; Leu may also be substituted for Ser and one or more Hyp. By "variants" it is also meant that the sequence need not be the entire nineteen (19) amino acids. Illustrative variants are shown in Table 3. In one preferred embodiment, variants contain one or more of the following three motifs: Ser-Hyp$_4$ (SEQ ID NO: 3), Ser-Hyp$_3$-Thr (SEQ ID NO: 15), and Xaa-Hyp-Xaa-Hyp (SEQ ID NO: 9), where Xaa is any amino acid other than hydroxyproline.

Indeed, it is not intended that the present invention be limited by the precise length of the purified polypeptide. In one embodiment, the peptide comprises more than twelve (12) amino acids from the nineteen (19) amino acids of the sequence. In another embodiment, a portion of the nineteen (19) amino acids (see SEQ ID NO:1 and SEQ ID NO:2) is utilized as a repetitive sequence. In yet another embodiment, all nineteen (19) amino acids (see SEQ ID NO:1 and SEQ ID NO:2) with or without amino acid substitutions) are utilized as a repetitive sequence.

It is not intended that the present invention be limited by the precise number of repeats. The sequence (i.e. SEQ ID NO:1 and SEQ ID NO:2) or variants thereof may be used as a repeating sequence between one (1) and up to fifty (50) times, more preferably between ten (10) and up to thirty (30) times, and most preferably approximately twenty (20) times. The sequence (i.e. SEQ ID NO:1 and SEQ ID NO:2) or variants thereof may be used as contiguous repeats or may be used as non-contiguous repeats (with other amino acids, or amino acid analogues, placed between the repeating sequences).

The present invention specifically contemplates fusion proteins comprising a non-gum arabic protein or glycoprotein sequence and a portion of the gum arabic glycoprotein sequence (SEQ ID NO:1 and SEQ ID NO:2). It is not intended that the present invention be limited by the nature of the non-gum arabic glycoprotein sequence. In one embodiment, the non-gum arabic glycoprotein sequence is a green fluorescent protein.

As noted above, the present invention contemplates synthetic genes encoding such peptides. By "synthetic genes" it is meant that the nucleic acid sequence is derived using the peptide sequence of interest (in contrast to using the nucleic acid sequence from cDNA). In one embodiment, the present invention contemplates an isolated polynucleotide sequence encoding a polypeptide comprising at least a portion of the polypeptide of SEQ ID NO:1 and SEQ ID NO:2 or variants thereof. The present invention specifically contemplates a polynucleotide sequence comprising a nucleotide sequence encoding a polypeptide comprising one or more repeats of SEQ ID NO:1 and SEQ ID NO:2 or variants thereof. Importantly, it is not intended that the present invention be limited to the precise nucleic acid sequence encoding the polypeptide of interest.

The present invention contemplates synthetic genes encoding portions of HRGPs, wherein the encoded peptides contain one or more of the highly conserved Ser-Hyp$_4$ (SEQ ID NO:3) motif(s). The present invention also contemplates synthetic genes encoding portions of RPRPs, wherein the encoded peptides contain one or more of the pentapeptide motif: Pro-Hyp-Val-Tyr-Lys (SEQ ID NO:4) and variants of this sequence such as X-Hyp-Val-Tyr-Lys (SEQ ID NO:5) and Pro-Hyp-Val-X-Lys (SEQ ID NO:6) and Pro-Pro-X-Tyr-Lys (SEQ ID NO: 7) and Pro-Pro-X-Tyr-X (SEQ ID NO:8), where "X" can be Thr, Glu, Hyp, Pro, His and Ile. The present invention also contemplates synthetic genes encoding portions of AGPs, wherein the encoded peptides contain one or more Xaa-Hyp-Xaa-Hyp (SEQ ID NO:9) repeats. Such peptides can be expressed in a variety of forms, including but not limited to fusion proteins.

With regard to motifs for HRGPs, the present invention contemplates a polynucleotide sequence comprising the sequence: 5'-CCA CCA CCT TCA CCT CCA CCC CCA TCT CCA-3' (SEQ ID NO:10). With regard to motifs for AGPs, the present invention contemplates a polynucleotide sequence comprising the sequence: 5'-TCA CCA TCA CCA TCT CCT TCG CCA TCA CCC-3' (SEQ ID NO:11). Of course, it is not intended that the present invention be limited by the particular sequence. Indeed, the present invention specifically contemplates sequences that are not identical but are nonetheless homologous to the sequences of SEQ ID NOS: 10 and 11. The present invention also contemplates sequences that are complementary (including sequences that are only partially complementary) sequences to the sequences of SEQ ID NOS: 10 and 11. Such complementary sequences include sequences that will hybridize to the sequences of SEQ ID NOS: 10 and 11 under low stringency conditions as well as high stringency conditions (see Definitions below).

The present invention also contemplates the mixing of motifs (i.e. modules) which are not found in wild-type sequences. For example, one might add GAGP modules to extensin and RPRP crosslinking modules to AGP-like molecules.

The present invention contemplates using the polynucleotides of the present invention for expression of the polypeptides in vitro and in vivo. Therefore, the present invention contemplates polynucleotide sequences encoding two or more repeats of the sequence of SEQ ID NO:1 and SEQ ID NO:2 or variants thereof, wherein said polynucleotide sequence is contained on a recombinant expression vector. It is also contemplated that such vectors will be introduced into a variety of host cells, both eukaryotic and prokaryotic (e.g. bacteria such as *E. coli*).

In one embodiment, the vector further comprises a promoter. It is not intended that the present invention be limited to a particular promoter. Any promoter sequence which is capable of directing expression of an operably linked nucleic acid sequence encoding a portion of a plant gum polypeptide (or other hydroxyproline-rich polypeptide of interest as described above) is contemplated to be within the scope of the invention. Promoters include, but are not limited to, promoter sequences of bacterial, viral and plant origins. Promoters of bacterial origin include, but are not limited to, the octopine synthase promoter, the nopaline synthase promoter and other promoters derived from native Ti plasmids. Viral promoters include, but are not limited to, the 35S and 19S RNA promoters of cauliflower mosaic virus (CaMV), and T-DNA promoters from *Agrobacterium*. Plant promoters include, but are not limited to, the ribulose-1,3-bisphosphate carboxylase small subunit promoter, maize ubiquitin promoters, the phaseolin promoter, the E8 promoter, and the Tob7 promoter.

The invention is not limited to the number of promoters used to control expression of a nucleic acid sequence of interest. Any number of promoters may be used so long as expression of the nucleic acid sequence of interest is controlled in a desired manner. Furthermore, the selection of a promoter may be governed by the desirability that expression be over the whole plant, or localized to selected tissues of the plant, e.g., root, leaves, fruit, etc. For example, promoters active in flowers are known (Benfy et al. (1990) Plant Cell 2:849-856).

The promoter activity of any nucleic acid sequence in host cells may be determined (i.e., measured or assessed) using methods well known in the art and exemplified herein. For example, a candidate promoter sequence may be tested by ligating it in-frame to a reporter gene sequence to generate a reporter construct, introducing the reporter construct into host cells (e.g. tomato or potato cells) using methods described herein, and detecting the expression of the reporter gene (e.g., detecting the presence of encoded mRNA or encoded protein, or the activity of a protein encoded by the reporter gene). The reporter gene may confer antibiotic or herbicide resistance. Examples of reporter genes include, but are not limited to, dhfr which confers resistance to methotrexate [Wigler M et al., (1980) *Proc Natl Acad Sci* 77:3567-70]; npt, which confers resistance to the aminoglycosides neomycin and G-418 [Colbere-Garapin F et al., (1981) *J. Mol. Biol.* 150:1-14] and als or pat, which confer resistance to chlorsulfuron and phosphinotricin acetyl transferase, respectively. Recently, the use of a reporter gene system which expresses visible markers has gained popularity with such markers as β-glucuronidase and its substrate (X-Gluc), luciferase and its substrate (luciferin), and β-galactosidase and its substrate (X-Gal) being widely used not only to identify transformants, but also to quantify the amount of transient or stable protein expression attributable to a specific vector system [Rhodes C A et al. (1995) Methods Mol Biol 55:121-131].

In addition to a promoter sequence, the expression construct preferably contains a transcription termination sequence downstream of the nucleic acid sequence of interest to provide for efficient termination. In one embodiment, the termination sequence is the nopaline synthase (NOS) sequence. In another embodiment the termination region comprises different fragments of sugarcane ribulose-1,5-biphosphate carboxylase/oxygenase (rubisco) small subunit (scrbcs) gene. The termination sequences of the expression constructs are not critical to the invention. The termination sequence may be obtained from the same gene as the promoter sequence or may be obtained form different genes.

If the mRNA encoded by the nucleic acid sequence of interest is to be efficiently translated, polyadenylation sequences are also commonly added to the expression construct. Examples of the polyadenylation sequences include, but are not limited to, the *Agrobacterium* octopine synthase signal, or the nopaline synthase signal.

The invention is not limited to constructs which express a single nucleic acid sequence of interest. Constructs which contain a plurality of (i.e., two or more) nucleic acid sequences under the transcriptional control of the same promoter sequence are expressly contemplated to be within the scope of the invention. Also included within the scope of this invention are constructs which contain the same or different nucleic acid sequences under the transcriptional control of different promoters. Such constructs may be desirable to, for example, target expression of the same or different nucleic acid sequences of interest to selected plant tissues.

As noted above, the present invention contemplates using the polynucleotides of the present invention for expression of a portion of plant gum polypeptides in vitro and in vivo. Where expression takes place in vivo, the present invention contemplates transgenic plants. The transgenic plants of the invention are not limited to plants in which each and every cell expresses the nucleic acid sequence of interest. Included within the scope of this invention is any plant (e.g. tobacco, tomato, maize, algae, etc.) which contains at least one cell which expresses the nucleic acid sequence of interest. It is preferred, though not necessary, that the transgenic plant express the nucleic acid sequence of interest in more than one cell, and more preferably in one or more tissue. It is particularly preferred that expression be followed by proper glycosylation of the plant gum polypeptide fragment or variant thereof, such that the host cell produces functional (e.g. in terms of use in the food or cosmetic industry) plant gum polypeptide.

The fact that transformation of plant cells has taken place with the nucleic acid sequence of interest may be determined using any number of methods known in the art. Such methods include, but are not limited to, restriction mapping of genomic DNA, PCR analysis, DNA-DNA hybridization, DNA-RNA hybridization, and DNA sequence analysis.

Expressed polypeptides (or fragments thereof) can be immobilized (covalently or non-covalently) on solid supports or resins for use in isolating HRGP-binding molecules from a variety of sources (e.g. algae, plants, animals, microorganisms). Such polypeptides can also be used to make antibodies.

The invention further provides a substantially purified polypeptide comprising at least a portion of the gum arabic consensus sequence. In particular, the invention provides a substantially purified polypeptide comprising at least a portion of amino acid sequence A-Hyp-B-C-D-E-F-Hyp-G-H-I-Hyp-J-Hyp-Hyp-K-L-Pro-M (SEQ ID NO:136), wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His and Pro; and wherein the portion is greater than twelve contiguous amino acids of the amino acid sequence. In a preferred embodiment, the portion occurs in the polypeptide as a repeating sequence. In a more preferred embodiment, the repeating sequence repeats from 1 to 64 times. In an alternative preferred embodiment, A is Ser; B is selected from Hyp, and Leu; D is selected from Hyp, Ser, and Thr; E is Leu; F is Ser; G is selected from Ser, Leu, and Hyp; H is selected from Hyp, Pro, and Leu; I is selected from Thr and Ala; J is Thr; K is selected from Thr, Leu, and Hyp; L is selected from Gly and Leu; and M is selected from His and Pro. In another alternative embodiment, the amino acid sequence is selected from Ser-Hyp-Hyp-Hyp-Hyp-Leu-Ser-Hyp-Ser-Hyp-Thr-Hyp-Thr-Hyp-Hyp-Leu-Gly-Pro-His (SEQ ID NO:143), Ser-Hyp-Hyp-Hyp-Thr-Leu-Ser-Hyp-Ser-Hyp-Thr-Hyp-Thr-Hyp-Hyp-Hyp-Gly-Pro-His (SEQ ID NO:144), Ser-Hyp-Hyp-Hyp-Ser-Leu-Ser-Hyp-Ser-Hyp-Thr-Hyp-Thr-Hyp-Hyp-Thr-Gly-Pro-His (SEQ ID NO:145), Ser-Hyp-Hyp-Hyp-Leu-Ser-Hyp-Ser-Hyp-Thr-Hyp-Thr-Hyp-Hyp-Gly-Pro-Hyp (SEQ ID NO:146), Ser-Hyp-Leu-Pro-Thr-Leu-Ser-Hyp-Leu-Pro-Thr-Hyp-Thr-Hyp-Hyp-Hyp-Gly-Pro-His (SEQ ID NO:147), Ser-Hyp-Leu-Pro-Thr-Leu-Ser-Hyp-Leu-Pro-Ala-Hyp-Thr-Hyp-Hyp-Hyp-Gly-Pro-His (SEQ ID NO:148), Ser-Hyp-Hyp-Hyp-Hyp-Leu-Ser-Hyp-Ser-Leu-Thr-Hyp-Thr-Hyp-Hyp-Leu-Gly-Pro-Hyp (SEQ ID NO: 149), Ser-Hyp-Hyp-Hyp-Hyp-Leu-Ser-Hyp-Ser-Hyp-Thr-Hyp-Thr-Hyp-Hyp-Hyp-Gly-Pro-His (SEQ ID NO:150), Ser-Hyp-Hyp-Hyp-Thr-Leu-Ser-Hyp-Ser-Hyp-Thr-Hyp-Thr-Hyp-Hyp-Hyp-Gly-Pro-His (SEQ ID NO:151), Ser-Hyp-Hyp-Hyp-Hyp-Leu-Ser-Hyp-Ser-Hyp-Ala-Hyp-Thr-Hyp-Hyp-Hyp-Gly-Pro-His (SEQ ID NO:152), Ser-Hyp-Hyp-Hyp-Hyp-Leu-Ser-Hyp-Leu-Pro-Thr-Hyp-Thr-Hyp-Hyp-Leu-Gly-Pro-His (SEQ ID NO:153), Ser-Hyp-Hyp-Hyp-Ser-Leu-Ser-Hyp-Leu-Pro-Thr-Hyp-Thr-Hyp-Hyp-Leu-Gly-Pro-His (SEQ ID NO:154), Ser-Hyp-Hyp-Hyp-Thr-Leu-Ser-Hyp-Hyp-Leu- Thr-Hyp-Thr-Hyp-Hyp-Leu-Leu-Pro-His (SEQ ID NO:155), Hyp-Hyp-Thr-Leu-Ser-Hyp-Hyp-Leu-Thr-Hyp-Thr-Hyp-Hyp-Leu-Leu-Pro (SEQ ID NO:156), Ser-Hyp-Hyp-Hyp-Ser-Leu-Ser-Hyp-Leu-Pro-Thr-Hyp-Thr-Hyp-Hyp-Leu (SEQ ID NO:157), Hyp-Hyp-Leu-Ser-Hyp-Leu-Pro-Thr-Hyp-Thr-Hyp-Hyp-Leu-Gly-Pro-His (SEQ ID NO:158), Ser-Hyp-Hyp-Hyp-Thr-Leu-Ser-Hyp-Ser-Hyp-Thr-Hyp-Thr-Hyp (SEQ ID NO:159), Leu-Ser-Hyp-Ser-Leu-Thr-Hyp-Thr-Hyp-Hyp-Leu-Gly-Pro-Hyp (SEQ ID NO:160), Hyp-Thr-Leu-Ser-Hyp-Leu-Pro-Ala-Hyp-Thr-Hyp-Hyp-Hyp-Gly (SEQ ID NO:161), Ser-Hyp-Hyp-Hyp-Hyp-Leu-Ser-Hyp-Ser-Hyp-Thr-Hyp (SEQ ID NO:162), Ser-Leu-Ser-Hyp-Ser-Hyp-Thr-Hyp-Thr-Hyp-Hyp-Thr (SEQ ID NO:163), Hyp-Hyp-Thr-Leu-Ser-Hyp-Ser-Hyp-Thr-Hyp-Thr-Hyp (SEQ ID NO:164), Hyp-Thr-Hyp-Thr-Hyp-Hyp-Leu-Gly-Pro-His (SEQ ID NO:165), Hyp-Hyp-Thr-Leu-Ser-Hyp-Hyp-Leu-Thr-Hyp (SEQ ID NO:166), Ser-Hyp-Hyp-Hyp-Ser-Leu-Ser-Hyp-Leu-Pro (SEQ ID NO:167), Hyp-Thr-Hyp-Hyp-Leu-Gly-Pro-His (SEQ ID NO:168), Hyp-Leu-Ser-Hyp-Ser-Hyp-Ala-Hyp (SEQ ID NO:169), Hyp-Hyp-Hyp-Thr-Leu-Ser-Hyp-Ser (SEQ ID NO:170), Thr-Hyp-Hyp-Hyp-Gly-Pro (SEQ ID NO:171), Hyp-Hyp-Leu-Ser-Hyp-Ser (SEQ ID NO:172), Ser-Hyp-Leu-Pro-Ala-Hyp (SEQ ID NO:173), Leu-Pro-Thr-Leu-Ser-Hyp (SEQ ID NO:174), Ser-Hyp-Ser-Hyp (SEQ ID NO:175), Ser-Hyp-Thr-Hyp (SEQ ID NO:176), Thr-Hyp-Thr-Hyp (SEQ ID NO:177), Thr-Hyp-Hyp-Hyp (SEQ ID NO:178), Ser-Hyp-Pro-Pro-Pro-Leu-Ser-Hyp-Ser-Hyp-Thr-Hyp-Thr-Hyp-Hyp-Leu-Gly-Pro-His (SEQ ID NO:217), Ser-Hyp-Hyp-Pro-Pro-Leu-Ser-Hyp-Ser-Hyp-Thr-Hyp-Thr-Hyp-Hyp-Leu-Gly-Pro-His (SEQ ID NO:218), Ser-Hyp-Pro-Hyp-Pro-Leu-Ser-Hyp-Ser-Hyp-Thr-Hyp-Thr-Hyp-Hyp-Leu-Gly-Pro-His (SEQ ID NO:219), Ser-Hyp-Pro-Pro-Hyp-Leu-Ser-Hyp-Ser-Hyp-Thr-Hyp-Thr-Hyp-Hyp-Leu-Gly-Pro-His (SEQ ID NO:220), Ser-Hyp-Hyp-Hyp-Pro-Leu-Ser-Hyp-Ser-Hyp-Thr-Hyp-Thr-Hyp-Hyp-Leu-Gly-Pro-His (SEQ ID NO:221), Ser-Hyp-Hyp-Pro-Hyp-Leu-Ser-Hyp-Ser-Hyp-Thr-Hyp-Thr-Hyp-Hyp-Leu-Gly-Pro-His (SEQ ID NO:222), Ser-Hyp-Pro-Hyp-Hyp-Leu-Ser-Hyp-Ser-Hyp-Thr-Hyp-Thr-Hyp-Hyp-Leu-Gly-Pro-His (SEQ ID NO:223), Ser-Hyp-Hyp-Hyp-Hyp-Leu-Ser-Hyp-Ser-Pro-Thr-Hyp-Thr-Hyp-Hyp-Leu-Gly-Pro-His (SEQ ID NO:224), Ser-Hyp-Hyp-Hyp-Hyp-Leu-Ser-Hyp-Ser-Leu-Thr-Hyp-Thr-Hyp-Hyp-Leu-Gly-Pro-His (SEQ ID NO:225), Ser-Hyp-Hyp-Hyp-Thr-Leu-Ser-Hyp-Ser-Hyp-Thr-Hyp-Thr-Hyp-Hyp-Hyp-Gly-Pro-His-Ser-Hyp-Hyp-Hyp-(Hyp) (SEQ ID NO:18), Ser-Hyp-Ser-Hyp-Thr-Hyp-Thr-Hyp-Hyp-Leu-Gly-Pro-His (SEQ ID NO:23), Ser-Hyp-Hyp-Hyp-A-Leu-Ser-Hyp-Ser-Hyp-Thr-Hyp-Thr-Hyp-Hyp-B-Gly-Pro-His (SEQ ID NO:179), where A is selected from Hyp, Thr, and Ser, and B is selected from Hyp and Lys, SEQ ID NO:131, and SEQ ID NO:133. In yet another alternative embodiment, the portion comprises a motif selected from (Xaa-Hyp)$_x$ (SEQ ID NO:182) and Xaa-Hyp-Xaa-Xaa-Hyp-Xaa (SEQ ID NO:183), wherein Xaa is any amino acid other than hydroxyproline, and wherein x is from 2 to 1000. In a preferred embodiment, the portion comprises the sequence Xaa-Hyp-Xaa-Hyp (SEQ ID NO:9), and wherein Xaa is selected from Ser, Thr, and Ala. In a further alternative embodiment, the portion comprises a motif selected from Xaa-Hyp-Hyp$_n$ (SEQ ID NO:209) and Xaa-Pro-Hyp$_n$ (SEQ ID NO:210), wherein n is from 1 to 100, and wherein Xaa is any amino acid other than hydroxyproline. In a preferred embodiment, the portion comprises a peptide sequence selected from Ser-Hyp$_2$ (SEQ ID NO:211), Ser-Hyp$_3$ (SEQ ID NO:212), Ser-Hyp$_4$ (SEQ ID NO:3), Thr-Hyp$_2$ (SEQ ID NO:213), and Thr-Hyp$_3$ (SEQ ID NO:214).

In an additional alternative embodiment, the portion comprises a peptide sequence selected from Ser-Hyp$_2$-Pro (SEQ ID NO:215) and Ser-Hyp$_2$-Pro-Hyp (SEQ ID NO:216).

The invention further provides a substantially purified polypeptide comprising a non-contiguous hydroxyproline motif. In particular, the invention provides a substantially purified polypeptide comprising a first motif selected from (Xaa-Hyp)$_x$ (SEQ ID NO:182) and Xaa-Hyp-Xaa-Xaa-Hyp-Xaa (SEQ ID NO:183), wherein Xaa is any amino acid other than hydroxyproline, and wherein x is from 2 to 1000. In one embodiment, the sequence is Xaa-Hyp-Xaa-Hyp (SEQ ID NO:9), wherein Xaa is selected from Ser, Thr, and Ala. In an alternative embodiment, the polypeptide further comprises a contiguous hydroxyproline motif (i.e., a second motif) selected from Xaa-Hyp-Hyp$_n$ (SEQ ID NO:209) and Xaa-Pro-Hyp$_n$ (SEQ ID NO:210), wherein n is from 1 to 100, and wherein Xaa is any amino acid other than hydroxyproline. In a preferred embodiment, the first and second motifs alternate in the polypeptide. In a more preferred embodiment, the alternating first and second motifs repeat from 1 to 500 times.

Also provided herein is a substantially purified polypeptide comprising a motif selected from Xaa-Hyp-Hyp$_n$ (SEQ ID NO:209) and Xaa-Pro-Hyp$_n$ (SEQ ID NO:210), wherein n is from 1 to 100, and wherein Xaa is any amino acid other than hydroxyproline. In one embodiment, the portion comprises a peptide sequence selected from Ser-Hyp$_2$ (SEQ ID NO:211), Ser-Hyp$_3$ (SEQ ID NO:212), Ser-Hyp$_4$ (SEQ ID NO:3), Thr-Hyp$_2$ (SEQ ID NO:213), and Thr-Hyp$_3$ (SEQ ID NO:214).

The invention also provides a fusion protein comprising a first sequence selected from a non-gum arabic protein sequence and a non-gum arabic glycoprotein sequence operably linked to at least a portion of an amino acid sequence selected from (a) A-Hyp-B-C-D-E-F-Hyp-G-H-I-Hyp-J-Hyp-Hyp-K-L-Pro-M (SEQ ID NO:136), wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His and Pro; and wherein the portion is greater than twelve contiguous amino acids of the amino acid sequence, (b) a polypeptide comprising a first motif selected from (Xaa-Hyp)$_x$ (SEQ ID NO:182) and Xaa-Hyp-Xaa-Xaa-Hyp-Xaa (SEQ ID NO:183), wherein x is from 2 to 1000, (c) a polypeptide comprising a second motif selected from Xaa-Hyp-Hyp$_n$ (SEQ ID NO:209) and Xaa-Pro-Hyp$_n$ (SEQ ID NO:210), wherein n is from 1 to 500, and (d) a polypeptide comprising the first motif and the second motif, wherein Xaa is any amino acid other than hydroxyproline. In one embodiment, the first sequence is a green fluorescent protein amino acid sequence.

Also provided by the invention is an isolated polynucleotide sequence encoding at least a portion of an amino acid sequence selected from (a) A-Hyp-B-C-D-E-F-Hyp-G-H-I-Hyp-J-Hyp-Hyp-K-L-Pro-M (SEQ ID NO:136), wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His and Pro; and wherein the portion is greater than twelve contiguous amino acids of the amino acid sequence, (b) a polypeptide comprising a first motif selected from (Xaa-Hyp)$_x$ (SEQ ID NO: 182) and Xaa-Hyp-Xaa-Xaa-Hyp-Xaa (SEQ ID NO: 183), wherein x is from 2 to 1000, (c) a polypeptide comprising a second motif selected from Xaa-Hyp-Hyp$_n$ (SEQ ID NO:209) and Xaa-Pro-Hyp$_n$ (SEQ ID NO:210), wherein n is from 1 to 500, and (d) a polypeptide comprising the first motif and the second motif, wherein Xaa is any amino acid other than hydroxyproline.

The invention further provides a recombinant expression vector comprising a polynucleotide sequence encoding a portion of an amino acid sequence selected from (a) A-Hyp-B-C-D-E-F-Hyp-G-H-I-Hyp-J-Hyp-Hyp-K-L-Pro-M (SEQ ID NO:136), wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His and Pro; and wherein the portion is greater than twelve contiguous amino acids of the amino acid sequence, (b) a polypeptide comprising a first motif selected from (Xaa-Hyp)$_x$ (SEQ ID NO:182) and Xaa-Hyp-Xaa-Xaa-Hyp-Xaa (SEQ ID NO:183), wherein x is from 2 to 1000, (c) a polypeptide comprising a second motif selected from Xaa-Hyp-Hyp$_n$ (SEQ ID NO:209) and Xaa-Pro-Hyp$_n$ (SEQ ID NO:210), wherein n is from 1 to 500, and (d) a polypeptide comprising the first motif and the second motif, wherein Xaa is any amino acid other than hydroxyproline. In one embodiment, the expression vector further comprises a promoter operably linked to the polynucleotide sequence. In a preferred embodiment, the promoter is a viral promoter. In a more preferred embodiment, the viral promoter is selected from the group consisting of the 35S and 19S RNA promoters of cauliflower mosaic virus. In an alternative preferred embodiment, the expression vector further comprises a signal sequence selected from extensin signal sequence (SEQ ID NO:14), and tomato arabinogalactan-protein signal sequence (SEQ ID NO:215). In a more preferred embodiment, the expression vector further comprises a reporter gene. In a yet more preferred embodiment, the reporter gene is the green fluorescence protein gene. In another embodiment, the vector is contained within a host cell. In a preferred embodiment, the host cell is a plant cell. In a more preferred embodiment, the plant cell expresses a glycoprotein comprising the portion.

Also provided herein is a method for producing at least a portion of a glycoprotein, comprising: a) providing: i) a recombinant expression vector comprising a polynucleotide sequence encoding at least a portion of an amino acid sequence selected from (a) A-Hyp-B-C-D-E-F-Hyp-G-H-I-Hyp-J-Hyp-Hyp-K-L-Pro-M (SEQ ID NO:136), wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His and Pro; and wherein the portion is greater than twelve contiguous amino acids of the amino acid sequence, (b) a polypeptide comprising a first motif selected from (Xaa-Hyp)$_x$ (SEQ ID NO:182) and Xaa-Hyp-Xaa-Xaa-Hyp-Xaa (SEQ ID NO:183), wherein x is from 2 to 1000, (c) a polypeptide comprising a second motif selected from Xaa-Hyp-Hyp$_n$ (SEQ ID NO:209) and Xaa-Pro-Hyp$_n$ (SEQ ID NO:210), wherein n is from 1 to 500, and (d) a polypeptide comprising the first motif and the second motif, wherein Xaa is any amino acid other than hydroxyproline; and ii) a host cell; and b) introducing the vector into the host cell under conditions such that the portion is expressed. In one embodiment, the host cell is growing in culture. In a preferred embodiment, the method further comprises the step of c) recovering the portion from the host cell culture. In an alternative embodiment, the host cell is a plant cell. In a more preferred embodiment, the plant cell is derived from a plant selected from the family Leguminoseae.

One aspect of the present invention contemplates an isolated polypeptide, comprising alternating rigid and non-rigid modules, wherein said rigid modules are directed by contiguous hydroxyproline residues and said non-rigid modules are directed by non-contiguous hydroxyproline residues. In one embodiment, an isolated polypeptide includes, but is not limited to, non-naturally occurring polypeptides and naturally occurring polypeptides. Preferably, the naturally occurring polypeptides are modified by insertion of modules or motifs described herein. In one embodiment, the rigid module comprises at least two contiguous hydroxyproline residues. In one embodiment, the rigid module is arabinosylated. In one embodiment, the polypeptide further comprises a glycoprotein having a crosslinkage motif. In one embodiment, the crosslinkage motif comprises tyrosine. In another embodiment, the crosslinkage motif comprises VYK (SEQ ID NO: 256). In one embodiment, the tyrosine forms an intramolecular crosslink. In another embodiment, the tyrosine forms an intermolecular crosslink.

One aspect of the present invention contemplates a polypeptide, comprising a first elastin module flanked on the N-terminal side by a first extensin module having a first crosslinkage motif and a second elastin module flanked on the C-terminal side by a second extension module having a second crosslinkage motif. In one embodiment, the first elastin module is repeated six times. In one embodiment, the second elastin module is repeated three times. In one embodiment, the first crosslinkage motif comprises VYK (SEQ ID NO: 256) and contiguous hydroxyproline residues. In one embodiment, the second crosslinkage motif comprises VYK (SEQ ID NO: 256) and contiguous hydroxyproline residues. In one embodiment, the polypeptide further comprises a central stretch of rigid arabinosylated SOOOO (SEQ ID NO: 134) repeats flanked on either side by said first and said second elastin module.

One aspect of the present invention comprises a nucleotide acid encoding a polypeptide variant of Le-APG-1. In one embodiment, the variant lacks a glycosylphosphatidylinositol anchor signal sequence. In one embodiment, the variant lacks an internal lysine rich region. In one embodiment, the nucleotide acid further comprises an enhanced green fluorescent protein fusion glycoprotein. In one embodiment, the nucleotide acid is expressed in *Nicotiana tabacum*.

DESCRIPTION OF THE DRAWINGS

FIG. 1 shows the nucleic acid sequence (SEQ ID NO:12) of one embodiment of a synthetic gene of the present invention. Protein sequence disclosed as SEQ ID NO: 297.

FIG. 11 shows the oligonucleotide sequence (SEQ ID NOs:112, 113, 115, 116, 118-121, 123 and 124) sets used to build the synthetic genes which encode the Ser-Pro internal repeat polypeptide (SEQ ID NO:114), the GAGP internal repeat polypeptide (SEQ ID NO:117), the 5'-linker (SEQ ID NO:122) and 3'-linker (SEQ ID NO:125).

FIG. 14 shows polypeptide sequences of (Ser-Hyp)$_{32}$-EGFP ((Ser-Hyp)$_{32}$ disclosed as SEQ ID NO: 275) and (GAGP)$_3$-EGFP before and after deglycosylation. (A) N-terminal amino acid sequence of the glycoprotein, (Ser-Hyp)$_{32}$-EGFP ((Ser-Hyp)$_{32}$ disclosed as SEQ ID NO: 275), with partial sequence of both the glycoprotein (upper sequence) (SEQ ID NO:126) and its polypeptide after deglycosylation (lower sequence) (SEQ ID NO:127). X denotes blank cycles which correspond to glycosylated Hyp; glycoamino acids tend to produce blank cycles during Edman degradation, an exception being arabinosyl Hyp. (B) Polypeptide sequence of glycosylated (GAGP)$_3$-EGFP (upper sequence) (SEQ ID NO:128) and deglycosylated (GAGP)$_3$-EGFP (lower sequence) (SEQ ID NO:129). Residues marked with an asterisk (*) denote low molar yields of Hyp and likely sites of arabinogalactan polysaccharide attachment in glycosylated (GAGP)$_3$-EGFP. For example, yields were 480 pM Asp in the first cycle, 331 pM Ser in the second, 194 pM Hyp in the third, and 508 pM Ser in the fourth cycle.

FIGS. 16A and 16B depict the exemplary (A) nucleotide sequence (SEQ ID NO:130) and amino acid sequence (SEQ ID NO:131) of two GAGP repeats, and (B) nucleotide sequence (SEQ ID NO:132) and amino acid sequence (SEQ ID NO:133) of four GAGP repeats (SEQ ID NOs:133).

FIG. 20 shows sample photographs of expressed EGFP fusion proteins. Panel A: VYK-EGFP; Panel B: VFL-EGFP.

FIG. 22 shows the DNA sequence of EGFP-LeAGP-1 (SEQ ID NO: 265) and the corresponding primary amino acid sequence (SEQ ID NO: 266). Underlined are the regions of this gene common to the oligonucleotides used to introduce the restriction sites (bold and labeled), enabling the construction of plasmids described in Example 26. The chymotrypsin-labile Try residue engineered into the fusion glycoprotein to allow removal of EGFP form LeAGP-1 is encoded in the BsrG1 restriction site.

DEFINITIONS

Figure 2:
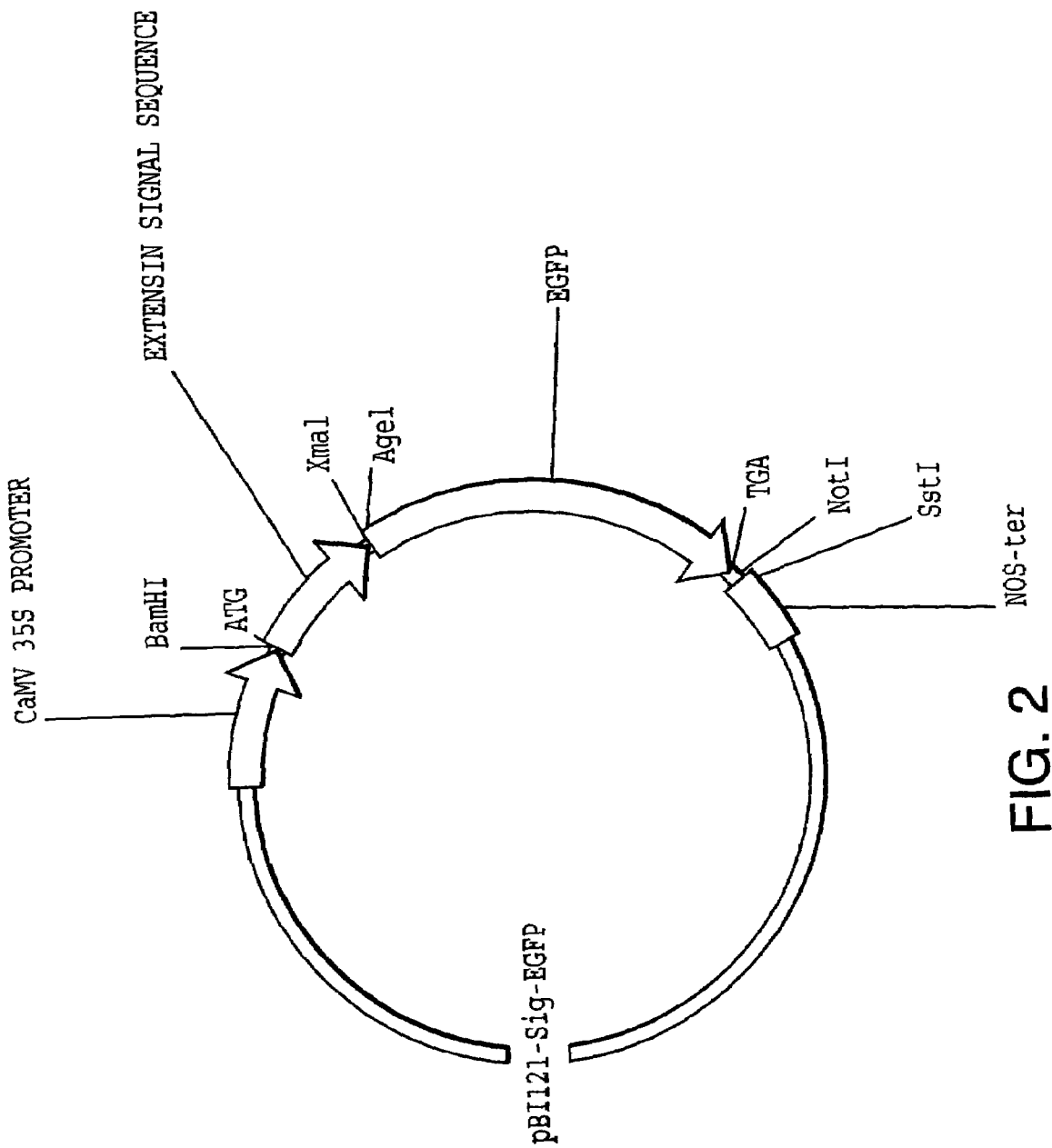
FIG. 2 shows one embodiment of a synthetic gene in one embodiment of an expression vector.

The term "gene" refers to a DNA sequence that comprises control and coding sequences necessary for the production of a polypeptide or its precursor. The polypeptide can be encoded by a full length coding sequence or by any portion of the coding sequence.

The term "nucleic acid sequence of interest" refers to any nucleic acid sequence the manipulation of which may be deemed desirable for any reason by one of ordinary skill in the art (e.g., confer improved qualities).

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "targeting vector" or "targeting construct" refer to oligonucleotide sequences comprising a gene of interest flanked on either side by a recognition sequence which is capable of homologous recombination of the DNA sequence located between the flanking recognition sequences.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "transformation" as used herein refers to the introduction of foreign DNA into cells. Transformation of a plant cell may be accomplished by a variety of means known in the art including particle mediated gene transfer (see, e.g., U.S. Pat. No. 5,584,807 hereby incorporated by reference); infection with an *Agrobacterium* strain containing the foreign DNA for random integration (U.S. Pat. No. 4,940,838 hereby incorporated by reference) or targeted integration (U.S. Pat. No. 5,501,967 hereby incorporated by reference) of the foreign DNA into the plant cell genome; electroinjection (Nan et al. (1995) In "Biotechnology in Agriculture and Forestry," Ed. Y. P. S. Bajaj, Springer-Verlag Berlin Heidelberg, Vol 34:145-155; Griesbach (1992) HortScience 27:620); fusion with liposomes, lysosomes, cells, minicells or other fusible lipid-surfaced bodies (Fraley et al. (1982) *Proc. Natl. Acad. Sci. USA* 79:1859-1863; polyethylene glycol (Krens et al. (1982) *Nature* 296:72-74); chemicals that increase free DNA uptake; transformation using virus, and the like.

The terms "infecting" and "infection" with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens,* (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208) are referred to as "nopaline-type" *Agrobacteria; Agrobacterium* strains which cause production of octopine (e.g., strain LBA4404, Ach5, B6) are referred to as "octopine-type" *Agrobacteria;* and *Agrobacterium* strains which cause production of agropine (e.g., strain EHA105, EHA101, A281) are referred to as "agropine-type" *Agrobacteria*.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

The term "microwounding" when made in reference to plant tissue refers to the introduction of microscopic wounds in that tissue. Microwounding may be achieved by, for example, particle or biolistic bombardment.

The term "transgenic" when used in reference to a plant cell refers to a plant cell which comprises a transgene, or whose genome has been altered by the introduction of a transgene. The term "transgenic" when used in reference to a plant refers to a plant which comprises one or more cells which contain a transgene, or whose genome has been altered by the introduction of a transgene. These transgenic cells and transgenic plants may be produced by several methods including the introduction of a "transgene" comprising nucleic acid (usually DNA) into a target cell or integration into a chromosome of a target cell by way of human intervention, such as by the methods described herein.

The term "transgene" as used herein refers to any nucleic acid sequence which is introduced into the genome of a plant cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include mutated wild-type genes (i.e., wild-type genes that have been modified such that they are no longer wild-type genes), reporter genes, transcriptional and translational regulatory sequences, selectable marker proteins (e.g., proteins which confer drug resistance), etc.

As used herein, the term "probe" when made in reference to an oligonucleotide (i.e., a sequence of nucleotides) refers to an oligonucleotide, whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. Oligonucleotide probes may be labelled with a "reporter molecule," so that the probe is detectable using a detection system. Detection systems include, but are not limited to, enzyme, fluorescent, radioactive, and luminescent systems.

The term "selectable marker" as used herein, refer to a gene which encodes an enzyme having an activity that confers resistance to an antibiotic or drug upon the cell in which the selectable marker is expressed. Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "amplification" is defined as the production of additional copies of a nucleic acid sequence and is generally carried out using polymerase chain reaction technologies well known in the art [Dieffenbach C W and G S Dveksler (1995) *PCR Primer, a Laboratory Manual,* Cold Spring Harbor Press, Plainview N.Y.]. As used herein, the term "polymerase chain reaction" ("PCR") refers to the method disclosed in U.S. Pat. Nos. 4,683,195, 4,683,202 and 4,965,188, all of which are hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With modern methods of PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

The present invention contemplates using amplification techniques such as PCR to obtain the cDNA (or portions thereof) of plant genes encoding plant gums and other hydroxyproline-rich polypeptides. In one embodiment, primers are designed using the synthetic gene sequences (e.g. containing sequences encoding particular motifs) described herein and PCR is carried out (using genomic DNA or other source of nucleic acid from any plant capable of producing a gum exudate) under conditions of low stringency. In another embodiment, PCR is carried out under high stringency. The amplified products can be run out on a gel and isolated from the gel.

The term "hybridization" as used herein refers to any process by which a strand of nucleic acid joins with a complementary strand through base pairing [Coombs J (1994) *Dictionary of Biotechnology,* Stockton Press, New York N.Y.].

As used herein, the terms "complementary" or "complementarity" when used in reference to polynucleotides refer to polynucleotides which are related by the base-pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions when used in reference to nucleic acid hybridization comprise conditions equivalent to binding or hybridization at 68° C. in a solution consisting of 5×SSPE (43.8 g/l NaCl, 6.9 g/l $NaH_2PO_4.H_2O$ and 1.85 g/l EDTA, pH adjusted to 7.4 with NaOH), 1% SDS, 5× Denhardt's reagent [50× Denhardt's contains the following per 500 ml: 5 g Ficoll (Type 400, Pharmacia), 5 g BSA (Fraction V; Sigma)] and 100 µg/ml denatured salmon sperm DNA followed by washing in a solution comprising 0.2× SSPE, and 0.1% SDS at room temperature when a DNA probe of about 100 to about 1000 nucleotides in length is employed.

High stringency conditions when used in reference to nucleic acid hybridization comprise conditions equivalent to binding or hybridization at 68° C. in a solution consisting of 5×SSPE, 1% SDS, 5× Denhardt's reagent and 100 µg/ml denatured salmon sperm DNA followed by washing in a solution comprising 0.1×SSPE, and 0.1% SDS at 68° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

As used herein, the term "fusion protein" refers to a chimeric protein containing the protein of interest (i.e., GAGP and fragments thereof) joined to an exogenous protein fragment (the fusion partner which consists of a non-GAGP sequence). The fusion partner may provide a detectable moiety, may provide an affinity tag to allow purification of the recombinant fusion protein from the host cell, or both. If desired, the fusion protein may be removed from the protein of interest (i.e., GAGP protein or fragments thereof) by a variety of enzymatic or chemical means known to the art. In an alternative embodiment, the fusion proteins of the invention may be used as substrates for plant glycosyl transfgerases. For example after deglycosylation, the exemplary (Ser-Hyp)$_{32}$-EGFP (see Example 23;(Ser-Hyp)$_{32}$ disclosed as SEQ ID NO: 275) may be used as an acceptor for galactose addition, with UDP-galactose as co-substrate, catalyzed by galactosyl transferase. The fusion partner EGFP allows facile isolation of the newly galactosyalted polypeptide. Fusion proteins containing sequences of the invention may be isolated using methods known in the art, such as gel filtration (Example 22), hydrophobic interaction chromatograph (HIC), reverse phase chromatography, and anion exchange chromatography.

As used herein the term "non-gum arabic glycoprotein" or "non-gum arabic glycoprotein sequence" refers to that portion of a fusion protein which comprises a protein or protein sequence which is not derived from a gum arabic glycoprotein.

The term "protein of interest" as used herein refers to the protein whose expression is desired within the fusion protein. In a fusion protein the protein of interest (e.g., GAGP) will be joined or fused with another protein or protein domain (e.g., GFP), the fusion partner, to allow for enhanced stability of the protein of interest and/or ease of purification of the fusion protein.

As used herein, the term "purified" or "to purify" refers to the removal of contaminants from a sample. For example, recombinant HRGP polypeptides, including HRGP-GFP fusion proteins are purified by the removal of host cell components such as nucleic acids, lipopolysaccharide (e.g., endotoxin). "Substantially purified" molecules are at least 60% free, preferably at least 75% free, and more preferably at least 90% free from other components with which they are naturally associated.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

As used herein the term "portion" when in reference to a protein (as in "a portion of a given protein") refers to fragments of that protein. The fragments may range in size from four (4) amino acid residues to the entire amino acid sequence minus one amino acid. Thus, a portion of an amino acid sequence which is 30 nucleotides long refers to any fragment of that sequence which ranges in size from 4 to 29 contiguous amino acids of that sequence. A polypeptide comprising "at least a portion of" an amino acid sequence comprises from four (4) contiguous amino acid residues of the amino acid sequence to the entire amino acid sequence. When made in reference to a nucleic acid sequence, the term "portion" means a fragment which ranges in size from twelve (12) nucleic acids to the entire nucleic acid sequence minus one nucleic acid. Thus, a nucleic acid sequence comprising "at least a portion of" a nucleotide sequence comprises from twelve (12) contiguous nucleotide residues of the nucleotide sequence to the entire nucleotide sequence.

The term "isolated" when used in relation to a nucleic acid, as in "an isolated nucleic acid sequence" refers to a nucleic acid sequence that is identified and separated from at least one contaminant nucleic acid with which it is ordinarily associated in its natural source.

The terms "motif" and "module" are equivalent terms when made in reference to an amino acid sequence, and refer to the particular type, number, and arrangement of amino acids in that sequence. For example, an elastin module comprises at least four amino acids (i.e., for example, VGVP (SEQ ID NO: 276), GVPG (SEQ ID NO: 277) or VPGVP (SEQ ID NO: 278). Preferably, an elastin module comprises at least ten amino acids (i.e., for example, VGVPGVGVPG). (SEQ ID NO: 279). For example, an extensin module comprises repeated SOOOOTO (SEQ ID NO: 280) segments interspersed by VKY (SEQ ID NO: 256). Preferably, an extension module comprises at least six amino acids, more preferably ten amino acids, and most preferably twenty-five amino acids. For example, a "crosslinkage motif" comprises any amino acid that is capable of crosslinking. Preferably, a crosslinkage motif comprises tyrosine, more preferably an amino acid triplet VKY (SEQ ID NO: 256), and most preferably an amino acid quadruplet YYYK (SEQ ID NO: 250).

The term "glycomodule" refers to a glycopeptide in which the carbohydrate portion is covalently linked to an amino acid sequence motif.

The term "repeating sequence" when made in reference to a peptide sequence that is contained in a polypeptide sequence means that the peptide sequence is reiterated from 1 to 10 times, more preferably from 1 to 100 times, and most preferably from 1 to 1000 times, in the polypeptide sequence. The repeats of the peptide sequence may be non-contiguous or contiguous. The term "non-contiguous repeat" when made in reference to a repeating peptide sequence means that at least one amino acid (or amino acid analog) is placed between the repeating sequences. The term "contiguous repeat" when made in reference to a repeating peptide sequence means that there are no intervening amino acids (or amino acid analogs) between the repeating sequences.

The term "self-orientation" or "self-alignment" as used herein, refers to a final molecular configuration driven by inherent forces. Preferably, these forces are ionic and steric interactions between neighbooring molecular groups.

The term "crosslinking" as used herein, refers to any covalent, ionic, or Van der Waals bonding occurring between neighbooring molecular groups. Crosslinking may be either intramolecular or intermolecular. Preferably, a covalent crosslink comprises isodityrosine.

The term "rigid molecule" as used herein, refers to a polymer compound that resists any conformation changes.

The term "non-rigid molecule" as used herein, refers to a polymer compound that is flexible and does not resist conformational changes.

GENERAL DESCRIPTION OF THE INVENTION

The present invention relates generally to the field of plant gums and other hydroxyproline-rich glycoproteins, and in particular, to the expression of synthetic genes designed from repetitive peptide sequences. The hydroxyproline-rich glycoprotein (HRGP) superfamily is ubiquitous in the primary cell wall or extracellular matrix throughout the plant kingdom. Family members are diverse in structure and implicated in all aspects of plant growth and development. This includes plant responses to stress imposed by pathogenesis and mechanical wounding.

Plant HRGPs have no known animal homologs. Furthermore, hydroxyproline residues are O-glycosylated in plant glycoproteins but never in animals. At the molecular level the function of these unique plant glycoproteins remains largely unexplored.

HRGPS are, to a lesser or greater extent, extended, repetitive, modular proteins. The modules are small (generally 4-6 amino acid residue motifs), usually glycosylated, with most HRGPs being made up of more than one type of repetitive module. For purposes of constructing the synthetic genes of the present invention, it is useful to view the glycosylated polypeptide modules not merely as peptides or oligosaccharides but as small functional motifs.

The description of the invention involves A) the design of the polypeptide of interest, B) the production of synthetic genes encoding the polypeptide of interest, C) the construction of the expression vectors, D) selection of the host cells, E) introduction of the expression construct into a particular cell (whether in vitro or in vivo), F) preferred consensus sequences and portions thereof, and G) O-glycosylation codes.

A. Design of the Polypeptide of Interest

The present invention contemplates polypeptides that are fragments of hydroxyproline-rich glycoproteins (HRGPs), repetitive proline-rich proteins (RPRPs) and arabinogalactan-proteins (AGPs). The present invention contemplates portions of HRGPs comprising one or more of the highly conserved Ser-Hyp$_4$ (SEQ ID NO:3) motif(s). The present invention also contemplates portions of RPRPs comprising one or more of the pentapeptide motif: Pro-Hyp-Val-Tyr-Lys (SEQ ID NO:4). The present invention also contemplates portions of AGPs comprising one or more Xaa-Hyp-Xaa-Hyp (SEQ ID NO:9) repeats.

While an understanding of the natural mechanism of glycosylation is not required for the successful operation of the present invention, it is believed that in GAGP and other HRGPs, repetitive Xaa-Hyp motifs constitute a Hyp-glycosylation code where Hyp occurring in contiguous motifs (Xaa-Hyp-Hyp) and Hyp occurring in non-contiguous Hyp repeats is recognized by different enzymes: arabinosyltransferases and galactosyltransferases, respectively.

The RPRPs (and some nodulins) consist of short repetitive motifs (e.g. Soybean RPRP1: [POVYK]$_n$ where O=Hyp; SEQ ID NO: 281) containing the least amount of contiguous Hyp. They also exemplify the low end of the glycosylation range with relatively few Hyp residues arabinosylated and no arabinogalactan polysaccharide. For example, in soybean RPRP1, L-arabinofuranose is attached to perhaps only a single Hyp residue in the molecule.

The Extensins occupy an intermediate position in the glycosylation continuum, containing about 50% carbohydrate which occurs mainly as Hyp-arabinosides (1-4 Ara residues), but not as Hyp-arabinogalactan polysaccharide. Extensins contain the repetitive, highly arabinosylated, diagnostic Ser-Hyp$_4$ (SEQ ID NO:3) glycopeptide module. The precise function of this module is unknown, but earlier work indicates that these motifs of arabinosylated Hyp help stabilize the extended polyproline-II helix of the extensins. Monogalactose also occurs on the Ser residues.

The classical Ser-Hyp$_4$ (SEQ ID NO:3) glycopeptide module is of special interest. A tetra-L-arabinofuranosyl oligosaccharide is attached to each Hyp residue in the motif. Three uniquely b-linked arabinofuranosyl residues and an a-linked nonreducing terminus comprise the tetraarabinooligosaccharide. While an understanding of the natural mechanism of glycosylation is not required for the successful operation of the present invention, it is believed that the arabinosylated Hyp residues together with the single galactosyl-serine residue undoubtedly form a unique molecular surface topography which interacts with and is recognized by other wall components, possibly including itself. Shorter motifs of Hyp, namely $Hyp_3$ and $Hyp_2$, lack the fourth (a-linked) arabinose residue, again suggesting that the fourth Ara unique to the $Hyp_4$ motif (SEQ ID NO: 282), has a special role and is presented for recognition or cleavage.

Tetra-arabinose and tri-arabinose are attached to known tetra-Hyp motifs (SEQ ID NO: 282). Those Ser-$Hyp_4$ (SEQ ID NO: 3) isolated from native extensins have every Hyp residue arabinosylated. However, the Ser-$Hyp_4$ (SEQ ID NO: 3) repeats fused to EGFP as disclosed herein showed that some Hyp residues were nonglycosylated, while some were mono- and di-arabinosylated. Mainly, the Hyp residues were tri-arabinosylated and tetra-arabinosylated. For example, Hyp-$Ara_4$ (SEQ ID NO: 200) was 31% of total Hyp, Hyp-$Ara_3$ (SEQ ID NO: 201) was 52% of total Hyp, Hyp-$Ara_2$ (SEQ ID NO: 202) was 8% of total Hyp, and Hyp-Ara (SEQ ID NO: 203) was 2% of total Hyp. 7% of the total Hyp was not glyscosylated. Most of the serine residues in the invention's exemplary Ser-$Hyp_4$ (SEQ ID NO: 3) repeats fused to EGFP were not galactosylated. This is in contrast to naturally occurring Ser-$Hyp_4$ (SEQ ID NO: 3) in which Ser is often mono-galactosylated. Importantly, Hyp-polysaccharide were never detected by the inventors in the Ser-$Hyp_4$ (SEQ ID NO: 3)repeats fused to EGFP.

At the high end of the glycosylation range (~90% sugar), the arabinogalactan-proteins (AGPs) and the related gum arabic glycoprotein (GAGP) are uniquely glycosylated with arabinogalactan polysaccharides. GAGP and all AGPs so far characterized by Hyp-glycoside profiles contain Hyp-linked arabinosides assigned to contiguous Hyp residues by the Hyp contiguity hypothesis. However these glycoproteins also uniquely contain Xaa-Hyp-Xaa-Hyp (SEQ ID NO:9) repeats. These repeats are putative polysaccharide attachment sites.

The present invention contemplates in particular fragments of gum arabic glycoprotein (GAGP). As noted above, GAGP has been largely refractory to chemical analysis. Prior to the inventors' discovery of the sequences disclosed herein, the largest peptide obtained and sequenced from gum arabic was a peptide of twelve (12) amino acids having the sequence Ser-Hyp-Ser-Hyp-Thr-Hyp-Thr-Hyp-Hyp-Hyp-Gly-Pro (SEQ ID NO:13). C. L. Delonnay, "Determination of the Protein Constituent Of Gum Arabic" Master of Science Thesis (1993). The present invention contemplates using this Delonnay sequence as well as (heretofore undescribed) larger peptide fragments of GAGP (and variants thereof) for the design of synthetic genes. In this manner, "designer plant gums" can be produced ("designer extensins" are also contemplated).

In one embodiment, the present invention contemplates a substantially purified polypeptide comprising at least a portion of the amino acid consensus sequence Ser-Hyp-Hyp-Hyp-[Hyp/Thr]-Leu-Ser-Hyp-Ser-Hyp-Thr-Hyp-Thr-Hyp-Hyp-Hyp-Gly-Pro-His (SEQ ID NO:1 and SEQ ID NO:2) or variants thereof. While an understanding of the natural mechanism of glycosylation is not required for the successful operation of the present invention, it is believed that this GAGP 19-amino acid consensus repeat (which contains both contiguous Hyp and non-contiguous Hyp repeats) is glycosylated in native GAGP with both Hyp-arabinosides and Hyp-polysaccharide in molar ratios. It is further believed that the high molecular weight protein component of gum arabic (i.e. GAGP) is responsible for the remarkable (and advantageous) emulsifying and stabilizing activity exploited by the food and soft drink industries.

The sequences of the invention may be used to isolate hydroxyproline rich glycoprotein-binding molecules. For example, polypeptides encoded by the invention's polynucloetide sequences may be immobilized (covalently or non-covalently) on solid supports or resins for use in isolating HRGP-binding molecules from a variety of sources (e.g. algae, plants, animals, microorganisms). Generic methods for immobilizing polypeptides are known in the art using commercially available kits. For example, the desired polypeptide sequence may be expressed as a fusion protein with heterologous protein A which allows immobilization of the fusion protein on immobilized immunoglobulin. Additionally, pGEX vectors (Promega, Madison Wis.) may be used to express the desired polypeptides as a fusion protein with glutathione S-transferase (GST) which may be adsorbed to glutathione-agarose beads.

The invention's sequences may also be used to make polyclonal and monoclonal antibodies. Generic methods for generating polyclonal and monoclonal antibodies are known in the art. For example, monoclonal antibodies may be generated using the methods of Kohler and Milstein (1976) Eur. J. Immunol. 6:511-519 (Exhibit B) and of J. Goding (1986) In "Monoclonal Antibodies: Principles and Practice," Academic Press, pp 59-103.

B. Production of Synthetic Genes

The present invention contemplates the use of synthetic genes engineered for the expression of repetitive glycopeptide modules in cells, including but not limited to callus and suspension cultures. It is not intended that the present invention be limited by the precise number of repeats.

In one embodiment, the present invention contemplates the nucleic acid sequences encoding the consensus sequence for GAGP (i.e. SEQ ID NO: 1 and SEQ ID NO:2) or variants thereof may be used as a repeating sequence between two (2) and up to fifty (50) times, more preferably between ten (10) and up to thirty (30) times, and most preferably approximately twenty (20) times. The nucleic acid sequence encoding the consensus sequence (i.e. SEQ ID NO:1 and SEQ ID NO:2) or variants thereof may be used as contiguous repeats or may be used as non-contiguous repeats.

In designing any HRGP gene cassette the following guidelines are employed:

1) Minimization of the repetitive nature of the coding sequence while still taking into account the HRGP codon bias of the host plant (e.g., when tomato is the host plant, the codon usage bias of the tomato which favors CCA and CCT [but not CCG] for Pro residues, and TCA and TCC for Ser residues is employed). *Zea mays (such as corn) and perhaps other graminaceous monocotyledons (e.g. rice barley, wheat and all grasses) prefer CCG and CCC for proline; GTC and CTT for valine; and AAG for lysine. Dicotyledons (including legumes) prefer CCA and CCT for proline and TCA and TCT for serine.*

2) Minimization of strict sequence periodicity.

3) Non-palindromic ends are used for the monomers and end linkers to assure proper "head-to-tail" polymerization.

4) The constructs contain no internal restriction enzyme recognition sites for the restriction enzymes employed for the insertion of these sequences into expression vectors or during subsequent manipulations of such vectors. Typically, the 5' linker contains a XmaI site downstream of the BamHI site used for cloning into the cloning vector (e.g., pBluescript). The XmaI site is used for insertion of the HRGP gene cassette into the expression vector (e.g., pBI121-Sig-EGFP). Typically, the 3' linker contains a AgeI site upstream of the EcoRI site used for cloning into the cloning vector (e.g., pBluescript). The AgeI site is used for insertion of the HRGP gene cassette into the expression vector. [For plasmid pBI121-Sig—which does not contain GFP for the fusion protein—the same signal sequence (SS) is used, but the 3' linkers contain an Sst I restriction site for insertion as an Xma I/Sst I fragment behind the signal sequence and before the NOS terminator].

5) The oligonucleotides used are high quality (e.g., from GibcoBRL, Operon) and have been purified away from unwanted products of the synthesis.

6) The $T_M$ of correctly aligned oligomers is greater than the $T_M$ of possible dimers, hairpins or crossdimers.

One of skill in the art appreciates that the hydroxyproline (Hyp) residues in the sequences of the invention are produced as the result of post-translational modification of proline (Pro) residues in the polypeptide which is encoded by the gene. Thus, where a hydroxyproline residue is desired to be present in the sequences of the invention, the corresponding codon would be selected to encode proline. The Edman degradation may be used to identify which Pro residues had been hydroxylated to Hyp as described in Example 23, infra.

C. Construction of Expression Vectors

It is not intended that the present invention be limited by the nature of the expression vector. A variety of vectors are contemplated. In one embodiment, two plant transformation vectors are prepared, both derived from pBI121 (Clontech). Both contain an extensin signal sequence (SS) for transport of the constructs through the ER/Golgi for posttranslational modification. A first plasmid construct contained Green Fluorescent Protein (GFP) as a reporter protein instead of GUS. A second plasmid does not contain GFP.

pBI121 is the Jefferson vector in which the BamHI and SstI sites can be used to insert foreign DNA between the 35S CaMV promoter and the termination/polyadenylation signal from the nopaline synthase gene (NOS-ter) of the *Agrobacterium* Ti plasmid); it also contains an RK2 origin of replication, a kanamycin resistance gene, and the GUS reporter gene.

Signal Sequences. As noted above, the GUS sequence is replaced (via BamHI/SstI) with a synthetic DNA sequence encoding a peptide signal sequence based on the extensin signal sequences of *Nicotiana plumbaginifolia* and *N. tabacum*

MGKMASLFATFLVVLVSLSLAQTTRVVPVASSAP (SEQ ID NO:14) The DNA sequence also contains 15 bp of the 5' untranslated region, and restriction sites for Bam HI in its 5'terminus and Sst I in its extreme 3' terminus for insertion into pBI121 in place of GUS. An XmaI restriction site occurs 16 bp upstream from the Sst I site to allow subsequent insertion of EGFP into the plasmid as a Xma I/Sst I fragment.

The sequence underlined above targets *N. plumbaginifolia* extensin fusion proteins through the ER and Golgi for post-translational modifications, and finally to the wall. The signal sequence proposed also involves transport of extensins and extensin modules in the same plant family (*Solanaceae*). Alternatively, one can use the signal sequence from tomato P1 extensin itself.

TABLE 1

GFP MUTANTS

| MUTANT | WAVELENGTH (nm) | |
|---|---|---|
| | Excitation | Emitting |
| mGFPX10; F99S, M153T, V163A | Excites at 395 | |
| mGFPX10-5 | Excites at 489 | Emits at 508 |
| GFPA2; I167T | Excites at 471 | |
| GFPB7; Y66H | Excites at 382 | Emits at 440 (blue fluorescence) |
| GFPX10-C7; F99S, M153T, V163A, I167T, S175G | Excites at 395 and 473 | |
| GFPX10-D3; F99S, M153T, V163A, Y66H | Excites at 382 | Emits at 440 |

In yet another alternative, the tomato arabinogalactan-protein (Le-AGP-1) signal sequence may be used. This sequence has previously been cloned [Li (1996) "Isolation and characterization of genes and complementary DNAs encoding a tomato arabiogalactan protein, PhD. Dissertation, Ohio University, Athens, Ohio] and encodes the protein sequence MDRKFVFLVSILCIVVASVTG (SEQ ID NO:283). This sequence has successfully been used by the inventors to target expression of the inventions's sequences to the extracellular medium of tobacco cell cultures and is being used to target (Ala-Pro)$_n$-EGFP and (Thr-Pro)$_n$-EGFP to the extracellular matrix of tobacco cell cultures.

Addition of GFP. The repetitive HRGP-modules can be expressed as GFP fusion products rather than GUS fusions, and can also be expressed as modules without GFP. Fusion with a green fluorescent protein reporter gene appropriately red-shifted for plant use, e.g. EGFP (an S65T variant recommended for plants by Clontech) or other suitable mutants (see Table 1 above) allows the detection of <700 GFP molecules at the cell surface. GFP requires aerobic conditions for oxidative formation of the fluorophore. It works well at the lower temperatures used for plant cell cultures and normally it does not adversely affect protein function although it may allow the regeneration of plants only when targeted to the ER.

Promoters. As noted above, it is not intended that the present invention be limited by the nature of the promoter(s) used in the expression constructs. The CaMV35S promoter is preferred, although it is not entirely constitutive and expression is "moderate". In some embodiments, higher expression of the constructs is desired to enhance the yield of HRGP modules; in such cases a plasmid with "double" CaMV35S promoters is employed.

D. Selection of Host Cells

A variety of host cells are contemplated (both eukaryotic and prokaryotic). It is not intended that the present invention be limited by the host cells used for expression of the synthetic genes of the present invention. Plant host cells are preferred, including but not limited to legumes (e.g. soy beans) and solanaceous plants (e.g. tobacco, tomato, etc.). Other cells contemplated to be within the scope of this invention are green algae [e.g., *Chlamydomonas*, Volvox, and duckweed (Lemna)].

The present invention is not limited by the nature of the plant cells. All sources of plant tissue are contemplated. In one embodiment, the plant tissue which is selected as a target for transformation with vectors which are capable of expressing the invention's sequences are capable of regenerating a plant. The term "regeneration" as used herein, means growing a whole plant from a plant cell, a group of plant cells, a plant part or a plant piece (e.g., from seed, a protoplast, callus, protocorm-like body, or tissue part). Such tissues include but are not limited to seeds. Seeds of flowering plants consist of an embryo, a seed coat, and stored food. When fully formed, the embryo consists basically of a hypocotyl-root axis bearing either one or two cotyledons and an apical meristem at the shoot apex and at the root apex. The cotyledons of most dicotyledons are fleshy and contain the stored food of the seed. In other dicotyledons and most monocotyledonss, food is stored in the endosperm and the cotyledons function to absorb the simpler compounds resulting from the digestion of the food.

Species from the following examples of genera of plants may be regenerated from transformed protoplasts: Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura.

For regeneration of transgenic plants from transgenic protoplasts, a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. These three variables may be empirically controlled to result in reproducible regeneration.

Plants may also be regenerated from cultured cells or tissues. Dicotyledonous plants which have been shown capable of regeneration from transformed individual cells to obtain transgenic whole plants include, for example, apple (*Malus pumila*), blackberry (*Rubus*), Blackberry/raspberry hybrid (*Rubus*), red raspberry (*Rubus*), carrot (*Daucus carota*), cauliflower (*Brassica oleracea*), celery (*Apium graveolens*), cucumber (*Cucumis sativus*), eggplant (*Solanum melongena*), lettuce (*Lactuca sativa*), potato (*Solanum tuberosum*), rape (*Brassica napus*), wild soybean (*Glycine canescens*), strawberry (*Fragaria x ananassa*), tomato (*Lycopersicon esculentum*), walnut (*Juglans regia*), melon (*Cucumis melo*), grape (*Vitis vinifera*), and mango (*Mangifera indica*). Monocotyledonous plants which have been shown capable of regeneration from transformed individual cells to obtain transgenic whole plants include, for example, rice (*Oryza sativa*), rye (*Secale cereale*), and maize.

In addition, regeneration of whole plants from cells (not necessarily transformed) has also been observed in: apricot (*Prunus armeniaca*), asparagus (*Asparagus officinalis*), banana (hybrid *Musa*), bean (*Phaseolus vulgaris*), cherry (hybrid *Prunus*), grape (*Vitis vinifera*), mango (*Mangifera indica*), melon (*Cucumis melo*), ochra (*Abelmoschus esculentus*), onion (hybrid *Allium*), orange (*Citrus sinensis*), papaya (*Carrica papaya*), peach (*Prunus persica*), plum (*Prunus domestica*), pear (*Pyrus communis*), pineapple (*Ananas comosus*), watermelon (*Citrullus vulgaris*), and wheat (*Triticum aestivum*).

The regenerated plants are transferred to standard soil conditions and cultivated in a conventional manner. After the expression vector is stably incorporated into regenerated transgenic plants, it can be transferred to other plants by vegetative propagation or by sexual crossing. For example, in vegetatively propagated crops, the mature transgenic plants are propagated by the taking of cuttings or by tissue culture techniques to produce multiple identical plants. In seed propagated crops, the mature transgenic plants are self crossed to produce a homozygous inbred plant which is capable of passing the transgene to its progeny by Mendelian inheritance. The inbred plant produces seed containing the nucleic acid sequence of interest. These seeds can be grown to produce plants that would produce the desired polypeptides. The inbred plants can also be used to develop new hybrids by crossing the inbred plant with another inbred plant to produce a hybrid.

It is not intended that the present invention be limited to only certain types of plants. Both monocotyledons and dicotyledons are contemplated. Monocotyledons include grasses, lilies, irises, orchids, cattails, palms, *Zea mays* (such as corn), rice barley, wheat and all grasses. Dicotyledons include almost all the familiar trees and shrubs (other than confers) and many of the herbs (non-woody plants).

Tomato cultures are the ideal recipients for repetitive HRGP modules to be hydroxylated and glycosylated: Tomato is readily transformed. The cultures produce cell surface HRGPs in high yields easily eluted from the cell surface of intact cells and they possess the required post-translational enzymes unique to plants—HRGP prolyl hydroxylases, hydroxyproline O-glycosyltransferases and other specific glycosyltransferases for building complex polysaccharide side chains. Furthermore, tomato genetics, and tomato leaf disc transformation/plantlet regeneration are well worked out.

Other preferred recipients for the invention's sequences include tobacco cultured cells and plants.

E. Introduction of Nucleic Acid

Expression constructs of the present invention may be introduced into host cells (e.g. plant cells) using methods known in the art. In one embodiment, the expression constructs are introduced into plant cells by particle mediated gene transfer. Particle mediated gene transfer methods are known in the art, are commercially available, and include, but are not limited to, the gas driven gene delivery instrument descried in McCabe, U.S. Pat. No. 5,584,807, the entire contents of which are herein incorporated by reference. This method involves coating the nucleic acid sequence of interest onto heavy metal particles, and accelerating the coated particles under the pressure of compressed gas for delivery to the target tissue.

Other particle bombardment methods are also available for the introduction of heterologous nucleic acid sequences into plant cells. Generally, these methods involve depositing the nucleic acid sequence of interest upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles which maximizes the number of cells receiving particles under uniform conditions, resulting in the introduction of the nucleic acid sample into the target tissue.

Alternatively, an expression construct may be inserted into the genome of plant cells by infecting them with a bacterium, including but not limited to an *Agrobacterium* strain previously transformed with the nucleic acid sequence of interest. Generally, disarmed *Agrobacterium* cells are transformed with recombinant Ti plasmids of *Agrobacterium tumefaciens* or Ri plasmids of *Agrobacterium rhizogenes* (such as those described in U.S. Pat. No. 4,940,838, the entire contents of which are herein incorporated by reference) which are constructed to contain the nucleic acid sequence of interest using methods well known in the art (Sambrook, J. et al., (1989) supra). The nucleic acid sequence of interest is then stably integrated into the plant genome by infection with the transformed *Agrobacterium* strain. For example, heterologous nucleic acid sequences have been introduced into plant tissues using the natural DNA transfer system of *Agrobacterium tumefaciens* and *Agrobacterium rhizogenes* bacteria (for review, see Klee et al. (1987) Ann. Rev. Plant Phys. 38:467-486).

One of skill in the art knows that the efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* [Shahla et al. (1987) Plant Molec. Biol. 8:291-298]. Alternatively, transformation efficiency may be enhanced by wounding the target tissue to be transformed. Wounding of plant tissue may be achieved, for example, by punching, maceration, bombardment with microprojectiles, etc. [see, e.g., Bidney et al. (1992) Plant Molec. Biol. 18:301-313].

It may be desirable to target the nucleic acid sequence of interest to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (Offringa et al., (1996), U.S. Pat. No. 5,501,967, the entire contents of which are herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

Where homologous recombination is desired, the targeting vector used may be of the replacement- or insertion-type (Offringa et al. (1996), supra). Replacement-type vectors generally contain two regions which are homologous with the targeted genomic sequence and which flank a heterologous nucleic acid sequence, e.g., a selectable marker gene sequence. Replacement type vectors result in the insertion of the selectable marker gene which thereby disrupts the targeted gene. Insertion-type vectors contain a single region of homology with the targeted gene and result in the insertion of the entire targeting vector into the targeted gene.

Other methods are also available for the introduction of expression constructs into plant tissue, e.g., electroinjection (Nan et al. (1995) In "Biotechnology in Agriculture and Forestry," Ed. Y. P. S. Bajaj, Springer-Verlag Berlin Heidelberg, Vol 34:145-155; Griesbach (1992) HortScience 27:620); fusion with liposomes, lysosomes, cells, minicells or other fusible lipid-surfaced bodies (Fraley et al. (1982) *Proc. Natl. Acad. Sci. USA* 79:1859-1863; polyethylene glycol (Krens et al. (1982) *Nature* 296:72-74); chemicals that increase free DNA uptake; transformation using virus, and the like.

In one embodiment, the present invention contemplates introducing nucleic acid via the leaf disc transformation method. Horsch et al. *Science* 227:1229-1231 (1985). Briefly, disks are punched from the surface of sterilized leaves and submerged with gentle shaking into a culture of *A. tumefaciens* that had been grown overnight in Luria Broth (LB) at 28° C. The disks are then blotted dry and placed upside-down onto nurse culture plates to induce the regeneration of shoots. Following 2-3 days, the leaf disks are transferred to petri plates containing the same media without feeder cells or filter papers, but in the presence of carbenicillin (500 μg/ml) and kanamycin (300 μg/ml) to select for antibiotic resistance. 2-4 weeks later, the shoots that developed are removed from calli and placed into root-inducing media with the appropriate antibiotic. These shoots were then further transplanted into soil following the presence of root formation.

Cells and tissues which are transformed with a heterologous nucleic acid sequence of interest are readily detected using methods known in the art including, but not limited to, restriction mapping of the genomic DNA, PCR-analysis, DNA-DNA hybridization, DNA-RNA hybridization, DNA sequence analysis and the like.

Additionally, selection of transformed cells may be accomplished using a selection marker gene. It is preferred, though not necessary, that a selection marker gene be used to select transformed plant cells. A selection marker gene may confer positive or negative selection.

A positive selection marker gene may be used in constructs for random integration and site-directed integration. Positive selection marker genes include antibiotic resistance genes, and herbicide resistance genes and the like. In one embodiment, the positive selection marker gene is the NPTII gene which confers resistance to geneticin (G418) or kanamycin. In another embodiment the positive selection marker gene is the HPT gene which confers resistance to hygromycin. The choice of the positive selection marker gene is not critical to the invention as long as it encodes a functional polypeptide product. Positive selection genes known in the art include, but are not limited to, the ALS gene (chlorsulphuron resistance), and the DHFR-gene (methothrexate resistance).

A negative selection marker gene may also be included in the constructs. The use of one or more negative selection marker genes in combination with a positive selection marker gene is preferred in constructs used for homologous recombination. Negative selection marker genes are generally placed outside the regions involved in the homologous recombination event. The negative selection marker gene serves to provide a disadvantage (preferably lethality) to cells that have integrated these genes into their genome in an expressible manner. Cells in which the targeting vectors for homologous recombination are randomly integrated in the genome will be harmed or killed due to the presence of the negative selection marker gene. Where a positive selection marker gene is included in the construct, only those cells having the positive selection marker gene integrated in their genome will survive.

The choice of the negative selection marker gene is not critical to the invention as long as it encodes a functional polypeptide in the transformed plant cell. The negative selection gene may for instance be chosen from the aux-2 gene from the Ti-plasmid of *Agrobacterium,* the tk-gene from SV40, cytochrome P450 from *Streptomyces griseolus,* the Adh-gene from Maize or Arabidopsis, etc. Any gene encoding an enzyme capable of converting a substance which is otherwise harmless to plant cells into a substance which is harmful to plant cells may be used.

It is not intended that the host cells which are transformed with the invention's sequences or with expression constructs containing these sequences be limited to cells which display any particular phenotype. All that is necessary is that the transformed cells express a polypeptide encoded by the invention's sequences. Such host cells may be used to purify the expressed polypeptides for subsequent use, (e.g., in the food or cosmetic industry, for isolating HRGP-binding molecules, and for making antibodies).

Nor is the invention intended to be limited to transformed cells which express the invention's nucleotide sequences at a particular level, a particular time during the cell's life cycle, or a particular part of a transformed plant. Rather, the invention expressly contemplates cells which express relatively low and relatively high levels of expression of the desired proteins, regardless of whether such expression occurs in some or all parts of the transformed plant, and whether it changes or is unchanged in level during cell growth or plant development.

F. Preferred Consensus Sequences and Portions Thereof

The present invention provides GAGP sequences, and in particular the consensus sequence of SEQ ID NO:136. Gum arabic glycoprotein (GAGP) is a large molecular weight, hydroxyproline-rich arabinogalactan-protein (AGP) component of gum arabic. GAGP has a simple, highly biased amino acid composition indicating a repetitive polypeptide backbone. It has been suggested that the repetitive polypeptide backbone contains repetitive small (Ã10 amino acid residues) repetitive peptide motifs each with three Hyp-arabinoside attachment sites and a single Hyp-arabinogalactan polysaccharide attachment site [Qi et al. (1991) supra]. The inventors have tested this hypothesis by generating and sequencing peptides of GAGP, and determining the glycosyl and linkage analysis of an isolated Hyp-polysaccharide. Surprisingly, the inventors discovered a 19-amino acid consensus sequence, which is roughly twice the size of that previously postulated by Qi et al. (1991). In addition to the difference in size of the repeating motif, the inventors also surprisingly discovered that the peptides in the invention's 19-amino acid consensus sequence lacked some of the amino acids present in Qi et al.'s the empirical formula [i.e., $Hyp_4$ $Ser_2$ Thr Pro Gly Leu His (SEQ ID NO:135)] of the repeat motif suggested by Qi et. al.[Qi et al. (1991) supra], most notably His (Table 6, peptide PH3G2.) The inventors also surprisingly discovered that the invention's 19-amino acid GAGP consensus motif contains approximately nine Hyp residues, with only a single polysaccharide attachment site. Judging from the Hyp-glycoside profile of GAGP, the invention's consensus motif contained six Hyp-arabinosides rather than Qi et al.'s three, and two Hyp-polysaccharides rather than Qi et al's one.

The invention provides the consensus sequence (SEQ ID NO:136): A-Hyp-B-C-D-E-F-Hyp-G-H-I-Hyp-J-Hyp-Hyp-K-L-Pro-M, wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His, and Pro (Example 18, e.g., Tables 3 and 6). Also included within the scope of the invention are portions of the consensus sequence, having from 4 to 19 contiguous amino acid residues of the consensus sequence.

Figure 9:
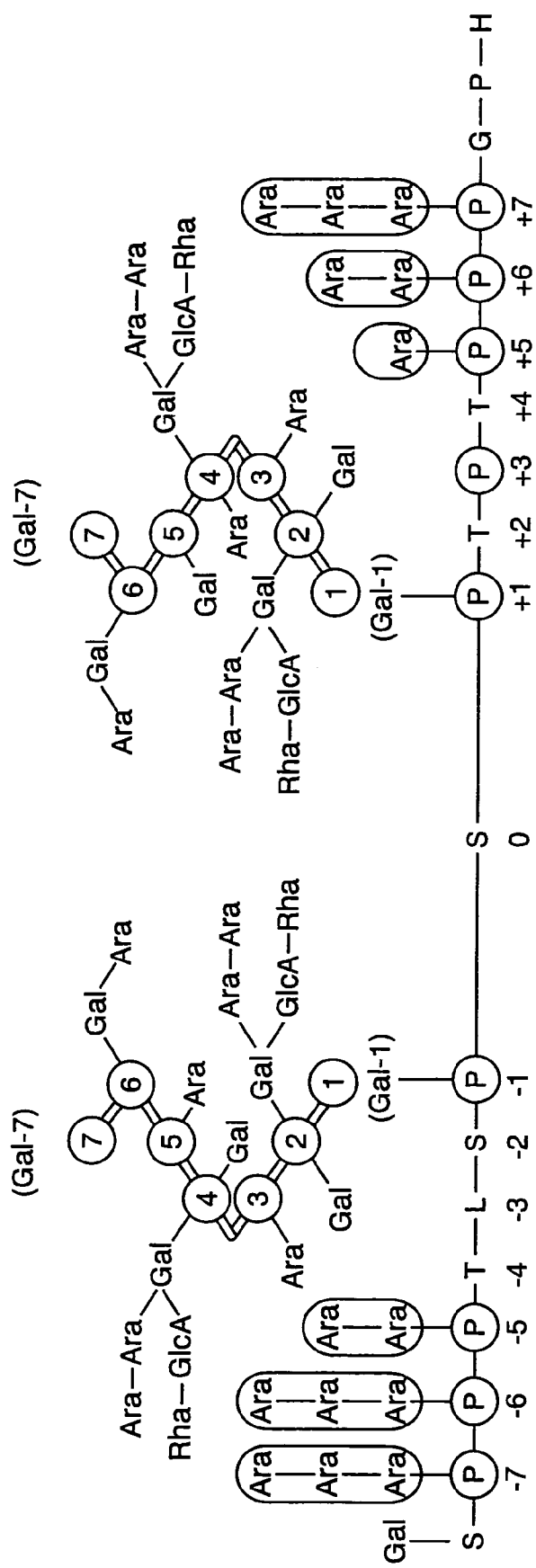
FIG. 9 shows a proposed model for an exemplary glycopeptide containing an exemplary consensus sequence. (SEQ ID NO: 296).

In a preferred embodiment, the invention's GAGP consensus sequence contains 19 amino acids, of which approximately nine are Hyp residues. Judging from the Hyp-glycoside profile of GAGP (Table 7) about one in every five Hyp residues is polysaccharide-substituted. Thus, in one preferred embodiment, there are approximately two Hyp-polysaccharide sites in the consensus sequence and portions thereof. Without limiting the invention to any particular mechanism, the inventors predicted arabinosylation of contiguous Hyp residues and arabinogalactan-polysaccharide addition to clustered non-contiguous Hyp residues, such as the X-Hyp-X-Hyp (SEQ ID NO: 9) modules common in AGPs [Nothnagel (1997) International Review of Cytology 174:195]. Also without limiting the invention to a particular theory, the inventors are of the view that the inventions's 19-amino acid consensus motif preferably contains approximately two polysaccharide attachment sites in the clustered non-contiguous Hyp motif [F-Hyp-G-H-I-Hyp (SEQ ID NO:137), where F is selected from Ser, Thr, and Ala; G is selected from Ser, Leu, Hyp, Thr, Ala, and Ile; H is selected from Hyp, Pro, Leu, and Ile; and I is selected from Thr, Ala, and Ser] which is exemplified by Ser-Hyp-Ser-Hyp-Thr-Hyp (SEQ ID NO:138)], and which is flanked by arabinosylated contiguous Hyp residues such as A-Hyp-B-C-D-E (SEQ ID NO:139) where A is selected from Ser, Thr, and Ala; B is selected from Hyp, Leu, and Ile; C is selected from Pro and Hyp; D is selected from Hyp, Ser, Thr, and Ala; E is selected from Leu and Ile; and more preferably Ser-Hyp-Hyp-Hyp-(Hyp/Thr/Ser)-Leu (SEQ ID NO:140), and such as J-Hyp-Hyp-K-L-Pro-M (SEQ ID NO:141) where J is selected from Thr, Ser, and Ala; K is selected from Thr, Leu, Hyp, Ser, Ala, and Ile; L is selected from Gly, Leu, Ala, and Ile; and M is selected from His, and Pro; and more preferably Hyp-Ser-Hyp-Thr-Hyp-Thr-Hyp-Hyp-(Hyp/Leu)-Gly-Pro-His (SEQ ID NOs:142) (FIG. 9). The following Table 2 shows 45 illustrative sequences which have from 4 to 19 amino acids and which are encompassed by the inventions' SEQ ID NO:136.

TABLE 2

Exemplary Sequences*

| Motif Number | Motif Sequence |
|---|---|
| 1 | Ser-Hyp-Hyp-Hyp-Hyp-Leu-Ser-Hyp-Ser-Hyp-Thr-Hyp-Thr-Hyp-Hyp-Leu-Gly-Pro-His (SEQ ID NO: 143) |
| 2 | Ser-Hyp-Hyp-Hyp-Thr-Leu-Ser-Hyp-Ser-Hyp-Thr-Hyp-Thr-Hyp-Hyp-Hyp-Gly-Pro-His (SEQ ID NO: 144) |
| 3 | Ser-Hyp-Hyp-Hyp-Ser-Leu-Ser-Hyp-Ser-Hyp-Thr-Hyp-Thr-Hyp-Hyp-Thr-Gly-Pro-His (SEQ ID NO: 145) |
| 4 | Ser-Hyp-Hyp-Hyp-Hyp-Leu-Ser-Hyp-Ser-Hyp-Thr-Hyp-Thr-Hyp-Hyp-Hyp-Gly-Pro-Hyp (SEQ ID NO: 146) |
| 5 | Ser-Hyp-Leu-Pro-Thr-Leu-Ser-Hyp-Leu-Pro-Thr-Hyp-Thr-Hyp-Hyp-Hyp-Gly-Pro-His (SEQ ID NO: 147) |
| 6 | Ser-Hyp-Leu-Pro-Thr-Leu-Ser-Hyp-Leu-Pro-Ala-Hyp-Thr-Hyp-Hyp-Hyp-Gly-Pro-His (SEQ ID NO: 148) |
| 7 | Ser-Hyp-Hyp-Hyp-Hyp-Leu-Ser-Hyp-Ser-Leu-Thr-Hyp-Thr-Hyp-Hyp-Leu-Gly-Pro-Hyp (SEQ ID NO: 149) |
| 8 | Ser-Hyp-Hyp-Hyp-Hyp-Leu-Ser-Hyp-Ser-Hyp-Thr-Hyp-Thr-Hyp-Hyp-Hyp-Gly-Pro-His (SEQ ID NO: 150) |
| 9 | Ser-Hyp-Hyp-Hyp-Thr-Leu-Ser-Hyp-Ser-Hyp-Thr-Hyp-Thr-Hyp-Hyp-Hyp-Gly-Pro-His (SEQ ID NO: 151) |
| 10 | Ser-Hyp-Hyp-Hyp-Hyp-Leu-Ser-Hyp-Ser-Hyp-Ala-Hyp-Thr-Hyp-Hyp-Hyp-Gly-Pro-His (SEQ ID NO: 152) |
| 11 | Ser-Hyp-Hyp-Hyp-Hyp-Leu-Ser-Hyp-Leu-Pro-Thr-Hyp-Thr-Hyp-Hyp-Leu-Gly-Pro-His (SEQ ID NO: 153) |
| 12 | Ser-Hyp-Hyp-Hyp-Ser-Leu-Ser-Hyp-Leu-Pro-Thr-Hyp-Thr-Hyp-Hyp-Leu-Gly-Pro-His (SEQ ID NO: 154) |
| 13 | Ser-Hyp-Hyp-Hyp-Thr-Leu-Ser-Hyp-Hyp-Leu-Thr-Hyp-Thr-Hyp-Hyp-Leu-Leu-Pro-His (SEQ ID NO: 155) |
| 14 | Hyp-Hyp-Thr-Leu-Ser-Hyp-Hyp-Leu-Thr-Hyp-Thr-Hyp-Hyp-Leu-Leu-Pro (SEQ ID NO: 156) |
| 15 | Ser-Hyp-Hyp-Ser-Leu-Ser-Hyp-Leu-Pro-Thr-Hyp-Thr-Hyp-Hyp-Leu (SEQ ID NO: 157) |
| 16 | Hyp-Hyp-Leu-Ser-Hyp-Leu-Pro-Thr-Hyp-Thr-Hyp-Hyp-Leu-Gly-Pro-His (SEQ ID NO: 158) |
| 17 | Ser-Hyp-Hyp-Hyp-Thr-Leu-Ser-Hyp-Ser-Hyp-Thr-Hyp-Thr-Hyp (SEQ ID NO: 159) |

TABLE 2-continued

Exemplary Sequences*

| Motif Number | Motif Sequence |
|---|---|
| 18 | Leu-Ser-Hyp-Ser-Leu-Thr-Hyp-Thr-Hyp-Hyp-Leu-Gly-Pro-Hyp (SEQ ID NO: 160) |
| 19 | Hyp-Thr-Leu-Ser-Hyp-Leu-Pro-Ala-Hyp-Thr-Hyp-Hyp-Hyp-Gly (SEQ ID NO: 161) |
| 20 | Ser-Hyp-Hyp-Hyp-Hyp-Leu-Ser-Hyp-Ser-Hyp-Thr-Hyp (SEQ ID NO: 162) |
| 21 | Ser-Leu-Ser-Hyp-Ser-Hyp-Thr-Hyp-Thr-Hyp-Hyp-Thr (SEQ ID NO: 163) |
| 22 | Hyp-Hyp-Thr-Leu-Ser-Hyp-Ser-Hyp-Thr-Hyp-Thr-Hyp (SEQ ID NO: 164) |
| 23 | Hyp-Thr-Hyp-Thr-Hyp-Hyp-Leu-Gly-Pro-His (SEQ ID NO: 165) |
| 24 | Hyp-Hyp-Thr-Leu-Ser-Hyp-Hyp-Leu-Thr-Hyp (SEQ ID NO: 166) |
| 25 | Ser-Hyp-Hyp-Hyp-Ser-Leu-Ser-Hyp-Leu-Pro (SEQ ID NO: 167) |
| 26 | Hyp-Thr-Hyp-Hyp-Leu-Gly-Pro-His (SEQ ID NO: 168) |
| 27 | Hyp-Leu-Ser-Hyp-Ser-Hyp-Ala-Hyp (SEQ ID NO: 169) |
| 28 | Hyp-Hyp-Hyp-Thr-Leu-Ser-Hyp-Ser (SEQ ID NO: 170) |
| 29 | Thr-Hyp-Hyp-Hyp-Gly-Pro (SEQ ID NO: 171) |
| 30 | Hyp-Hyp-Leu-Ser-Hyp-Ser (SEQ ID NO: 172) |
| 31 | Ser-Hyp-Leu-Pro-Ala-Hyp (SEQ ID NO: 173) |
| 32 | Leu-Pro-Thr-Leu-Ser-Hyp (SEQ ID NO: 174) |
| 33 | Ser-Hyp-Ser-Hyp (SEQ ID NO: 175) |
| 34 | Ser-Hyp-Thr-Hyp (SEQ ID NO: 176) |
| 35 | Thr-Hyp-Thr-Hyp (SEQ ID NO: 177) |
| 36 | Thr-Hyp-Hyp-Hyp (SEQ ID NO: 178) |
| 37 | Ser-Hyp-Pro-Pro-Pro-Leu-Ser-Hyp-Ser-Hyp-Thr-Hyp-Thr-Hyp-Hyp-Leu-Gly-Pro-His (SEQ ID NO: 217) |
| 38 | Ser-Hyp-Hyp-Pro-Pro-Leu-Ser-Hyp-Ser-Hyp-Thr-Hyp-Thr-Hyp-Hyp-Leu-Gly-Pro-His (SEQ ID NO: 218) |
| 39 | Ser-Hyp-Pro-Hyp-Pro-Leu-Ser-Hyp-Ser-Hyp-Thr-Hyp-Thr-Hyp-Hyp-Leu-Gly-Pro-His (SEQ ID NO: 219) |
| 40 | Ser-Hyp-Pro-Pro-Hyp-Leu-Ser-Hyp-Ser-Hyp-Thr-Hyp-Thr-Hyp-Hyp-Leu-Gly-Pro- |

TABLE 2-continued

Exemplary Sequences*

| Motif Number | Motif Sequence |
|---|---|
| | His<br>(SEQ ID NO: 220) |
| 41 | Ser-Hyp-Hyp-Hyp-Pro-Leu-Ser-Hyp-Ser-Hyp-Thr-Hyp-Thr-Hyp-Hyp-Leu-Gly-Pro-His<br>(SEQ ID NO: 221) |
| 42 | Ser-Hyp-Hyp-Pro-Hyp-Leu-Ser-Hyp-Ser-Hyp-Thr-Hyp-Thr-Hyp-Hyp-Leu-Gly-Pro-His<br>(SEQ ID NO: 222) |
| 43 | Ser-Hyp-Pro-Hyp-Hyp-Leu-Ser-Hyp-Ser-Hyp-Thr-Hyp-Thr-Hyp-Hyp-Leu-Gly-Pro-His<br>(SEQ ID NO: 223) |
| 44 | Ser-Hyp-Hyp-Hyp-Hyp-Leu-Ser-Hyp-Ser-Pro-Thr-Hyp-Thr-Hyp-Hyp-Leu-Gly-Pro-His<br>(SEQ ID NO: 224) |
| 45 | Ser-Hyp-Hyp-Hyp-Hyp-Leu-Ser-Hyp-Ser-Leu-Thr-Hyp-Thr-Hyp-Hyp-Leu-Gly-Pro-His<br>(SEQ ID NO: 225) |

*It is preferred, for gene design, that the last three amino acid sequences (e.g., Gly-Pro-Xaa) be moved from the end to the front of the DNA sequence. Most of the Pro residues will be post-translationally modified to Hyp and glycosylated when expressed in plants - Hyp glycosylation is crucial for function. This table does not list every variation that can be derived from the consensus sequence.

In one preferred embodiment, the consensus sequence and portions thereof is selected from Ser-Hyp-Hyp-Hyp-A-Leu-Ser-Hyp-Ser-Hyp-Thr-Hyp-Thr-Hyp-Hyp-B-Gly-Pro-His (SEQ ID NO:179), where A is selected from Hyp, Thr and Ser, and B is selected from Hyp and Leu (Table 6). Remarkably, fifteen amino acid residues of this sequence are "quasi-palindromic," i.e., the side chain sequence is almost the same whether read from the N-terminus or C-terminus. Without limiting the invention to a particular theory or mechanism, it is the inventors' consideration that such peptide symmetry, which occurs frequently in extensins and AGPs, may enhance molecular packing, recognition, and self-assembly. Indeed, palindromic symmetry rigidified by contiguous Hyp motifs in the motifs: Ser-Hyp-Hyp-Hyp-(Hyp) (SEQ ID NO: 3) and Thr-Hyp-Hyp-(Hyp) (SEQ ID NO: 212), may impart self-ordering properties in GAGP and other HRGPs. Thus, it is the inventor's consideration that GAGP properties are related to the polysaccharide substituents. In particular, the repeating glycopeptide symmetry of two central polysaccharides flanked by Hyp arabinosides may enhance gum arabic's remarkable properties which include: an anomalously low viscosity [Churms et al. (1983) Carbohydrate Research 123:267], the ability to act as a flavor emulsifier and stabilizer, and GAGP's biological role as a component of a plastic sealant.

In one embodiment, the invention's sequences and portions thereof may be used as repeats. The repeats preferably range from 1 to 500, more preferably from 1 to 100 and most preferably from 1 to 10. Data disclosed herein demonstrates the production of 8, 16, 20, 32, and 64 repeats of gum arabic motifs (Example 19).

The repeats may be contiguous or noncontiguous. Contiguous repeats are those without intervening amino acids, or amino acid analogues, placed between the repeating sequences. The repeats may contain two or more sequences which are described by the consensus sequence (SEQ ID NO:136) and portions thereof. The two or more sequences may be the same or different. Examples of a single repeat in which the two 19-amino acid sequences are different are those of motif 1-motif 2 [motif 1 (SEQ ID NO:143)=Ser-Hyp-Hyp-Hyp-Hyp-Leu-Ser-Hyp-Ser-Hyp-Thr-Hyp-Thr-Hyp-Hyp-Leu-Gly-Pro-His; motif 2 (SEQ ID NO: 144) =Ser-Hyp-Hyp-Hyp-Thr-Leu-Ser-Hyp-Ser-Hyp-Thr-Hyp-Thr-Hyp-Hyp-Hyp-Gly-Pro-His], described below in Example 19. Another example of a single repeat in which the two 19-amino acid sequences are different are those of motif 7-motif 13 of Table 2, having the sequence (SEQ ID NO:180): Gly-Pro-Hyp-Ser- Hyp- Hyp- Hyp- Thr- Leu-Ser-Hyp-Hyp-Leu-Thr-Hyp-Thr-Hyp-Hyp-Leu-Leu-Pro-His-Ser -Hyp-Hyp-Hyp-Hyp-Leu-Ser-Hyp-Ser-Leu-Thr-Hyp-Thr-Hyp-Hyp-Leu, in which motif 13 is underlined, and is flanked by motif 7. Yet another example of a single repeat in which the two 19-amino acid sequences are different are those of Table 2's motif 10-motif 12 having the sequence (SEQ ID NO:181): Gly-Pro-His-Ser- Hyp-Hyp- Hyp-Hyp- Leu-Ser- Hyp-Ala-Hyp-Thr-Hyp-Hyp-Hyp-Gly-Pro-His-Ser-Hyp-Ala-Hyp-Thr-Hyp-Hyp-Hyp-Gly-Pro-His-Ser-Hyp-Hyp-Hyp-Ser-Leu-Ser-Hyp-Leu-Pro-Thr-Hyp-Thr-Hyp-Hyp-Leu, in which motif 10 is underlined and is flanked by motif 12. Examples of a single repeat in which the two 19-amino acid sequences are the same are those of (motif 1-motif 1), (motif 2-motif 2), (motif 3-motif 3), etc.

In an alternative embodiment, the invention's sequences and portions thereof are used as noncontiguous repeats, i.e., with from 1 to 1000, more preferably from 1 to 100, and even more preferably from 1 to 10, intervening amino acids, or amino acid analogues, placed between the repeating sequences. The term "amino acid analog" refers to an amino acid is a chemically modified amino acid. Illustrative of such modifications would be replacement of hydrogen by an alkyl, acyl, or amino group, or formation of covalent adducts with biotin or fluorescent groups. Amino acids include biological amino acids as well as non-biological amino acids. The term "biological amino acid" refers to any one of the known 20 coded amino acids that a cell is capable of introducing into a polypeptide translated from an mRNA. The term "non-biological amino acid" refers to an amino acid that is not a biological amino acid. Non-biological amino acids are useful, for example, because of their stereochemistry or their chemical properties. The non-biological amino acid norleucine, for example, has a side chain similar in shape to that of methionine. However, because it lacks a side chain sulfur atom, norleucine is less susceptible to oxidation than methionine. Other examples of non-biological amino acids include aminobutyric acids, norvaline and allo-isoleucine, that contain hydrophobic side chains with different steric properties as compared to biological amino acids. The term "derivative" when in reference to an amino acid sequence means that the amino acid sequence contains at least one amino acid analog.

The production of repeating sequences may be achieved using methods known in the art [for example, Lewis et al. (1996) Protein Expression & Purification 7:400-406] and the methods described herein (Example 19).

In a preferred embodiment, the consensus sequence and portions thereof contains at least one noncontiguous hydroxyproline sequence and/or at least one contiguous hydroxyproline sequence. In a more preferred embodiment, the consensus sequence and portions thereof contains at least one noncontiguous hydroxyproline sequence and at least one contiguous hydroxyproline sequence.

The term "noncontiguous hydroxyproline sequence" refers to a sequence selected from (Xaa-Hyp)$_x$ (SEQ ID NO: 182) and Xaa-Hyp-Xaa-Xaa-Hyp-Xaa (SEQ ID NO: 183), wherein Xaa is any amino acid other than hydroxyproline, and wherein x is from 2 to 1000, more preferably from 2 to 100, and most preferably from 2 to 50. In a preferred embodiment, the noncontiguous hydroxyproline sequence is Xaa-Hyp-Xaa-Hyp (SEQ ID NO:9), wherein Xaa is selected from Ser, Thr, and Ala.

The term "contiguous hydroxyproline sequence" refers to a sequence selected from Xaa-Hyp-Hyp$_n$ (SEQ ID NO:209) and Xaa-Pro-Hyp$_n$ (SEQ ID NO:210), wherein n is from 1 to 100, and wherein Xaa is any amino acid other than hydroxyproline. In a preferred embodiment, the contiguous hydroxyproline sequence is selected from Ser-Hyp$_2$ (SEQ ID NO:211), Ser-Hyp$_3$ (SEQ ID NO:212), Ser-Hyp$_4$ (SEQ ID NO:3), Thr-Hyp$_2$ (SEQ ID NO:213), and Thr-Hyp$_3$ (SEQ ID NO:214).

Data presented herein demonstrates that noncontiguous hydroxyproline sequences [e.g., (Xaa-Hyp)$_x$ (SEQ ID NO: 182) where x is preferably at least 2] are functional glycomodules which direct the exclusive addition of arabinogalactan polysaccharide to Hyp, while contiguous hydroxyproline sequences are functional glycomodules which direct arabinosylation (Example 23). The term "functional" when made in reference to a noncontiguous hydroxyproline sequence or to sequences containing a noncontiguous hydroxyproline sequence means that the sequence directs exclusive addition of arabinogalactan polysaccharide to Hyp residues in that sequence. The addition of arabinogalactan polysaccharide to Hyp residues may be determined using methods described herein (Example 23). The term "functional" when made in reference to a contiguous hydroxyproline sequence or to sequences containing a contiguous hydroxyproline sequence a means that the sequence directs arabinosylation of Hyp residues in that sequence as determined by methods disclosed herein (Example 23).

The invention contemplates sequences that are complementary, and partially complementary to SEQ ID NO:136 and portions thereof, such as those which hybridize under low stringency conditions and high stringency conditions to these sequences.

The sequences of the invention may be used to isolate hydroxyproline rich glycoprotein-binding molecules and to make polyclonal and monoclonal antibodies as described supra. In addition, the invention's sequences may be used as emulsifying agents and/or to stabilize emulsions, both of which are properties which are highly valued by the food industry for GAGP. The emulsifying and emulsion stabilizing activities of the invention's proteins, glycoproteins, and portions thereof may be determined using generic methods known in the art [Kevin & John (1978) J. Agric. Food Chem 26(3):716-723; James & Patel, "Development of a standard oil-in-water emulsification test for proteins," Leatherhead Food RA Res. Rep. No. 631] which employ commercially available reagents.

For example, the following assay may be employed using orange oil (Sigma) following essentially the manufacturer's instructions. Freeze-dried glycoproteins are dissolved in 0.05 M phosphate buffer (pH 6.5) at a concentration of 0.5% (m/v). The aqueous solutions are combined with orange oil in a 60:40 (v/v) ratio. A 1 ml emulsion is prepared in a glass tube at 0° C. with a Sonic Dismembrator (Fisher Scientific) equipped with a Microtip probe. The amplitude value is set at 4 and mixing time is set to 1 min. For the determination of emulsifying ability (EA), the emulsion is diluted serially with a solution containing 0.1 M NaCl and 0.1% SDS to give a final dilution of 1/1500. The optical density of the diluted emulsion is then determined in a 1-cm pathlenght cuvette at a wavelength of 50 nm and defined as EA. The emulsion is stored vertically in a glass tube for 3 h at room temperature, then the optical density of 1:1500 dilution of the low phase of the stored sample is measured. Emulsifying stability (ES) is defined as the percentage optical density remaining after 2 hour of storage. BSA is used as a positive control. This assay has been used to determine the activity of sequences within the scope of the invention, as described in Example 24.

G. O-Glycosylation Codes

The invention further provides sequences which signal O-glycosylation. The O-glycosylation sequences are the noncontiguous hydroxyproline sequences (Xaa-Hyp)$_x$ (SEQ ID NO:182) and Xaa-Hyp-Xaa-Xaa-Hyp-Xaa (SEQ ID NO: 183), wherein Xaa is any amino acid other than hydroxyproline, and wherein x is a number from 1 to 1000, more preferably from 2 to 100, and yet more preferably from 2 to 50. In a more preferred embodiment, the sequence is Xaa-Hyp-Xaa-Hyp (SEQ ID NO:9), wherein Xaa is selected from Ser, Thr, and Ala.

The inventors' discovery of these sequences was based on their hypothesis that clustered, non-contiguous Hyp residues are sites for arabinogalactan polysaccharide attachment. In particular, the inventors predicted that Hyp galactosylation of clustered non-contiguous Hyp residues, such as the Xaa-Hyp-Xaa-Hyp (SEQ ID NO: 9) repeats of AGPs, results in the addition of a galactan core with sidechains of arabinose and other sugars to form characteristic Hyp-arabinogalactan polysaccharides. Hitherto, these sites of arabinogalactan polysaccharide attachment have been poorly defined because AGPs resist proteases, and because degradation by partial alkaline hydrolysis yields arabinogalactan-glycopeptides that are difficult to purify.

The inventor's discovery of the O-glycosylation sequences relied on a new approach to HRGP glycosylation site mapping as disclosed herein. To test their hypothesis that non-contiguous Hyp residues are sites for arabinogalactan polysaccharide attachment, the inventors designed three synthetic genes: The first synthetic gene, dubbed Sig-(Ser-Pro)$_{32}$-EGFP ((Ser-Pro)$_{32}$ disclosed as SEQ ID NO: 284), encoded a signal sequence (Sig) at the N-terminus followed by a repetitive Ser-Hyp motif [i.e., (Ser-Pro)$_{32}$ (SEQ ID NO: 284)] which encoded only clustered non-contiguous Hyp residues, which the inventors predicted would code as polysaccharide addition sites. The (Ser-Pro)$_{32}$ (SEQ ID NO: 284) was followed by EGFP at the C-terminus (FIG. 11). The inventors predicted that polysaccharide addition to noncontiguous Hyp should yield an expression product containing Hyp-polysaccharide exclusively. The second synthetic gene, dubbed Sig-(GAGP)$_3$-EGFP, encoded three repeats of a slightly modified 19-amno acid residue GAGP consensus sequence (FIG. 14) and was used by the inventors to determine whether it yielded an expression product that contains Hyp arabinosides as well as Hyp-polysaccharide. The third synthetic gene was a control construct (Sig-EGFP) that encoded only the signal sequence and EGFP. The expression product was a control to test whether or not any Hyp glycosylation could be attributed to EGFP modification that encode putative AGP glycomodules. Data presented herein shows that, when expressed and targeted for secretion, the two experimental sequence modules behaved as simple endogenous substrates for HRGP glycosyl transferases. The first construct expressing noncontiguous Hyp showed exclusive polysaccharide addition with polysaccharide O-linked to all Hyp residues. In contrast, the second construct containing noncontiguous Hyp and additional contiguous Hyp showed both polysaccharide and arabinooligosaccharide. From this data, the inventors arrived at the invention's O-glycosylation sequences.

The invention's sequences find use as substrates for O-Hyp arabinosyl- and galactosyltransferases. These substrates may be used to isolate and unambiguously identify these enzymes as well as to determine the enzymes' substrate preferences.

Yet another use for the inventions' sequences is in the identification of potential sites of oligoarabinoside addition in HRGPs, which may be inferred from their genomic sequences. Furthermore, these sequences would permit the transfer of useful products like exudate gum glycoproteins [Breton et al. (1998) *J. Biochem.* (Tokyo) 123, 1000-1009; Islam et al. (1997) *Food Hydrocolloids* 11, 493-505] such as GAGP from thorny desert scrub like *Acacia* to other desirable crop plants.

A further use for the invention's sequences is that they facilitate the de novo design of new HRGPs and their manipulation to enhance desirable properties. For example, glycoproteins which contain the O-glycosylation sequences of the invention may be used as emulsifying agents and/or to stabilize emulsions, as described supra as well as in Example 24.

H. Intermolecular and Intramolecular Crosslinking

Hydroxyproline-rich glycoproteins (HRGPs), comprising extensins proline-rich proteins (PRPs) and arabinogalactan proteins (AGPs) are among the most abundant proteins on this planet. HRGPs are extended macromolecules consisting of small repetitive peptide and glycopeptide motifs that form peptide modules and glycomodules of functional significance, as in "mix and match" mode they define the molecular properties of the overall macromolecule. Glycomodules result from a combination of posttranslational modifications unique to plants, namely proline hydroxylation/glycosylation that leads either to short arabinooligosaccharide or larger arabinogalactan polysaccharide addition to the glycosylation of Hyp residues. These glycomodules, as discussed herein, impart specific structural characteristics to HRGPs. These characteristics include, but are not limited to, self-orientation and crosslinking.

Extensins are about 50% glycosylated and have a Ser-Hyp$_4$ repeat module that provides Hyp-arabinoside attachment. Extensins play a structural role in the cell wall and comprise amino acids including, but not limited to, Hyp, Ser, Lys, and Tyr. It is known that there are two groups of extensins, a cross-linkable extensin (i.e., CL-extensins) and a non-cross-linkable extensin (i.e., NCL-extensins). Schnabelrauch et al., *Plant J.* 9, 477-489 (1996). The CL-extensins are known to contain the tripeptide repeat sequence Val-Tyr-Lys (i.e., VYK; SEQ ID NO: 256). Although it is not necessary to understand the mechanism of an invention, it is believed that their is a relationship between crosslinking and glycosylation as HF-deglycosylated tomato PI extensin is not crosslinked by pI 4.6 extensin peroxidase. Further, since the crosslinking kinetics of extensin show a sigmoidal curve that suggests cooperative assembly the Ser-Hyp$_4$ (SEQ ID NO: 3) motif may facilitate extensin monomer alignment prior to peroxidase-induced crosslinking.

One aspect of this invention contemplates a precise oligosaccharides or polysaccharide addition driven by a sequence-dependent O-Hyp glycosylation code (supra). In one embodiment, synthetic gene technology results in the design of novel glycoproteins. Surprisingly, the properties of these glycoproteins are contemplated for optimization to provide new fibers, filters, films, pharmaceuticals and foods.

One aspect of the present invention contemplates a functional P3-type extensin glycomodule. In one embodiment, variations in glycomodule crosslink sites are useful to predict the precise molecular nature of P3-type extensin crosslinking. Preferably, tobacco cell suspension cultures are used for synthesis and isolation of these glycomodules.

Highly repetitive extensin precursors are known to be glycosylated and localized to the primary cell wall where they are readily insolublized, presumably by covalent, intermolecular crosslinking. Mort et al., *Analyt. Biochem.*, 82:289-309 (1977). Extensin orientation and positioning in the wall is, however, self-mediated and determined by densely glycosylated molecular surfaces. Schnabelrauch et al., *Plant J.,* 9:477-489 (1996).

Although it is not necessary to understand the mechanism of an invention, it is believed that the protein sequence of extensin and other hydroxyproline-rich glycoproteins (HRGP's) ultimately dictate the extent and type of glycosylation moieties that determine self-alignment. For example, the Hydroxyproline Contiguity Hypothesis (supra) predicts that contiguous blocks of hydroxyproline residues (i.e., Hyp; hereinafter designated "O") are arabinosylated via the hydroxyl group (i.e., O-arabinosylation). However, repetitive, non-contiguous Hyp residues are also believed sites of polysaccharide attachment. Kieliszewski et al., *Plant J.,* 5:157-172 (1994).

Although hydroxyproline-rich proteins are essential structural components of the extracellular matrix in both plants and animals, glycosylation of hydroxyproline (Hyp) residues is unique to plants; animals never glycosylate hydroxyproline. Lamport et al., "Hydroxyproline in primary cell walls of higher plants" *Nature*, 188, 665-666 (1960); Lamport et al., "Hydroxyproline arabinosides in the plant kingdom" *Plant Physiol.*, 48, 454-456 (1971); and Lamport. D. T. A. "The Primary Cell Wall" *Ph.D. Thesis*, University of Cambridge—181 p., (1963). The result is a superfamily of Hyp-rich glycoproteins unique to plants. As shown in Table 2.1, HRGPs include, but are not limited to, extensins, arabinogalactan-proteins (AGPs) and proline-rich proteins (PRPs). Kieliszewski et al., "Extensin: repetitive motifs, functional sites, posttranslational codes and phylogeny" *Plant J.*, 5:157-172 (1994). Some AGPs, including gum arabic glycoprotein, are massively secreted as a wound-response ("gummosis") and form a protective plastic sealant. Qi et al., "Gum arabic glycoprotein is a twisted hairy rope: a new model based on O-galactosylhydroxyproline as the polysaccharide attachment site" *Plant Physiol.*, 96:848-855 (1991).

TABLE 2.1

Repetitive Sequences Common In Hydroxyproline-rich Glycoproteins

| Characteristic Sequence | HRPG |
| --- | --- |
| Ser-Hyp-Hyp-Hyp-Hyp-Thr-Hyp-Val-Tyr-Lys (SEQ ID NO: 237) | P1-type Extensin |
| Ser-Hyp-Hyp-Hyp-Hyp-Ser-Hyp-Ser-Hyp-Hyp-Hyp-Hyp-Hyp-Tyr-Tyr-Tyr-Lys (SEQ ID NO: 238) | P3 Extensin |
| Pro-Hyp-Val-Tyr-Lys (SEQ ID NO: 239) | Proline-rich protein |
| Ala-Hyp-Ala-Hyp (SEQ ID NO: 240) | Arabinogalactan-protein |

HRGPs are modular proteins comprising small modules (i.e, for example, generally 4-6 amino acid residue motifs) and include glycosylated motifs (glycomodules) and peptide motifs. (See Table 2.2). These modules can be viewed as small functional units, wherein most HRGPs are made up of more than one type of repetitive module.

TABLE 2.2

HRGP repetitive glycomodules, peptide modules and their corresponding properties.

| Repetitive Module | Properties |
| --- | --- |
| X-Hyp-Hyp-Hyp-Hyp (SEQ ID NO: 241) | Glycomodule common in extensins; this module has a polyproline-II extended conformation; Extensive arabinosylation of Hyp enhances the polyproline-II conformation and rigidifies the module (X = Ser, Ala, or Thr). |
| X-Hyp-Hyp (SEQ ID NO: 242) | Glycomodule common in arabinogalactan-proteins; Less polyproline-II conformation than the X-Hyp-Hyp-Hyp-Hyp glycomodule: First Hyp is always arabinosylated, the second Hyp is occasionally arabinosylated (X = Ser, Ala or Thr). |
| X-Hyp-X-Hyp (SEQ ID NO: 243) | Glycomodule which defines the arabinogalactan-proteins (i.e., for example, clustered non-contiguous Hyp; An extended random coil conformation further enhanced by arabinogalactan-polysaccharide addition to each Hyp (X = Ser or Ala). |
| X-Hyp-Val-Tyr-Lys (SEQ ID NO: 244) | Peptide module of extensins and PRPs: adhesion; peroxidase-catalyzed intermolecular cross-linking: Possible reverse β-turns: tandem repeats of this module may increase elasticity (X = Thr. Glu, Pro, His or Ile). |
| Tyr-Tyr-Tyr-Lys (SEQ ID NO: 245) Tyr-Lys-Tyr-Lys (SEQ ID NO: 246) | Peptide crosslinking modules common in extensin; Peroxidase-catalyzed intramolecular isodityrosine cross-linking sequences; probable intermolecular crosslinks that enhance hydrophobicity, intramolecular crosslink rigidifies these modules. |
| Lys-Pro (SEQ ID NO: 247) | Ionic/covalent cross-linking motif of extensins and PRPs. |

Highly glycosylated extensins comprise HRPGs with the cell wall proper and create insoluble networks crosslinked inter- and intramolecularly to varying degrees. Epstein et al., "An intramolecular linkage involving isodityrosine in extensin" *Phytochem.*, 23, 1241-1246 (1984); Lamport D. T. A., "The primary cell wall: a new model" In: *Cellulose: Structure, Modification and Hydrolysis*, edited by R. A. Young, et al, pp. 77-89, 1986, Wiley Interscience, New York.

Crosslinks often involve tyrosine derivatives, including, but not limited to, a unique biphenylether, isodityrosine. Schnabelrauch et al., "Isolation of pI 4.6 extensin peroxidase from tomato cell suspension cultures and identification of Val-Tyr-Lys as putative intermolecular cross-link site" Plant J. 9:477-489 (1996); Brady et al., "Diisodityrosine, a novel tetrameric derivative of tyrosine in plant cell wall proteins: a new potential cross-link" Biochem J. 315: 323-337 (1996).

Soluble hyperglycosylated HRGPs of the arabinogalactan-protein family, however, are often initially anchored to the outer surface of the plasma membrane. Serpe et al., "Arabinogalactan-proteins in the multiple domains of the plant cell surface" Adv. Bot. Res. 30: 207-289 (1999); Svelelc et al., "Presence of a glycosylphosphatidylinositol lipid anchor on rose arabinogalactan proteins" J Biol Chem 274:14724-1473 (1999); and Youl et al., "Arabinogalactan-proteins from Nicotiana alata and Pyrus communis contain glycosylphosphatidylinositol membrane anchors." Proc. Natl. Acad. Sci. USA 95:7921-7926 (1998). Soluble HRGPs contribute substantially to the formation of a protective glycocalyx interface.

Extensins and AGPs are among the most highly glycosylated glycoproteins known, ranging from approximately 50% to 95% carbohydrates. Thus, the interactive molecular surface of HRGPs consists mainly of saccharides rather than amino acid sidechains. The identity and arrangement of saccharide substituents along an extended highly repetitive polypeptide backbone characterizes the HRGPs and largely defines their molecular properties. One mechanism of directing the placement of glycosylation sites involves the HRGP O-glycosylation code (supra). Shpak et al., "Synthetic genes for glycoprotein design and the elucidation of hydroxyproline-O- glycosylation codes" Proc. Natl. Acad. Sci. 96:14736-14741 (1999); Shpak et al., "Contiguous hydroxyproline residues direct hydroxyproline arabinosylation in Nicotiana tabacum" J Biol Chem 276:11272-11278 (2001).

The glycosubstituents of HRGPs fall into two major categories, namely short chains of arabinooligosaccharides and longer arabinogalactan heteropolysaccharides. Two fundamental modes of O-Hyp glycosylation control the addition of glycosubstituents, namely arabinosylation which gives rise to arabinooligosaccharide addition and galactosylation which gives rise to the larger acidic arabinogalactan polysaccharides. The Hyp residue sequence directs the arrangement of the different Hyp-glycoside substituents. Shpak (supra). The key to this glycosylation code is Hyp contiguity. Our recent elucidation of the fundamental O-glycosylation code for HRGP-glycosylation shows that contiguous Hyp residues direct the addition of homo-arabinooligosaccharides to Hyp (i.e., the degree of polymerization is approximately 1-5), while clustered noncontiguous Hyp residues direct the addition of a complex arabinogalactan heteropolysaccharide (i.e., the degree of polymerization is approximately 15-75) containing glucuronic acid and rhamnose in addition to arabinose and galactose.

These two distinct modes of glycosylation create unique glycomodules, small functional units that confer distinctly different molecular properties: addition of short oligosaccharides of arabinose to Hyp residues locks the contiguous Hyp-rich glycomodules into an extended polyproline-II conformation resulting in rigid, rodlike regions. In contrast, regions that lack contiguous Hyp remain flexible while subsequent addition of arabinogalactan polysaccharide to clustered non-contiguous Hyp residues promotes an extended random coil conformation as shown above in Table 23.

One aspect of the present invention contemplates successful synthesis, isolation, and partial characterization of a soluble P3-type extensin. In one embodiment, soluble P3-type glycomodules are suitable substrates for defining precise molecular interactions of P3 extensin.

P3 extensin comprises a repeat unit having the amino acid sequence SOOOOSOSOOOOYYYK (SEQ ID NO. 248). Lamport, D. T. A. 1st International Protoplast Colloquium, Versailles. I. N. R. A., pp. 27-31 (1973). P3 extensin further comprises a primary amino acid sequence symmetry module (i.e., Ser-Hyp$_4$-Ser-Hyp-Ser-Hyp$_4$; the palindromic module: SEQ ID NO: 249) that provides direction for in vivo glycosylation sites. The present invention contemplates a variety of methods comprising a P3 extensin as a substrate for studying carbohydrate mediated self-alignment and extensin intra- and intermolecular crosslinking. In one embodiment, a primary amino acid sequence symmetry module comprises a crosslinking module, wherein the crosslinking may be intramolecular or intermolecular. In one embodiment, the crosslinking module comprises the amino acid sequence YYYK (SEQ ID NO. 250). In another embodiment, the crosslinking module comprises the amino acid sequence FFFK (SEQ ID NO. 251). In another embodiment, the crosslinking module comprises the amino acid sequence YYYL (SEQ ID NO. 252). In another embodiment, the crosslinking module comprises the amino acid sequence FFFL (SEQ ID NO. 253).

Figure 4:
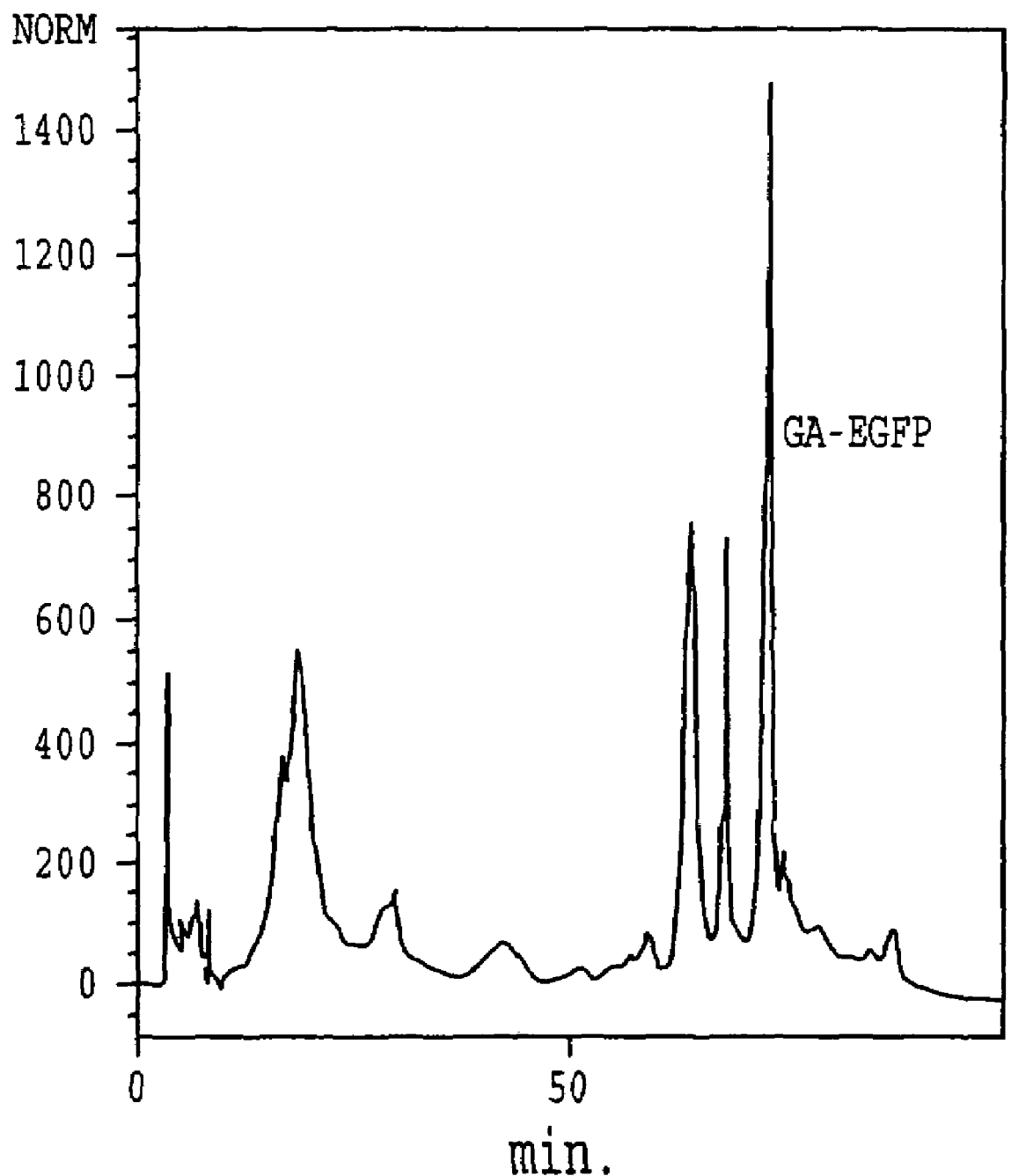
FIG. 4 is a graph showing the isolation of GA-EGFP by reverse phase chromatography.

The present invention contemplates a P3 crosslink module comprising three contiguous tyrosine residues. In one embodiment, at least one tyrosine residue forms a crosslink, wherein the crosslink isodityrosine. In one embodiment, the crosslink is intramolecular. In another embodiment, the crosslink is intermolecular. Although it is not necessary to understand the mechanism of an invention, it is believed that the first and third tyrosine residues provide oxidative coupling to form a biphenylether (i.e., for example, isodityrosine (IDT) resulting in an intramolecular crosslink: FIG. 4-inset) that may be directly responsible for intramolecular crosslinking. Dimers of IDT may couple to form di-isodityrosine (di-IDT) and are thus responsible for intermolecular extensin crosslinking. Brady et al., Biochem J., 315:323-327 (1996).

Gum arabic glycoprotein (GAGP) is the HRGP model that best illustrates the modular approach to the molecular design of new HRGPs. GAGP is a component of gum arabic, gum arabic being a gum exudate produced in response to mechanical wounding and widely used as an emulsifier, encapsulator, and excipient in the pharmaceutical, paint, print, and food industries. Gum arabic is colorless, odorless, tasteless, and non-toxic, with beneficial effects on human health. Phillips G. V., "Acacia gum (Gum Arabic): a nutritional fiber, metabolism and calorific value" Food Addit. Contam. 15:251-264 (1998); Al-Othman et al., "Plasma total, lipoprotein cholesterol, organs cholesterol and growth performance in rats fed dietary gum arabic" Food Chem., 67:69-72 (1998); and Teichberg et al., "Effect of gum arabic in an oral rehydration solution on recovery from diarrhea in rats" J. Pediatr. Gastroenterol. Nutr. 29:411-417 (1999).

Although gum arabic consists of a complex mixture of related arabinogalactan polysaccharides, GAGP is the active emulsifying component. Goodrum et al., "Gum arabic glycoprotein contains glyconodules of both extensin and arabinogalactanglycoproteins" Phytochem. 54:99-106 (2000); and X-F Xu and M. Kieliszewski, unpublished data). GAGP is believed an amphiphilic ~150 nm flexuous rodlike HRGP with a highly repetitive modular structure that combines features of other HRGPs and comprises a 19-residue repeat, and variations thereof, that occurs about 20 times within a glycoprotein (See Table 2). In one representative GAGP sequence (i.e., SEQ ID NO: 143) below, the alternation of rigid (underlined)and non-rigid (italicized and bolded) modules are directed mainly by contiguous and non-contiguous Hyp glycomodules.

[Ser-Hyp-Hyp-Hyp-Hyp-Leu-Ser-Hyp-Ser-Hyp-Thr-Hyp-Thr-Hyp-Hyp-Leu-Gly-Pro-His]$_n$

Selection of glycomodules (and peptide modules) in "mix and match" mode can fine-tune molecular flexibility, glycosylation, crosslinking anal other properties to create biopolymers with a wide range of desirable properties.

Plants uniquely catalyze two posttranslational modifications essential to the formation of the complex interpenetrating glycoprotein and polysaccharide polymeric networks that comprise the cell wall and extracellular microcomposite. The ability to hydroxylate prolyl residues is absent from prokaryotes while hydroxyproline glycosylation is lacking in both prokaryotes and animals. Thus, plants are the only possibility for producing HRGP-based hydrocolloids. Furthermore, plants are polymer factories par excellence. With this in mind, the scope and potential for designing long extended-chain co-polymers by glycoengineering in plants is enormous. Willmitzer et al., "Production of new or modified carbohydrates in transgenic plants" *Schriftenr. Bundesminist. Ernaehr. Sonderh.,* 110 (1997); Wee et al., "Targeting of active sialyltransferase to the plant Golgi apparatus" *Plant Cell,* 10:1759-1768 (1998).

The idea of polymer chemistry based on solar energy, and renewable resources that are biodegradable and can be recycled is currently attractive when considering both the short term and long term implications of over-reliance on petrochemicals. Furthermore, the availability of diverse crops, crop products, and markets benefits agriculture in general by providing flexibility find choice both for farmer-producers and consumers, thereby contributing to a robust stable economy.

One aspect of the present invention contemplates the construction and expression of synthetic genes regarding the determinants of the hydroxyproline O-glycosylation code. As discussed above, this code is based upon the Hydroxyproline Contiguity Hypothesis. In one embodiment, the code predicts hydroxyproline-rich glycoprotein design. In one embodiment, blocks of contiguous hydroxyproline have a high degree of O-arabinosylation with little, or no, attachment of arabinogalactan-polysaccharides. In another embodiment, the code predicts clustered non-contiguous Hyp residues are sites of arabinogalactan-polysaccharide addition (See Table 23). In one embodiment, the present invention accurately predicts the hydroxyproline glycosylation sites of a naturally occurring arabinogalactan-protein, wherein said prediction is based on the gene sequence.

The hydroxyproline O-glycosylation code elucidated herein is the first that predicts precise placement of very different O-linked glycans along a polypeptide backbone. Furthermore, the ability to use the hydroxylproline O-glycosylation code for molecular design greatly extends the range of properties and structures that can be engineered into glycoprotein hydrocolloids. While the ultimate significance cannot be foreseen, precision glycoengineering has ramifications ranging from new foodstuffs to nanotechnology and molecular machines.

One aspect of the present invention contemplates creating HRGP synthetic genes from oligonucleotide pairs. In one embodiment, an overlapping internal repeat set encoded a repetitive HRGP motif. McGrath et al., "Chemical and biosynthetic approaches to the production of novel polypeptide materials" *Biotechnol. Prog.* 6:186-192 (1990). Preferably, the internal repeat oligonucleotide pair may be polymerized head-to-tail in the presence of a 5'-end linker set containing a BamHI restriction site. After ligation, a 3'-end linker set containing a LcoR1 site was added and ligated, and the resulting oligomers were inserted as BamHI/EcoRI fragments into a vector. This approach produced a range of synthetic genes differing only in the extent of internal repeat polymerization. Although this approach was suitable for the elucidation of the glycosylation code, it is unsuitable for designing long repetitive genes of precise lengths. One aspect of the present invention contemplates a method comprising spider silk protein production in *E. coli* involving compatible but nonrengenerable restriction sites, which allows construction of very large repetitive genes in a precisely controlled manner. Lewis et al., "Expression and purification of a spider silk protein, a new strategy for producing repetitive proteins" *Protein Expression Purif* 7:400-406 (1996).

One aspect of the present invention contemplates crosslink motifs of P1 extensin comprising hydroxyproline-rich glycoprotein (HRGP). In one embodiment, the present invention contemplates a P1 extensin having an amino acid sequence comprising SPPPPTPVYK (SEQ ID NO: 254). In another embodiment, the present invention contemplates a P1 extensin having an amino acid sequence comprising SPPPPVKPYHPTPVYK (SEQ ID NO: 255).

Another aspect of the present invention contemplates an extensin crosslinking site comprising VYK (i.e., Val-Tyr-Lys; SEQ ID NO: 256). Although it is not necessary to understand the mechanism of an invention, it is believed that tyrosine and lysine contain reactive groups which mediate both intra- and intermolecular extensin crosslinking. In one embodiment, the present invention contemplates synthetic genes that encode for these P1 crosslinking motifs. In one embodiment, synthetic genes encoding P1 extensin proteins comprise substitutions of phenylalanine for tyrosine residues. In another embodiment, synthetic genes encoding P1 extensin proteins comprise substitutions of leucine for lysine residues.

One aspect of the present invention contemplates the expression P1 extensin as recombinant proteins by transformation techniques known in the art. In one embodiment, a tobacco extensin signal sequence initiates the expression of synthetic proteins to the cell wall. In one embodiment, enhanced green fluorescent protein (EGFP) identifies transformed cells and detects isolated expression products. In one embodiment, isolated P1 extensin proteins have crosslinking activity. In another embodiment, VYK (SEQ ID NO: 256) site crosslinks in vitro.

One aspect of the present invention contemplates a method comprising a controlled approach to design GAGP analogs of various lengths (i.e., for example, 8, 16, 20, 32, and 64 repeats of the 19-residue consensus repeats: SEQ ID NOs: 27 and 28). Shpak E., "Synthetic genes for the elucidation of hydroxyproline O-glycosylation codes" *Ph. D. Thesis,* University of Ohio. 179 p. (2000); and Shpak and M. Kieliszewski, unpublished data). In one embodiment, this method results in the design and expression of novel extensins comprising alternating Ser-Hyp-Hyp-Hyp-Hyp glycomodules and crosslinking modules Tyr-Tyr-Tyr-Lys (SEQ ID NO: 245) or Thr-Hyp-Val-Tyr-Lys (SEQ ID NO: 267).

The present invention contemplates that synthetic gene technology is useful to design repetitive peptide motifs that can be spliced together, expressed under the control of appropriate promoters and targeting signals, plus a suitable reporter gene for transfer to the ER/Golgi for posttranslational modification and secretion. Shpak et al., "Synthetic genes for glycoprotein design and the elucidation of hydroxyproline-O-glycosylation codes" *Proc. Natl. Acad. Sci. USA.*, 96:14736-14741 (1999); and Kieliszewski. M. J. "The latest hype on Hyp-O-glycosylation codes" *Phytochem.*, 57, 319-323 (2001).

One aspect of the present invention contemplates a method to express repetitive modules, including the elastin module, in plants. Zhang et al., "Expression of an environmentally friendly synthetic protein- based polymer gene in transgenic tobacco plants" *Plant Cell Reports*, 16:174-179 (1996). In one embodiment, peroxidase-catalyzed intermolecular crosslinking of a Thr-Hyp-Val-Tyr-Lys (SEQ ID NO: 267) module produces long fibers. In one embodiment, PI extensin lysine residues are resistant to trypsin. Smith. J. J., "Isolation and characterization of extensin precursors from suspension cultured tomato cells" *Ph. D. Thesis*, Michigan State University, 129 p. (1985). Preferably, these crosslinked extensin modules are tough, rigid, protease resistant, elastic fibers of high tensile strength, analogous to fibers found in mussel byssus threads but with enhanced water holding ability in the glycosylated regions.

One aspect of the present invention contemplates crosslinked extensin modules comprising SOOOOTOVYK (SEQ ID NO: 268), wherein "O" represents a Hyp residue, at the N- and C-termini, and a central stretch composed of rigid arabinosylated SOOOO (SEQ ID NO: 134) repeats (bolded below) flanked on either side with elastin sequences (italicized below). In one embodiment, a crosslinked extension module comprises SEQ ID NO: 269.

(SEQ ID NO: 269)
SOOOOTOVYKSOOOOTOVYKSOOOO-[*VGVPGVGVPG*]$_6$-

[SOOOOSOOOOSOOOO]$_6$-[*VG*

*VPGVGVPG*]$_3$-SOOOOTOVYKSOOOOTOVYKSOOOO

Another aspect of the present invention contemplates a crosslinked extensin module comprising SOOOOTOVYK (SEQ ID NO: 268) at the N- and C-termini and a central stretch composed of SOOOO (SEQ ID NO: 134) repeats with the more flexible SOSOSO (SEQ ID NO: 285)repeats (bolded), or AOAOAO (SEQ ID NO: 286) repeats, flanked on either side with elastin sequences (italics). In one embodiment, an SO or AO repeat sequence provides arabinogalactan-polysaccharide addition sites. In another embodiment, a crosslinked extensin modules comprises SEQ ID NO: 254. In another embodiment, a crosslinked extensin modules comprises SEQ ID NO: 255. While it is not necessary to understand the mechanism of an invention, it is believed that these polysaccharide additions sites: i) greatly increase the amount of carbohydrate on the molecule, ii) impart a negative charge due to the abundance of uronic acids in the polysaccharide, and iii) promote an extended conformation. Gottschalk, A., "Correlation between composition, structure, shape and function of a salivary mucoprotein" *Nature* 186:949-957 (1960).

(SEQ ID NO: 270)
SOOOOTOVYKSOOOOTOVYKSOOOO-[*VGVPGVGVPG*]$_6$-

[SOSOSOSOSOSOSOSOSO-SOSOSO]$_6$-

[*VGVPGVGVPG*]$_3$-SOOOOTOVYKSOOOOTOVYKSOOOO (SEQ ID NO: 271)
SOOOOTOVYKSOOOOTOVYKSOOOO-[*VGVPGVGVPG*]$_6$-

[AOAOAOAOAOAOAOAO-AOAOAOAO]$_6$-

[*VGVPGVGVPG*]$_3$-SOOOOTOVYKSOOOOTOVYKSOOOO

One aspect of the present invention contemplates a composition comprising hydroxyproline-rich glycoproteins, wherein said composition is an emulsifier. In one embodiment, the hydroxyproline-rich glycoprotein includes, but is not limited to, GAGP. Preferably, HRGP emulsifiers lack crosslinking motifs and the elastin repeats. In one embodiment, an HRGP emulsifier comprises a modified extensin module. In one embodiment, the modified extensin module comprises twelve residues and a Pro-rich but flexible, hydrophobic module. In one embodiment, a modified extensin module comprises SEQ ID NO: 256. In one embodiment, rhamnoglucuronoarabinogalactan polysaccharide sidechains attached to the AOAO (SEQ ID NO: 287) repeats stabilize an oil-in-water emulsion by preventing aggregation and flocculation. In another embodiment, the composition further comprises at least one crosslinking module, wherein said crosslinking module induces emulsion stabilization. One skilled in the art would understand that many variations contemplated by this invention include glycoproteins having only a single hydrophobic module and a single glycosylated HRGP module or many of each type dispersed regularly throughout the chain.

(SEQ ID NO: 272)
*VPGVPGVGPVPG*-[AOAOAOAOAOAOAOAOAOAO]$_3$-*VPGVPGVPGVPCG*

One aspect of the present invention contemplates an emulsifier composition comprising a GAGP repeat and an extensin crosslink motif. In one embodiment, said extensin crosslink motif (underlined below) comprises TOVYK (SEQ ID NO: 288), wherein said crosslinking is intermolecular. The C-terminus variation of the GAGP repeat (italicized and bolded) has decreased glycosylation, increased flexibility, and increased hydrophobicity which is believed to allow the molecule to interact with the surface of an oil droplet. Such a molecule might facilitate slow-release drug delivery from an oil-in-water emulsion.

SOOOTLSOSOTOTOOLGPHSOOOTLSOSOTOTOOLGPHTOVYKSOOOTLSOSOT (SEQ ID NO: 273)

OTOOLGPHSOOOTLSOSOTOTOOLGPHTOVYKSOOOTLSOSOTOTOOLGPHSOO

OTLSOSOTOTOOLGPHTOVYKSOOOTLSOSOTOTOOLPGH*SOLPTLSOLPTOTO*

*OLLPHSOLPTLSOLPTOTOOLLPH*

Although it is not necessary to understand the mechanism of an invention, it is believed that these expressed novel hydrocolloids have the following properties:
1. Determination Of Crosslinking
   a. Size exclusion chromatography
   b. Cyanoethylation of free crosslink lysine residues.
   c. Dityrosine or isodityrosine formation.
   d. Cis-parinaric acid assay for surface hydrophobicity.
2. Mechanical properties of biopolymer films
   a. Compression isotherms via Langmuir film balance.
3 Emulsifying properties will be evaluated as follows:
   a. At different pH levels
   b. At different ionic strengths
   c. Stability of the emulsion
   d. Droplet size and surface charge: Emulsions containing the smallest globules tend to be the most stable (200-500 n.m), as do emulsions that have a high surface charge. Droplet size cane measured in a Coulter counter. Zeta potential measurements are typically carried out using a Doppler electrophoresis apparatus or via moving-boundary electrophoresis.
4. Fiber formation and properties
   a. Extrusion of crosslinked products through an appropriately sized nozzle will yield fibers. After a curing stage the physical properties of the fibers will be determined by measuring their elastic modules and tensile strength.
5. Elastic properties/viscoelasticity can be measured using a rheometer.
6. Lipid encapsulation
   a. Chloroform extraction.

The above proposed work outlines an approach that uses green plants as biopolymer "factories". This view will undoubtedly become increasingly popular as the new era of biotechnology gathers momentum and fulfills its promise of providing diverse, sustainable and ecologically sound products rouging from edible vaccines to biodegradable plastics. Indeed, of those drugs in use today, a majority originate from complex biosynthetic pathways unique to plants, emphasizing the great potential of future bioengineering in plants. In our examples here we have suggested how to harness synthetic gene technology with the unique post-translational modifications used by plants, to construct new polymers, giving new meaning to the term designer genes.

I. Variants of Le-APG-1

Functional analysis of hyperglycosylated arabinogalactan-proteins (AGPs) attempts to relate biological roles to the molecular properties that result largely from O-hydroxyproline glycosylation believed coded by the primary amino acid sequence. Naturally occurring hydroxyproline-rich glycoproteins (HRGPs) and HRGPs designed by synthetic genes are consistent with a sequence-driven code.

One aspect of the present invention contemplates a method comprising expression in tobacco (*Nicotlana tabacum*) of the most predominant tomato (*Lycopersicon esculentum*) AGP, LeAGP-1, as an enhanced green fluorescent protein fusion glycoprotein (EGFP)-LeAGP-1, wherein hydrophobicity of said APG is sufficiently improved for chromatographic purification. In one embodiment, the method is contemplated to design and purify two variants of LeAGP-1. In one embodiment, the variant lacks a glycosylphosphatidylinositol (GPI)-anchor signal sequence. In another embodiment, the variant lacks a 12-residue internal lysine-rich region. Fluorescence microscopy of plasmolysed cells confirms the location of LeAGP-1 at the plasma membrane outer surface and in Hechtian threads. Hyp glycoside profiles of the fusion glycoproteins gave ratios of Hyp-polysaccharides to Hyp-arabinosides plus non-glycosylated Hyp consistent with those predicted from DNA sequences by the Hyp contiguity hypothesis. These results demonstrate a route to the purification of AGPs and the use of the Hyp contiguity hypothesis for predicting the Hyp D-glycosylation profile of an HRGP from its DNA sequence.

Experimental

The following examples serve to illustrate certain preferred embodiments and aspects of the present invention and are not to be construed as limiting the scope thereof.

In the experimental disclosure which follows, the following abbreviations apply: g (gram); mg (milligrams); µg (microgram); M (molar); mM (milliMolar); µM (microMolar); nm (nanometers); L (liter); ml (milliliter); µl (microliters); ° C. (degrees Centigrade); m (meter); sec. (second); DNA (deoxyribonucleic acid); cDNA (complementary DNA); RNA (ribonucleic acid); mRNA (messenger ribonucleic acid); X-gal (5-bromo-4-chloro-3-indolyl-β-D-galactopyranoside); LB (Luria Broth), PAGE (polyacrylamide gel electrophoresis); NAA (α-naphtaleneacetic acid); BAP (6-benzyl aminopurine); Tris (tris(hydroxymethyl)-aminomethane); PBS (phosphate buffered saline); 2×SSC (0.3 M NaCl, 0.03 M $Na_3$citrate, pH 7.0); Agri-Bio Inc. (North Miami, Fla.); Analytical Scientific Instruments (Alameda, Calif.); BioRad (Richmond, Calif.); Clontech (Palo Alto Calif.); Delmonte Fresh Produce (Kunia, Hawaii); Difco Laboratories (Detroit, Mich.); Dole Fresh Fruit (Wahiawa, Hawaii); Dynatech Laboratory Inc. (Chantilly Va.); Gibco BRL (Gaithersburg, Md.); Gold Bio Technology, Inc. (St. Louis, Mo.); GTE Corp. (Danvers, Mass.); MSI Corp. (Micron Separations, Inc., Westboro, Mass.); Operon (Operon Technolies, Alameda, Calif.); Pioneer Hi-Bred International, Inc. (Johnston, Iowa); 5 Prime 3 Prime (Boulder, Colo.); Sigma (St. Louis, Mo.); Promega (Promega Corp., Madison, Wis.); Stratagene (Stratagene Cloning Systems, La Jolla, Calif.); USB (U.S. Biochemical, Cleveland, Ohio).

EXAMPLE 1

Determination of the Peptide Sequence of *Acacia* Gum Arabic Glycoproteins

In this example, GAGP (SEQ ID NO:15) was isolated and (by using chymotrypsin) the deglycosylated polypeptide backbone was prepared. Although GAGP does not contain the usual chymotryptic cleavage sites, it does contain leucyl and histidyl residues which are occasionally cleaved. Chymotrypsin cleaved sufficient of these "occasionally cleaved" sites to produce a peptide map of closely related peptides.

Purification and Deglycosylation of GAGP (SEQ ID NO:15). GAGP was isolated via preparative Superose-6 gel filtration. Anhydrous hydrogen fluoride deglycosylated it (20 mg powder/mL HF at 4° C., repeating the procedure twice to ensure complete deglycosylation), yielding dGAGP which gave a single symmetrical peak (data not shown) after re-chromatography on Superose-6. Further purification of dGAGP by reverse phase chromatography also gave a single major peak, showing a highly biased but constant amino acid composition in fractions sampled across the peak. These data indicated that dGAGP was a single polypeptide component sufficiently pure for sequence analysis.

Sequence Analysis. An incomplete pronase digest gave a large peptide PRP3 which yielded a partial sequence (Table 3) containing all the amino acids present in the suggested dGAGP repeat motif. In view of the limitations of pronase, for further peptide mapping and to obtain more definitive sequence information, dGAGP was digested with chymotrypsin, followed by a two-stage HPLC fractionation scheme. Initial separation of the chymotryptides on a PolySULFO-ETHYL A™ (designated PSA, PolyLC, Inc. Ellicott City, Md.) cation exchanger yielded three major fractions: S1 and S2 increased with digestion time while S3 showed a concomitant decrease. Further chromatography on PRP-1 resolved PSA fractions S1 and S2 into several peptides.

EXAMPLE 2

Construction of Synthetic HRGP Gene Cassettes

Synthetic gene cassettes encoding contiguous and non-contiguous Hyp modules are constructed using partially overlapping sets consisting of oligonucleotide pairs, "inter-

TABLE 3

AMINO ACID SEQUENCES OF THE GUM ARABIC GLYCOPROTEIN POLYPEPTIDE BACKBONE

| Peptide | Sequence |
|---|---|
| S1P5 | Ser-Hyp-Hyp-Hyp-Hyp-Leu-Ser-Hyp-Ser-Leu-Thr-Hyp-Thr-Hyp-Hyp-Leu-Gly-Pro-(Pro) (SEQ ID NO: 16) |
| S1P3 | Ser-Hyp-Hyp-Hyp-Hyp-Leu-Ser-Hyp-Ser-Hyp-Thr-Hyp-Thr-Hyp-Hyp-Leu-Gly-Pro-(Pro) (SEQ ID NO: 17) |
| S3 | Ser-Hyp-Hyp-Hyp-Thr-Leu-Ser-Hyp-Ser-Hyp-Thr-Hyp-Thr-Hyp-Hyp-Hyp-Gly-Pro-His-Ser-Hyp-Hyp-Hyp-(Hyp) (SEQ ID NO: 18) |
| S1P2 | Ser-Hyp-Hyp-Hyp-Ser-Leu-Ser-Hyp-Ser-Hyp-Thr-Hyp-Thr-Hyp-Hyp-Thr-Gly-Pro-His (SEQ ID NO: 19) |
| S2P1 | Ser-Hyp-Ser-Hyp-Thr-Hyp-Thr-Hyp-Hyp-Hyp-Gly-Pro-His (SEQ ID NO: 20) |
| S2P2a | Ser-Hyp-Ser-Hyp-Ala-Hyp-Thr-Hyp-Hyp-Leu-Gly-Pro-His (SEQ ID NO: 21) |
| S2P2b | Ser-Hyp-Leu-Pro-Thr-Hyp-Thr-Hyp-Hyp-Leu-Gly-Pro-His (SEQ ID NO: 22) |
| S2P3a | Ser-Hyp-Ser-Hyp-Thr-Hyp-Thr-Hyp-Hyp-Leu-Gly-Pro-His (SEQ ID NO: 23) |
| S2P4 | Ser-Hyp-Hyp-Leu-Thr-Hyp-Thr-Hyp-Hyp-Leu-Leu-Pro-His (SEQ ID NO: 24) |
| S1P4 | Ser-Hyp-Leu-Pro-Thr-Leu-Ser-Hyp-Leu-Pro-Ala/Thr-Hyp-Thr-Hyp-Hyp-Hyp-Gly-Pro-His (SEQ ID NOS: 25 and 26) |
| Consensus: | (SEQ ID NOS: 27 and 28) Ser-Hyp-Hyp-Hyp-Thr/Hyp-Leu-Ser-Hyp-Ser-Hyp-Thr-Hyp-Thr-Hyp-Hyp-Leu-Gly-Pro-His ↑ ↑ ↑        ↑ ↑ ↑        ↑     ↑ (Leu) (Pro) (Ser)  (Leu) (Leu) (Ala)  (Hyp)  (Pro) ↑ (Pro) |

Edman degradation showed that these chymotryptides were closely related to each other, to the partial sequence of the large pronase peptide (Table 3), and to the major pronase peptide of GAGP isolated earlier by Delonnay (see above). Indeed, all can be related to a single 19-amino acid residue consensus sequence with minor variation in some positions (Table 3). These peptides also reflect the overall amino acid composition and are therefore evidence of a highly repetitive polypeptide backbone with minor variations in the repetitive motif, these include occasional substitution of Leu for Hyp and Ser. Remarkably, fifteen residues of the consensus sequence are "quasi-palindromic" i.e. the side chain sequence is almost the same whether read from the N-terminus or C-terminus.

nal repeat pairs" and "external 3'- and 5'-linker pairs" respectively, all with complementary "sticky" ends. The design strategy for the repetitive HRGP modules combines proven approaches described earlier for the production in *E.coli* of novel repetitive polypeptide polymers (McGrath et al. [1990] Biotechnol. Prog. 6:188), of a repetitious synthetic analog of the bioadhesive precursor protein of the mussel *Mytilus edulis*, of a repetitive spider silk protein (Lewis et al. [1996] Protein Express. Purif. 7:400), and of a highly repetitive elastin-like polymer in tobacco [Zhang, X., Urry, D. W., and Daniell, H. "Expression of an environmentally friendly synthetic protein-based polymer gene in transgenic tobacco plants," *Plant Cell Reports*, 16: 174 (1996)].-

The basic design strategy for synthetic HRGP cassettes is illustrated by the following illustrative constructs.

a) Ser-Hyp$_4$ (SEQ ID NO:3) Gene Cassette

A synthetic gene encoding the extensin-like Ser-Hyp$_4$ (SEQ ID NO:3) module is constructed using the following partially overlapping sets of oligonucleotide pairs.

```
                    5'-Linker:

Amino Acid (SEQ ID NO: 29):  A   G   S   S   T   R
                             A   S   P   (P  P)

5'-GCT GGA TCC TCA ACC CGG GCC  (SEQ ID NO: 30)
    TCA CCA

CGA CCT AGG AGT TGG GCC CCG  (SEQ ID NO: 31)
        AGT GGT GGT GGT GGA-5'

3' Linker (for pBI121-Sig-EGFP):

Amino Acid (SEQ ID NO: 32):  P   P   P   S   P   V
                             A   R   N   S   P   P

5'-CCA CCA CCT TCA CCG GTC GCC  (SEQ ID NO: 33)
    CGG AAT TCA CCA CCC

AGT GGC CAG CGG  (SEQ ID NO: 34)
    GCC TTA AGT GGT GGG-5'

3' Linker (for pBI121-Sig):

Amino Acid:

5'-CCA CCA CCT TAA TAG AGC TCC  (SEQ ID NO: 35)
    CCC

ATT ATC TCG AGG  (SEQ ID NO: 36)
        GGG-5'

Internal Repeat

Amino Acid (SEQ ID NO: 37):  P   P   P   S   P   P
                             P   P   S   P

5'-CCA CCA CCT TCA CCT CCA CCC  (SEQ ID NO: 38)
    CCA TCT CCA

AGT GGA GGT GGG  (SEQ ID NO: 39)
    GGT AGA GGT GGT GGT GGA-5'
```

Conversion of the "internal" and 5' & 3' "external" gene cassettes to long duplex DNA is accomplished using the following steps:

1. Heat each pair of complementary oligonucleotides to 90° and then anneal by cooling slowly to 60° thereby forming short duplex internal and external DNAs.
2. Combine the 5' external linker duplex with the internal repeat duplexes in an approximately 1:20 molar ratio and anneal by further cooling to yield long duplex DNA capped by the 5' linker. The 5' linker is covalently joined to the internal repeat duplex by ligation using T4 DNA ligase. (Preferably up to 50, more preferably up to 30, repeats of the internal repeat duplex can be used).
3. In molar excess, combine the 3' external linker duplex with the above 5' linker-internal repeat duplex, anneal and ligate as described above.
4. Digest the 5' linker-internal repeat-3' linker duplex with BamHI (cuts within the 5'-linker) and EcoR1 (cuts within the 3'-linker).
5. Size fractionate the reaction products using Sephacryl gel permeation chromatography to select constructs greater than 90 bp.
6. Insert the sized, digested synthetic gene cassette into a plasmid having a polylinker containing BamHI and EcoRI sites (e.g., pBluescript SK$^+$ or KS$^+$ [Stratagene]).
7. Transform *E. coli* cells (e.g., by electroporation or the use of competent cells) with the plasmid into which the synthetic gene construct has been ligated.
8. Following *E. coli* transformation, the internal repeat oligonucleotides are used to screen and identify Ampicillin-resistant colonies carrying the synthetic gene construct.
9. The insert contained on the plasmids within the Ampicillin-resistant colonies are sequenced to confirm the fidelity of the synthetic gene construct.

b) GAGP (SEQ ID NO:15) Consensus Sequence Cassette

A synthetic gene cassette encoding the GAGP consensus sequence is generated as described above using the following 5' linker, internal repeat and 3' linker duplexes.

```
                    5'-Linker

Amino Acid (SEQ ID NO: 40):  A   A   G   S   S   T
                             R   A   (S   P   S)

5'-GCT GCC GGA TCC TCA ACC CGG  (SEQ ID NO: 41)
    GCC-3'

3'-CGA CGG CCT AGG AGT TGG GCC  (SEQ ID NO: 42)
    CGG AGT GGC AGT-5'

3'-Linker (for pBI121-Sig-EGFP)

Amino Acid (SEQ ID NO: 43):  S   P   S   P   V   A
                             R   N   S   P   P

5'-TCA CCC TCA CCG GTC GCC CGG  (SEQ ID NO: 44)
    AAT TCA CCA CCC-3'

3'GGC CAG CGG GCC  (SEQ ID NO: 45)
    TTA AGT GGT GGG-5'

3'-Linker (for pBI121-Sig)

Amino Acid:

5'-TCA CCC TCA TAA TAG AGC TCC  (SEQ ID NO: 46)
    CCC-3'

3'ATT ATC TCG AGG  (SEQ ID NO: 47)
        GGG-5'

Internal Repeat

Amino Acid (SEQ ID NO: 48):  S   P   S   P   T   P
                             T   P   P   G   P
                             H   S   P   P   P   T
                             L 5'-TCA CCC TCA CCA ACT CCT ACC  (SEQ ID NO: 49)
    CCA CCA CCT GGT CCA CAC TCA CCA
    CCA CCA ACA TTG-3'

3'-GGT TGA GGA TGG  (SEQ ID NO: 50)
    GGT GGT GGA CCA GGT GTG AGT GGT
    GGT GGT TGT AAC AGT GGG AGT-5'
```

Conversion of the "internal" AGP-like motif and 5' & 3' "external" gene cassettes to long duplex DNA is accomplished using the steps described in section a) above. Up to fifty (50) repeats of the internal repeat duplex are desirable (more preferably up to thirty (30) repeats, and more preferably approximately twenty (20) repeats) (i.e., the wild-type protein contains 20 of these repeats).

Since the above GAGP internal repeat is a consensus sequence, it is also desirable to have repeats that comprise a repeat sequence that varies from the consensus sequence (see e.g. Table 3 above). In this regard, the variant sequences are likely to be glycosylated in a slightly different manner, which may confer different properties (e.g. more soluble etc.). Other constructs are shown for other illustrative modules in Table 4.

EXAMPLE 3

Isolation of Tomato P1 Extensin cDNA Clones

In order to obtain the tomato P1 extensin signal sequence (i.e., signal peptide), P1 extensin cDNA clones were isolated using oligonucleotides designed after the P1-unique protein sequence (SEQ ID NO:51): Val-Lys-Pro-Tyr-His-Pro-Thr-Hyp-Val-Tyr-Lys. When present at the N-terminus of a protein sequence, the P1 extensin signal sequence directs the nascent peptide chain to the ER.

EXAMPLE 4

Construction of One Embodiment of an Expression Vector pBI121 is an expression vector which permits the high level expression and secretion of inserted genes in plant cells (e.g., tomato, tobacco, members of the genus Solanaceae, members of the family Leguminoseae, non-graminaceous monocotyledons). pBI121 contains the 35S CaMV promoter, the tobacco (*Nicotiana plumbaginifolia*) extensin signal sequence, a EGFP gene, the termination/polyadenylation signal from the nopaline synthetase gene (NOS-ter), a kanamycin-resistance gene (nptII) and the right and left borders of T-DNA to permit transfer into plants by *Agrobacterium*-mediated transformation.

TABLE 4

ILLUSTRATIVE HRGP SYNTHETIC GENE MODULES

1. MODULES FOR AGP-LIKE SEQUENCES a. The $[SP]_n$ Module $[SP]_n$ Internal Repeat Oligo's:

5'-TCA CCC TCA CCA TCT CCT TCG      (SEQ ID NO: 52)
CCA TCA CCC

GGT AGA GGA AGC      (SEQ ID NO: 53)
GGT AGT GGG AGT GGG AGT-5'

The $[SP]_n$ 3' & 5' External Linkers for both plasmids are the same as for the GAGP module.

b. The $[AP]_n$ Module $[AP]_n$ Internal Repeat Oligo's:

5'-GCT CCA GCA CCT GCC CCA GCC      (SEQ ID NO: 54)
CCT GCA CCA -3'

GGA CGG GGT CGG      (SEQ ID NO: 55)
GGA CGT GGT -5'

$[AP]_n$ External Linker Oligo's for plasmid pBI121-Sig-EGFP

5'-Linker:  5'-GCT GCC GGA TCC TCA      (SEQ ID NO: 56)
            ACC CGG

3'-CGA CGG CCT AGG AGT      (SEQ ID NO: 57)
            TGG GCC CGA GGT CGT-5'

TABLE 4-continued

ILLUSTRATIVE HRGP SYNTHETIC GENE MODULES

3'-Linker:  5'-GCT CCA GCA CCG GTC      (SEQ ID NO: 58)
            GCC CGG AAT TCA CCA
            CCC-3'

3'- GGC CAG CGG GCC TTA     (SEQ ID NO: 59)
            AGT
            GGT GGG-5'

$[AP]_n$ External 3' Linker Oligos for plasmid pBI121-Sig

5'-GCT CCA GCA TAA TAG      (SEQ ID NO: 60)
            AGC TCC CCC

ATT ATC TCG        (SEQ ID NO: 61)
            AGG GGG-5' c. The $[TP]_n$ Module $[TP]_n$ Internal Repeat Oligo's:

5'-ACA CCA ACC CCT ACT CCC ACG      (SEQ ID NO: 62)
CCA ACA CCT ACA CCC ACT CCA

GGA TGA GGG TGC      (SEQ ID NO: 63)
GGT TGT GGA TCT GGG TGA GGT TGT
GGT TGG-5'

$[TP]_n$ External Linker Oligo's for
  pBI121-Sig-EGFP:

5'Linker:   5'-GCT GCC GGA TCC TCA      (SEQ ID NO: 64)
            ACC CGG

3'-CGA CGG CCT AGG AGT      (SEQ ID NO: 65)
            TGG GCC TGT GGT TGG-5'

3'Linker:   5'-ACA CCA ACC CCG GTC      (SEQ ID NO: 66)
            GCC CGG AAT TCA CCA
            CCC-3'

GGC CAG            (SEQ ID NO: 67)
            CGG GCC TTA AGT GGT
            GGG-5'

$[TP]_n$ External 3' Linker Oligos for pBI121-Sig

5'-ACA CCA ACC TAA TAG AGC TCC  (SEQ ID NO: 68)
            CCC

ATT ATC TCG AGG    (SEQ ID NO: 69)
            GGG-5'

2. MODULES FOR EXTENSIN-LIKE SEQUENCES a. The $[SPP]_n$ Module $[SPP]_n$ Internal Repeat Oligo's:

5'-CCA CCA TCA CCA CCC TCT CCT      (SEQ ID NO: 70)
CCA TCA CCC CCA TCC CCA CCA TCA

GGT GGG AGA GGA      (SEQ ID NO: 71)
GGT AGT GGG GGT AGG GGT GGT AGT
GGT GGT AGT-5'

$[SPP]_n$ External Linkers for pBE121-Sig-EGFP:

5'Linker:   5'-GCT GCC GGA TCC TCA      (SEQ ID NO: 72)
            ACC CGG GCC

3'-CGA CGG CCT AGG AGT      (SEQ ID NO: 73)
            TGG GCC CGG GGT GGT
            AGT-5'

3'Linker:   5'-CCA CCA TCA CCG GTC      (SEQ ID NO: 74)
            GCC CGG AAT TCA CCA

TABLE 4-continued

ILLUSTRATIVE HRGP SYNTHETIC GENE MODULES

```
                         CCC-3'
                             GGC CAG    (SEQ ID NO: 75)
                     CGG GCC TTA AGT GGT
                                    GGG-5'

[SPP]ₙ External 3' Linker for pBE121-Sig:

5'-CCA CCA TCA TAA TAG      (SEQ ID NO: 76)
               AGC TCC CCC
                             ATT ATC    (SEQ ID NO: 77)
                         TCG AGG GGG-5' b. The [SPPP]ₙ Module

[SPPP]ₙ Internal Repeat Oligo's:

5'-CCA CCA CCT TCA CCA CCT CCA         (SEQ ID NO: 78)
   TCT CCC CCA CCT TCC CCT CCA CCA
   TCA
                AGT GGT GGA GGT         (SEQ ID NO: 79)
AGA GGG GGT GGA AGG GGA GGT GGT
AGT GGT GGT GGA-5'

[SPPP]ₙ External Linker Oligo's for pBI121-
Sig-EGFP:

5'-Linker:  5'-GCT GGA TCC TCA ACC      (SEQ ID NO: 80)
               CGG GCC TCA
            3'-CGA CCT AGG ACT TGG      (SEQ ID NO: 81)
               GCC CGG AGT GGT GGT
               GGA-5'

3'-Linker:  5'-CCA CCA CCT TCA CCG      (SEQ ID NO: 82)
               GTC GCC CGG AAT TCA
               CCA CCC-3'
                             AGT GGC    (SEQ ID NO: 83)
                         CAG CGG GCC TTA AGT
                         GGT GGG-5'

[SPPP]ₙ External 3' Linker Oligos for pBI121-Sig:

5'-CCA CCA CCT TAA TAG      (SEQ ID NO: 84)
               AGC TCC CCC
                             ATT ATC    (SEQ ID NO: 85)
                         TCG AGG GGG-5' d. The P3-Type Extensin Palindromic Module:

P3-Type Extensin Palindromic Internal Repeat
    Oligo's:

5'-CCA CCA CCT TCA CCC TCT CCA         (SEQ ID NO: 86)
   CCT CCA CCA TCT CCG TCA CCA
                AGT GGG                 (SEQ ID NO: 87)
AGA GGT GGA GGT GGT AGA GGC AGT
GGT GGT GGT GGA-5'

P3-Type Extensin Palindromic External Linker
Oligo's: Use the [SPPP]ₙ linkers (SEE ABOVE)

e. The Potato Lectin HRGP Palindromic Module:

Potato Lectin HRGP Palindromic External Linker
    Oligo's:

5'-CCA CCA CCT TCA CCC CCA TCT         (SEQ ID NO: 88)
   CCA CCT CCA CCA TCT CCA CCG TCA
   CCA
                AGT GGG GGT AGA         (SEQ ID NO: 89)
```

TABLE 4-continued

ILLUSTRATIVE HRGP SYNTHETIC GENE MODULES

```
GGT GGA GGT GGT AGA GGT GGC AGT
GGT GGT GGT GGA-5'

Potato Lectin HRGP Palindromic External Linker
Oligo's: Use the [SPPP]ₙ linkers (SEE ABOVE)

f. P1-Extensin-Like Modules:

i.  The SPPPPTPVYK Module:
        (SEQ
         ID
         NO:
         254)

SPPPPTPVYK Internal Repeat Oligo's:
    (SEQ ID NO: 254)

5'-CCA CCA CCT ACT CCC GTT TAC         (SEQ ID NO: 90)
   AAA TCA CCA CCA CCT ACT CCC
   GTT TAC AAA TCA CCA
                TGA GGG CAA ATG         (SEQ ID NO: 91)
TTT AGT GGT GGT GGT GGA TCA GGG
CAA ATG TTT AGT GGT GGT GGT
GGA-5'

SPPPPTPVYK External Linker Oligo's: Use the
    [SPPP]ₙ linkers (SEE ABOVE)    (SEQ ID NO: 254)

ii. The SPPPPVKPYHPTPVFL Module:
        (SEQ
         ID
         NO:
         255)

SPPPPVKPYHPTPVFL Internal Repeat Oligo's:
    (SEQ ID NO: 255)

5'-CCA CCA CCT GTC AAG CCT TAC         (SEQ ID NO: 92)
   CAC CCC ACT CCC GTT TTT CTT TCA
   CCA
                CAG TTC GGA ATG         (SEQ ID NO: 93)
GTG GGG TGA GGG CAA AAA GAA AGT
GGT GGT GGT GGA-5'

SPPPPVKPYHPTPVFL External Linker Oligo's: Use
    the [SPPP]ₙ linkers (SEE ABOVE) (SEQ ID NO: 255)

iii. The SPPPPVLPFHPTPVYK Module:
         (SEQ
          ID
          NO:
          290)

SPPPPVLPFHPTPVYK Internal Repeat Oligo's:
    (SEQ ID NO: 290)

5'-CCA CCA CCT GTC TTA CCT TTC         (SEQ ID NO: 94)
   CAC CCC ACT CCC GTT TAC AAA TCA
   CCA
                CAG AAT GGA AAG         (SEQ ID NO: 95)
GTG GGG TGA GGG CAA ATG TTT AGT
GGT GGT GGT GGA-5'

SPPPPVLPFHPTPVYK External Linker Oligo's: Use
    the [SPPP]ₙ linkers (SEE ABOVE) (SEQ ID NO: 290)

EGFP 3' Linker Oligo's needed to insert EGFP into
pBI121-Sig-EGF

5'-GGC CGC GAG CTC CAG CAC GGG         (SEQ ID NO: 96)
                   CG CTC GAG GTC GTG   (SEQ ID NO: 97)
CCC-5'
```

The presence of the extensin signal sequence at the N-terminus of proteins encoded by genes inserted into the pBI121 expression vector (e.g., HRGPs encoded by synthetic gene constructs). The tobacco signal sequence was demonstrated to target extensin fusion proteins through the ER and Golgi for posttranslational modifications, and finally to the wall. The targeted expression of recombinant HRGPs is not dependent upon the use of the tobacco extensin signal sequence. Signal sequences involved in the transport of extensins and extensin modules in the same plant family (Solanaceae) as tobacco may be employed; alternatively, the signal sequence from tomato P1 extensin may be employed.

The EGFP gene encodes a green fluorescent protein (GFP) appropriately red-shifted for plant use (the EGFP gene encodes a S65T variant optimized for use in plants and is available from Clontech). Other suitable mutants may be employed (see Table 1). These modified GFPs allow the detection of less than 700 GFP molecules at the cell surface. The use of a GFP gene provides a reporter gene and permits the formation of fusion proteins comprising repetitive HRGP modules. GFPs require aerobic conditions for oxidative formation of the fluorophore. It is functional at the lower temperatures used for plant cell cultures, normally it does not adversely affect protein function.

Plasmids pBI121-Sig and pBI121-Sig-EGFP are constructed as follows. For both plasmids, the GUS gene present in pBI121 (Clontech) is deleted by digestion with BamHI and SstI and a pair of partially complementary oligonucleotides encoding the tobacco extensin signal sequence is annealed to the BamHI and SstI ends. The oligonucleotides encoding the 21 amino acid extensin signal sequence have the following sequence:

```
            5'-GA TCC GCA ATG    (SEQ ID NO: 98)
GGA AAA ATG GCT TCT CTA TTT GCC
ACA TTT TTA GTG GTT TTA GTG TCA
CTT AGC TTA GCA CAA ACA ACC GGG
GTA CCG GTC GCC ACC ATG GTG TAA
AGC GGC CGC GAG CT-3'
and 5'-C GCG GCC GCT TTA CAC CAT GGT    (SEQ ID NO: 99)
GGC GAC CGG TAC CGG GGT TGT TTG
TGC TAA GCT AAG TGA CAC TAA AAC
CAC TAA AAA TGT GGC AAA TAG AGA
AGC CAT TTT TCC ATG TGC G-3'.
```

In addition to encoding the extensin signal sequence, this pair of oligonucleotides, when inserted into the digested pBI121 vector, provides a BamHI site (5' end) and XmaI and SstI sites (3' end). The XmaI and SstI sites allow the insertion of the GFP gene. The modified pBI121 vector lacking the GUS gene and containing the synthetic extensin signal sequence is termed pBI121-Sig. Proper construction of pBI121 is confirmed by DNA sequencing.

The GFP gene (e.g., the EGFP gene) is inserted into pBI121-Sig to make pBI121-Sig-EGFP as follows. The EGFP gene is excised from pEGFP (Clontech) as a 1.48 kb XmaI/NotI fragment (base pairs 270 to 1010 in pEGFP). This 1.48 kb XmaI/NotI fragment is then annealed and ligated to a synthetic 3' linker (see above). The EGFP-3' linker is then digested with SstI to produce an XmaI/SstI EGFP fragment which in inserted into the XmaI/SstI site of pBI121-Sig to create pBI121-Sig-EGFP. The AgeI (discussed below), XmaI and SstI sites provide unique restriction enzyme sites. Proper construction of the plasmids is confirmed by DNA sequencing.

The EGFP sequences in pBI121-Sig-EGFP contain an AgeI site directly before the translation start codon (i.e., ATG) of EGFP. Synthetic HRGP gene cassettes are inserted into the plasmid between the signal sequence and the EGFP gene sequences as XmaI/AgeI fragments; the HRGP gene cassettes are excised as XmaI/AgeI fragments from the pBluescript constructs described in Ex.2. Proper construction of HRGP-containing expression vectors is confirmed by DNA sequencing and/or restriction enzyme digestion.

Expression of the synthetic HRGP gene cassettes is not dependent upon the use of the pBI121-Sig and pBI121-Sig-EGFP gene cassette. Analogous expression vectors containing other promoter elements functional in plant cells may be employed (e.g., the CaMV region IV promoter, ribulose-1, 6-biphosphate (RUBP) carboxylase small subunit (ssu) promoter, the nopaline promoter, octopine promoter, mannopine promoter, the β-conglycinin promoter, the ADH promoter, heat shock promoters, tissue-specific promoters, e.g., promoters associated with fruit ripening, promoters regulated during seed ripening (e.g., promoters from the napin, phaseolin and glycinin genes). For example, expression vectors containing a promoter that directs high level expression of inserted gene sequences in the seeds of plants (e.g., fruits, legumes and cereals, including but not limited to corn, wheat, rice, tomato, potato, yam, pepper, squash cucumbers, beans, peas, apple, cherry, peach, black locust, pine and maple trees) may be employed. Expression may also be carried out in green algae.

In addition, alternative reporter genes may be employed in place of the GFP gene. Suitable reporter genes include β-glucuronidase (GUS), neomycin phosphotransferase II gene (nptII), alkaline phosphatase, luciferase, CAT (Chloramphenicol AcetylTransferase). Preferred reporter genes lack Hyp residues. Further, the proteins encoded by the synthetic HRGP genes need not be expressed as fusion proteins. This is readily accomplished using the pBI121-Sig vector.

EXAMPLE 5

Expression of Recombinant HRGPs in Tomato Cell Suspension Cultures

The present invention contemplates recombinant HRGPs encoded by expression vectors comprising synthetic HRGP gene modules are expressed in tomato cell suspension cultures. The expression of recombinant HRGPs in tomato cell suspension cultures is illustrated by the discussion provided below for recombinant GAGP expression.

a) Expression of Recombinant GAGP

An expression vector containing the synthetic GAGP gene cassette (capable of being expressed as a fusion with GFP or without GFP sequences) is introduced into tomato cell suspension cultures. A variety of means are known to the art for the transfer of DNA into tomato cell suspension cultures, including *Agrobacteriuln*-mediated transfer and biolistic transformation.

*Agrobacterium*-mediated transformation: The present invention contemplates transforming both suspension cultured cells (Bonnie Best cultures) and tomato leaf discs by mobilizing the above-described plasmid constructions (and others) from E. coli into Agrobacterium tumefaciens strain LBA4404 via triparental mating. Positive colonies are used to infect tomato cultures or leaf discs (Lysopersicon esculentum). Transformed cells/plants are selected on MSO medium containing 500 mg/mL carbenicillin and 100 mg/mL kanamycin. Expression of GFP fusion products are conveniently monitored by fluorescence microscopy using a high Q FITC filter set (Chroma Technology Corp.). FITC conjugates (e.g. FITC-BSA) can be used along with purified recombinant GFP as controls for microscopy set-up. Cultured tomato cells show only very weak autofluorescence. Thus, one can readily verify the spatiotemporal expression of GFP-Hyp module fusion products.

Transgenic cells/plants can be examined for transgene copy number and construct fidelity genomic Southern blotting and for the HRGP construct mRNA by northern blotting, using the internal repeat oligonucleotides as probes. Controls include tissue/plants which are untransformed, transformed with the pBI121 alone, pBI121 containing only GFP, and pBI121 having the signal sequence and GFP but no HRGP synthetic gene.

Microprojectile bombardment: 1.6 M gold particles are coated with each appropriate plasmid construct DNA for use in a Biolistic particle delivery system to transform the tomato suspension cultures/callus or other tissue. Controls include: particles without DNA, particles which contain PBI121 only, and particles which contain PBI121 and GFP.

b) Expression of Other HRGPs of Interest

As noted above, the present invention contemplates expressing a variety of HRGPs, fragments and variants. Such HRGPs include, but are not limited to, RPRps, extensins, AGPs and other plant gums (e.g. gum Karaya, gum Tragacanth, gum Ghatti, etc.). HRGP chimeras include but are not limited to HRGP plant lectins, including the solanaceous lectins, plant chitinases, and proteins in which the HRGP portion serves as a spacer (such as in sunflower). The present invention specifically contemplates using the HRGP modules (described above) as spacers to link non-HRGP proteins (e.g. enzymes) together.

EXAMPLE 6

Construction of a Synthetic HRGP Gene Cassette Incorporating a GAGP Construct

Synthetic gene cassettes encoding contiguous and non-contiguous Hyp modules were constructed using partially overlapping sets consisting of oligonucleotide pairs, "internal repeat pairs" and "external 3'- and 5'-linker pairs" respectively, all with complementary "sticky" ends. The following 5'-linker, internal repeat and 3'-linker duplexes were employed:

```
                  5'-Linker
      A    A   G    S    S    T    R    A (SEQ ID NO: 40)
    (S    P   S)

5'-GCT GCC GGA TCC TCA ACC CGG    (SEQ ID NO: 41)
GCC-3'

3'-CGA CGG CCT AGG AGT TGG GCC    (SEQ ID NO: 42)
CGG AGT GGG AGT-5'

3'-Linker

S    P   S    P    V    A    R    N (SEQ ID NO: 43)
    S    P   P
```

```
5'-TCA CCC TCA CCG GTC GCC CGG    (SEQ ID NO: 44)
AAT TCA CCA CCC-3'

3'-GGC CAG CGG GCC    (SEQ ID NO: 45)
TTA AGT GGT GGG-5'

Internal Repeat
      S    P   S    P    T    P    T    (SEQ ID NO: 100)
    A    P   P    G    P    H    S    P
    P    P   T    L

[5'-TCA CCC TCA CCA ACT CCT ACC    (SEQ ID NO: 101)]
GCA CCA CCT GGT CCA CAC TCT CCA
CCA CCA ACA TTG-3'

[3'-AGT GGG AGT GGT TGA GGA TGG    (SEQ ID NO: 102)]₂
CGT GGT GGA CCA GGT GTG AGA GGT
GGT GGT TGT AAC-5'
then:

S    P   S    P    T    P    T    (SEQ ID NO: 103)
    A    P   P    G    P    H    S    P
    P    P   S    L

5'-TCA CCC TCA CCA ACT CCT ACC    (SEQ ID NO: 104)
GCA CCA CCT GGT CCA CAC TCT CCA
CCA CCA TCA TTG-3'

3'-AGT GGG AGT GGT TGA GGA TGG    (SEQ ID NO: 105)
CGT GGT GGA CCA GGT GTG AGA GGT
GGT GGT AGT AAC-5'
```

The following synthetic gene (SEQ ID NO:106: protein disclosed as SEQ ID NO: 107) was eventually expressed in tobacco and tomato cell cultures and tobacco plants using the above constructs:

```
                   M    G    K    M    A    S    L    F    A
     T    F    L   V    V    L    V

5'-GGA TCC GCA ATG GGA AAA ATG GCT TCT CTA TTT GCC
ACA TTT TTA GTC GTT TTA GTG

3'-CCT AGG CGT TAC CCT TTT TAC CGA AGA GAT AAA CGG
TGT AAA AAT CAC CAA AAT CAC

S    L    S   L    A    Q    T    T    R    D    S    P    S
     P    T    P   T    A    P

TCA CTT AGC TTA GCA CAA ACA ACC CGG GAC TCA CCC
TCA CCA ACT CCT ACC GCA CCA

AGT GAA TCG AAT CGT GTT TGT TGG GCC CTG AGT GGG
AGT GGT TGA GGA TGG CGT GGT

P    G    P   H    S    P    P    P    T    L    S    P    S
     P    T    P   T    A    P

CCT GGT CCA CAC TCT CCA CCA CCA ACA TTG TCA CCC
TCA CCA ACT CCT ACC GCA CCA

GGA CCA GGT GTG AGA GGT GGT GGT TGT AAC AGT GGG
AGT GGT TGA GGA TGG CGT GGT

P    G    P   H    S    P    P    P    T    L    S    P    S
     P    T    P   T    A    P

CCT GGT CCA CAC TCA CCA CCA CCA ACA TTG TCA CCC
TCA CCA ACT CCT ACC GCA CCA

GGA CCA GGT GTG AGT GGT GGT GGT TGT AAC AGT GGG
AGT GGT TGA GGA TGG CGT GGT

P    G    P   H    S    P    P    P    S    L    S    P    S
     P    V
```

-continued

```
CCT GGT CCA CAC TCA CCA CCA CCA TCA TTG TCA CCC
TCA CCG GTC GCC ACC-gfp-3'

GGA CCA GGT GTG AGT GGT GGT GGT AGT AAC AGT GGG
AGT GGC CAG CGG TGG-gfp-5'
```

This example involved: (A) Oligonucleotide pair preparation; (B) Oligonucleotide polymerization; (C) Construct precipitation; (D) Restriction of gene 3'-linker and 5'-linker capped ends; (E) Size-fractionation and removal of enzyme contaminants; (F) Gene insertion into SK plasmid vector. All SDS-PAGE purified oligonucleotides were synthesized by Gibco-BRL.

(A) Oligonucleotide Pair Preparation

In separate Eppendorf tubes were combined:

Tube 1) 5.5 µl GAGP internal repeat sense oligonucleotide (0.5 m-nol/µl), 5.5 µl GAGP internal repeat antisense oligonucleotide (0.5 nmol/µl), 11 µl T4 ligase 10× ligation buffer (New England Biolabs);

Tube 2) 2 µl 5'-sense linker (0.05 nmol/µl), 2 µl 5'-antisense linker (0.05 nmol/µl), 1 µl H2O, 5 µl T4 ligase 10× ligation buffer (New England Biolabs);

Tube 3) 2 µl 3'-sense linker (1 nmol/µl), 2 µl 3'-antisense linker (1 nmol/µl), 1 µl water, 5 µl T4 ligase 10× ligation buffer (New England Biolabs).

All tubes were heated to 90-95° C. for 5 minutes, then slowly cooled over the next 3 hours to 45° C. The tubes were then incubated at 45° C. for 2 hours.

(B) Oligonucleotide Polymerization

10 µl of solution from Tube 1 (internal repeat pair) was combined with 10 µl of solution from Tube 2 (5' linker pair), and incubated at 17° C. for 3 hours. To this mixture was added 80 µl water and 2 µl (4000 U) T4 DNA ligase (New England Biolabs), and again incubated at 12-15° C. for 36 hours. The degree of polymerization was verified on 2.2% agarose gel (Fisher).

The 3'-end of the polymer was then capped by adding 50 µl of the ligated GAGP 5'-linker mixture from above to 5 µl of solution from Tube 3 (3'-linker), heating to 30° C., and incubating at 17° C. for 3 hours. 20 µl water and 2 µl T4 DNA ligase (New England Biolabs) was then added, and the solution incubated at 12-15° C. for 36 hr. Finally, the solution was heated at 65° C. for 10 minutes to denature the ligase.

(C) Construct Precipitation

10 µl GAGP construct from (B) above was combined with 25 µl water and 5 µl 3 M NaAcetate. 150 µl EtOH was then added and the solution incubated at 4° C. for 30 minutes The solution was then centrifuged at 10,000 rpm for 30 minutes The resultant pellet was washed with 70% EtOH and dried.

(D) Restriction of Gene 3'-Linker and 5'-Linker Capped Ends

The pellet from (C) above was dissolved in 14 µl water. 2 µl 10× EcoRI restriction buffer (New England Biolabs), 2 µl EcoRI 10 U/µl (New England Biolabs), and 2 µl BamHI 20 U/µl (New England Biolabs) was then added and the mixture incubated at 37° C. overnight.

(E) Size-Fractionation and Removal of Enzyme Contaminants

10 µl water was added to 20 µl of the restricted genes from Step (D) above. This mixture was then loaded onto a Sephacryl S-400 (Pharmacia Microspin™) minicolumn and spun to remove small (<90 bp) oligonucleotide fragments. The first effluent from the column (i.e. the large MW material) was collected. Finally, the enzymes were removed using a Qiaquick Nucleotide removal kit (Qiagen). The final volume of mixture was approximately 50 µl.

(F) Gene Insertion into SK Plasmid Vector

SK plasmid vector (Strategene) was restricted with BamHI and EcoRI and restricted large plasmid fragments were isolated from agarose gel. To 2-3 µg restricted SK plasmid in 10 µl water was added 6 µl restricted GAGP gene construct from Step (E), 2 µl T4 DNA ligase buffer (New England Biolabs), and 1 µl T4 DNA ligase (New England Biolabs). The solution was then kept at 8° C. overnight for ligation. 100 µl competent XL1-Blue cells (Stratagene) were then transformed with 3 µl ligation mixture. Clones were selected via Blue/White assay (Promega Corporation), as described by Promega Protocols and Applciations Guide, 2 ed. (1991), by hybridization with 32P-labeled antisense internal oligonucleotide, and by restriction mapping.

EXAMPLE 7

Construction of a Synthetic HRGP Gene Cassette Incorporating an SP Construct Synthetic gene cassettes encoding contiguous and non-contiguous Hyp modules were constructed using partially overlapping sets consisting of oligonucleotide pairs, "internal repeat pairs" and "external 3'- and 5'-linker pairs" respectively, all with complementary "sticky" ends. The following 5'-linker, internal repeat and 3'-linker duplexes were employed:

```
                     5'-Linker

A   A   G   S   S   T   R   A       (SEQ ID NO: 40)
       (S   P   S)

5'-GCT GCC GGA TCC TCA ACC CGG              (SEQ ID NO: 41)
GCC-3'

3'-CGA CGG CCT AGG AGT TGG GCC CGG          (SEQ ID NO: 42)
AGT GGG AGT-5'

3'-Linker

S   P   S   P   V   A   R   N       (SEQ ID NO: 43)
        S   P   P

5'-TCA CCC TCA CCG GTC GCC CGG AAT          (SEQ ID NO: 44)
TCA CCA CCC-3'

3'-GGC CAG CGG CCC TTA            (SEQ ID NO: 45)
AGT GGT GGG-5'

Internal Repeat

S   P   S   P   S   P   S   P       (SEQ ID NO: 108)
        S   P  (S   P   S)

5'-TCA CCC TCA CCA TCT CCT TCC CCA          (SEQ ID NO: 109)
TCA CCC

3'-GGT ACA GGA AGC GGT            (SEQ ID NO: 110)
AGT GGG AGT GGG AGT-5'
```

The following synthetic gene (SEQ ID NO:111: protein disclosed as SEQ ID NO: 236) was eventually expressed in tobacco and tomato cell cultures and tobacco plants using the above constructs:

```
        G    S    A    M    G    K    M    A    S    L    F    A
   T    F    L    V    V    L    V

5'-GGA TCC GCA ATG GGA AAA ATG GCT TCT CTA TTT GCC
ACA TTT TTA GTG GTT TTA GTG

3'-CCT AGG CGT TAC CCT TTT TAC CGA AGA GAT AAA CGG
TGT AAA AAT CAC CAA AAT CAC

S    L    S    L    A    Q    T    T    R    A  [ S    P
   S    P    S    P    S    P    S

TCA CTT AGC TTA GCA CAA ACA ACC CGG GCC [TCA CCC
TCA CCA TCT CCT TCG CCA TCA

AGT GAA TCG AAT CGT GTT TGT TGG GCC CGG [AGT GGG
AGT GGT AGA GGA AGC GGT AGT

P ]  S    P    S    P    V    A    T

CCC] 6 TCA CCC TCA CCG GTC GCC ACC-gfp-3'

GGG] 6 AGT GGG AGT GGC CAG CGG TGG-gfp-5'
```

This example involved: (A) Oligonucleotide pair preparation; (B) Oligonucleotide polymerization; (C) Construct precipitation; (D) Restriction of gene 3'-linker and 5'-linker capped ends; (E) Size-fractionation and removal of enzyme contaminants; (F) Gene insertion into SK plasmid vector. All SDS-PAGE purified oligonucleotides were synthesized by Gibco-BRL.

(A) Oligonucleotide Pair Preparation
In separate Eppendorf tubes were combined:
Tube 1) 5.5 µl SP internal repeat sense oligonucleotide (0.5 nmol/µl), 5.5 µl SP internal repeat antisense oligonucleotide (0.5 nmol/µl), 11 µl T4 ligase 10× ligation buffer (New England Biolabs);
Tube 2) 2 µl 5'-sense linker (0.05 nmol/µl), 2 µl 5'-antisense linker (0.05 nmol/µl), 1 µl H2O, 5 µl T4 ligase 10× ligation buffer (New England Biolabs);
Tube 3) 2 µl 3'-sense linker (1 nmol/µl), 2 µl 3'-antisense linker (1 nmol/µl), 1 µl water, 5 µl T4 ligase 10× ligation buffer (New England Biolabs).

All tubes were heated to 90-95° C. for 5 minutes, then slowly cooled over the next 3 hours to 45° C. The tubes were then incubated at 45° C. for 2 hours.

(B) Oligonucleotide Polymerization
10 µl of solution from Tube 1 (internal repeat pair) was combined with 10 µl of solution from Tube 2 (5' linker pair), and incubated at 17° C. for 3 hours. To this mixture was added 80 µl water and 2 µl (4000 U) T4 DNA ligase (New England Biolabs), and again incubated at 12-15° C. for 36 hours. The degree of polymerization was verified on 2.2% agarose gel (Fisher).

The 3' end of the polymer was then capped by adding 50 µl of the ligated SP-5' linker mixture from above to 5 µl of solution from Tube 3 (3' linker), heating to 30° C., and incubating at 17° C. for 3 hours. 20 µl water and 2 µl T4 DNA ligase (New England Biolabs) was then added, and the solution was incubated at 12-15° C. for 36 hr. Finally, the solution was heated at 65° C. for 10 minutes to denature the ligase.

(C) Construct Precipitation
10 µl SP construct from (B) above was combined with 25 µl water and 5 µl 3 M NaAcetate. 150 µl EtOH was then added and the solution incubated at 4° C. for 30 minutes The solution was then centrifuged at 10,000 rpm for 30 minutes The resultant pellet was washed with 70% EtOH and dried.

(D) Restriction of Gene 3'-Linker and 5'-Linker Capped Ends

The pellet from (C) above was dissolved in 14 µl water. 2 µl 10× EcoRI restriction buffer (New England Biolabs), 2 µl EcoRI 10 U/µl (New England Biolabs), and 2 µl BamHI 20 U/µl (New England Biolabs) was then added and the mixture incubated at 37° C. overnight.

(E) Size-Fractionation and Removal of Enzyme Contaminants

10 µl water was added to 20 µl of the restricted genes from Step (D) above. This mixture was then loaded onto a Sephacryl S-400 (Pharmacia Microspin™) minicolumn and spun to remove small (<90 bp) oligonucleotide fragments. The first effluent from the column (i.e. the high molecular weight material) was collected. Finally, the enzymes were removed using a Qiaquick Nucleotide removal kit (Qiagen). The final volume of mixture was approximately 50 µl.

(F) Gene Insertion into SK Plasmid Vector

SK plasmid vector (Strategene) was restricted with BamHI and EcoRI and restricted large plasmid fragments were isolated from agarose gel. To 2-3 µg restricted SK plasmid in 10 µl water was added 6 µl restricted SP gene construct from Step (E), 2 µl T4 DNA ligase buffer (New England Biolabs), and 1 µl T4 DNA ligase (New England Biolabs). The solution was then kept at 8° C. overnight for ligation. 100 µl competent XL1-Blue cells (Stratagene) were then transformed with 3 µl ligation mixture. Clones were selected via Blue/White assay (Promega Corporation), as described by Promega Protocols and Applications Guide, 2 ed. (1991), by hybridization with 32P-labeled antisense internal oligonucleotide, and by restriction mapping.

EXAMPLE 8

Gene Subcloning into pEGP, pKS, pUC18 and pBI121 and Signal Sequence Synthesis

The methods of the following example were used to incorporate the synthetic genes of Examples 6 and 7 into the pBI121 plasmid. Restriction digests, ligations, subclonings, and *E. Coli* transformations were performed generally according to F. M. Ausubel, ed., "Current Protocols in Molecular Biology," (1995), Chapter 3: Enzymatic Manipulation of DNA and DNA Restriction Mapping,; Subcloning of DNA Fragments. The restriction digests used were 1-2 µg of plasmid DNA, 5-10 U of restriction enzyme, and 1× recommended restriction buffer (starting with the 10× buffer provided by the company). Samples were run on 1-2.2% agarose gels in TBE buffers. Plasmid and DNA fragments were isolated from gels using QIAEX II gel extraction kits (Qiagen). The DNA ligase employed was 400 U T4 (New England Biolabs). Vector:fragment ratios employed were 1:2-1:6, and ligation volumes were 20 µl.

Transformation of *E. coli* was done in 5-10 µl ligation reaction volumes with XL-Blue competent cells (Stratagene). Cells were plated on LB plates containing 50 µg/ml ampicillin or 30 µg/ml kanamycin.

Plasmid isolation was performed by growing transformed XL-Blue cells in 3 mL LB-ampicillin or LB-kanamycin medium. The plasmids were then isolated using a Wizard Plus Miniprep DNA Purification System (Promega).

This example involved: (A) Insertion of the synthetic gene into pEGFP; (B) Insertion of GAGP-EGFP or SP-EGFP fragment into pKS; (C) Construction of the Signal Sequence and cloning into pUC18; (D) Insertion of GAGP- EGFP or SP-EGFP construct into pUC18; (E) Insertion of SS-GAGP-EGFP or SS-SP-EGFP genes into pBI121.

(A) Insert Synthetic Gene for GAGP or SP into pEGFP

This step was carried out to allow directional cloning of the gene at the 5' end of EGFP. First, the GAGP or SP gene was isolated from pSK [from Examples 6(F) and 7(F)] as a BamHI (New England Biolabs) and AgeI (New England Biolabs) fragment. The pEGFP (Clontech) was then restricted with BamHI and AgeI. Finally, the BamHI/AgeI-restricted gene was annealed with BamHI/AgeI-restricted pEGFP, and ligated to yield pEGFP containing the synthetic gene inserted at the 5' end of the EGFP.

(B) Insert GAGP-EGFP or SP-EGFP Fragment into pKS

This step was carried out to obtain an Sst I site at the 3' end of EGFP. The GAGP-EGFP or SP-EGFP construct from (A) above was isolated from pEGFP as an XmaI/NotI fragment. pKS (Strategene) was then restricted with XmaI and NotI (New England Biolabs). Finally, the GAGP-EGFP or SP-EGFP construct was annealed with cut pKS and ligated to yield pKS containing GAGP-EGFP or SP-EGFP.

(C) Construct of the Signal Sequence and Cloning into pUC18

In order to anneal the partially overlapping sense and antisense oligonucleotides encoding the extensin signal sequence, 2 µl signal sequence sense oligonucleotide (0.1 nmol/µl), 2 µl signal sequence antisense oligonucleotide (0.1 nmol/µl), 2 µl 10× DNA Polymerase Buffer (New England Biolabs), and 14 µl H$_2$O was combined and heated to 85° C. for 5 minutes The mixture was then slowly cooled to 40° C. over 1 hour.

The annealed oligonucleotides were then extended via primer extension. To the above mixture was added 2 µl dNTP 2.5 mM (New England Biolabs) and 1 µl DNA Polymerase 5 U/µl (New England Biolabs), and the resultant mixture incubated at 37° C. for 10 minutes The polymerase was then denatured by heating at 70° C. for 10 minutes Then 8 µl Buffer 4 (New England Biolabs), 66 µl H$_2$O, 2 µl BamHI 20 U/µl (New England Biolabs), and 2 µl SstI 14 U/µl (Sigma) was added and the mixture incubated at 37° C. overnight. The restriction enzymes were then denatured by heating at 70° C. for 10 minutes.

The mixture was then precipitated with EtOH/NaAcetate (6 µl NaAcetate/300 µl EtOH), and pelletized in a centrifuge. The pellet was washed with 70% EtOH and dried. The pellet was then dissolved in 20 µl H$_2$O and 4 µl was used for ligation into 2 µg pSK (Stratagene) as a BamHI/SstI fragment. Finally, the signal sequence was subcloned into pUC18 as a BamHI/SstI fragment.

(D) Insertion of GAGP-EGFP or SP-EGFP Construct into pUC18

This step was carried out to insert the GAGP-EGFP or SP-EGFP construct "behind" the signal sequence. The GAGP-EGFP or SP-EGFP construct from (B) above was removed from pKS as an XmaI/SstI fragment. pUC18 containing the signal sequence (SS-pUC18) was restricted with XmaI/Sst. The GAGP-EGFP or SP-EGFP fragment was then annealed with cut SS-pUC18, and ligated. The SS-GAGP-EGFP or SS-SP-EGFP gene sequence was then confirmed through DNA sequencing using the pUC18 17-residue sequencing primer (Stratagene).

(E) Insertion of SS-GAGP-EGFP or SS-SP-EGFP Genes into pBI121

The SS-GAGP-EGFP or SS-SP-EGFP gene from (D) above was removed from pUC18 as BamHI/SstI fragments.

pBI121 (Clontech) was restricted with BamHI and SstI and the larger plasmid fragments recovered. The smaller fragments, containing the GUS reporter gene, were discarded. The SS-GAGP-EGFP or SS-SP-EGFP fragment was annealed with the restricted pBI121 fragment and ligated.

EXAMPLE 9

*Agrobacterium* Transformation with pBI121-Derived Plasmids

2 µg of the pBI121 containing SS-GAGP-EGFP or SS-SP-EGFP from Example 8 above was used to transform *Agrobacterium tumefaciens* (Strain LB4404, from Dr. Ron Sederoff, North Carolina State University) according to An et al., Plant Molecular Biology Manual A3:1-19 (1988).

EXAMPLE 10

Transformation of Tobacco Cultured Cells with pBI121-Derived Plasmids

All steps were carried out under sterile conditions. Tobacco cells were grown for 5-7 days in NT-1 medium (pH 5.2, per liter: 1 L packet of MS Salts (Sigma #S5524), 30 g sucrose, 3 ml 6% KH$_2$PO$_4$, 100 mg Myo-Inositol, 1 mL Thiamine•HCl (1 mg/ml stock), 20 µl 2,4-D (10 mg/ml stock) ) containing 100 µg/ml kanamycin. The cells were grown in 1 L flasks containing 500 mL medium on a rotary shaker (94 rpm, 27° C.) to between 15-40% packed cell volume. *Agrobacterium* cells transformed with pBI121-derived plasmid (Example 9) were grown overnight in Luria Broth containing 30 µg/ml kanamycin. The *Agrobacterium* cell broth was pelletized for 1 minutes at 6000 rpm, and the pellet resuspended in 200 µl NT-1 medium.

Excess medium was removed from the tobacco cell broth until the broth had a consistency approximate to applesauce. The tobacco cells were placed in petri dish, and 200 µl of the *Agrobacterium* preparation was added. The mixture was then incubated at room temperature, no light, for 48 hours.

The mixture was then washed 4 times with 20 ml NT-1 to remove the *Agrobacterium* cells, and the plant cells were plate-washed on NT-1 plates containing 400 µg/ml timentin and 100 µg/ml kanamycin. Cells which grew on the antibiotics were selected and checked for green fluorescence through fluorescence microscopy, excitation wavelength 488 nm (see Example 16).

EXAMPLE 11

Transformation of Tomato Cultured Cells with pBI121-Derived Plasmids

All steps were carried out under sterile conditions. Tomato cells were grown for 5-7 days in Schenk-Hildebrand medium (pH 5.8, per liter: 1 L packet of S-H basal salt (Sigma #S6765), 34 g sucrose, 1 g Schenck-Hildebrandt vitamin powder (Sigma #S3766), 100 µl Kinetin 1 mg/ml stock (Sigma #K32532), 44 µl 2,4-D 10 mg/ml stock, 2.1 ml p-chlorophenoxy acetic acid 1 mg/ml stock (Sigma)) containing 200 µg/ml kanamycin. The cells were grown in 1 L flasks containing 500 mL medium on a rotary shaker (94 rpm, 27° C.) to between 15-40% packed cell volume. *Agrobacterium* cells transformed with pBI121-derived plasmid (Example 9) were grown overnight in Luria Broth containing 30 µg/ml kanamycin. The *Agrobacterium* cell broth was pelletized for 1 minutes at 6000 rpm, and the pellet resuspended in 200 µl NT-1 medium.

Excess medium was removed from the tomato cell broth until the broth had a consistency approximate to applesauce. The tomato cells were placed in petri dish, and 200 µl of the Agrobacterium preparation was added. The mixture was then incubated at room temperature, no light, for 48 hours.

The mixture was then washed 4 times with 20 ml NT-1 to remove the Agrobacterium cells, and then the plant cells were plate-washed on NT-1 plates containing 400 µg/ml timentin and 200 µg/ml kanamycin. Cells which grew on the antibiotics were selected and checked for green fluorescence through fluorescence microscopy, excitation wavelength 488 nm.

EXAMPLE 12

Isolation of GAGP-EGFP from Tobacco Cell Suspension Culture Medium

Figure 3:
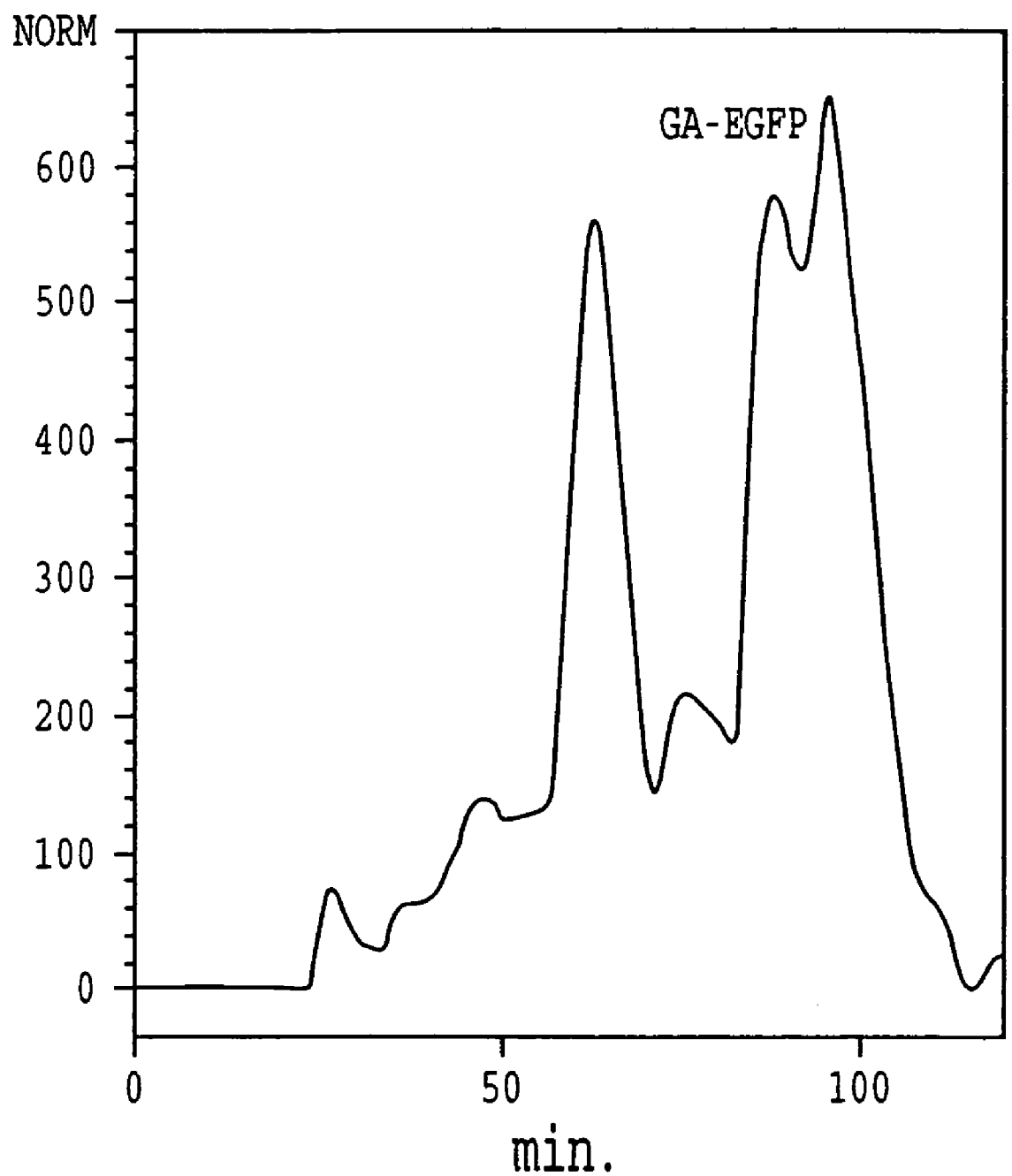
FIG. 3 is a graph showing size-fractionation of expressed protein from transformed tobacco cells.

Transformed tobacco cells were grown on rotary shaker as described in Example 11 above. The medium was separated from the cells by filtration on a glass sintered funnel (coarse grade), and the medium concentrated by freeze-drying. The medium was then resuspended in water (~50 ml/500 mL original volume before lyophilization), and dialyzed against cold water for 48 hours (water changed 6 times). The precipitated pectin contaminants were removed by centrifuge, the pellet discarded, and the supernatant freeze-dried. The dried supernatant was then dissolved in Superose Buffer 20 mg/ml (200 mM sodium phosphate buffer, pH 7, containing 0.05% sodium azide), and spun in a centrifuge to pelletize insolubles. 1.5 ml of this preparation (18-30 mg) was then injected into a semi-preparative Superose-12 gel filtration column (Pharmacia), equilibrated in Superose Buffer and eluted at 1 ml/minutes The UV absorbance was monitored at 220 nm. 2 ml fractions were collected throughout, with GAGP-EGFP expected to elute between 59 and 70 minutes (~2.5 Vo). GAGP-EGFP actually eluted at 65 minutes (see FIG. 3, Example 15 for method used to analyze peaks).

The Superose peak containing GAGP-EGFP was dialyzed against cold water for 24 hours (4 water changes), and freeze-dried. The dried GAGP-EGFP peak was then dissolved in 250 µl 0.1% aqueous TFA (Pierce) and loaded onto a PRP-1 column (Polymeric Reverse Phase, Hamilton) equilibrated in Buffer A (0.1% aqueous TFA). The column was then eluted with Buffer B (0.1% TFA/80% acetonitrile in water; gradient=0-70% B/100 min) at a rate of 0.5 mL/minutes UV absorbance was monitored at 220 nm, and GAGP-EGFP eluted at 63 minutes (see FIG. 4, Example 15 for method used to analyze peaks). Finally, the TFA/acetonitrile was removed through $N_2$ (g) blowdown.

EXAMPLE 13

Characterization of GAGP-EGFP by Neutral Sugar Analysis

100 µg of GAGP-EGFP isolated from tobacco cells was aliquoted into a 1 ml glass microvial and dried under $N_2$ (g). 200 µl 2N TFA was added and the vial capped. The vial was heated at 121° C. for 1 hour, then blown down under $N_2$ at 50° C. to rid the sample of acid. 25 µl of sodium borohydride solution (20 mg/ml in 3 M ammonium hydroxide) was added and the mixture kept at room temperature for 1 hour. 1-3 drops of concentrated acetic acid were added until fizzing stops, and the mixture blown down under $N_2$ at 40° C. 100 µl MeOH was added, the mixture vortexed, and blown down under $N_2$ at 40° C., then this step was repeated. A mixture of 100 µl MeOH and 100 µl $H_2O$ was added, vortexed, and blown down under $N_2$ at 40° C., then the procedure of adding 100 µl MeOH, vortexing, and $N_2$ treatment was repeated 3 times. The resultant mixture was then dried under vacuum overnight.

50 µl reagent grade acetic anhydride was added and the mixture heated at 121° C. for 0.5 hour. The sample was then analyzed by gas chromatography as described in Kieliszewski et al., Plant Physiol. 98:919 (1992). The sample was shown to contain hydroxyproline and sugar, accounting for ~50% of the fusion product on a dry weight basis. Galactose, arabinose, and rhamnose occur in 3:3:1 molar ratio similar to that of native GAGP's 3.5:4:1 molar ratio. This is consistent with the likely presence of both Hyp-arabinosides and Hyp-arabinogalactan polysaccharide in the expresssed construct. The lower ratio of Ara in the GAGP-EGFP fusion glycoprotein is consistent with the Ala for Pro substitution (See Example 6), which removes one arabinosylation site in the peptide.

EXAMPLE 14

Characterization of GAGP-EGFP by Hydroxyproline Assay

100 µg purified GAGP-EGFP was hydrolyzed with 6N HCl (Pierce) at 110° C. for 18 hours. The excess acid was then removed by blowing down under $N_2$. Hydroxyproline was then determined following Kivirikko and Liesma, Scand. J. Clin. Lab. Invest. 11:128 (1959).

EXAMPLE 15

Characterization of Tobacco and Tomato Expression Products by Enyzme-Linked Immunosorbant Assay GAGP-EGFP and SP-EGFP products from tomato and tobacco cell medium and column peaks (see Example 12) were detected by Enyzme-Linked Immunosorbant Assays (ELISA) using the method of Kieliszewski and Lamport, "Cross-reactivities of polyclonal antibodies against extension precursors determined via ELISA techniques," Phytochemistry 25:673-677 (1986). The GAGP-EGFP product was also assayed using anti-EGFP antibodies. Anti-EGFP antibodies (Clontech) were the primary antibody, diluted 1000-fold as recommended by the manufacturer. The secondary antibody was Peroxidase conjugated goat-anti-rabbit IGG diluted 5000-fold (Sigma). Recombinant EGFP (Clontech) was used as a control. This assay was used to generate FIGS. 3 and 4 from Example 12 above.

EXAMPLE 16

Characterization of Tobacco and Tomato Expression Products by Fluorescence

Culture medium from both tobacco and tomato cells transformed with the GAGP-EGFP and the SP-EGFP genes was collected. The EGFP tag fluoresces when exposed to UV light; the excitation wavelength used here was 488 nm. These media were compared with media which included EGFP expressed behind the signal sequence and secreted into the medium, cells transformed with unaltered pBI121 and medium from untransformed cells. The unmistakable bright green fluorescence (data not shown) allowed visualization of the targeted products during their transit through the ER/Golgi membrane system. As *Agrobacterium* lacks the posttranslational machinery to make HRGPs, the fluorescing proteins must be of plant origin.

EXAMPLE 17

Tobacco Leaf Disc Transformation

Sterile tobacco leaves were cut into small pieces and wounded with a needle. 4 ml NT-1 medium without hormones (NT-1 medium of Example 10, omitting 2-4 D) and 150 ul concentrated overnight culture of *Agrobacterium* (see Example 9) was added to the leaves, and the leaf discs incubated for 48 hours, no light. The leaf discs were then washed with NT-1 medium, no hormones. The discs were then put on NT-1 solid medium plates (NT-1 medium of Example 10 plus 7.5 g Bactoagar (Difco Laboratories) ), 400 ul/ml timentin, and 100 ug/ml kanamycin.

After 3 weeks, shoots were transferred from NT-B solid medium without hormones [NT-1 Medium of Example 10, omitting 2-4 D, and adding 300 ul/L benzyl adenine, made from a 2 mg/ml stock made up in DMSO (N-benzyl-9-(tetrahydropyranyl) adenine (Sigma)] to root. Transformed plants have expressed SP-EGFP and GAGP-EGFP in leaf and root cells, as determined by the fluorescence assay of Example 16 (data not shown)

EXAMPLE 18

Sequence Analysis of GAGP and Determination of a Consensus Sequence

This Example describes amino acid sequencing, glycosyl and linkage analysis of GAGP which yielded sequences (including preferred consensus sequences) within the scope of SEQ ID NO:136.

1. Experimental

The following experimental protocols were used to arrive at preferred embodiments of the invention's sequences.

A. Size Fractionation

GAGP was isolated via preparative Superose-6 gel filtration using the method of Qi et al. [Qi et al. (1991) supra] as follows. Nodules of gum arabic (Kordofan Province, Sudan) were a gift from Gary Wine of AEP Colloids (Ballston Spa, N.Y.). Nodules were ground to a fine flour (ca. 2 min.) in a Tekmar A-10 mill. Samples of gum arabic (100 mg/ml) were dissolved in water then diluted to 50 mg/ml in 0.2 M sodium phosphate buffer (pH 7). Samples were spun to pellet insoluble material and 1 ml aliquots were injected onto a semi-preparative Superose-6 gel filtration column (1.6 cm i.d.×50 cm, Pharmacia), eluted isocratically as described previously [Qi et al. (1991) supra]. The protein peaks corresponding to GAGP were dialyzed against water to remove salt and then freeze-dried.

B. HF-Deglycosylation

For chymotryptic peptide mapping GAGP was HF-deglycosylated as follows. The Superose-6 fractionated GAGP (designated dGAGP) was deglycosylated in anhydrous hydrogen fluoride (HF) (20 mg powder/ml HF for 1 h at 4°) as described earlier [Qi et al. (1991) supra], repeating the procedure twice to ensure complete deglycosylation.

C. Purification of Size-Fractionated GAGP and dGAGP by Reverse Phase HPLC

Superose-fractionated GAGP was purified for glycoside analyses, or dGAGP samples were used for peptide mapping on a Hamilton PRP-1 semi-preparative column (10 mm, 250×4.1 mm) by equilibrating with Buffer A (0.1% TFA, aqueous) and eluting with Buffer B (0.1% TFA, 80% acetonitrile, aqueous) by gradient elution (0-100% B/80 min.; 0.5 mL/min flow rate). The eluate was monitored at 220 nm. The collected peaks were blown down to dryness with $N_2(g)$, redissolved in $ddH_2O$, then freeze-dried.

D. Proteolysis of Deglycosylated GAGP with Chymotrypsin or Pronase 2-9 mg samples of dGAGP were digested with pronase or chymotrypsin as detailed earlier [Kieliszewski et al (1992) Plant Physiology 99:538]. The digests were then freeze-dried.

E. Fractionation of dGAGP Chymotryptic Peptides by Cation Exchange HPLC dGAGP chymotryptic peptides (400 mg/injection) were fractionated on a PolySULFOETHYL A™ cation exchange column (9.4 mm i.d.×200 mm; PolyLC, Ellicot City, Md.) equilibrated with Buffer A (5 mM potassium phosphate/phosphoric acid buffer, pH 3, containing 25% v/v acetonitrile) and eluted with Buffer B (Buffer A containing 1 M KCl) using programmed gradient elution. The elution gradient was 0-4% Buffer B in 45 min., 4-8% Buffer B from 45 to 50 min, and 8-30% Buffer B from 50-65 min. The flow rate was 0.4 mL/min and the absorbance was monitored at 220 nm. The collected peaks were pooled, blown down with $N_2$ (g), redissolved in $ddH_2O$, then freeze dried.

F. Peptide Isolation Via Reverse Phase HPLC

The partial pronase digest of dGAGP and major peaks S1 and S2 PolySULFOETHYL Aspartamide column were dissolved in Buffer A (0.1% TFA, aqueous) and injected onto a Hamilton PRP-1 analytical reverse phase column (4.1 mm i.d.×150 mm) which was eluted at 0.5 mL/min with a Buffer B (0.1% TFA and 80% v/v acetonitrile) gradient of 0-50% in 100 min. The effluent was monitored at 220 nm and collected peaks were blown down with $N_2(g)$, re-dissolved in $ddH_2O$, and then freeze dried prior to sequencing. For increased resolution of pronase peptide P3 (FIG. 6), P3 was run through the PRP-1 column a second time, eluting with a 0-30% Buffer B gradient.

G. Automated Edman Degradation of dGAGP Chymotryptic Peptides dGAGP peptides were sequenced at the Michigan State University Macromolecular Facility on a 477A Applied Biosystems (Foster City, Calif.) gas phase sequencer.

H. Amino Acid Analysis

Amino acid compositions were determined by precolumn derivatization of amino acids with 6-aminoquinolyl-N-hydroxysuccinimidyl carbamate followed by reverse-phase HPLC (Nova-Pak™ $C_{18}$ column) using the Waters AccQ-Tag Chemistry Package and the gradient recommended by Waters for analyzing collagen hydrolysates [Crimmins and Cherian (1997) Analytical Biochemistry 244:407; van Wandelen and Cohen (1997) Journal of Chromatography A 763:11].

Hydroxyproline Glycoside Profile. The distribution of GAGP hydroxyproline glycosides was determined after alkaline hydrolysis (105°, 18 h, 0.22 N $Ba(OH)_2$) and neutralization followed by chromatography on a 75×0.6 cm Technicon Chromobeads C2 cation exchange resin as described earlier [Lamport and Miller (1971) Plant Physiology 48:454].

I. Isolation of the Hyp-Polysaccharide

Alkaline hydrolysates (see above) of Superose-6 and PRP-1 purified GAGP were loaded onto a G-50 Sephadex gel permeation column eluted isocratically with 100 mM ammonium acetate buffer, pH 6.8, at a flow rate of 0.3 ml/min. One ml fractions were collected and 40 ml aliquots of each fraction were assayed for Hyp as described earlier [Kivirikko and Liesmaa (1959) Scandinavian Journal of Clinical Laboratories 11:128; Kieliszewski et al. (1990) Plant Physiology 92:316]. The fractions were freeze-dried, then weighed, and the amounts of Hyp and sugar in the fractions were calculated from the recovered weights, Hyp assays, and monosaccharide composition analyses.

J. Partial Alkaline Hydrolysis of GAGP

Superose-fractionated GAGP (10 mg/ml) was dissolved in 0.2 N NaOH/NaBH$_4$ and heated it at 50° C. as described earlier [Akiyama and Kato (1984) Agricultural and Biological Chemistry 48:235]. A 200 ml aliquot was removed immediately (time zero control) and hourly for 6 h, cooled in ice, then 20 ml glacial acetic acid was added (final pH=5.8). Each sample was assayed for Hyp as described earlier [Kivirikko and Liesmaa (1959) Scandinavian Journal of Clinical Laboratories 11:128; Kieliszewski et al. (1990) Plant Physiology 92:316].

K. Saccharide Composition and Linkage Analysis

Monosaccharide compositions and linkage analyses were determined at the Complex Carbohydrate Research Center, University of Georgia following the methods of York et al [York et al.(1985) Methods in Enzymology 118:3] and Merkle and Poppe [Merkle and Poppe (1994) Methods Enzymology 230:1].

2. Determination of an Exemplary Consensus Sequence

Figure 5:
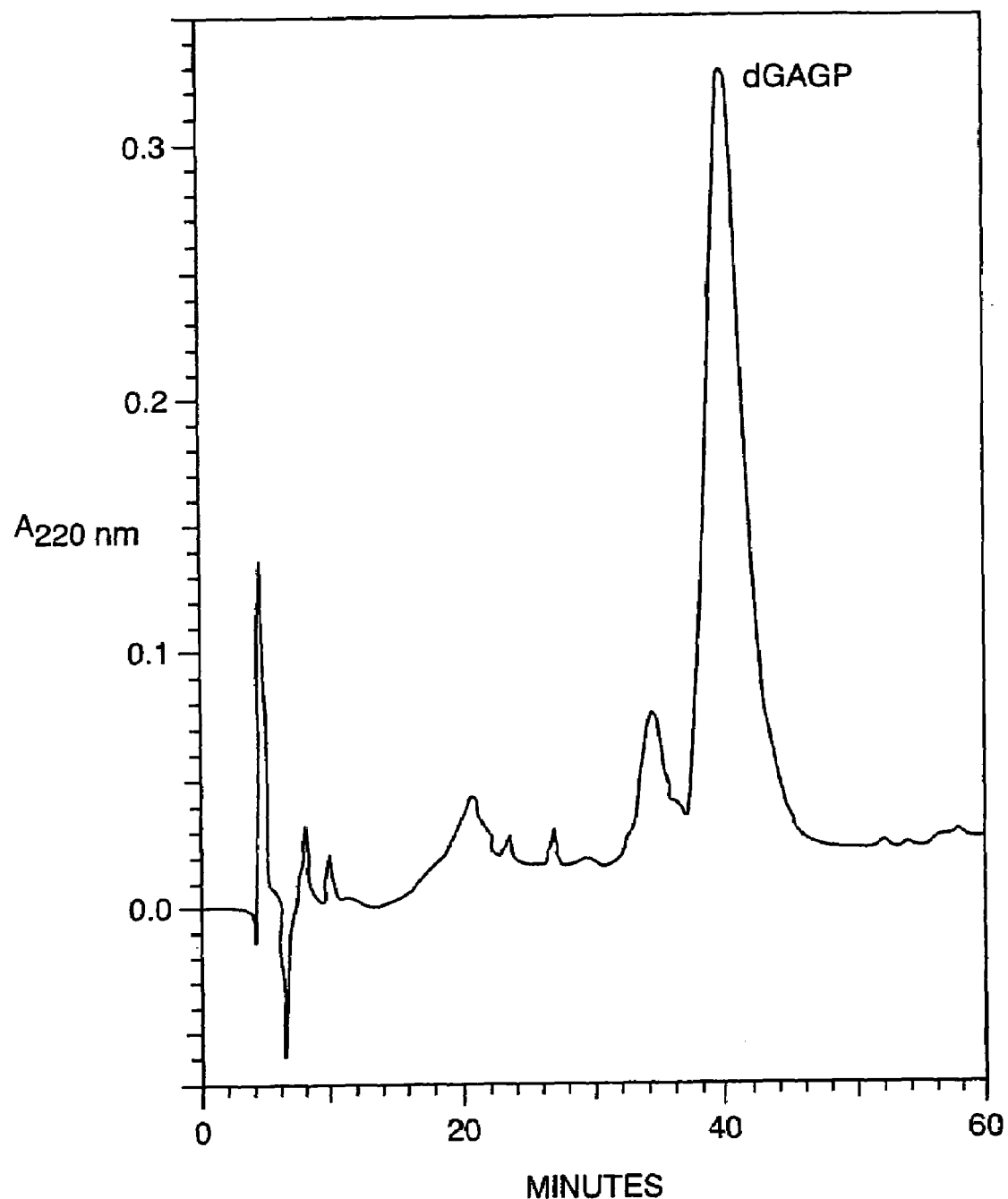
FIG. 5 is the elution profile for dGAGP by reverse phase chromatography on a Hamilton PRP-1 column and fractionation by gradient elution.

Using the method of Qi et al. [Qi et al. (1991) supra] the inventors isolated GAGP via preparative Superose-6 gel filtration. For chymotryptic peptide mapping HF-deglycosylated GAGP was used. This gave a major symmetrical peak (designated dGAGP) when further fractionated by reverse phase chromatography as shown in FIG. 5. FIG. 5 is the elution profile for dGAGP by reverse phase chromatography on a Hamilton PRP-1 column and fractionation by gradient elution. The component at 35 min. was a Hyp-poor contaminant.

Amino acid analysis showed dGAGP had a highly biased but constant amino acid composition in fractions sampled across the peak (Table 5), indicating that dGAGP was a single polypeptide component sufficiently pure for sequence analysis.

TABLE 5

Amino acid compositions of glycosylated GAGP (GAGP) and deglycosylated GAGP (dGAGP) fractions obtained by reverse phase HPLC compared to dGAGP isolated by Qi et. al. [Qi et al. (1991) Plant Physiology 96: 848] dGAGP Peak Fractions *

| Amino Acid [+] | GAGP | Ascending | Center | Descending | GAGP [Qi et al. (1991) supra] |
|---|---|---|---|---|---|
| Hyp | 40.0 | 38.4 | 36.7 | 36.3 | 36.9 |
| Asx | 0.0 | 0.0 | 0.0 | 0.0 | 1.6 |
| Ser | 22.2 | 21.6 | 21.6 | 22.5 | 19.4 |
| Glx | 0.0 | 0.0 | 0.0 | 0.0 | 1.9 |
| Gly | 4.5 | 4.8 | 4.4 | 4.3 | 6.4 |
| His | 6.6 | 8.7 | 8.2 | 8.4 | 7.1 |
| Arg | 0.0 | 0.0 | 0.0 | 0.0 | 0.0 |
| Thr | 10.2 | 10.6 | 12.2 | 11.4 | 8.8 |
| Ala | 1.2 | 0.7 | 0.8 | 1.0 | 1.3 |
| Pro | 8.0 | 7.6 | 8.3 | 8.1 | 6.8 |
| Tyr | 0.0 | 0.0 | 0.0 | 0.0 | 0.3 |
| Val | 0.0 | 0.0 | 0.0 | 0.0 | 0.8 |
| Met | n.d. [++] | n.d. [++] | n.d. [++] | n.d. [++] | n.d. [++] |
| Lys | 0.0 | 0.0 | 0.0 | 0.0 | 1.0 |
| Ile | 0.2 | 0.0 | 0.0 | 0.0 | 0.4 |
| Leu | 6.4 | 7.6 | 7.8 | 8.1 | 6.4 |
| Phe | 0.5 | 0.0 | 0.0 | 0.0 | 0.9 |
| Trp | n.d. [++] | n.d. [++] | n.d. [++] | n.d. [++] | n.d. [++] |
| Cys | 0.0 | 0.0 | 0.0 | 0.0 | 0.0 |

* To check peak homogeneity, three consecutive fractions across the dGAGP peak were analyzed (designated Ascending, Center, and Descending).

[+] represented as mole percent.

[++] not determined.

This was confirmed by the isolation of peptides (Table 6) similar in composition to one other and to the parent GAGP (Table 5).

TABLE 6

Pronase and chymotryptic peptide sequences from the dGAGP Polypeptide Backbone

| | | Sequence |
|---|---|---|
| Pronase Peptide | | |
| P1 | (SEQ ID NOs: 184, 185) | SOOOTLSOSOTOTOOOGPHSOOO(O)- |
| P3 | (SEQ ID NOs: 186, 187) | SOOO(T/S)LSOSOTOTXOO- |
| PH3G2+ | (SEQ ID NO: 188) | SOSOTOTOOOGP |
| Chymotryptic Peptide | | |
| S1P2 | (SEQ ID NO: 189) | SOOOSLSOSOTOTOOTGPH |
| S1P3 | (SEQ ID NO: 190) | SOOOOLSOSOTOTOOOGP- |

TABLE 6-continued

Pronase and chymotryptic peptide sequences from
the dGAGP Polypeptide Backbone

| | | Sequence |
|---|---|---|
| S1P4 | (SEQ ID NOs: 191, 192) | SOLPTLSOLP(A/T)OTOOOGPH |
| S1P5 | (SEQ ID NO: 193) | SOOOOLSOSLTOTOOLGP- |
| S2P1 | (SEQ ID NO: 194) | SOSOTOTOOOGPH |
| S2P2a | (SEQ ID NO: 195) | SOSOAOTOOLGPH |
| S2P2b | (SEQ ID NO: 196) | SOLPTOTOOLGPHS |
| S2P3 | (SEQ ID NO: 197) | SOSOTOTOOLGPH |
| S2P4 | (SEQ ID NO: 198) | SOOLTOTOOLLPH |
| Consensus++ | (SEQ ID NO: 179) | SOOO(O/T/S)LSOSOTOTOO(O/L)GPH |

*O denotes hydroxyproline in the peptide sequences;
X denotes a blank cycle.
+From Delonnay et al. (1993)
++Derived from the major peptides P1, P3, S1P3, S1P5, S2P1, S2P3 and PH3G2.

Figure 6:
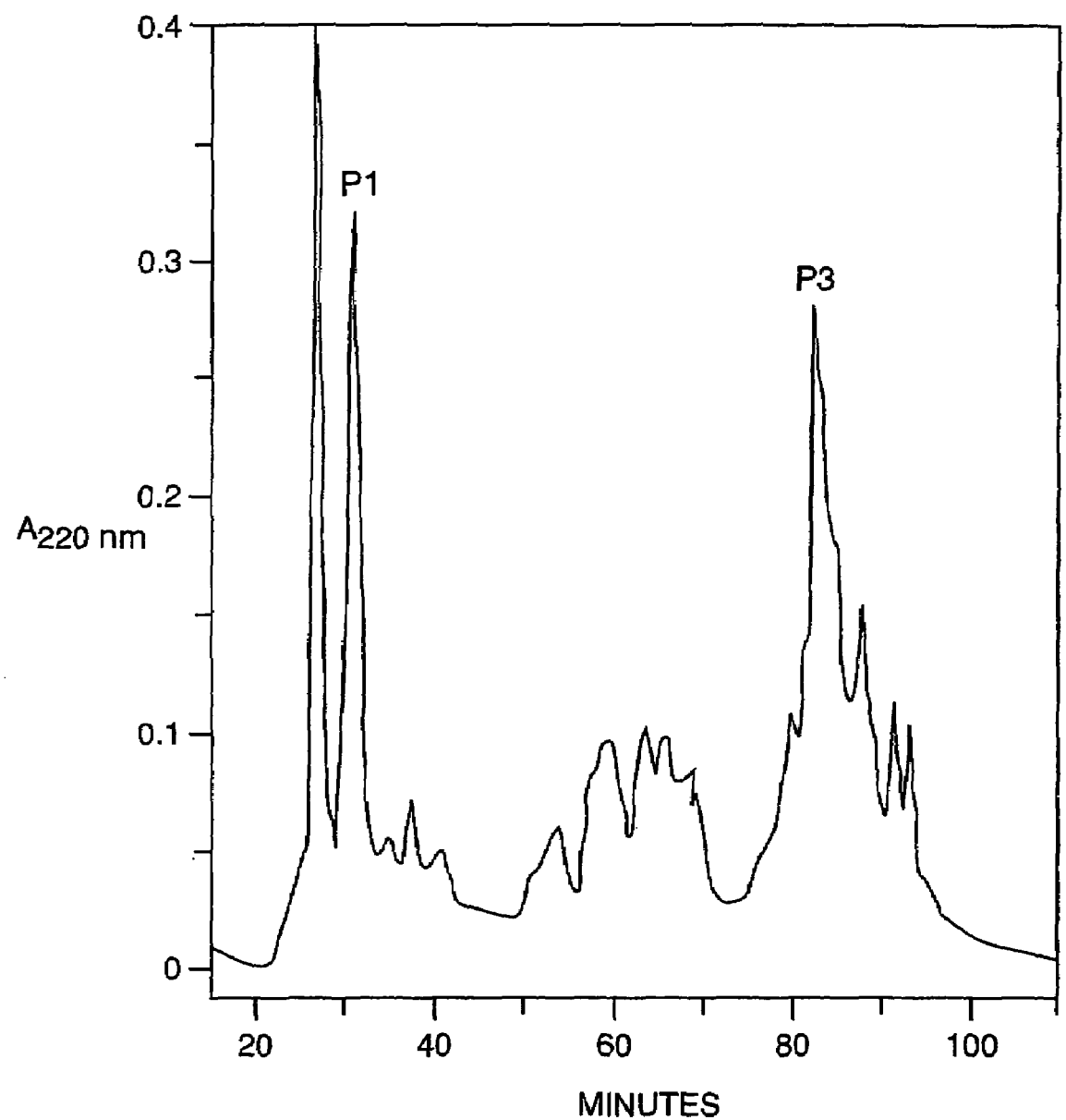
FIG. 6 is the elution profile for dGAGP incomplete pronase digest by reverse phase chromatography. An incomplete digest of dGAGP fractionated on the Hamilton PRP-1 reverse phase column yielded two major peptide fractions, designated P1 and P3.
Figure 7:
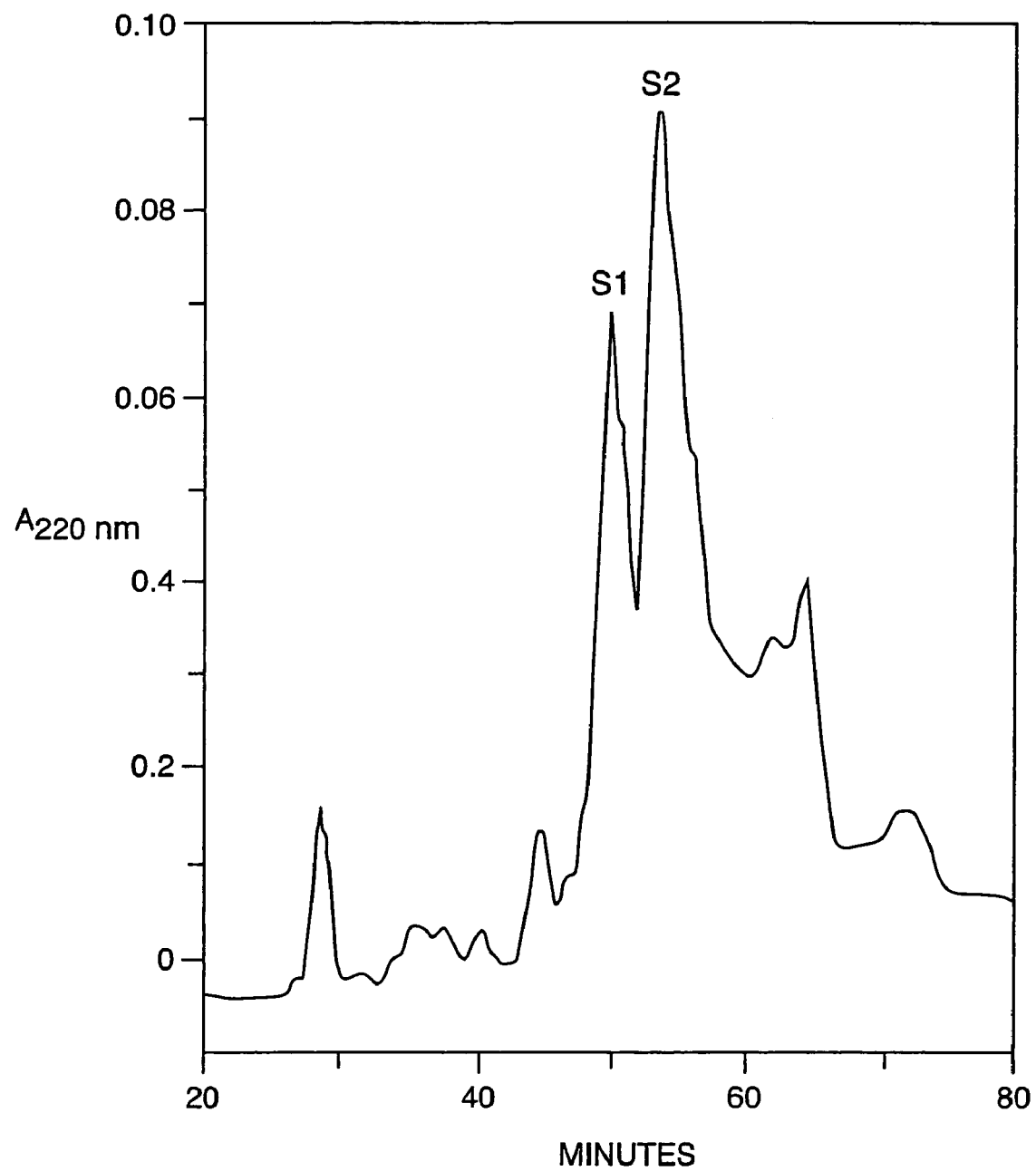
FIG. 7 is the elution profile for a chymotryptic digest of dGAGP fractionated on a Polysulfoethyl aspartamide cation exchange column.
Figure 8A:
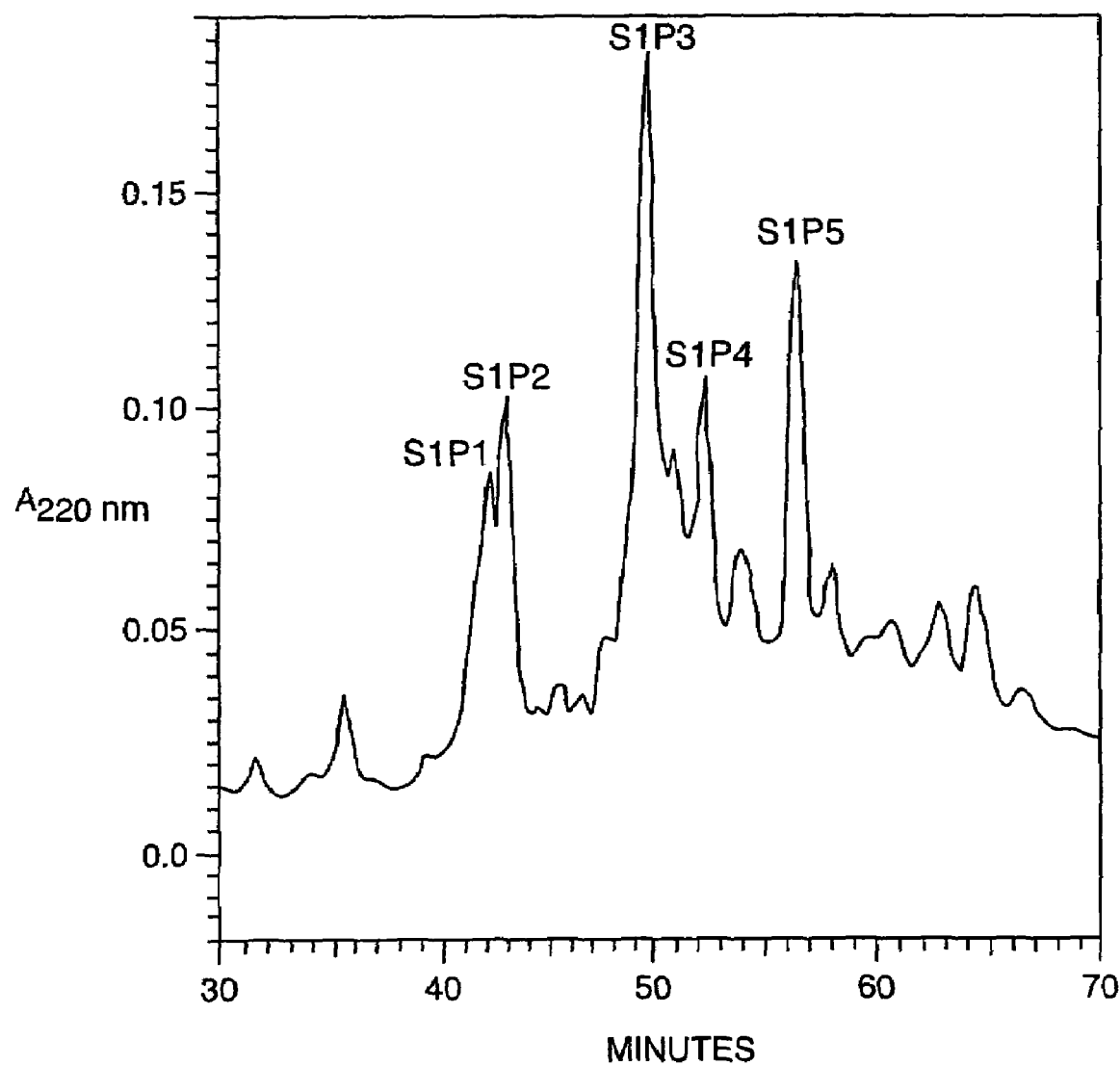
FIGS. 8A and 8B are the elution profiles of dGAGP chymotryptic peptides by reverse phase column chromatography of a) S1, and b)S2.
Figure 8B:
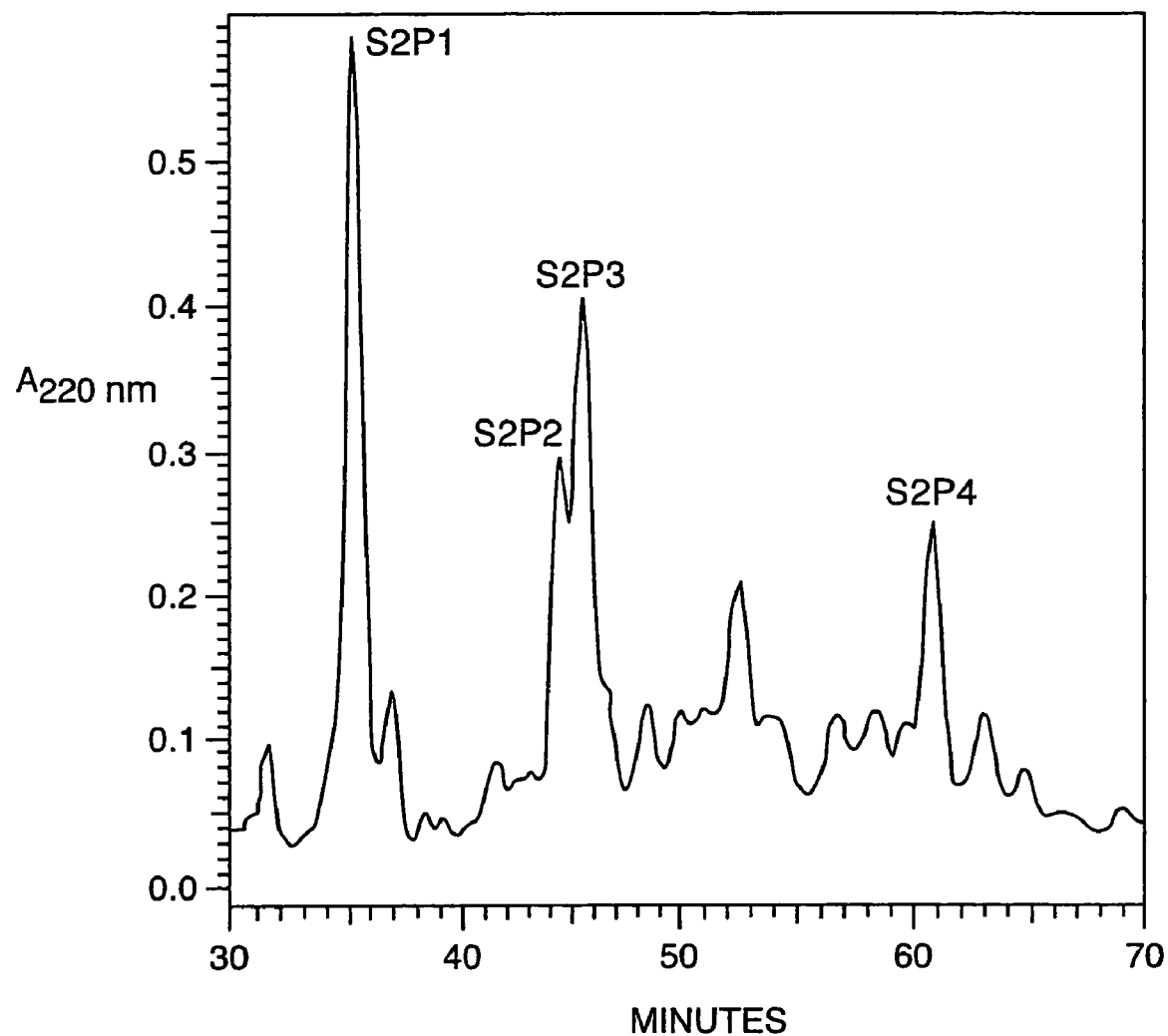

Although native GAGP resists pronase digestion [Akiyama and Kato (1984) Agricultural and Biological Chemistry 48:235; Chikamai et al (1996) Food Hydrocolloids 10:309], which only generates large fragments of ~200 kDa [Connolly et al. (1988) Carbohydrate Polymers 8:23], preliminary work in Lamport's laboratory showed that exhaustive digestion with pronase effectively cleaved dGAGP to small peptides [Delonnay (1993) Masters Thesis, Michigan State University, MI.]. However, the peptides lacked some of the amino acids present in Qi et al's empirical formula: Hyp$_4$ Ser$_2$ Thr Pro Gly Leu His (SEQ ID NO:199) of the repeat motif suggested by Qi et. al. [Qi et al. (1991) supra], most notably His (Table 6, peptide PH3G2.) Therefore, a partial pronase digestion of dGAGP was performed. This gave two large major peptides P1 and P3, as shown in FIG. 6, with partial sequences (Table 6) containing all of the amino acids in the empirical formula.

dGAGP was also digested with chymotrypsin, which slowly cleaved leucyl and histidyl bonds, followed by a two-stage HPLC fractionation scheme. Initial separation of the chymotryptides on a PolySULFOETHYL A™ (PolyLC, Inc. Ellicott City, Md.) cation exchanger yielded two major fractions designated S1 and S2 (FIG. 7). The major chymotryptic fractions, S1 and S2, were collected for further fractionation by reverse phase column chromatography. Further chromatography on a Hamilton PRP-1 reverse phase column resolved fraction S1 into five major peptides labeled S1P1-S1P5, while fractionation of S2 resolved four major peptides, designated S2P1-S2P4, which were sequenced (FIGS. 8a & b). Edman degradation showed that these chymotryptides were closely related to each other and to the pronase peptides (Table 6). These peptides reflect the overall amino acid composition of GAGP and can be related to the 19-amino acid residue consensus sequence (SEQ ID NO:179) shown in Table 6.

From the above data, the inventors concluded that GAGP possesses a highly repetitive polypeptide, albeit with minor variations in the sequence. Based on a linear GAGP molecule of 150 nm [Qi et al. (1991) supra], and presuming the extended polyproline II helix present in both extensins and AGPs [Kieliszewski and Lamport (1994) Plant Journal 5:157; Nothnagel (1997) International Review of Cytology 174:195], the inventors estimate that GAGP contains about 20 peptide repeats with occasional partial repeats. Partial repeats of the consensus sequence may account for the somewhat higher serine content in native GAGP compared to that in the consensus sequence.

The exemplary 19-amino acid residue GAGP consensus sequence of Table 6 contains approximately nine Hyp residues and is roughly twice the size of that previously postulated to contain only a single polysaccharide attachment site [Qi et al. (1991) supra]. Judging from the Hyp-glycoside profile of GAGP (Table 7) [Qi et al. (1991) supra], about one in every five Hyp residues is polysaccharide-substituted.

TABLE 7

GAGP Hydroxyproline glycoside profile

| Hydroxyproline glycoside | Percent of total hydroxyproline |
|---|---|
| Hyp-polysaccharide | 20 |
| Hyp-Ara$_4$ (SEQ ID NO: 200) | 5 |
| Hyp-Ara$_3$ (SEQ ID NO: 201) | 27 |
| Hyp-Ara$_2$ (SEQ ID NO: 202) | 27 |
| Hyp-Ara (SEQ ID NO: 203) | 10 |
| Nonglycosylated Hyp | 11 |

Thus, there are approximately two Hyp-polysaccharide sites in the invention's exemplary consensus sequence. In order to determine which Hyp residues are involved in polysaccharide attachment, without limiting the invention to any particular mechanism, the inventors predict arabinosylation of contiguous Hyp residues and arabinogalactan-polysaccharide addition to clustered non-contiguous Hyp residues, such as the X-Hyp-X-Hyp (SEQ ID NO: 9) modules common in AGPs [Nothnagel (1997) International Review of Cytology 174:195]. Based on this prediction, it is the inventor's view that the exemplary consensus sequence of Table 6 contains approximately two polysaccharide attachment sites in the clustered non-contiguous Hyp motif: Ser-Hyp-Ser-Hyp-Thr-Hyp (SEQ ID NO: 138) which is flanked by arabinosylated contiguous Hyp residues as depicted in FIG. 9. FIG. 9 uses the standard single letter code for amino acids except for Hyp which is denoted by [Du et al.(1994) Plant Cell 6:1643], and the standard three letter code for sugars, except for glucuronic acid which is denoted as GlcA. This model depicts a symmetrical distribution of arabinosides and polysaccharide substituents which is directed by the palindrome-like arrangement of the Hyp residues in the peptide backbone; Ser-0 is the palindromic center. However degenerate variations occur (Table 6). The inventors base this structure on compositional and linkage analyses of the isolated Hyp-polysaccharide fraction (Tables 7 & 8) [Qi et al. (1991) supra] and on the pentasaccharide side-chain structure elucidated for crude gum arabic by Defaye and Wong [Defaye and Wong (1986) Carbohydrate Research 150:221] (corresponding to $Rha_f$, $Ara_f$, 3-Ara, 4-GlcA, and 2,3,6-Gal in Table 9).

Hydroxyproline-O-glycosidic linkages are stable in base [Lamport (1967) Nature 216:1322; Miller et al. (1972) Science 176:918; Pope (1977) Plant Physiology 59:894], in contrast to other O-glycosylated hydroxyamino acids such as serine and threonine, which undergo β-elimination [Lamport et al (1973) Biochemical Journal 133:125]. Therefore, alkaline hydrolysis was used to isolate and characterize Hyp-arabinogalactan polysaccharides from GAGP as demonstrated earlier [Qi et al. (1991) supra].

Figure 10:
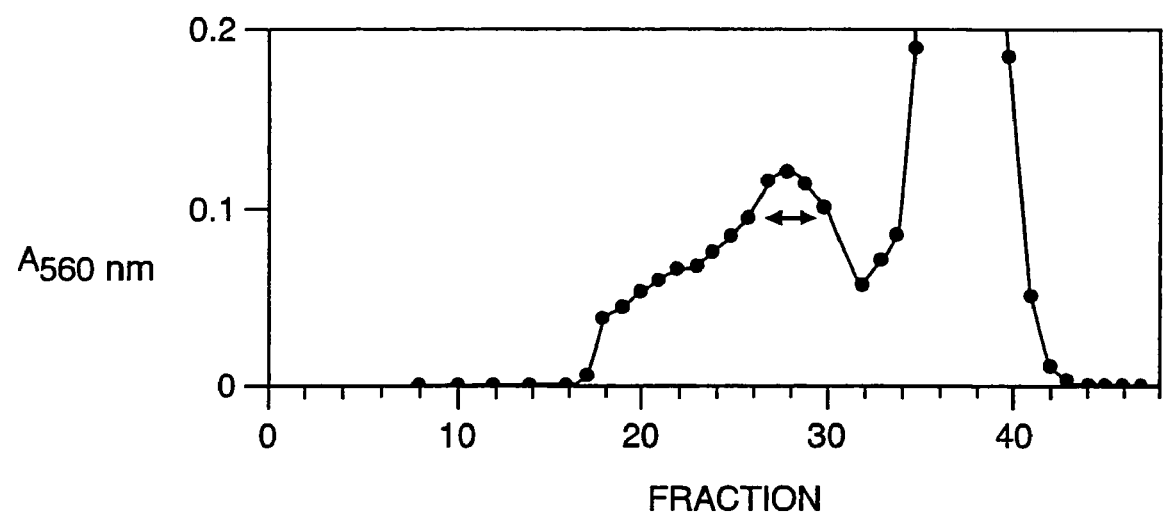
FIG. 10 is the elution profile of the GAGP base hydrolysate by Sephadex G-50 gel permeation chromatography.
Figure 12A:
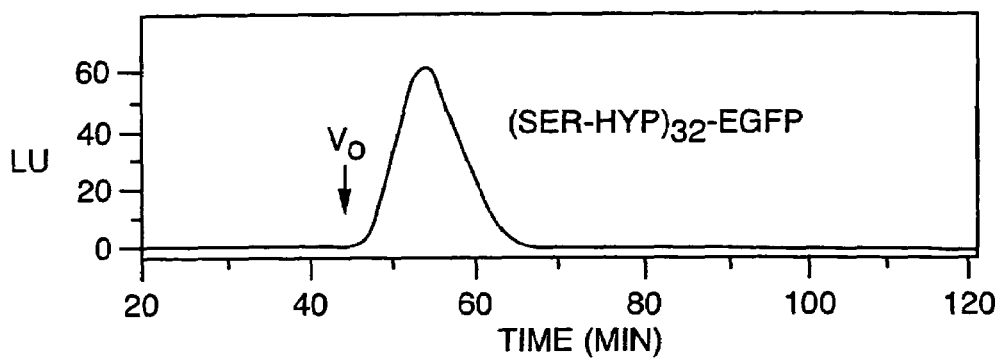
FIG. 12 shows Superose-12 gel permeation chromatography with fluorescence detection of (A) culture medium containing (Ser-Hyp)$_{32}$-EGFP ((Ser-Hyp)$_{32}$ disclosed as SEQ ID NO: 275), (B) (GAGP)$_3$-EGFP medium concentrated four-fold, (C) Medium of EGFP targeted to the extracellular matrix (concentrated ten-fold), and (D) 10 mg standard EGFP from Clontech.
Figure 12B:
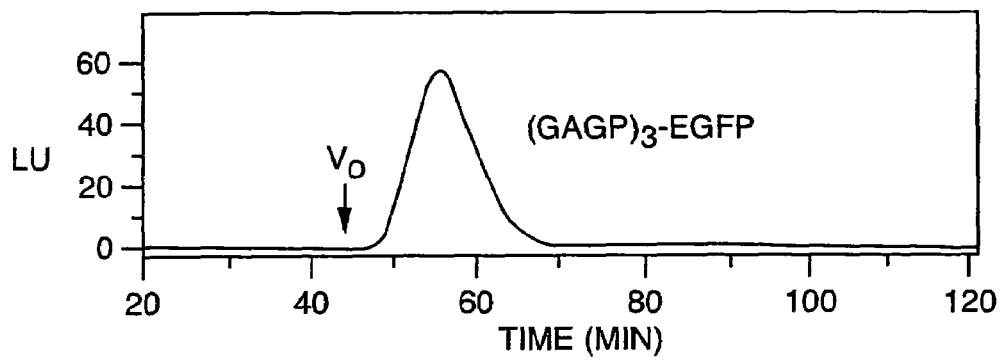
Figure 12C:
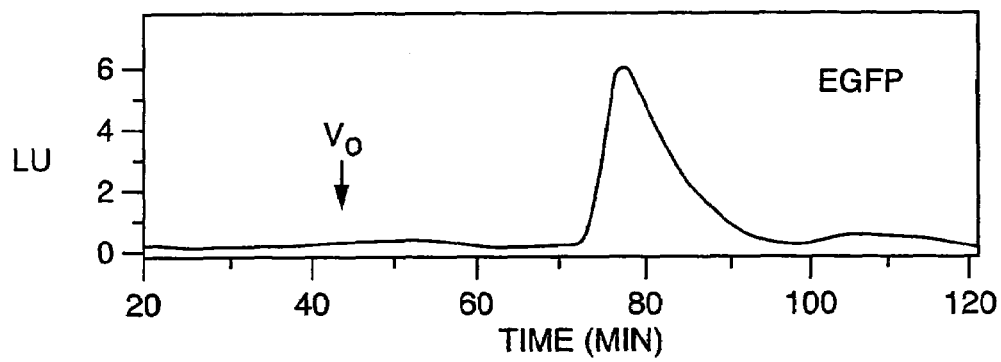
Figure 12D:
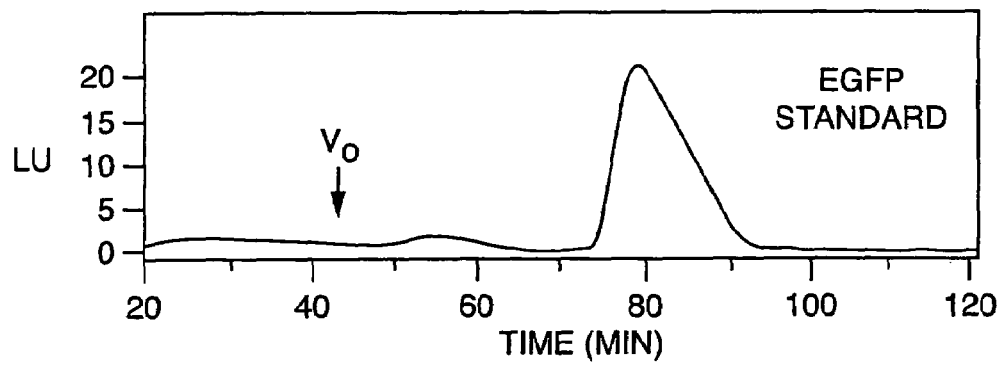

Compositional analysis of the small Hyp-polysaccharides isolated from GAGP after fractionation of the alkaline hydrolysate on Sephadex G-50 (FIG. 10; Table 8) indicated a content of 5158 nM sugar.

TABLE 8

Glycosyl compositions of intact GAGP and a GAGP Hyp-polysaccharide isolated from GAGP base hydrolysates

| | Mol % | |
|---|---|---|
| Glycosyl Residue | GAGP[Qi et al. (1991) supra] | GAGP Hyp-polysaccharide |
| Ara | 36 | 38 |
| Gal | 46 | 34 |
| Rha | 10 | 13 |
| GlcUA | 9 | 15 |

In FIG. 10, assay of Hyp across the recovered fractions indicated a broad size range for the Hyp-polysaccharide (fractions 17-32). Fractions 27-30 were collected for linkage and composition analyses. Hyp arabinosides and non-glycosylated Hyp eluted in fractions 33-42. Corresponding quantitative Hyp assays showed a total of 220 nm Hyp in the peak isolated and analyzed (FIG. 10). The molar ratio of 220 nm Hyp: 5156 nm sugar indicated a ~23-residue rhamno-glucuronoarabinogalactan Hyp-polysaccharide substituent in this fraction. Methylation analysis of the polysaccharide (Table 9) showed linkages consistent with the model featured in FIG. 9, but containing 21-22 sugar residues rather than the 23 featured in FIG. 9.

TABLE 9

Glycosyl linkages of Intact GAGP and a GAGP Hyp-polysaccharide isolated from the GAGP base hydrolysate

| | Mol % | | |
|---|---|---|---|
| Glycosyl Linkage | GAGP | GAGP Hyp-Polysaccharide | |
| t-Rha | 6.7 | 10.4 | (2)* |
| 2,3,4-Rha | 3.3 | 0.0 | |
| t-Ara (f) | 13.3 | 16.2 | (4) |
| t-Ara (p) | 1.7 | 2.3 | (0-1) |

TABLE 9-continued

Glycosyl linkages of Intact GAGP and a GAGP Hyp-polysaccharide isolated from the GAGP base hydrolysate

| | Mol % | | |
|---|---|---|---|
| Glycosyl Linkage | GAGP | GAGP Hyp-Polysaccharide | |
| 2-Ara (f) | 2.5 | 0.0 | |
| 3-Ara (f) | 8.3 | 11.0 | (2-3) |
| 4-Ara (p) or 5-Ara (f) | 1.7 | 0.0 | |
| 2,4-Ara or 2,5-Ara (f) | 0.8 | 0.0 | |
| 2,3,4-Ara or 2,3,5-Ara (f) | 2.5 | 0.0 | |
| t-Gal | 5.8 | 11.8 | (3) |
| 2-Gal | 0.8 | 0.0 | |
| 3-Gal | 2.7 | 4.5 | (1) |
| 4-Gal | 0.8 | 0.5 | |
| 6-Gal | 2.5 | 2.4 | (0-1) |
| 3,4-Gal | 2.5 | 7.7 | (2) |
| 3,6-Gal | 11.7 | 12.7 | (3) |
| 3,4,6-Gal | 10.0 | 9.4 | (2) |
| 2,3,6-Gal | 3.3 | 0.0 | |
| 2,3,4,6-Gal | 5.8 | 0.0 | |
| t-GlcUA | 1.7 | 0.9 | |
| 4-GlcUA | 7.5 | 10.2 | (2) |
| 3,4-GlcUA | 1.7 | 0.0 | |
| 2,4-GlcUA | 0.8 | 0.0 | |
| 2,3,4-GlcUA | 0.8 | 0.0 | |
| 4-Glc | 0.8 | 0.0 | |

*Estimated number of residues/polysaccharide.

Based on the above data, the inventors conclude that each small polysaccharide contains two pentasaccharide side chains (Gal, $Ara_2$, GlcA, Rha) arranged along a ~7-residue (1-3)β-D-galactan backbone helix which also contains monosaccharide side chains of Ara and Gal.

Data presented herein demonstrates that the linkage analyses of both Hyp-polysaccharide and GAGP (Table 9) are similar, thus providing evidence of similarity between GAGP and gum arabic polysaccharides. These results suggest that the larger Hyp-polysaccharides (FIG. 10) may be comprised of repeat units containing approximately 12 galactose residues/repeat. Hence, without limiting the invention to any particular theory or mechanism, the inventors estimate that as many as five side-chains (~40 sugars) occur in the larger arabinogalactan moieties which eluted in fractions 18-26 from the G-50 Sephadex column (FIG. 10). The inventors further believe that GAGP and other AGP sensitivity to alkaline degradation involves peptide bonds rather than glycosidic linkages.

EXAMPLE 19

Construction of 8, 16, 20, 32, and 64 Repeats of Gum Arabic Motifs and Expression in Plant Cells This Example discloses construction of synthetic genes for the expression of gum arabic glycoprotein repeats based on the invention's consensus sequences. The genes had 8, 20, 32, or 64 contiguous units of two motifs [motif 1 (SEQ ID NO:143)=Ser-Hyp-Hyp-Hyp-Hyp-Leu-Ser-Hyp-Ser-Hyp-Thr-Hyp-Thr-Hyp-Hyp-Leu-Gly-Pro-His; motif 2 (SEQ ID NO:144)=Ser-Hyp-Hyp-Hyp-Thr-Leu-Ser-Hyp-Ser-Hyp-Thr-Hyp-Thr-Hyp-Hyp-Hyp-Gly-Pro-His], each of which is encompassed by the invention's consensus sequence. The 64 contiguous units [i.e., (motif 1-motif 2)$_{32}$] were constructed using a modification of the previously described [Lewis et al. (1996) Protein Expression & Purification 7:400-406] strategy involving compatible but nonregenerable restriction sites, which allowed construction of very large inserts with precise control over the number of DNA repeat number.

1. Site-Directed Mutagenesis of pUC18 to Eliminate BsrFI Restriction Site from the Amp$^r$ Gene Plasmid pUC18 has an endogenous BsrFI site in the Amp$^r$ gene. This site was eliminated by mutation to make the plasmid amenable to subcloning of the XmaI-BsrFI synthetic gene fragments, using the PCR core system I kit (Promega). The PCR Primer 1: (upstream primer) had the sequence (SEQ ID NO:204) GATACCGCGAGAC-CCACGCTC ACC<u>A</u>GCTCC; this primer was designed from nucleotides 1756 to 1785 of pUC18 except for 1 substitution (A for G) at position 1780 (bolded and underlined). This changes one Ala codon (GCC) for another (GCT), retaining the Amp$^r$ amino acid sequence while mutating the BsrFI site. PCR Primer 2: (downstream primer) had the sequence (SEQ ID NO:205) CTCGGTCGCCG-CATACACTAT and was designed from nt 2220 to 2198 of pUC18. The PCR reaction conditions were 2 min @ 95° C., 30 sec @ 95° C., 1 min @ 48° C., 1 min @ 72° C. (30 cycles), 5 min @ 72° C. PCR products were separated on a 1.5% agarose gel. The 464 bp PCR fragment was extracted from the gel using the QIAEX II gel extraction kit. The isolated fragment was restricted and subcloned into pUC 18 as a ScaI-BpmI fragment. The new plasmid was designated MpUC18 and has an active Amp$^r$ gene and no BsrFI site.

2. Synthesis of Gum Arabic Glycoproteins (GAGP) Repeats Using Mutually Priming Oligonucleotides DNA encoding gum arabic glycoprotein contiguous units of motif 1 linked to motif was constructed using previously described methods [Current Protocols in Molecular Biology section 8.2.8-8.2.10]. A DNA fragment encoding the two GAGP motifs was synthesized by primer extension of two partially overlapping synthetic oligonucleotides: First oligonucleotide (SEQ ID NO:206): 5'- G GCA AGC TTC CGG AGT GCC GGC CCT CAT AGC CCA CCT CCA CCA TTA TCA CCA TCA CCT ACT CCA ACT CCTCCTTTGGGACCACACAG-3'; second oligonucleotide (SEQ ID NO:207): 5'-GGT CCC GGG GGG TGG TGT TGG GGT TGG TGA AGG GGA AAG TGT AGG GGG TGG ACTGTGTGGTCCCAAAGGAGG-3'. The oligonucleotides (0.05 nm of each) were heated for 5 min @ 95° C., annealed for 5 min @ 48° C., then extended by DNA polymerase I Klenow fragment (Promega) for 30 min @ 37° C. The reaction was stopped by heating 10 min at 75° C. and the buffer was exchanged via a Sephacryl S-200 column (Pharmacia Microspin™). The plasmid was then subcloned into MpUC18 as a Hind I-XmaI fragment. The plasmid was sequenced with the pUC/M13 forward primer (17-mer).

Figure 15:
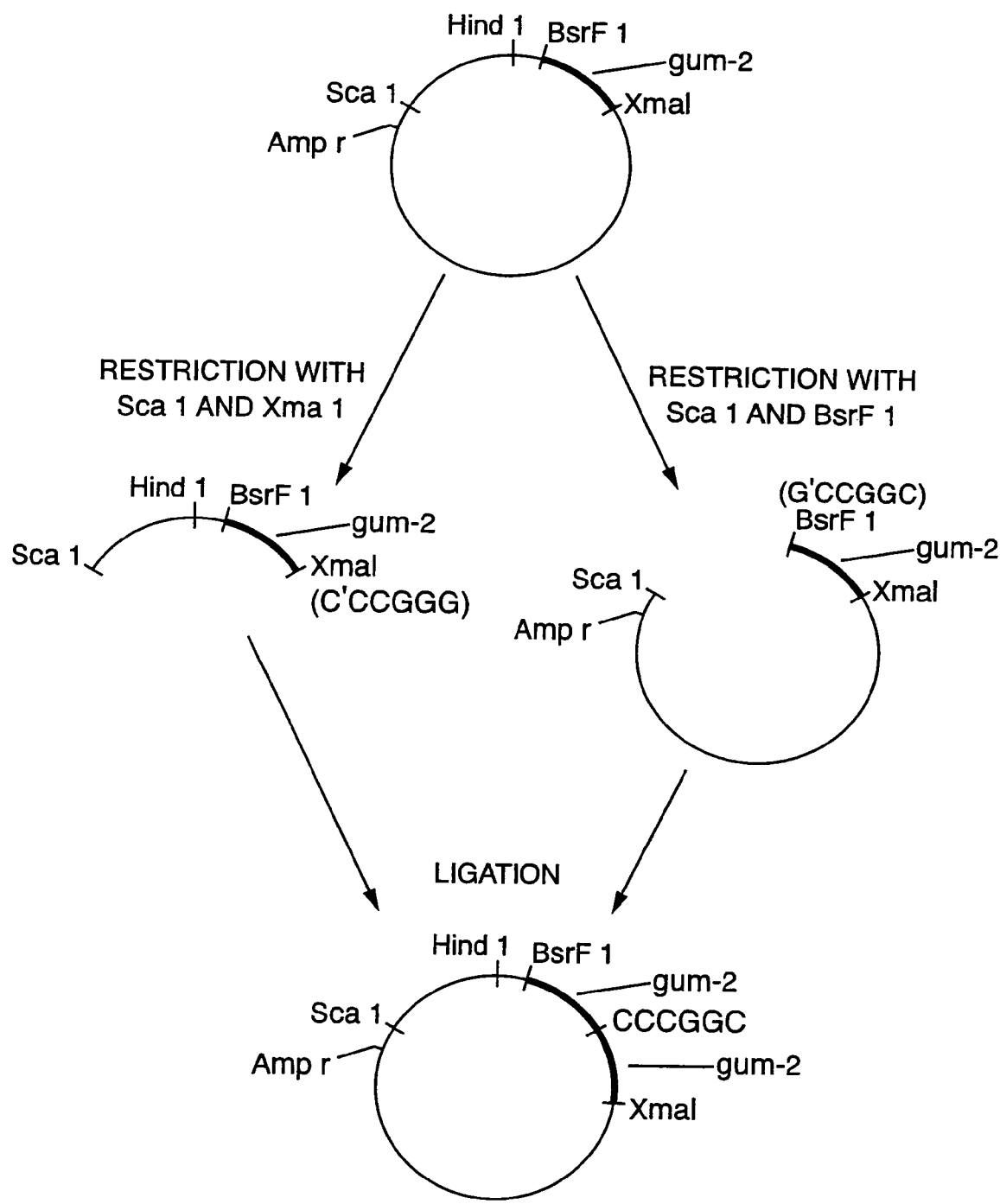
FIG. 15 is a diagram of the cloning strategy for generating repeats of GAGP sequences.

3. Multiplication of GAGP Internal Repeat Using Nonregenerable Restriction Sites Synthetic genes containing controlled numbers of GAGP repeats were synthesized as follows, and as illustrated in FIG. 15. MpUC18 containing the PCR product described above (two GAGP motifs as shown in FIG. 16A) (designated MpUC gum-2) was divided between two tubes. MpUC gum-2 in tube 1 was restricted with ScaI and BsrFI; MpUC gum-2 in tube 2 was restricted with ScaI and XmaI. The digests were separated on a 1% agarose gel. The 1884 kb band from tube 1 (ScaI/BsrFI digest) and the 1044 kb band from the tube 2 (ScaI/XmaI digest) were excised from the gel, combined and ligated together. The resulting plasmid (MpUC gum-4) contained 4 GAGP internal repeats [i.e., (motif 1-motif 2)$_2$] (FIG. 16B). This strategy was successfully used to build plasmids containing 8, 16, 20, 32, and 64 internal repeats of GAGP.

4. Subcloning of Synthetic Gum Repeats into pUC ss-EGFP Plasmid

The gum genes (gum-8, gum-20, and gum-32) were removed from MpUC18 plasmid as BspEI/SacI fragments and subcloned into pUC ss-EGFP plasmid behind the signal sequence. During this subcloning, EGFP was removed from pUC ss-EGFP as XmaI/SacI fragment. XmaI and BspEI restriction sites are compatible but nonregenerable.

The next subcloning was done to put the EGFP gene in frame behind the gum sequences. pUC ss-EGFP plasmid was cut with XmaI and treated with Mung Bean endonuclease (New England Biolabs). The enzymes were inactivated by phenol/chloroform extraction followed by ethanol precipitation. Then plasmid was cut with SacI. The EGFP fragment isolated after restriction was subcloned into pUC ss-gum plasmids which was cut with SmaI/SacI restriction enzymes. The signal sequence-synthetic gene-EGFP fragments were removed from MpUC18 plasmid as BamHI/SacI fragments and subcloned into pBI121, replacing the β-glucuronidase reporter gene. The MpUC ss-gum$_{20}$-EGFP and MpUC ss-gum$_{32}$-EGFP plasmids were sequenced with pUC/M13 forward (17 mer) primer and with GFP primer GAA-GATGGTGCGCTCCTGGACGT (SEQ ID NO:226) from nucleotide 566 to nucleotide 588 of pEGFP.

5. Transformation of Tobacco Cultured Cells, Tobacco Leaf Discs, and Tomato Cultured Cells, and Expression of Multiple GAGP Internal Repeats The expression vectors contained an extension signal sequence or a tomato signal sequence for transport of the constructs through the ER/Golgi for posttranslational modification, as well as Green Fluorescent Protein (GFP) as a reporter protein as described below.

A. Extensin Signal Sequence

Transformation vectors were derived from pBI121 (Clontech). These vectors contained an extensin signal sequence (SS) as well as Green Fluorescent Protein (GFP) as a reporter protein. 8, 20, 32, and 64 internal repeats of GAGP were inserted between the signal sequence and GFP to yield plasmids SS-GAGP$_8$-EGFP, SS-GAGP$_{20}$-EGFP, SS-GAGP$_{32}$-EGFP, and SS-GAGP$_{64}$-EGFP, respectively. Because preliminary data showed that the gene encoding the 64 repeats of GAGP was unstable in pBI12, plasmids SS-GAGP$_8$-EGFP, SS-GAGP$_{20}$-EGFP, and SS-GAGP$_{32}$-EGFP were used to transform *Agrobacterium tumefacienes* as described supra (Example 9).

B. Tomato LeAGP-1 Signal Sequence

As an alternative to the extensin signal sequence, the tomato LeAGP-1 signal sequence was used. Cloning of the LeAGP-1 signal sequence was as follows using the sense primer 5'-CTC TTT TTC TCT G↓GATCC GGT CTA TAT TTT CTT TTA GC-3' (SEQ ID NO:227) (Tm: 68° C.) with the arrow showing the BamHI restriction site, and the antisense primer 5'-CGG GTG CTG C↓CCGGG TTG TCT GAC CCG TGA CAC TTG C-3' (SEQ ID NO:228) (Tm: 80° C.) with the arrow showing the XmaI restriction site.

PCR was carried out using 52.8 pmol of sense primer and 47 pmol of antisense primer. The LeAGP-1 signal sequence template (0.01 µg) was added together with the PCR mixture. The reaction solution was covered with oil and the incubation was at 95° C. 5 min (circle one); 95° C. 45 sec, 58° C. 1 min, 74° C. 1 min (circle 2-30); 74° C. 5 min. 20 µl out of 50 µl total PCR solution was removed and purified using 2% agarose gel. The PCR product was 127-bp in size and was isolated by using QIAEXII kit. This fragment was digested as follows at 37° C. overnight.:

| Purified PCR fragment | 100 ng | pUC-SS$^{Tob}$GFP | 200 ng |
|---|---|---|---|
| BamH1 | 5 u | BamH1 | 2 u |
| XmaI | 4 u | XmaI | 2 u |
| Buffer B | 3 μl | Buffer B | 3 μl |
| Add water to 30 μl | | Add water to 30 μl | |

The digested samples were run on an agarose gel. The vector and fragment were cut from the gel and were isolated with the QIAEXII kit. The ligation reaction [pUC-SS$^{Tob}$GFP (BX) 100 ng, PCR fragment(BX) 20 ng, Ligase Buffer (10×) 1 μl, Ligase 1 μl] was incubated at 10° C. overnight.

Transformation was carried out and 3 clones were cultured separately in LB media containing ampicillin overnight. Plasmids were isolated from the transformed cells and digested with BamHI and XmaI to confirm that the fragments were 99 bp long. The plasmid containing the tomato signal sequence was named pUC-SS$^{Tom}$-GFP.

Plasmids containing the tomato signal sequence in tandem with repeating GAGP sequences and with EGFP as a reporter gene is used to transform *Agrobacterium tumefacienes* as described supra (Example 9).

The transformed *Agrobacterium* cells were used to transform tobacco cultured cells as described above (Example 10). Transformed cells were selected by detection of fluorescent cells which express GFP.

Transformed *Agrobacterium* cells will be used to transform tomato cultured cells and tobacco discs as described above (Examples 11 and 17, supra). Transformed cells will be selected by detection of fluorescent cells which express GFP. Successful expression of 8, 20, and 32, internal repeats of GAGP in tobacco cultured cells, tobacco leaf discs, and tomato cultured cells will be confirmed using the methods described in the above Examples.

EXAMPLE 20

Construction of Genes and Vectors Containing Contiguous and Noncontiguous Hydroxyproline Glycomodules (SP)$_{32}$ (SEQ ID NO: 284), (GAGP)$_3$, (SPP)$_{24}$ (SEQ ID NO: 292), (SPPP)$_{16}$ (SEQ ID NO: 293), and (SPPPP)$_{18}$ (SEQ ID NO: 294)

This Example describes construction of three plasmids, each encoding a tobacco signal sequence and EGFP, as well as subcloning of (SP)$_{32}$ (SEQ ID NO: 284), (GAGP)$_3$, EGFP, (SPP)$_{24}$ (SEQ ID NO: 292), (SPPP)$_{16}$ (SEQ ID NO: 293), (SPPPP)$_{18}$ (SEQ ID NO: 294). In the three plasmids described here, the signal sequence was used to direct the products through the ER and Golgi, then out to the extracellular matrix [Goodenough et al. (1986) *J. Cell Biol.* 103, 403; Gardiner & Chrispeels (1975) *Plant Physiol.* 55, 536-541]. Two of the plasmids also contained a synthetic gene (SEQ ID NOs:112, 113, 115, 116) encoding either six (Ser-Pro) (SEQ ID NO: 295) internal repeat units (SEQ ID NO:117) or three (GAGP) internal repeat units (SEQ ID NO:122) (FIG. 11) sandwiched between the signal sequence and gene-enhanced green fluorescent protein (EGFP). In FIG. 11, internal repeat oligonucleotide sets encoding Ser-Pro repeats or the GAGP sequence were polymerized head-to-tail in the presence of the 5'-linker set [SEQ ID NOs:120 and 121 which encode SEQ ID NO:122]. Following ligation, the 3'-linker [SEQ ID NOs:123 and 124 which encode SEQ ID NO:125] was added and the genes then restricted with BamHI and EcoRI and inserted into pBluescript II SK. The signal sequence (SEQ ID NOs:118 and 119) was built by primer extension of the overlapping oligonucleotides featured here. The overlap is underlined.

The conserved (Ser-Hyp)$_n$ (SEQ ID NO: 182) motif was chosen because it occurs both in green algae (*Chlamydomonas*) and in higher plant AGPs. This noncontiguous Hyp motif is of particular interest because it also occurs together with a contiguous Hyp motif in the consensus sequence of GAGP which contains both oligoarabinoside and polysaccharide addition sites.

The signal sequence (FIG. 11) was modeled after an extensin signal sequence from *Nicotiana plumbaginifolia*; mutually priming oligonucleotides were extended by T7 DNA Polymerase and the duplex placed in pUC18 as a BamHI-Sst I fragment. Construction of a given synthetic gene involved the polymerization of three sets of partially overlapping, complementary oligonucleotide pairs as described earlier (FIG. 11). The following subclonings were required to create DNA fragments/restriction sites which allowed facile transfer of the Signal Sequence-synthetic gene-enhanced green fluorescent protein (EGFP) unit to the plant transformation vector pBI121 (Clontech): The synthetic genes were placed in pBluescript II SK (Stratagene) as BamHI-EcoRI fragments and then subcloned the genes into pEGFP (Clontech) as BamHI-AgeI fragments preceding the EGFP gene (Tsien, R. Y. (1998) *Annu.Rev.Biochem.* 67,509-544; Haseloff, J., Siemering, K. R., Prasher, D. C. & Hodge, S. (1997) *Proc.Natl.Acad.Sci.* 94, 2122-2127.22). The synthetic gene-EGFP fragments were then subcloned into pBluescript II KS (Stratagene) as XmaI/NotI fragments, removed as XmaI-SstI fragments and subcloned into pUC18 behind the signal sequence. DNA sequences were confirmed by sequence analysis before insertion into pBI121 as BamHI/SstI fragments, replacing the b-glucuronidase reporter gene. All constructs were under the control of the 35S cauliflower mosaic virus promoter. The oligonucleotides were synthesized by Lifesciences (Gibco/BRL). An Ala for Pro/Hyp substitution at residue 8 of the gum arabic glycoprotein (GAGP) internal repeat module (SEQ ID NO:208) (Ser-Pro-Ser-Pro-Thr-Pro-Thr-Pro-Pro-Pro-Gly-Pro-His-Ser-Pro-Pro-Pro-Thr-Leu) was inadvertently introduced during synthesis by a G for C base substitution in the sense strand.

The following is a more detailed description of the protocol used to subclone (SP)$_{32}$ (SEQ ID NO: 284), (GAGP)$_3$, EGFP, (SPP)$_{24}$ (SEQ ID NO: 292), (SPPP)$_{16}$ (SEQ ID NO: 293), (SPPPP)$_{18}$ (SEQ ID NO: 294). Briefly, Everything was first built and sequenced in pUC18, then transferred as a block (i.e., signal sequence-synthetic gene-EGFP) to pBI121. The constructs in pBI121 were not sequenced. The pBI121 plasmids were used to transform *Agrobacterium* and the transformed *Agrobacterium* was used to transform the plant cells, as described infra in Example 21.

1. Synthesis of the Signal Sequence

The signal sequence was assembled by using mutually priming oligonucleotides [Current Protocols in Molecular Biology," (1995) pages 8.2.8-8.2.10].

Oligonucleotides (0.2 nmol, 0.2 nmol) were annealed (5 min at 70° C. followed by 5 min at 40° C.) and extended by DNA polymerase I (Klenow) large fragment (Promega) (30 min at 37° C.). The reaction was stopped by heating 10 min at 75° C. The resulting DNA fragment was cut with BamHI and SstI enzymes and was placed in pUC18 plasmid. The plasmid was sequenced with pUC/M13 forward (17 mer) primer.

2. Synthesis and Subcloning of Synthetic Genes

Oligonucleotides were synthesized and SDS-PAGE purified by Gibco-BRL or Integrated DNA Technologies Inc. They were dissolved in water at appropriate concentrations.

A. $(SP)_{32}$ (SEQ ID NO: 284) and $(GAGP)_3$ Synthesis and Subcloning i. Annealing Reaction Oligonucleotide-pairs were combined in eppendorf tubes as follows:
a) 5.5 µl internal repeat sense oligonucleotide (0.5 nmol/µl) 5.5 µl internal repeat antisense oligonucleotide (0.5 nmol/µl) 11 µl T4 ligase 10× ligation buffer
b) 2 µl 5'-end sense linker (0.05 nmol/µl) 2 µl 5'-end antisense linker (0.05 nmol/µl) 1 µl water 5 µl T4 ligase 10× ligation buffer
c) 2 µl 3'-end sense linker (1 nmol/µl) 2 µl 3'-end antisense linker (1 nmol/µl) 1 µl water 5 µl T4 ligase 10× ligation buffer All tubes were heated 5 min at 90-95° C. Then they were cooled to 45° C. over next 3 hours and kept at 45° C. for 2 more hours.

ii. Oligonucleotide Polymerization

10 µl of the internal repeat pair was combined with 10 µl of the 5'-end linker pair (15:1 molar ratio). This mixture was incubated 3 hour at 17° C. Then, 80 µl of water (to receive 1× concentration of ligation buffer) and 2 µl of T4 DNA ligase (4,000 U) were added. The ligation reaction was incubated 36 hours at 12-15° C. The extent of polymerization was checked on 2.2% agarose gel.

The 5'-end linker-internal repeat polymers were capped with the 3'-end linker. 5 µl of the 3'-end linker were added to 50 µl of ligation reaction from the step above. The mixture was heated to 30° C. (to destroy unspecific hybridization), and incubated at 17° C. for 3 hours. 20 µl of water and 2 µl T4 DNA ligase (4,000 U) were added and the ligation reaction was incubated at 12-15° C. for 36 hours. The reaction was stopped by heating at 65° C. for 10 min.

The constructs were ethanol precipitated, washed with 70% ethanol and air dried. The pellet was dissolved in 80 µl of water. 10 µl was used for restriction with EcoRI (10 Units) and BamHI (20 Units). The Sephacryl S-400 column (Pharmacia Microspin™) was used to remove salts and small oligonucleotide fragments. Qiaquick Nucleotide removal kit (Qiagen) was used to remove enzymes. The resultant fragments were inserted in pBluescript II SK plasmid (Stratagene) The selection of clones was done by white-blue assay. The structure of synthetic genes was checked by sequencing with pUC/M13 forward (17 mer) primer.

iii. Subcloning

The synthetic genes were first removed from pBluescript II SK (Strategene) as BamHI/AgeI fragments and subcloned in pEGFP (Clontech). (This step allowed directional cloning). The synthetic gene—EGFP fragments were removed from pEGFP as XmaI/NotI fragments and subcloned in KS (Stratagene) (This step was done to obtain SstI site at the end of EGFP). The synthetic gene—EGFP fragments were removed from KS as XmaI/SstI fragments and subcloned in pUC-signal sequence plasmid behind the signal sequence. The structure of the synthetic genes was checked by sequencing with pUC/M13 forward (17 mer) primer. The signal sequence-synthetic gene-EGFP fragments were removed from pUC18 plasmid as BamHI/SstI fragments and subcloned in pBI121 (Clontech).

iv. EGFP Subcloning

The EGFP fragment was removed from pEGFP as XmaI/NotI fragments and subcloned in KS. (This step was done to obtain SstI site at the end of EGFP). The EGFP fragment was removed from KS as XmaI/SstI fragments and subcloned in pUC-signal sequence plasmid behind the signal sequence. The signal sequence-EGFP fragment was removed from pUC18 plasmid as BamHI/SstI fragments and subcloned in pBI121.

B. $(SPP)_{24}$ (SEQ ID NO: 292), $(SPPP)_{16}$ (SEQ ID NO: 293), $(SPPPP)_{18}$ (SEQ ID NO: 294), Palindromic Repeat Synthesis and Subcloning i. Annealing Reaction Oligonucleotide-pairs were combined in eppendorf tubes as follows:
a) 2 µl internal repeat sense oligonucleotide (0.25 nmol/µl) 2 µl internal repeat antisense oligonucleotide (0.25 nmol/µl) 3 µl T4 ligase 10× ligation buffer 23 µl water
b) 1 µl 5'-end sense linker (0.5 nmol/µl) 1 µl 5'-end antisense linker (0.5 nmol/µl) 4 µl T4 ligase 10× ligation buffer 34 µl water
c) 2 µl 3'-end sense linker (0.25 nmol/µl) 2 µl 3'-end antisense linker (0.25 nmol/µl) 3 µl T4 ligase 10× ligation buffer 23 µl water All tubes were heated to 90-95° C. for 5 min. Then they were cooled to annealing temperature ( ) over next 30 min and kept at that temperature for 1 more hour.

ii. Oligonucleotides Polymerization

25 µl of internal repeat pair was combined with 20 µl of 5'-end linker pair (1.5:1 ratio). The mixture was heated to 35° C. to destroy circular structures formed by internal repeat pair. After cooling to 20° C. 0.5 µl of T4 DNA ligase (1.5 U) was added. The ligation reaction was incubated 3 hours at 20° C. 3 µl of ligation mixture was used to check the extent of polymerization on 2% agarose gel.

The 5'-end linker-internal repeat polymers were capped with 3'-end linker. I added 15 µl of the 3'-end linker to 40 µl of ligation reaction from step above and 0.5 µl of T4 DNA ligase (1.5 U). The ligation reaction was incubated 3 hours at 20° C. The reaction was stopped by heating at 65° C. for 10 min. 3 µl of ligation mixture was used to check the extent of polymerization on 2% agarose gel. The Sephacryl S-200 column (Pharmacia Microspin)™ was used to remove salts. 4-6 µl of solution was used for restriction with EcoRI (10 Units) and BamHI (20 units). After restriction, 150-bp to 500-bp fragments were cut out of 2% agarose gel. QIAEX II gel extraction kit was used to isolate fragments from the gel.

The resultant fragments were inserted in pUC18 plasmid. The selection of clones was done by white-blue assay. The structure of synthetic genes was checked by sequencing with pUC/M13 forward (17 mer) primer.

iii. Subcloning

The synthetic genes were removed from pUC18 as XmaI/NcoI fragments and subcloned behind the signal sequence and in front of EGFP in pUC-signal sequence-EGFP plasmid. The signal sequence-synthetic gene-EGFP fragments were removed from pUC18 plasmid as BamHI/SstI fragments and subcloned in pBI121.

The above protocols yielded pBI121 expression constructs in which genes encoding each of (SP)$_{32}$ (SEQ ID NO: 284), (GAGP)$_3$, EGFP, (SPP)$_{24}$ (SEQ ID NO: 292), (SPPP)$_{16}$ (SEQ ID NO: 293), (SPPPP)$_{18}$ (SEQ ID NO: 294) palindromic repeats were ligated to sequences encoding the signal sequence and EGFP.

EXAMPLE 21

Transformation of Tobacco Cells and Selection of Transformed Cell Lines

This Example describes transformation of suspension cultured tobacco cells with the expression vectors of Example 20 and selection of transformants which express green fluorescent protein.

Suspension cultured tobacco cells (*Nicotiana tabacum*, BY2) were transformed with *Agrobacterium tumifaciens* strain LBA4404 containing the pBI121-derived plant transformation vector. Transformed cell lines were selected on solid Murashige-Skoog medium (Sigma # 5524) containing 100 mg/mL kanamycin. Timentin was initially included at 400 mg/mL to kill *Agrobacterium*. Cells were later grown in 1 L flasks containing 500 mL Shenck-Hildebrand medium (Sigma # 6765) and 100 mg/mL kanamycin, rotated at 100 rpm on a gyrotary shaker.

After transformation of tobacco cells with *Agrobacterium* harboring the plant transformation plasmid pBI121 outfitted with either Sig-(GAGP)$_3$-EGFP, Sig-(Ser-Pro)$_{32}$-EGFP ((Ser-Pro)$_{32}$ disclosed as (SEQ ID NO: 284), or Sig-EGFP (described in Example 20), selection on solid medium and subsequent growth in liquid culture yielded cells bathed in a green fluorescent medium. The fluorescence in these highly vacuolated, cultured cells surrounds the nuclei, but is not within judging by optical sections (not shown). The microscope was a Molecular Dynamics Sarastro 2000 confocal laser scanning microscope using a 488 nm laser wave length filter, 510 nm primary beam splitter and a 510 nm barrier filter.

Figure 13A:
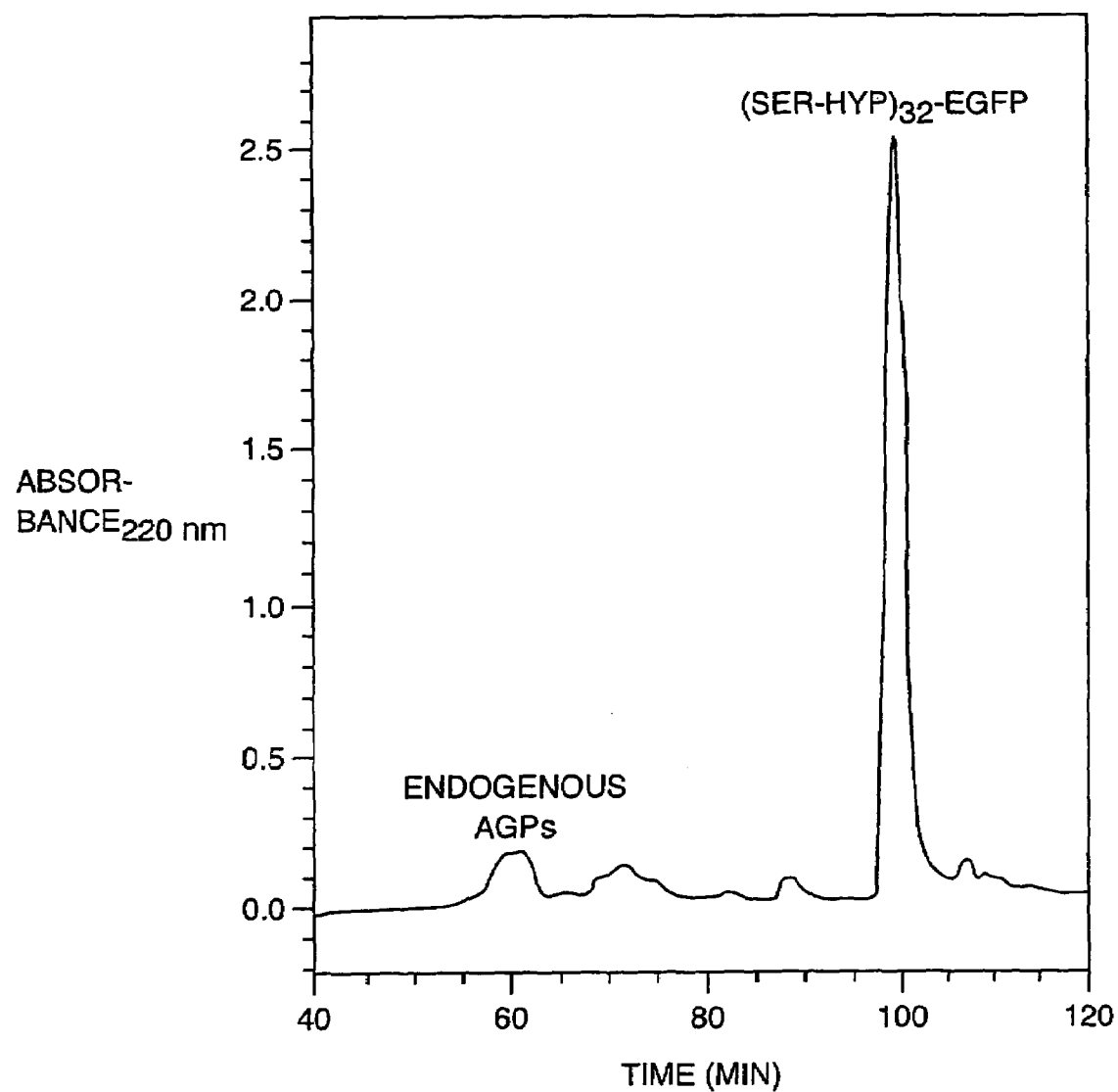
FIG. 13 shows PRP-1 reverse-phase fractionation of the Superose-12 peaks containing (A) (Ser-Hyp)$_{32}$-EGFP ((Ser-Hyp)$_{32}$ disclosed as SEQ ID NO: 275), (B) (GAGP)$_3$-EGFP, and (C) (Glyco)proteins in the medium of non-transformed tobacco cells.
Figure 13B:
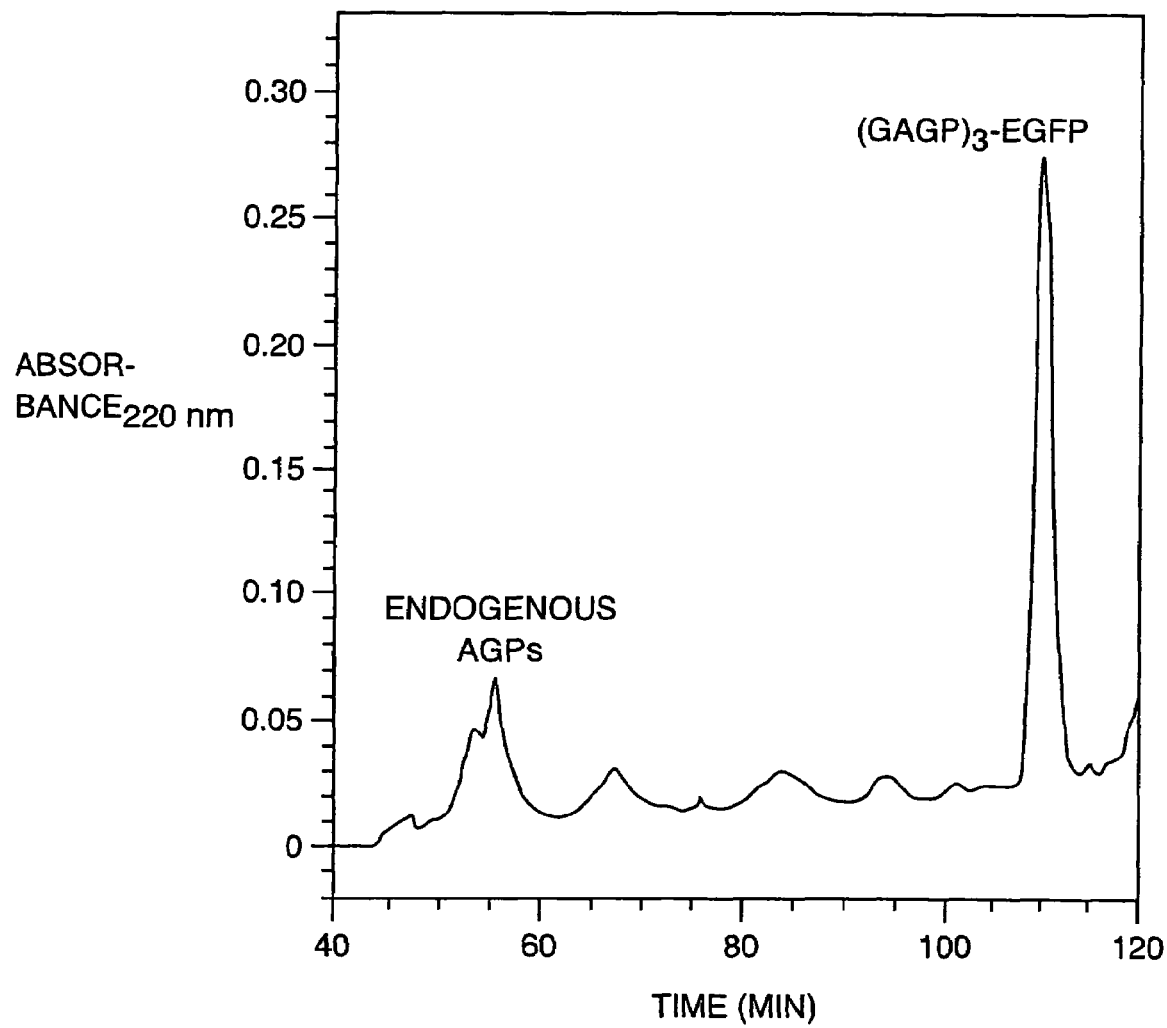
Figure 13C:
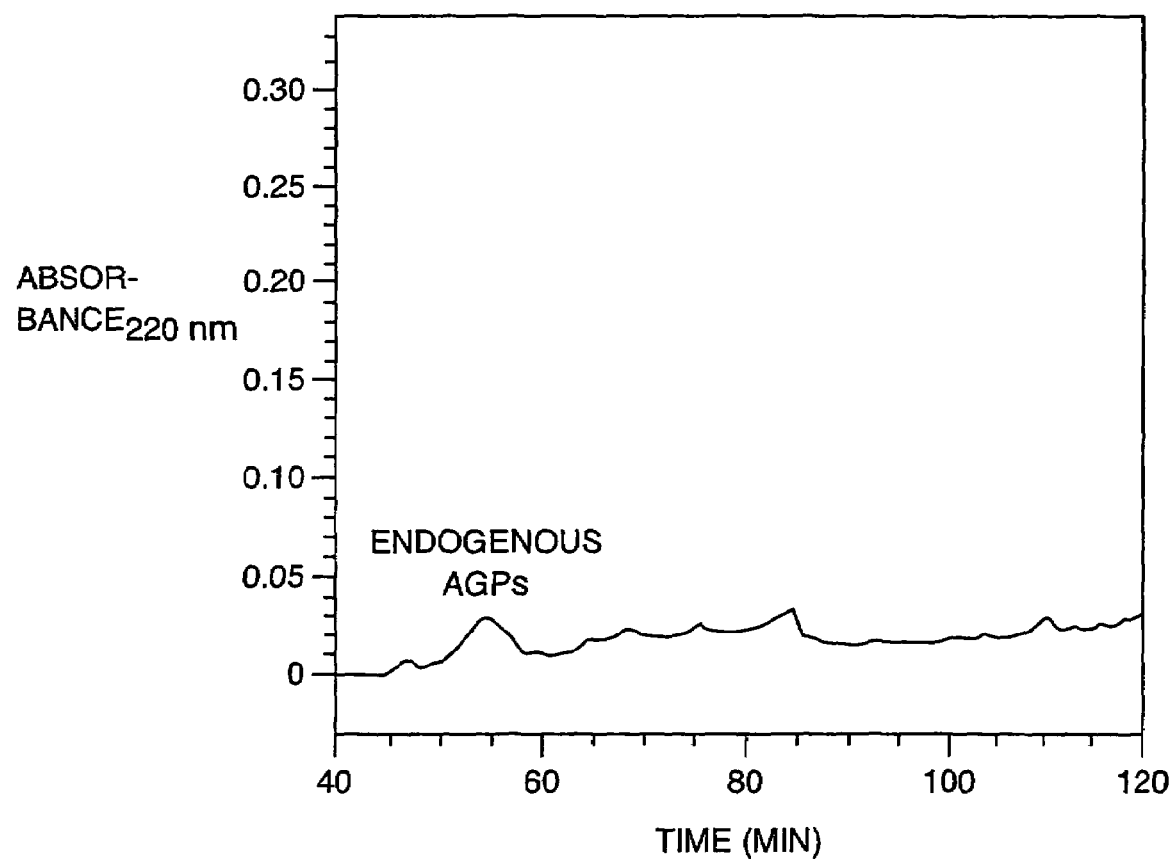

This Example demonstrates that inclusion of the EGFP reporter protein facilitated the selection of transformed cells and subsequent detection of the expression products during isolation (FIGS. 13 & 14). EGFP fluorescence in the growth medium was also a visual demonstration of Sig efficacy in directing secretion. The absence of any obvious cell lysis in the cultures and excellent product yields of the glycosylated expression products confirmed that the green fluorescence represented bona fide secretory products. Interestingly, EGFP without a glycomodule was secreted at very low levels, perhaps due to lower solubility.

EXAMPLE 22

Isolation of (Ser-Hyp)$_{32}$-EGFP, ((Ser-Hyp)$_{32}$ disclosed as (SEQ ID NO: 275), (GAGP)$_3$-EGFP, (SPP)$_{24}$-EGFP ((SPP)$_{24}$ disclosed as (SEQ ID NO: 292), (SPPP)$_{16}$-EGFP ((SPPP)$_{16}$ disclosed as (SEQ ID NO: 293), and (SPPPP)$_{18}$-EGFP ((SPPP)$_{18}$ disclosed as (SEQ ID NO: 294) from Transformed Cells This Example describes the isolation of sequences containing contiguous and noncontiguous Hyp residues from the growth medium of tobacco cells transformed with expression vectors which express these polypeptides.

Culture medium of cells described in Example 21, supra, was harvested 7 to 21 days after subculture, and the gene products were purified by gel permeation and reverse-phase chromatography (FIGS. 13 and 14) as follows. Culture medium was concentrated ten fold via rotovapping, then injected onto a Superose-12 gel filtration column (Pharmacia) equilibrated in 200 mM sodium phosphate buffer, pH 7, and eluted at a flow rate of 1 mL/min. EGFP fluorescence was monitored by a Hewlett-Packard 1100 Series flow-through fluorometer (Excitation=488 nm; Emission=520 nm). The Superose-12 column was calibrated with molecular weight standards (BSA, insulin, catalase, and sodium azide). Fluorescent Superose-12 fractions were injected directly onto a Hamilton PRP-1 reverse phase column and gradient eluted at a flow rate of 0.5 mL/min. Start buffer consisted of 0.1% TFA (aq) and elution buffer was 0.1% TFA/80% acetonitrile (aq). The sample was repeatedly injected (0.5 mL/minute) onto the column over 35 min, then eluted with a gradient of elution buffer (0-70% /135 min). Native GAGP was isolated from gum arabic nodules as described by Qi et. al. Endogenous tobacco AGPs were isolated as by PRP-1 reverse-phase and the results are shown in FIG. 13. FIG. 13 shows PRP-1 reverse-phase fractionation of the Superose-12 peaks containing (A) (Ser-Hyp)$_{32}$-EGFP ((Ser-Hyp)$_{32}$ disclosed as (SEQ ID NO: 275), (B) (GAGP)$_3$-EGFP, and (C) Glycoproteins in the medium of non-transformed tobacco cells. Endogenous tobacco AGPs eluted between 47 and 63 minutes; extensins eluted at Ã67 min. (C) Control medium collected from non-transformed tobacco cells was first fractionated on Superose-12 and the fractions eluting between 47 and 63 min collected for further separation on PRP-1 to determine if any endogenous AGPs/HRGPs co-chromatographed with (Ser-Hyp)$_{32}$-EGFP or with (GAGP)$_3$-EGFP, which they did not.

Six cell lines examined [three each of (Ser-Hyp)$_{32}$-EGFP ((Ser-Hyp)$_{32}$ disclosed as (SEQ ID NO: 275) and (GAGP)$_3$-EGFP] synthesized fluorescent glycoproteins of comparable sizes, although product yields between lines differed as much as ten-fold. For product characterization high-yielding lines were chosen which typically produced 23 mg/L of (Ser-Hyp)$_{32}$-EGFP ((Ser-Hyp)$_{32}$ disclosed as SEQ ID NO: 275) and 8 mg/L of (GAGP)$_3$-EGFP after isolation.

FIG. 12 shows Superose-12 gel permeation chromatography with fluorescence detection of (A) culture medium containing (Ser-Hyp)$_{32}$-EGFP, ((Ser-Hyp)$_{32}$ disclosed as SEQ ID NO: 275), (B) (GAGP)$_3$-EGFP medium concentrated four-fold, (C) Medium of EGFP targeted to the extracellular matrix (concentrated ten-fold), and (D) 10 mg standard EGFP from Clontech. Not shown is the fractionation of medium from non-transformed tobacco cells, which gave no fluorescent peaks consistent with the results discussed above. Superose-12 fractionation of the two fusion glycoproteins (FIG. 12) compared to molecular weight standards (not shown) indicated mass ranges of Ã95-115 kD for (Ser-Hyp)$_{32}$-EGFP ((Ser-Hyp)$_{32}$ disclosed as SEQ ID NO: 275) and Ã70-100 kD for (GAGP)$_3$-EGFP. The above data demonstrates successful isolation of GAGP sequences from cells which had been transformed with vectors that are capable of expressing these sequences.

The recombinant (SPP)$_{24}$-EGFP ((Ser-Hyp)$_{24}$ disclosed as SEQID NO: 292), (SPPP)$_{16}$-EGFP, and (SPPPP)$_{16}$-EGFP were isolated from transformed cells as described supra in this Example with respect to (SP)$_{32}$-EGFP ((SP)$_{32}$ disclosed as SEQ ID NO: 284) and (GAGP)$_3$-EGFP.

EXAMPLE 23

Characterization of Glycoproteins Isolated from Transformed Cells

The glycoproteins isolated from transformed tobacco cells as described in Example 22 were characterized as follows, and were shown to be new arabinogalactan-proteins (AGPs).

1. Co-Precipitation with Yariv Reagent (Ser-Hyp)$_{32}$-EGFP ((Ser-Hyp)$_{32}$ disclosed as SEQ ID NO:275), (GAGP)$_3$-EGFP, tobacco AGPs, and native GAGP were co-precipitated with the Yariv reagent as described earlier. Both (Ser-Hyp)$_{32}$-EGFP (Ser-Hyp)$_{32}$ disclosed as SEQ ID NO: 275) and (GAGP)$_3$-EGFP precipitated with Yariv reagent (Table 10), which is a specific property of b-1,3-linked arabinogalactan-proteins.

TABLE 10

Yariv Assay of (Ser-Hyp)$_{32}$ - EGFP ((SER-HYP)_disclosed as SEQ ID NO: 275) and (GAGP)$_3$ - EGFP

| | Absorbencies at 420 nm | | | |
|---|---|---|---|---|
| Sample | | | Standards | |
| Weight (μg) | (Ser-Hyp)$_{32}$ - EGFP | (GAGP)$_3$ - EGFP | GAGP | Tobacco AGP |
| 20 | 0.16 | 0.27 | 0.51 | 0.16 |
| 50 | 0.45 | 0.56 | 1.22 | 0.38 |
| 100 | 1.00 | 1.21 | 2.69 | 0.85 |

2. Hydroxyproline Glycoside Profiles

Hyp-glycoside profiles were determined as described by Lamport and Miller. We hydrolyzed 5.8-12.2 mg (Ser-Hyp)$_{32}$-EGFP ((Ser-Hyp)$_{32}$ disclosed as SEQ ID NO: 275) or (GAGP)$_3$-EGFP in 0.44 N NaOH and neutralized the hydrolysate with 0.3 M HCl before injection onto a C2 cation exchange column. Each Hyp residue in (Ser-Hyp)$_{32}$-EGFP ((Ser-Hyp)$_{32}$ disclosed as SEQ ID NO: 275) contained an arabinogalactan-polysaccharide substituent; (GAGP)$_3$-EGFP Hyp residues contained arabinooligosaccharide substituents in addition to arabinogalactan-polysaccharide (Table 11).

TABLE 11

Hyp-Glycoside Profiles of (Ser-Hyp)$_{32}$ - EGFP ((SER-HYP)_ disclosed as SEQ ID NO: 275) and (GAGP)$_3$ - EGFP and Native Crude GAGP

| | % of Total Hyp | | |
|---|---|---|---|
| Hyp-Glycoside | (Ser-Hyp)$_{32}$ - EGFP | GAGP$_3$ - EGFP | Native GAGP |
| Hyp-polysaccharide | 100 | 62 | 25 |
| Hyp-Ara (SEQ ID NO: 203) | 0 | 4 | 10 |
| Hyp-Ara$_2$ (SEQ ID NO: 202) | 0 | 12 | 17 |
| Hyp-Ara$_3$ (SEQ ID NO: 201) | 0 | 7 | 31 |
| Hyp-Ara$_4$ (SEQ ID NO: 200) | 0 | 4 | 5 |
| Non-glycosylated Hyp | 0 | 11 | 12 |

The Hyp-glycoside profile of (Ser-Hyp)$_{32}$-EGFP ((Ser-Hyp)$_{32}$ disclosed as SEQ ID NO: 275) gave a single peak of Hyp corresponding to Hyp-polysaccharide. Significantly, peaks corresponding to Hyp-arabinosides and non-glycosylated Hyp were absent. Importantly, this indicates that all of the Hyp residues in the glycomodule were linked to a polysaccharide.

In contrast, (GAGP)$_3$-EGFP yielded peaks corresponding to Hyp-arabinosides, non-glycosylated Hyp, and Hyp-polysaccharide. However, (GAGP)$_3$-EGFP (FIGS. 11 & 15) was designed with fewer contiguous Hyp residues than the consensus sequence of native GAGP and yielded fewer Hyp arabinosides consistent with fewer contiguous Hyp arabinosylation sites [Kieliszewski & Lamport (1994) Plant J. 5, 157-172; Kieliszewski et al. (1992) Plant Physiol. 98, 919-926.; Kieliszewski et al. (1995) J.Biol.Chem. 270, 2541-2549]. In addition, occasional incomplete hydroxylation of the middle proline residue in the Pro-Pro-Pro motif (FIG. 14B) converted a region of contiguous Hyp (putative arabinosylation site) to noncontiguous Hyp (polysaccharide addition sites). Control EGFP targeted to the extracellular matrix contained no Hyp, hence no glycosylated Hyp, judging by manual Hyp assays.

The following describes the sequences of the genes and the expressed proteins as well as the Hyp-glycoside glcoprotein profile which were obtained using the SPP, and SPPP (SEQ ID NO: 289) modules described in Table 4, as well as the SPPPP (SEQ ID NO: 291) module.

A. Ser-Pro-Pro Gene

The [SPP]$_n$ module described in Table 4, item 2.a. was expresed using the following sequence:

```
GGA TCC GCA ATG GGA AAA ATG GCT      (SEQ ID No: 229)
TCT CTA TTT GCC ACA TTT TTA GTG
GTT TTA

G   S   A   M   G   K   M   A
S   L   F   A   T   F   L   V
V   L

GTG TCA CTT AGC TTA GCA CAA ACA
ACC CGG GCC [CCA CCT TCA CCC CCA
TCT CCA

V   S   L   V   L   A   Q   T
T   R   A   [P  P   S   P   P
S   P

CCG AGT CCA CCA TCC]₆ CCA CCT TCA
TCC ATG GCA TAA TAG AGC TCG

P   S   P   P   S  ]₆ P   S   S      (SEQ ID No: 230)
M   A   Stop Stop.
```

The Ser-Pro-Pro gene expressed the protein sequence [Pro-Hyp-Ser-Hyp-Hyp-Ser-Hyp-Hyp-Ser-Hyp-Hyp-Ser]$_6$ (SEQ ID NO:231) which had the following Hyp-glycoside profile: Hyp (51% of total Hyp), Hyp-Ara (0% of total Hyp), Hyp-Ara$_2$ (0% of total Hyp), Hyp-Ara$_3$ (49% of total Hyp), Hyp-Ara$_4$ (0% of total Hyp), Hyp-Polysaccharide (0% of total Hyp).

B. Ser-Pro-Pro-Pro Gene

The [SPPP]$_n$ module described in Table 4, item b. was expresed using the following sequence:

```
GGA TCC TCA ACC CGG GCC TCA CCA      (SEQ ID NO: 232)
[CCA CCA CCT TCT CCA CCT CCA TCA
CCC CCA

G   S   S   T   R   A   S   P
[P  P   P   S   P   P   P   S
P   P
```

```
CCT TCG CCT CCA CCA TCC]₄ CCT TCC
ATG GCA TAA TAG AGC TCG AAT TCG

P   S   P   P   P   S  ]₄ P   S      (SEQ ID NO: 233)
 M   A           STOP STOP
```

The expressed the protein sequence had the following Hyp-glycoside profile: Hyp (0% of total Hyp), Hyp-Ara (0% of total Hyp), Hyp-Ara₂ (21% of total Hyp), Hyp-Ara₃ (39% of total Hyp), Hyp-Ara₄ (3% of total Hyp), Hyp-Polysaccharide (37% of total Hyp).

C. The Ser-Pro-Pro-Pro-Pro Gene

The [SPPPP]ₙ module was expresed using the following sequence:

```
GGA TCC TCA ACC CGG GCC TCA CCA        (SEQ ID NO: 234)
[CCA CCA CCT TCA CCT CCA CCC CCA
TCT

G   S   S   T   R   A   S   P
[P   P   P   S   P   P   P   P   S

CCA]₉ CCA CCA CCT TCC ATG GCA TTA
TAG AGC TCG

P  ]₉ P   P   P   S   M   A   Stop  (SEQ ID NO: 235)
Stop
```

The expressed the protein sequence had the following Hyp-glycoside profile: Hyp (7% of total Hyp), Hyp-Ara (2% of total Hyp), Hyp-Ara₂ (8% of total Hyp), Hyp-Ara₃ (52% of total Hyp), Hyp-Ara₄ (31% of total Hyp), Hyp-Polysacchride (0% of total Hyp).

3. Monosaccharide and Glycosyl Linkage Analysis

Monosaccharide compositions and linkage analyses were determined at the Complex Carbohydrate Research Center, University of Georgia as described earlier. The results are shown in Table 12.

TABLE 12

Glycosyl Compositions of (Ser-Hyp)₃₂ - EGFP ((SER-HYP)₃₂ disclosed as SEQ ID NO: 275)(GAGP)₃-EGFP, Native GAGP and Crude Gum Arabic Mol %

| Glycosyl Residue | (Ser-Hyp)₃₂-EGFP | (GAGP)₃-EGFPª | Native GAGP | Crude Gum Arabic |
|---|---|---|---|---|
| Ara | 28 | 23 | 36 | 28 |
| Gal | 45 | 49 | 46 | 37 |
| Rha | 8 | 8 | 10 | 13 |
| Xyl | 0 | 2 | 0 | 0 |
| GlcUA | 19 | 16 | 9 | 17 |
| Mann | 1 | 1 | 0 | 0 |

ªvalues corrected for a small amount of glucose contamination.

Gal and Ara accounted for the bulk of the saccharides in both fusion proteins, with lesser amounts of Rha and GlcUA (Table 12); saccharide accounted for 58% (dw) of (Ser-Hyp)₃₂-EGFP ((Ser-Hyp)₃₂ disclosed as SEQ ID NO: 275) and 48% (dw) of (GAGP)₃-EGFP. Methylation analyses indicated that 3- and 3,6-linked galactose species accounted for 50 mole % of the sugars in (Ser-Hyp)₃₂-EGFP ((Ser-Hyp)₃₂ disclosed as SEQ ID NO: 275) and 46 mole % of (GAGP)₃-EGFP; 2-linked arabinofuranose (Ara (f)) accounted for 1.6 and 3.1 mole % respectively; terminal Ara(f) accounted for 20 and 21 mole % respectively; 4-arabinopyranose or 5-Ara(f) accounted for 6 and 8% respectively; all rhamnose was terminal; and all GlcUA was 4-linked.

The sugar analysis data in Table 12 shows that both fusion glycoproteins had sugar compositions typical of AGPs: a galactose : arabinose molar ratio of Ã2:1 with lesser amounts of glucuronic acid and rhamnose. The predominantly 3- and 3,6-linked galactose and terminal arabinofuranose determined by methylation analysis, was in keeping with a (–1,3-linked galactan backbone having sidechains of arabinose, glucuronic acid and rhamnose [Nothnagel, E. A. (1997) Int.Rev.Cytol. 174, 195-291]. The very low amount of 1,2-linked arabinose in (Ser-Hyp)₃₂-EGFP ((Ser-Hyp)₃₂ disclosed as SEQ ID NO: 275) agreed with the absence of Hyp arabinosides while the presence of 1,2-linked arabinose in (GAGP)₃-EGFP agreed with the presence of Hyp arabinosides in its Hyp glycoside profile as they are known to be largely 1,2-linked [Sticher et al. (1993) Plant Physiol. 101, 1239-1247; Akiyama et al. (1980) Agric.Biol.Chem. 44, 2487-2489]. Thus, (GAGP)₃-EGFP contained both types of Hyp glycosylation consistent with the presence of a polypeptide having contiguous and non-contiguous Hyp as putative arabinosylation and polysaccharide addition sites, respectively.

With respect to the size of attached polysaccharide, Hyp glycoside profiles showed the molar ratio of Hyp-polysaccharide in each fusion glycoprotein (Table 11). This gives the number of (polysaccharide)-Hyp residues in each glycoprotein molecule. (e.g. Hyp-polysaccharide accounted for 100% of the Hyp glycosides in (Ser-Hyp)₃₂ (SEQ ID NO: 275) i.e. 31-32 Hyp-polysaccharide). Glycoprotein size before and after deglycosylation gave an approximate size for the attached polysaccharide. The size of each fusion protein before and after deglycosylation was Ã95-115 kDa and 34 kDa respectively for (Ser-Hyp)₃₂-EGFP ((Ser-Hyp)₃₂ disclosed as SEQ ID NO: 275) (Ã71 kDa carbohydrate), and Ã70-100 kDa and 34 kDa respectively for (GAGP)₃-EGFP (Ã51 kDa carbohydrate). Judging by the gene sequence (not shown) and FIG. 14, (Ser-Hyp)₃₂-EGFP ((Ser-Hyp)₃₂ disclosed as SEQ ID NO: 275) contains Ã31-32 Hyp residues, all noncontiguous, hence with an average polysaccharide size of 71 kDa/31=2.2-2.3 kDa which corresponds to 14-15 sugar residues (average sugar residue weight of 155 calculated from the sugar composition in Table 12) and is consistent with the empirical formula Gal₆ Ara₃ GlcA₂ Rha based on compositional data in Table 12. Similarly, (GAGP)₃-EGFP contains Ã23-25 Hyp residues of which 62% (Table 11), or Ã15 occur with polysaccharide attached. Hence the polysaccharide approximates 51 kDa/15=3.4 kDa corresponding to about 22 sugar residues, a modest overestimate as it includes arabinose from the Hyp arabinooligosaccharides.

The similarity of these fusion glycoproteins to native GAGP (Table 12) suggests a model for the Hyp-polysaccharide based on the general arabinogalactan structure [Akiyama et al. (1980) Agric.Biol.Chem. 44, 2487-2489; Aspinall & Knebl (1986) Carbohyd.Res. 157, 257-260; Defaye & Wong (1986) Carbohydr.Res. 150, 221-231] of a galactan core with small sidechains containing rhamnose, arabinose and glucuronic acid. Possibly larger arabinogalactan polysaccharide can be built up by repeated addition [Clarke et al. (1979) Phytochem. 18, 521-540; Bacic et al. (1987) Carbohyd.Res. 162, 85-93] of small ~12 residue motifs represented by the above empirical formula.

4. Hydroxyproline Assay of Secreted EGFP

Secreted EGFP, the product of the Sig-EGFP gene, was isolated by the Superose-12 fractionation. We removed EGFP from the fusion glycoproteins by overnight pronase digestion (1% ammonium bicarbonate, 5 mM $CaCl_2$; 27° C. 1:100 enzyme:substrate ratio) followed by isolation of EGFP by gel permeation chromatography as described above. After dialysis and freeze-drying, we assayed Hyp on 0.5 mg EGFP as described earlier. There was no Hyp in secreted EGFP or in EGFP removed from the fusion glycoproteins by pronase.

5. Anhydrous Hydrogen Fluoride (HF) Deglycosylation

We deglycosylated 4.5 mg each of $(Ser-Hyp)_{32}$-EGFP ($(Ser-Hyp)_{32}$ disclosed as SEQ ID NO: 275) and $(GAGP)_3$-EGFP in anhydrous HF containing 10% dry methanol for 1 hr at 0° C. then quenched the reactions in $ddH_2O$. After deglycosylation of 4.5 mg of each fusion glycoprotein, we recovered 1 mg of deglycosylated $(Ser-Hyp)_{32}$-EGFP ($(Ser-Hyp)_{32}$ disclosed as SEQ ID NO: 275) (i.e. Ã23% weight recovery) and 2.2 mg deglycosylated $(GAGP)_3$-EGFP (i.e. Ã50% recovery).

6. Protein and DNA Sequence Analysis

Protein sequence analysis was performed at the Michigan State University Macromolecular Facility on a 477-A Applied Biosystems Inc. gas phase sequencer. DNA sequencing was performed at the Guelph Molecular Supercentre, University of Guelph, Ontario, Canada. Edman degradation confirmed the gene sequences and identified which Pro residues had been hydroxylated to Hyp. In particular, N-terminal sequencing of both $(Ser-Hyp)_{32}$-EGFP ($(Ser-Hyp)_{32}$ disclosed as SEQ ID NO: 275) and $(GAGP)_3$-EGFP (FIG. 14) verified the synthetic gene sequences and identified hydroxyproline residues. Occasional incomplete proline hydroxylation has been observed elsewhere [de Blank et al. (1993) Plant Mol.Biol. 22, 1167-1171] and may simply signify a prolyl hydroxylase with less than 100% fidelity.

The above data demonstrates that the repetitive Ser-Hyp motif directed the exclusive addition of arabinogalactan polysaccharide to Hyp in $(Ser-Hyp)_{32}$-EGFP while Hyp arabinosylation was correlated with the presence of contiguous Hyp motifs in $(GAGP)_3$-EGFP. Thus the O-Hyp glycosyltransferases of plants seem to resemble the O-Ser and O-Thr glycosyltransferases of animals in their multiplicity and ability to discriminate based on primary sequence and site clustering [Bacic et al. (1987) supra; Gerken et al. (1997) J.Biol.Chem. 272, 9709-9719].

EXAMPLE 24

Assay of Emulsifying Activity and Emulsion Stabilizing Activity of GAGPs

This Example analyzes the emulsifying activity (EA) and emulsion stabilizing activity (ES) of recombinant $(GAGP)_3$-EGFP which was expressed in the medium of transformed tobacco cell cultures as described above (Example 23). These activities were compared with those for bovine serum albumin (BSA), crude gum arabic glycoprotein (crude GAGP) which was isolated from *Acacia senegal*, dialyzed gum arabic glycoprotein, and tobacco arabinogalactan-protein (AGP) which contains a mixture of at least four different arabinogalactan-proteins. In addition, this Example describes the emulsifying activity and emulsion stabilizing activity of $(GAGP)_3$-EGFP protein fractions which were fractionated on Superose-6 and reverse-phase columns (Example 23), as well as the effect of size and glycosylation of $(GAGP)_3$-EGFP on emulsifying activity and emulsion stabilizing activity. All GAGP emulsions used in Tables 14-17, infra, were prepared at a concentration of 0.5% (w/v).

The emulsifying activity and emulsion stabilizing activity were determined using orange oil (Sigma) following essentially the manufacturer's instructions. Freeze-dried glycoproteins were dissolved in 0.05 M phosphate buffer (pH 6.5) at a concentration of 0.5% (m/v): The aqueous solutions were combined with orange oil in a 60:40 (v/v) ratio. A 1 ml emulsion was prepared in a glass tube at 0° C. with a Sonic Dismembrator (Fisher Scientific) equipped with a Microtip probe. The amplitude value was set at 4 and mixing time was set to 1 min.

For the determination of emulsifying ability (EA), the emulsion was diluted serially with a solution containing 0.1 M NaCl and 0.1% SDS to give a final dilution of 1/1500. The optical density of the diluted emulsion was then determined in a 1-cm pathlength cuvette at a wavelength of 50 nm and defined as the emulsifying activity (EA). BSA was used as a positive control. Test samples which showed an emulsifying activity which was at least 10%, more preferably at least 50%, and most preferably at least 75% of the emulsifying activity of a BSA control are said to be "characterized by having emulsifying activity."

For emulsifying stability, the emulsion was stored vertically in a glass tube for 3 h at room temperature, then the optical density of 1:1500 dilution of the low phase of the stored sample was measured. Emulsifying stability (ES) was defined as the percentage optical density remaining after 2 hour of storage. BSA was used as a positive control. Test samples which showed an emulsion stabilizing activity which was at least 10%, more preferably at least 50%, and most preferably at least 75% of the emulsion stabilizing activity of a BSA control are said to be "characterized by having emulsion stabilizing activity."

To determine whether $(GAGP)_3$-EGFP had emulsifying activity and/or emulsion stabilizing activity, this glycoprotein was assayed as described above and its activities were compared with those for bovine serum albumin (BSA), crude gum arabic, dialyzed gum arabic, and tobacco AGP. The results are shown in Table 13, which demonstrates the emulsifying properties of native gum arabic when compared to BSA, the synthetic $GAGP_3$-EGFP, and native tobacco AGPs.

TABLE 13

Emulsions properties of crude Gum Arabic and other Materials[a]

| Materials | BSA (0.5%) | Crude GAGP (0.5%) | Crude GAGP (1.0%) | Dialyzed GAGP (0.5%) | Synthetic GAGP[b] (0.5%) | Tobacco AGP (0.5%) |
|---|---|---|---|---|---|---|
| EA | 0.801 | 0.102 | 0.472 | 0.146 | 0.007 | 0.035 |
| ES | 90.6% | 39.7% | 83.0% | 57.5% | 20.2% | 20.0% |

[a]Values in parentheses are of the concentration (wt %)
[b]Synthetic GAGP (i.e., $GAGP_3$-EGFP) was isolated from the medium of the recombinant tobacco cell culture. The fused GFP was knocked off by pronase digestion before emulsion property measurement.

In addition, different $(GAGP)_3$-EGFP fractions which were obtained from Superose-6 column fractionation were also assayed and the results are shown in Table 14 which demonstrates that fraction F-2, which contained native GAGP showed the highest emulsifying activity and emulsion stabilizing activity of all fractions tested. These results establish GAGP as the emulsifying component of gum arabic.

TABLE 14

Emulsion Properties of GAGP Protein Fractions separated by Superose-6 column

| Fractions | F-1 | F-2 | F-3 | F-4 | F-5 |
|---|---|---|---|---|---|
| EA | 0.442 | 0.558 | 0.299 | 0.081 | 0.019 |
| ES | 74.1% | 84.2% | 48.5% | 32.2% | 22.4% |

The F-2 fraction was further separated on Hydrophobic Interaction column (HIC). The F-2 fraction was dissolved in 4.2 M NaCl and injected onto the HIC column. The column was eluted, starting by 4.2 M NaCl, followed by 3.0 M NaCl, 2.0 M NaCl, 1.0 M NaCl, and distilled water. The resulting fractions were tested and the results are shown in Table 15, which demonstrates that F-2 contains GAGP which is characterized by having emulsifying activity and emulsion stabilizing activity. Table 15 also demonstrates that F-2 separates into four components which differ in hydrophobicity, with the 2.0M and 1.0M NaCl hydrolysates being good emulsifiers

TABLE 15

Emulsion Properties of F-2 Fractions Separated by Hydrophobic Interaction Column

| Fractions | 4.2 M NaCl 1 | 2 | 3.0 M NaCl | 2.0 M NaCl | 1.0 M NaCl | Distilled water |
|---|---|---|---|---|---|---|
| EA | 0.076 | 0.284 | 0.475 | 0.710 | 0.670 | 0.04 |
| ES | 28% | 60.5% | 78.5% | 93.5% | 94.6% | 21.0% |

In order to determine the effect of the size of GAGPs on their emulsion activity and emulsion stabilizing activity, the F-2 fraction containing native GAGP was incubated in 0.2 N NaOH at 50° C. for 0.5 hr, 1.0 hr, 2.0 hr, 4.0 hr, and 8.0 hr. and the emulsifying properties of each sample were determined as shown in Table 16.

TABLE 16

Emulsion Properties of Partially-deglycosylated F-2

| Samples | 0 hr | 0.5 hr | 1.0 hr | 2.0 hr | 4.0 hr | 8.0 hr |
|---|---|---|---|---|---|---|
| EA | 0.558 | 0.354 | 0.245 | 0.097 | 0.036 | 0.011 |
| ES | 84.2% | 61.2% | 41.5% | 23.2% | 0 | 0 |

The results in Table 16 demonstrate that both the emulsifying activity and emulsion stabilizing activity of GAGP decrease with decreasing GAGP size.

To determine whether the carbohydrate moiety of GAGPs affects their emulsion activity and emulsion stabilizing activity, the F-2 fraction was partially deglycosylated by anhydrous hydrogen fluoride (HF) as described above, and the emulsifying properties of the deglycosylated sample were determined. Deglycosylated F-2 fraction had an EA of 0.269, and an ES of 46.5%. These results demonstrate that the GAGP in the F-2 fraction lost most of its ability to emulsify, thus indicating the importance of the carbohydrate moiety of the GAGP for emulsification.

EXAMPLE 24

Tyrosine Mediated Extensin Crosslinking

This example demonstrates the construction, expression and composition of three extensin crosslinking modules.

Four putative P-3 type extensin crosslinking modules were designed and integrated into the Ser-Hyp$_4$-Ser-Hyp-Ser-Hyp$_4$ (SEQ ID NO: 249) palindromic module by methods known to those skilled in the art. These sequences were expressed as repeated sequences (i.e., for example 8, 9 or 20 repeats) comprising tyrosine triplets or phenylalanine triplets terminated by either a lysine or leucine residue as listed in Table 17 below.

TABLE 17

P3 Extensin Synthetic Gene Construct Monomers.

| Sequence Name | Palindromic Module (SEQ ID NO: 249) | Putative Cross-linking Module |
|---|---|---|
| YK (8 and 20 repeats) | Ser-Pro-Pro-Pro-Pro-Ser-Pro-Ser-Pro-Pro-Pro-Pro- | -Tyr-Tyr-Tyr-Lys SEQ ID NO: 250 |
| FK (9 repeats) | Ser-Pro-Pro-Pro-Ser-Pro-Ser-Pro-Pro-Pro-Pro- | -Phe-Phe-Phe-Lys SEQ ID NO: 251 |
| YL (8 and 20 repeats) | Ser-Pro-Pro-Pro-Pro-Ser-Pro-Ser-Pro-Pro-Pro-Pro- | -Tyr-Tyr-Tyr-Leu SEQ ID NO: 252 |
| FL (8 repeats) | Ser-Pro-Pro-Pro-Pro-Ser-Pro-Ser-Pro-Pro-Pro-Pro- | -Phe-Phe-Phe-Leu SEQ ID NO: 253 |

P3 gene constructs YK20, YL8 and FK9 were separately ligated into the recombinant binary plant expression vector pB1121 between a native tobacco signal sequence and an EGFP reporter gene. This vector was used to transform BY2 tobacco callus cells via *Agrobacterium tumefaciens* infection. Subsequent EGFP expression in this transformed cell line was verified by fluorescent microscopy. The fourth P3 gene construct, FL8, has not been successfully expressed at this time.

Figure 17A:
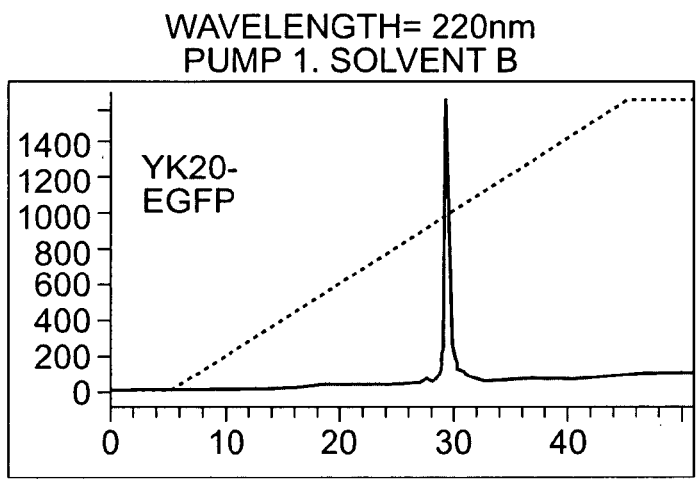
FIGS. 17A-17C show exemplary C4 reverse phase HPLC purification profiles depicting post-expression isolation and separation of: (A) YK20-EGFP (~300 µg); (B) YL8-EGFP (~200 µg); and (C) FK9-EGFP (~400 µg).
Figure 17B:
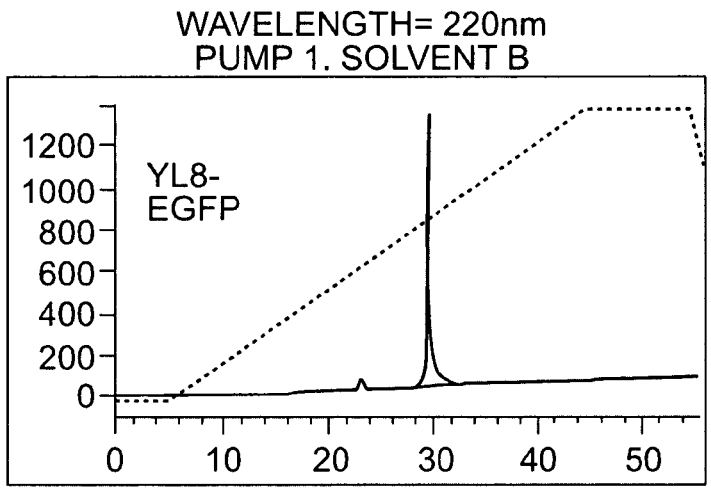
Figure 17C:
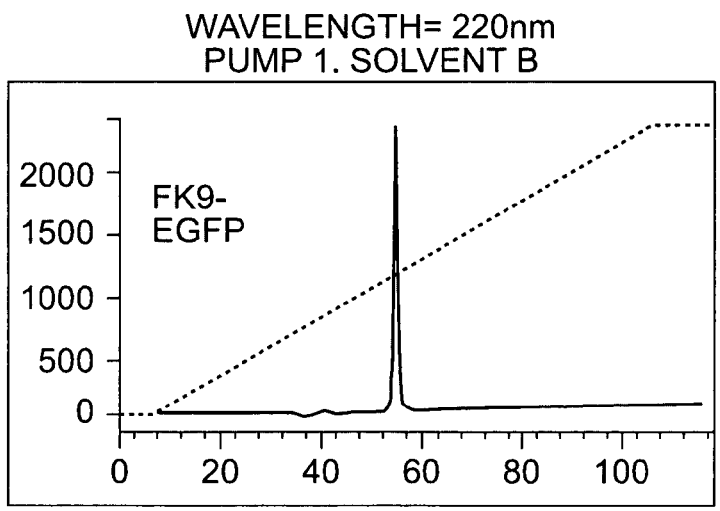

Expressed P3 extensin variants were collected from the culture medium and concentrated, desalted, and isolated by butyl sepharose hydrophobic interaction chromatography (HIC) followed by Superose-12 gel filtration chromatography and C4 reversed phase HPLC. FIG. 17 shows a clear and distinct separation and collection of the three P3 extensin variants.

The glycosylation patterns of these expressed P3 extensin variants were determined. Table 18 clearly shows that Hyp-Ara4 (SEQ ID NO: 200) glycosylation predominates in all three variants followed by a significant amount of Hyp-Ara3 (SEQ ID NO: 201) glycosylation. One having skill in the art should recognize that the apparent absence of Hyp-polysaccharide glycosylation is consistent with the Hydroxyproline Contiguity Hypothesis contemplated by the present invention. Specifically, the Hydroxyproline Contiguity Hypothesis predicts a high degree of arabinosylation due to the presence of two Ser-(Hyp)$_4$ (SEQ ID NO: 3) sequences per repeat.

TABLE 18

Hyp-glycoside profile of YK20-EGFP, YL8-EGFP, and FK9-EGFP.

| | Percentage of Total Hyp | | |
|---|---|---|---|
| Hyp-Glycoside | YK20-EGFP | YL8-EGFP | FK9-EGFP |
| Hyp-polysaccharide | 0 | 3 | 0 |
| Hyp-Ara4 (SEQ ID NO: 200) | 56 | 55 | 42 |
| Hyp-Ara3 (SEQ ID NO: 201) | 32 | 27 | 40 |
| Hyp-Ara2 (SEQ ID NO: 202) | 4 | 6 | 5 |
| Hyp-Ara1 (SEQ ID NO: 203) | 5 | 4 | 5 |
| Free Hyp | 3 | 5 | 8 |
| Total | 100 | 100 | 100 |

Performed according to Lamport et al. Plant Physiol., 48: 454-456 (1971).

The data in Table 18 is corroborated by a neutral sugar analysis, where high levels of arabinose were detected in all of the P3-type extensin variants. (see Table 19). A significant amount of galactose is present in all P3-type extensins suggesting the presence of a galactosyl-serine moiety (i.e., Ser-O-Gal), also common to native, network forming extensins. Lamport, D.T.A. 1st International Protoplast Colloquium, Versailles. I.N.R.A., pp. 27-31 (1973); and Lamport et al., Biochem J., 133:125-131 (1973). The low amounts of rhamnose and xylose are also consistent with the Hyp-glycoside profile data presented in Table 18, supporting the conclusion that a noncontiguous Hyp residue module is not sufficient for polysaccharide attachment.

TABLE 19

Neutral Sugar Analysis of YK20-EGFP, YL8-EGFP, and FK9-EGFP as determined by alditol acetate derivitization and gas chromatography.

| Glycosyl Residue | YK20-EGFP mol % | YL8-EGFP mol % | FK9-EGFP mol % |
|---|---|---|---|
| Arabinose | 90 | 84 | 91 |
| Galactose | 8 | 12 | 9 |
| Rhamnose | 1 | 2 | 0 |

TABLE 19-continued

Neutral Sugar Analysis of YK20-EGFP, YL8-EGFP, and FK9-EGFP as determined by alditol acetate derivitization and gas chromatography.

| Glycosyl Residue | YK20-EGFP mol % | YL8-EGFP mol % | FK9-EGFP mol % |
|---|---|---|---|
| Xylose | 0 | 1 | 0 |
| Glucose | 1 | 1 | 0 |
| Totals | 100 | 100 | 100 |

Performed according to Albersheim et al., Carbohydrate Research, 5: 340-345 (1967).

Figure 18:
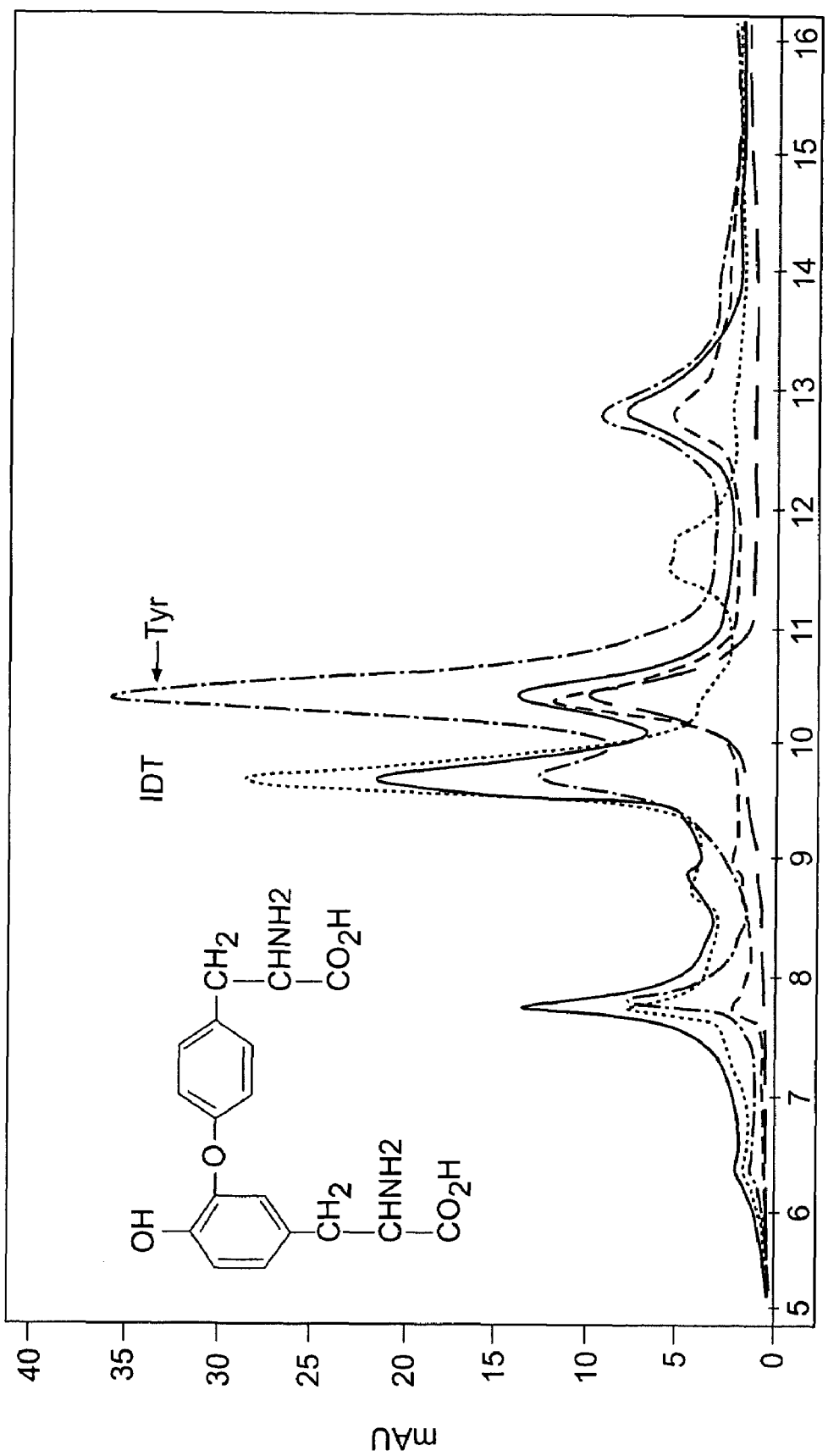
FIG. 18 shows the ability of C4 Reverse Phase HPLC to resolve isodityrosine derivatives of YK20-EGFP, YL8-EGFP, and FK9EGFP. Rank order of IDT elution peak heights (7.5 minutes): IDT Standard>YK20-EGFP=YL8-EGFP>FK9-EGFP. The structure of IDT is presented as an inset.

Participation of these three P3-type extensin variants in either intra- or intermolecular crosslinking is demonstrated in FIG. 18. The presence of isodityrosine indicates that a crosslinkage occurred. These data clearly show that tyrosine is necessary for these crosslinks to occur. Specifically, IDT was found in YK20-EGFP (second highest peak) and to a lesser degree YL8-EGFP (third highest peak). By contrast, no IDT was found in FK9-EGFP indicating that phenylalanine substitution of the tyrosine triplet effectively prevented the occurrence of crosslinking. This data answers the question left in the art regarding the complete extensin crosslink motif represented previously by (-Tyr-X-Tyr-). Epstein et al., Phytochemistry, 23:1241-1246 (1984). These data are also consistent with observations that P3 extensin tryptides are isolated from sycamore cell walls. Lamport, D.T.A. 1st International Protoplast Colloquium, Versailles. I.N.R.A., pp. 27-31 (1$^{973}$).

Finally, the amino acid composition of the expressed P3 extensin variants were verified. Predicted values, based on the known structure, are consistent with direct amino acid analysis data. See Table 20. Prior to C4 reverse phase HPLC separation the EGFP tag was removed by tryptic digestion.

TABLE 20

Amino Acid Composition Analysis of YK20, YL8, and FK9.

| Amino Acid | YK20 mol % (predicted mol %) | YL8 mol % (predicted mol %) | FK9 mol % (predicted mol %) |
|---|---|---|---|
| Hydroxyproline | 51 (55) | 52 (55) | 54 (55) |
| Serine | 17 (19) | 18 (19) | 18 (19) |
| Tyrosine | 16 (19) | 20 (19) | 9 (0) |
| Phenylalanine | 0 (0) | 0 (0) | 21 (19) |
| Lysine | 9 (7) | 9 (0) | 7 (7) |
| Leucine | 0 (0) | 8 (7) | 0 (0) |
| Isodityrosine | 7 (Not Predicted) | 2 (Not Predicted) | 0 (0) |
| Totals | 100 (100) | 100 (100) | 100 (100) |

Technical Acknowledgement: Joe Leykam (Michigan State University).

EXAMPLE 25

VYK (SEQ ID NO: 256) Crosslinking in P1 Extensin Proteins

This example demonstrates the design and expression of synthetic genes encoding P1 crosslinking motifs.

In particular, the design of the P1 extensin synthetic genes encode for proteins having at least one substitution of phenylalanine for tyrosine and at least one substitution of leucine for lysine. As illustrated in Table 21, these exemplary two variants were incorporated into the primary extensin module to create a complete P1 extensin variant as contemplated by this invention. Although it is not necessary to understand the mechanism of an invention it is believed that these these substitutions prevent crosslinking by the elimination of the reactive hydroxyl and amino groups of tyrosine and lysine, respectively.

The data shown in FIG. 21, demonstrates that VYK (SEQ ID NO: 256) peptide does cross-link, although to a much lesser extent than the complete P1 extensin protein. This is most likely due to the small size (Ã60 AA) of the VYK (SEQ ID NO: 256) module as compared to the complete P1 extensin protein (>300 AA). This strongly suggests that the

TABLE 21

P1 Extensin Modules to Test Putative Cross-linking Site

| Sequence Name | Extensin Module | Crosslink Module |
|---|---|---|
| VYK | Ser-Pro-Pro-Pro-Pro-Thr-Pro- (SEQ ID NO: 257) | Val-Tyr-Lys (SEQ ID NO: 256) |
| VFL | Ser-Pro-Pro-Pro-Pro-Thr-Pro- (SEQ ID NO: 257) | Val-Phe-Leu (SEQ ID NO: 258) |

Figure 19:
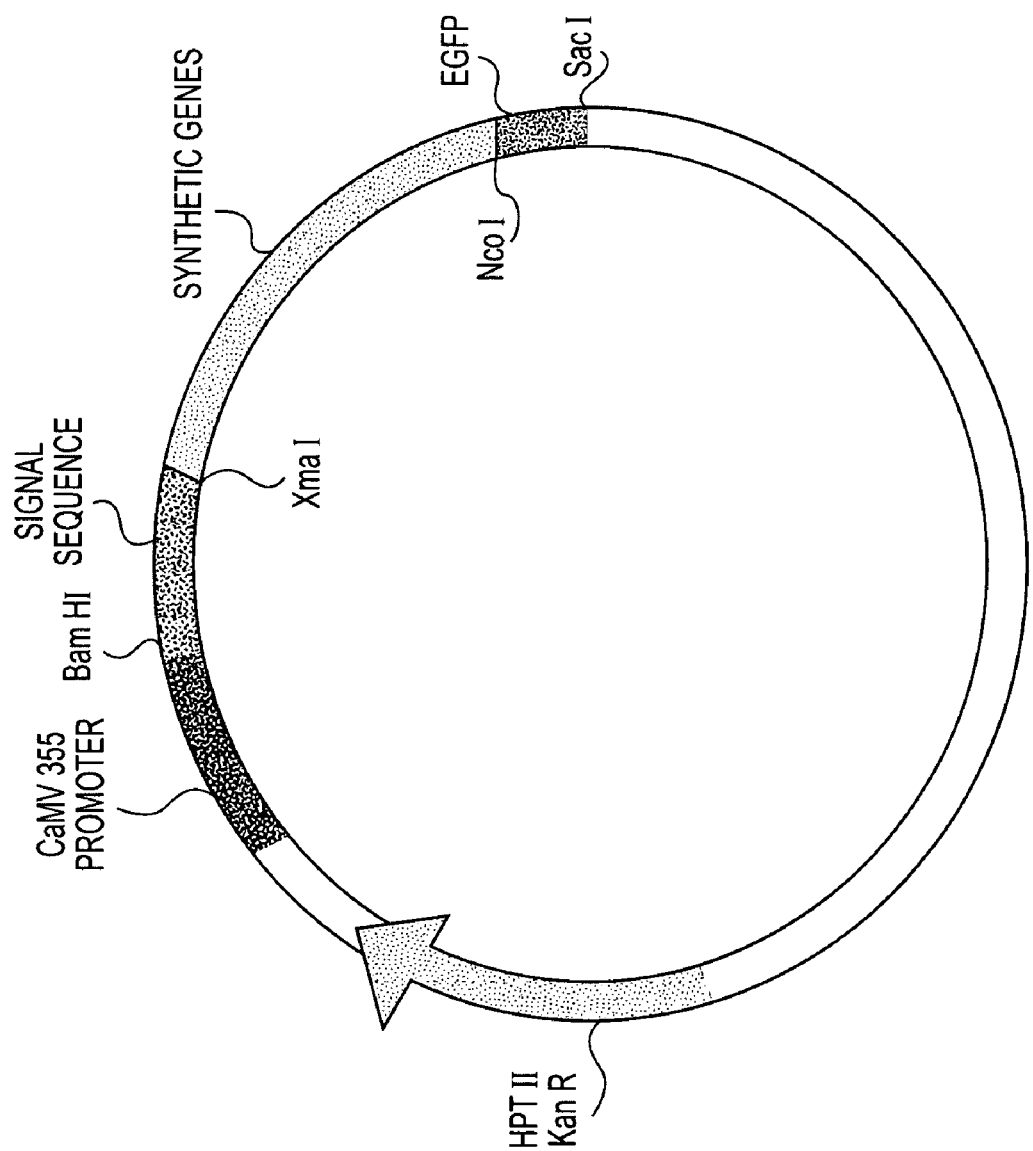
FIG. 19 depicts an exemplary pBI121 plasmid with a signal sequence synthetic gene-EGFP.
Figure 21A:
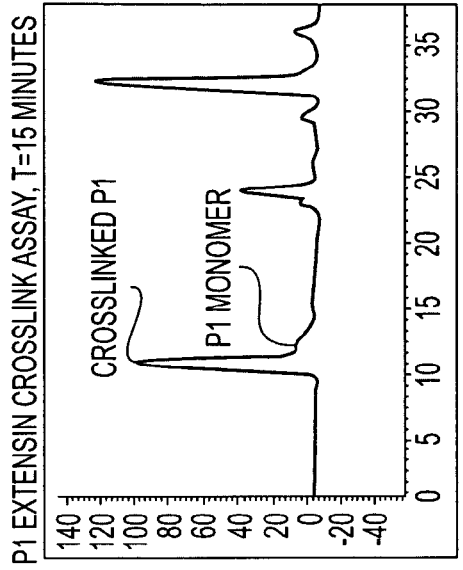
FIG. 21 shows exemplary data of P1 extension crosslinking development. Assays were performed on Superose 6 gel filtration columns and measured at 220 nm (a) P1 extensin protein crosslinking prior to peroxidase incubation; (b) P1 extensin protein crosslinking after 15 minutes of peroxidase incubation; (c) VYK (SEQ ID NO: 256) module crosslinking prior to peroxidase incubation; and (d) VYK (SEQ ID NO: 256) module crosslinking after 19 hours of peroxidase incubation. Note: As cross-linking occurs, the monomer peak decreases and a peak representing a larger cross-linked oligomer appears.
Figure 21B:
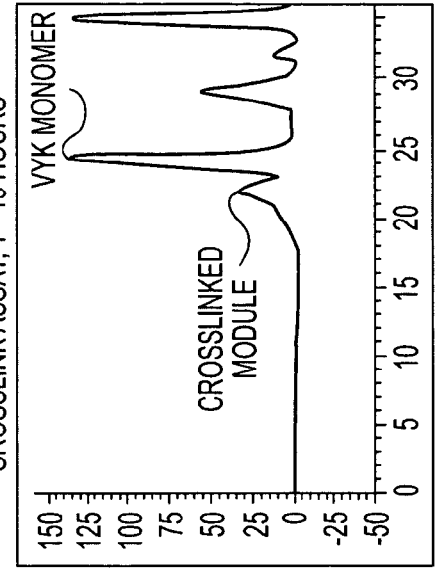
Figure 21C:
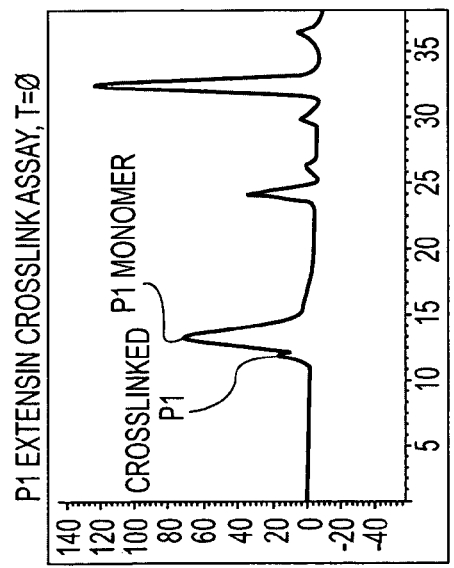
Figure 21D:
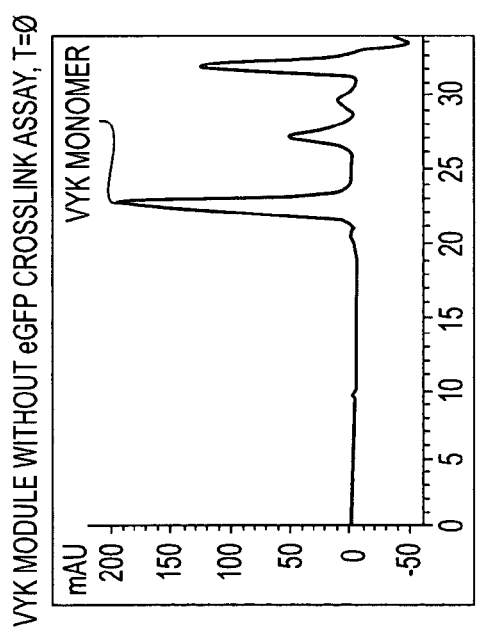

The method of gene construction was adapted from techniques known in the art and diagrammed in FIG. 19. Shpak et al., *Proc. Natl. Acad. Sci.* 96:14736-14741 (1999). Briefly, the appropriate overlapping oligonucleotide pairs were annealed and polymerized to create the desired synthetic gene. The synthetic gene was then inserted into pUC18 as a BamHI-EcoRl fragment, sequenced and then inserted between the signal sequence and EGFP in pUC18 as a XmaI-NcoI fragment. Finally, the signal sequence-synthetic gene-EGFP unit was placed in the plant transformation vector pBI121 as a BamHI-SacI fragment.

The pBI121-based plasmids were then delivered into *Agrobacterium tumifaciens* which was then used to transform suspension cultured tobacco cells. Plant cells are utilized for transformation and expression as bacteria are not capable of making the necessary posttranslational modifications. Specifically, mammalian cells have a different hydroxylation pattern and do not glycosylate hydroxyproline residues. Ruggiero et al., *FEBS Lett.* 469:132-136 (2000). The transformed tobacco cells were grown on solid and liquid SH media and selected for kanamycin resistance. Protein expression was verified using a confocal laser scanning fluorescence microscope by visualizing EGFP fluorescence. (FIG. 20).

Soluble P1 extensin fusion proteins containing six repeats were then isolated from the culture medium. The media was first concentrated by rotary evaporation, then dialyzed against water, and finally freeze-dried. The freeze-dried sample was redissolved in 2 M sodium chloride and injected onto a hydrophobic interaction column for purification verification. A step gradient of decreasing sodium chloride concentration was used to elute the column. Sequential fractions were monitored for fluorescence using a Hewlett Packard 1100 Series flow-through fluorometer and collected. The collected fluorescent P1 extensin fractions were further purified using gel filtration and reverse-phase chromatography.

The detection of crosslinkages was performed using a pI 4.6 peroxidase assay. Specifically, the isolated fusion proteins were treated with trypsin to remove EGFP and were then tested as substrates for isolated tomato pI 4.6 peroxidase. The cross-linked product and the resultant monomers was measured by a Superose 6 gel filtration assay. Everdeen et al., *Plant Physiol.* 87:616-621 (1988). Native P1 extensin served as the positive control and the SPPPPTPVFL (SEQ ID NO: 259) served as the negative control.

monomers must align themselves for cross-linking, possibly by the Ser-Hyp$_4$ (SEQ ID NO: 3) motifs.

EXAMPLE 26

Isolation of the LeAGP1 Signal Sequence and Creation of Plasmid pUC-SS$^{tom}$-EGFP This example describes the generation of two variants of the Le-APG1 protein. FIG. 22 shows the DNA sequence of EGFP-LeAGP-1 (SEQ ID NO: 265) and the corresponding primary amino acid sequence (SEQ ID NO: 266).

Tomato LeAGP-1 signal sequence was amplified using the cDNA LeAGP-1c and primers designed to introduce BamHl and Xmal restriction sites to the amplified fragment. (The LeAGP-1c sequence is available in the EMBL, Gen-Bank and DDBJ Nucleotide Sequence Databases under the accession number X99148) All primers were designed using PRIMER PREMIER software (Biosoft International, Palo Alto, Calif.) and synthesized by Integrated DNA Technologies, Inc. (Coralville, Iowa). The signal sequence sense primer introduced the BamHl site (underlined); 5'-CTC TTT TCT GGA TCC GGT CTA TAT CTT TTA GC-3' (SEQ ID NO: 274) and the antisense primer introduced an Xmal site (underlined): 5'-C GGG TGC TG C CCG GGT_TGT CTG ACC CGT GAC ACT TGC-3' (SEQ ID NO: 260). The isolated fragment was subcloned into plasmid pUC-SS$^{tob}$-EGFP as a BamHl/Xmal fragment in place of the tobacco extensin signal sequence (SS$^{tob}$). This new pUC19-derived plasmid was designated pUC-SS$^{tom}$-EGFP.

1. Creation of Plasmids pUC-SS$^{tom}$-EGFP-LeAGP-1ΔK and pUC-SS$^{tom}$-EGFP-LeAGP-1ΔGPI pUC-SS$^{tom}$-EGFP-LeAGP-1

A BsrGl restriction site was introduced to the 5'-end of LeAGP-1c immediately after the signal sequence and an Eagl restriction site introduced to the 3'- and of LeAGP-1c via PCR amplification. The 5' sense primer containing the BsrGl site (underlined) was: 5'-GCA ATGTACACG_GGT CAG ACA CCT GCC GCA GCA CCC GTT G-3' (SEQ ID NO: 261)

The 3'-antisense primer contained the Eagl site (underlined): 5'-GAC GTC ACGGCCGCT_TTA GAA CAA GAG CCA GCT CAT CAC AGC-3' (SEQ ID NO: 262). The amplified LeAGP-1 fragment was subcloned into pUC-SS$^{tom}$-EGFP immediately following EGFP as a BsrGl/Eagl fragment.

pUC-SS*tom*-EGFP-LeAGP-1ΔK

First, pUC.SS*tom*-EGFP-LeAGP-1 was digested with BsrGl and Naλ to remove the 5'-end of LeAGP-1 through the lysine-rich region. The smaller BsrGl/Ns/l fragment encoding the N-terminus of LeAGP-1 and the lysine-rich region was discarded, but the larger pUC-SS*tom*-EGFP plasmid fragment which still retained the nucleotides encoding the C-terminal AGP portion of LeAGP-1, the GPI-anchor addition signal sequence, the signal sequence and EGFP was retained.

Next, PCR amplification of a section of LeAGP-1c sandwiched between the signal sequence and the region encoding the lysine-rich region introduced a BsrGl site at the 5'-end of the amplified fragment and an NsiI site at the 3'-end. The sense primer for amplification was the 5'-sense primer with a BsrGl site (described above) for construction of pUC-SS*tom*-EGFP-LeAGP-1. The anti-sense primer contained an NsiI restriction site {underlined below}: 5'-AC TTT TC ATGCATT AGG AGC CGG AGC TGG AGT TGT CTC-3' (SEQ ID NO: 263)

The resulting BsrGl/NsiI fragment was subcloned into the isolated BsrGl/Nsl pUC-SS*tom*-EGFP plasmid fragment described above, generating the plasmid pUC-SS*tom*-EGFP-LeAGP1ΔK where ΔK denotes a LeAGP-1 clone lacking the lysine-rich region.

PUC-SS*tom*-EGFP-LeAGP-1ΔGPI

LeAGP-1ΔGPl was constructed which denotes the clone 1ΔGPl (i.e., lacking the putative GPI anchor-signal sequence) by PCR amplification of LeAGP-1c using the 5' sense primer with a BsrGI site (described above) for construction of pUc-SS*tom*-EGFP-LeAGP-1 and a 3' antisense primer having an EagI restriction site (underlined):

```
5'-CAA TTT GCG GCC GCT TTA CTC ATC   (SEQ ID NO: 264)
GTT AAG AGA TGG GCT GGG A-3'
```

The resulting PCR-amplified fragment was inserted into pUC-SS*tom*-EGFP as a BsrGl/Eagl fragment. Constructs were sequenced followed by subcloning into the plant vector pBI121 (Clontech Laboratories, Palo Alto, Calif.) as BamHI-SstI fragments in place of the glucuronidase reporter gene. All constructs were under control of the 36S cauliflower mosaic virus promoter, and can be obtained from the Kieliszewski Laboratory.

2. *Agrobacterium* and Tobacco Cell Transformation and Selection of Cell Lines

The pBI121-based plasmids containing the EGFP-LeAGP-1 constructs were delivered into *Agrobacterium tumefaciens* strain LBA4404 by the freeze-thaw method. Then suspension-cultured tobacco cells (*Nicotiana tabacum* BY-2) were transformed with the *Agrobacterium*. These transformed tobacco cell lines (three lines of each construction) were selected and maintained. Callus lines exhibiting the brightest green fluorescence when examined via fluorescence microscopy were chosen for propagation in liquid culture, and lines expressing the highest amount of fusion glycoprotein in the culture medium were further characterized biochemically. The number of transgenes present in each transformed cell was not determined. Transformed cells are available from the Kieliszewski laboratory.

From the above, it should be clear that the present invention provides a new approach and solution to the problem of producing plant gums. The approach is not dependent on environmental factors and greatly simplifies production of a variety of naturally-occurring gums, as well as designer gums.

The invention claimed is:

1. An isolated polypeptide, comprising a) a first elastin module comprising at least four amino acids, wherein the elastin module comprises amino acid sequence GVP (amino acids 1 to 3 of SEQ ID NO: 277), flanked on the N-terminal side by a first extensin module comprising amino acid sequence SOOOOTO (SEQ ID NO: 280), wherein S is serine and O is hydroxyproline, the extensin module further comprising a first crosslinkage motif chosen from amino acid sequences VYK (SEQ ID NO: 256) and YYYK (SEQ ID NO: 245) and b) a second elastin module comprising at least four amino acids, wherein the elastin module comprises amino acid sequence GVP (amino acids 1 to 3 of SEQ ID NO: 277), flanked on the C-terminal side by a second extensin module comprising amino acid sequence SOOOOTO (SEQ ID NO: 280), wherein S is serine and O is hydroxyproline, the extensin module further comprising a second crosslinkage motif chosen from amino acid sequences VYK (SEQ ID NO: 256) and YYYK (SEQ ID NO: 245).

2. The polypeptide of claim 1, wherein said first elastin module is repeated six times.

3. The polypeptide of claim 1, wherein said second elastin module is repeated three times.

4. The polypeptide of claim 1, wherein said first crosslinkage motif comprises VYK (SEQ ID NO: 256) and contiguous hydroxyproline residues.

5. The polypeptide of claim 1, wherein said second crosslinkage motif comprises VYK (SEQ ID NO: 256) and contiguous hydroxyproline residues.

6. The polypeptide of claim 1, further comprising a central stretch of rigid arabinosylated SOOOO (SEQ ID NO: 3), wherein S represents seine and O represents hydroxyproline, repeats flanked on either side by first and said second elastin module.

7. The polypeptide according to claim 1, wherein the first and second elastin modules comprise an amino acid sequence chosen from VGVP (SEQ ID NO: 276), GVPG (SEQ ID NO: 277), VPGVP (SEQ ID NO: 278), and VGVPGVGVPG (SEQ ID NO: 279).

* * * * *